United States Patent
Kadoma et al.

(10) Patent No.: US 8,142,911 B2
(45) Date of Patent: Mar. 27, 2012

(54) ORGANIC COMPOUND, BENZOXAZOLE DERIVATIVE, AND LIGHT-EMITTING ELEMENT, LIGHT-EMITTING DEVICE, AND ELECTRONIC DEVICE USING THE BENZOXAZOLE DERIVATIVE

(75) Inventors: Hiroshi Kadoma, Kanagawa (JP); Sachiko Kawakami, Kanagawa (JP); Hiroko Nomura, Kanagawa (JP); Takahiro Ushikubo, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 391 days.

(21) Appl. No.: 12/466,076
(22) Filed: May 14, 2009
(65) Prior Publication Data
US 2009/0284142 A1 Nov. 19, 2009
(30) Foreign Application Priority Data

May 16, 2008 (JP) .................................. 2008-129723

(51) Int. Cl.
*H01L 51/54* (2006.01)
(52) U.S. Cl. ........ 428/690; 428/917; 548/152; 548/440; 257/40; 313/504; 313/505; 313/506
(58) Field of Classification Search .................. 428/690, 428/917; 313/504, 505, 506; 548/152, 440; 257/40
See application file for complete search history.

(56) References Cited

U.S. PATENT DOCUMENTS
6,603,007 B1   8/2003   Shintou
(Continued)

FOREIGN PATENT DOCUMENTS
EP   1 231 207 A1   8/2002
(Continued)

OTHER PUBLICATIONS

Chan et. al., Synthesis and Characterization of Poly(benzobisoxazole)s and Poly(benzobisthiazole)s with 2,2'-Bipyridyl Units in the Backbone, 1998, Macromolecules, vol. 31, pp. 5639-5646.*

(Continued)

*Primary Examiner* — Jennifer Chriss
*Assistant Examiner* — Gregory Clark
(74) *Attorney, Agent, or Firm* — Husch Blackwell LLP

(57) ABSTRACT

Novel benzoxazole derivatives are provided to reduce driving voltage of light-emitting elements, and to reduce power consumption of light-emitting elements, light-emitting devices, and electronic devices. A benzoxazole derivative represented by the general formula (G1) is provided. Since the benzoxazole derivative represented by the general formula (G1) has an electron-injecting property, the benzoxazole derivative can be suitably used for light-emitting elements, light-emitting devices, and electronic devices.

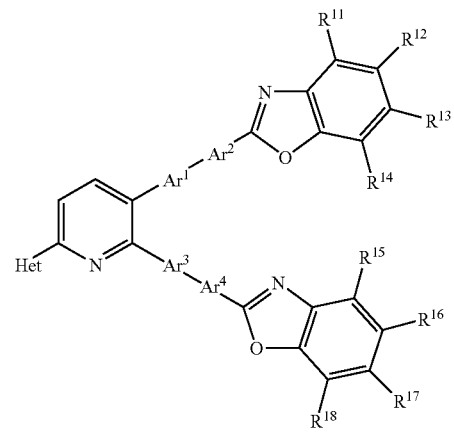

19 Claims, 48 Drawing Sheets

U.S. PATENT DOCUMENTS

| | | |
|---|---|---|
| 7,221,095 B2 | 5/2007 | Yamazaki et al. |
| 7,224,118 B2 | 5/2007 | Yamazaki et al. |
| 7,411,344 B2 | 8/2008 | Yamazaki et al. |
| 7,420,203 B2 | 9/2008 | Tsutsui et al. |
| 7,473,923 B2 | 1/2009 | Tsutsui et al. |
| 7,514,159 B2 | 4/2009 | Nakamura |
| 2008/0093981 A1 | 4/2008 | Nakamura et al. |

FOREIGN PATENT DOCUMENTS

| | | |
|---|---|---|
| JP | 2001-97950 | 4/2001 |
| WO | WO 01/19815 A1 | 3/2001 |

OTHER PUBLICATIONS

Tsuji, T. et al, "23.3: Distinguished Paper: Red-Phosphorescent OLEDs Employing Bis(8-Quinolinolato)-Phenolato-Aluminum(III) Complexes as Emission-Layer Hosts," SID 04 Digest: SID International Symposium Digest of Technical Papers, vol. 35, 2004, pp. 900-903.

* cited by examiner

ORGANIC COMPOUND, BENZOXAZOLE DERIVATIVE, AND LIGHT-EMITTING ELEMENT, LIGHT-EMITTING DEVICE, AND ELECTRONIC DEVICE USING THE BENZOXAZOLE DERIVATIVE

BACKGROUND OF THE INVENTION

1. Field of the Invention

The present invention relates to organic compounds and benzoxazole derivatives. Further, the present invention relates to light-emitting elements, light-emitting devices and electronic devices using the benzoxazole derivatives.

2. Description of the Related Art

An organic compound can take a wider variety of structures compared with an inorganic compound, and it is possible to synthesize a material having various functions by appropriate molecular-design of an organic compound. Owing to these advantages, photo electronics and electronics which use a functional organic material have been attracting attention in recent years.

For example, a solar cell, a light-emitting element, an organic transistor, and the like are exemplified as electronic devices utilizing an organic compound as a functional material. These are devices taking advantage of electric properties and optical properties of the organic compound. Among them, in particular, a light-emitting element has been making remarkable development.

It is considered that the light emission mechanism of a light-emitting element is as follows: when a voltage is applied between a pair of electrodes that interpose a light-emitting layer, electrons injected from a cathode and holes injected from an anode are recombined in an emission center of the light-emitting layer to form a molecular exciton, and energy is released to emit light when the molecular exciton relaxes to the ground state. An excited singlet state and an excited triplet state are known as excited states, and it is believed that light can be emitted through either state.

In an attempt to improve element characteristics, there are many problems which depend on a material used, and in order to solve these problems, improvement of element structure, development of a material, and the like have been carried out.

For example, as a material with an electron-transporting property for a light-emitting element, tris(8-quinolinolato)aluminum(III) (abbreviation: Alq) is widely used (e.g., Non-Patent Document 1). However, in the case of using Alq for a light-emitting element, there is a problem in that driving voltage is high. In particular, in view of commercialization, less power consumption is an important issue, and various researches and developments for a material and a light-emitting element with more superior characteristics have been carried out.

[Non-Patent Document 1]
Taishi TSUJI et al., SID 04 DIGEST, 35, PP. 900-903 (2004)

SUMMARY OF THE INVENTION

In order to reduce driving voltage of a light-emitting element, an electron-transporting material should easily accept electrons (i.e., excellent electron-injecting property). Also, in order to reduce driving voltage of a light-emitting element, it is important to have a high electron-transporting property.

Thus, it is an object of an embodiment of the present invention to provide a novel electron-transporting material.

In addition, it is another object of an embodiment of the present invention to provide a light-emitting element, a light-emitting device and an electronic device using the novel electron-transporting material.

Further, it is another object of an embodiment of the present invention to reduce driving voltage of light-emitting elements. Furthermore, it is another object of an embodiment of the present invention to reduce power consumption of light-emitting elements, light-emitting devices, and electronic devices.

An embodiment of the present invention is a benzoxazole derivative represented by a general formula (G1).

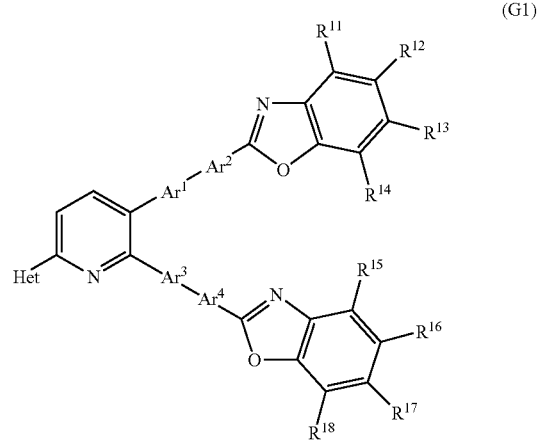

(G1)

In the formula, Het represents a pyridyl group or a pyrimidinyl group, $Ar^1$ to $Ar^4$ are independently a substituted or unsubstituted arylene group having 6 to 13 carbon atoms, and $R^{11}$ to $R^{18}$ are independently hydrogen, an alkyl group having 1 to 4 carbon atoms, a haloalkyl group having 1 to 4 carbon atoms, a substituted or unsubstituted aryl group having 6 to 13 carbon atoms, or halogen.

In the above structure, Het is preferably a substituent represented by a general formula (G1-1). In other words, Het is preferably 2-pyridyl, 4-pyridyl, pyrimidin-2-yl, or pyrimidin-4-yl.

(G1-1)

In the formula, one or two of $A^1$ to $A^3$ is/are nitrogen, and the other(s) is/are carbon.

In the general formula (G1), preferably, $Ar^1$ and $Ar^3$ have the same structure and $Ar^2$ and $Ar^4$ have the same structure.

Another embodiment of the present invention is a benzoxazole derivative represented by a general formula (G2).

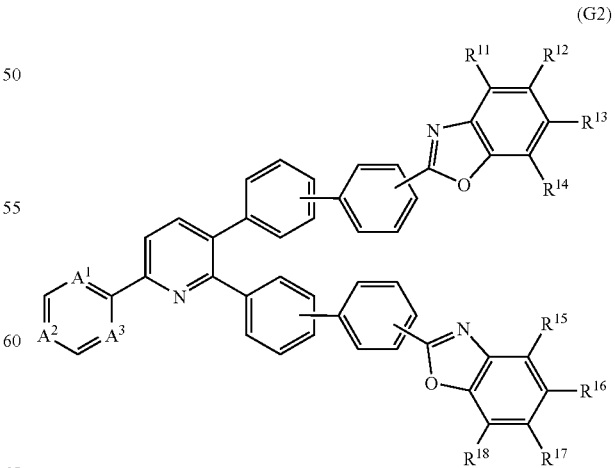

(G2)

In the formula, one or two of $A^1$ to $A^3$ is/are nitrogen, and the other(s) is/are carbon, and $R^{11}$ to $R^{18}$ are independently hydrogen, an alkyl group having 1 to 4 carbon atoms, a haloalkyl group having 1 to 4 carbon atoms, a substituted or unsubstituted aryl group having 6 to 13 carbon atoms, or halogen.

In addition, another embodiment of the present invention is a benzoxazole derivative represented by a general formula (G3).

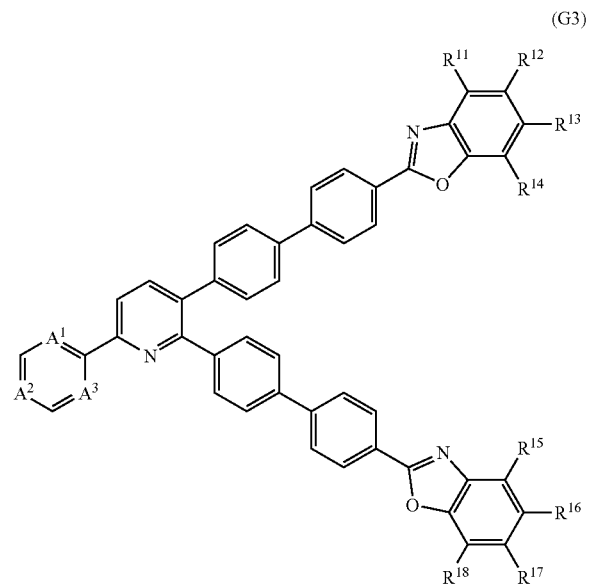

In the formula, one or two of $A^1$ to $A^3$ is/are nitrogen, and the other(s) is/are carbon, and $R^{11}$ to $R^{18}$ are independently hydrogen, an alkyl group having 1 to 4 carbon atoms, a haloalkyl group having 1 to 4 carbon atoms, a substituted or unsubstituted aryl group having 6 to 13 carbon atoms, or halogen.

Further, in the general formulae (G1) to (G3), preferably, $R^{11}$ and $R^{15}$ have the same structure, $R^{12}$ and $R^{16}$ have the same structure, $R^{13}$ and $R^{17}$ have the same structure, and $R^{14}$ and $R^{18}$ have the same structure.

In addition, any of the above benzoxazole derivatives can be suitably used for a light-emitting element.

Thus, one embodiment of the present invention is a light-emitting element including any of the benzoxazole derivatives described above between a pair of electrodes.

In particular, each of the above-described benzoxazole derivatives has an electron-transporting property, and thus is preferably used for an electron-transporting layer of a light-emitting element.

Therefore, another embodiment of the present invention is a light-emitting element having a light-emitting layer and a layer including any of the above-described benzoxazole derivatives between an anode and a cathode, in which the layer including the benzoxazole derivative is provided between the light-emitting layer and the cathode.

Moreover, the present invention includes light-emitting devices having the above described light-emitting element.

Thus, one embodiment of the present invention includes a light-emitting element including any of the benzoxazole derivatives described above and a control circuit which controls light emission of the light-emitting element.

Note that the light-emitting device in this specification includes image display devices, light-emitting devices, or light sources (including lighting device). Further, the following are all included in light-emitting devices: a module in which a connector, for example, an FPC (flexible printed circuit), a TAB (tape automated bonding) tape, or a TCP (tape carrier package) is attached to a panel provided with a light-emitting element; a module provided with a printed wiring board at the end of the TAB tape or the TCP; and a module in which an IC (integrated circuit) is directly mounted to a light-emitting element by a COG (chip on glass) method.

Further, electronic devices using a light-emitting element of the present invention in display portions are also included in the scope of the present invention. Thus, an embodiment of the present invention is an electronic device that has a display portion provided with the above-described light-emitting element and a control circuit controlling light emission of the light-emitting element.

Furthermore, the present invention also covers organic compounds used for the synthesis of the benzoxazole derivatives of the present invention because the organic compounds are novel substances. Therefore, one embodiment of the present invention is an organic compound represented by a general formula (G11).

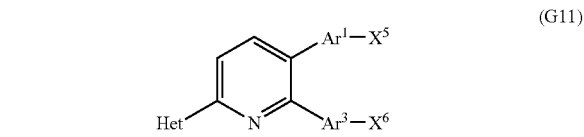

In the formula, Het is a pyridyl group or a pyrimidinyl group, $Ar^1$ and $Ar^3$ are independently a substituted or unsubstituted arylene group having 6 to 13 carbon atoms, and $X^5$ and $X^6$ are independently halogen or a triflate group (trifluoromethane sulfonyl group).

The benzoxazole derivatives of the present invention are electron-transporting materials having an excellent electron-injecting property. Thus, any of the above benzoxazole derivatives can be suitably used for a light-emitting element.

In addition, by using a benzoxazole derivative of the present invention for a light-emitting element, a light-emitting element with low driving voltage can be obtained. In addition, a light-emitting element with low power consumption can be obtained.

Further, by applying a light-emitting element of the present invention to light-emitting devices and electronic devices, power consumption of the light-emitting devices and the electronic devices can be lowered.

DETAILED DESCRIPTION OF THE INVENTION

Figure 1:
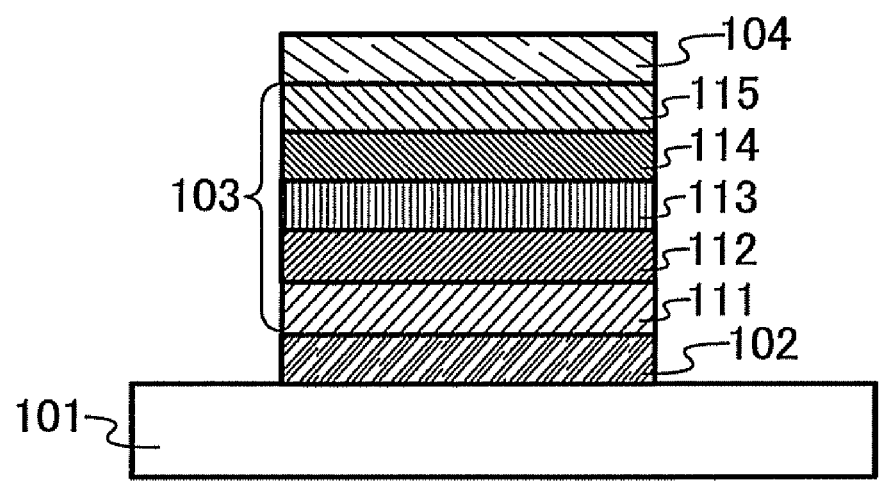
FIG. 1 illustrates a light-emitting element according to an embodiment of the present invention.

Hereinafter, embodiments of the present invention will be described in detail with reference to the accompanying drawings. However, the present invention is not limited to the following description, and various changes and modifications for the modes and details thereof will be apparent to those skilled in the art unless such changes and modifications depart from the spirit and scope of the present invention. Therefore, the present invention should not be interpreted as being limited to description in the embodiments described below.

Embodiment 1

In Embodiment 1, benzoxazole derivatives of the present invention will be described. The benzoxazole derivatives of the present invention include a heterocycle and a benzoxazole skeleton.

Specifically, one of the benzoxazole derivatives of the present invention is a benzoxazole derivative represented by a general formula (G1).

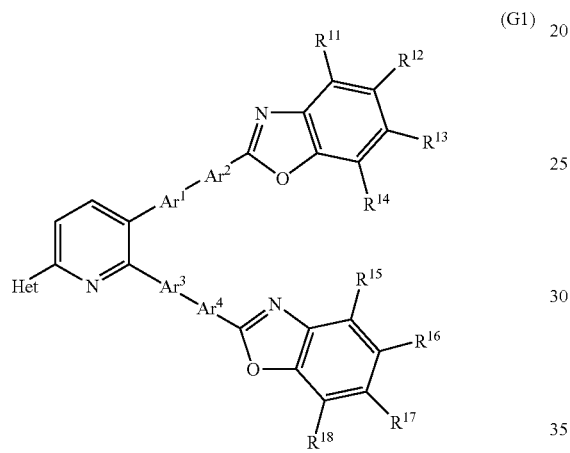

(G1)

In the formula, Het represents a pyridyl group or a pyrimidinyl group, $Ar^1$ to $Ar^4$ are independently a substituted or unsubstituted arylene group having 6 to 13 carbon atoms, and $R^{11}$ to $R^{18}$ are independently hydrogen, an alkyl group having 1 to 4 carbon atoms, a haloalkyl group having 1 to 4 carbon atoms, a substituted or unsubstituted aryl group having 6 to 13 carbon atoms, or halogen.

In the general formula (G1), examples of the arylene groups represented by $Ar^1$ to $Ar^4$ include arylene groups represented by structural formulae (11-1) to (11-13). The arylene group represented by $Ar^1$ to $Ar^4$ may further have a substituent as represented by the structural formulae (11-7) to (11-9) and the structural formulae (11-11) to (11-13).

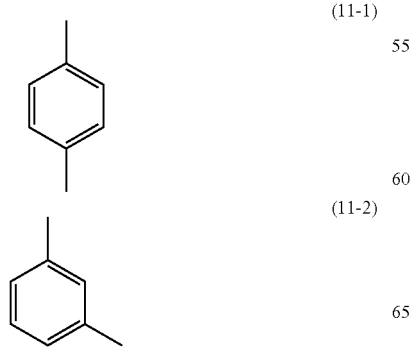

(11-1)

(11-2)

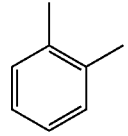

(11-3)

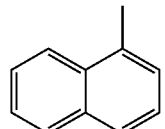

(11-4)

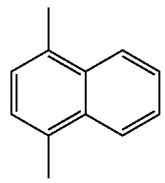

(11-5)

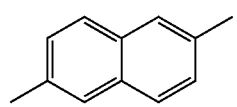

(11-6)

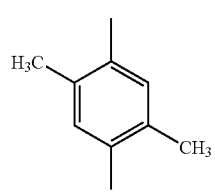

(11-7)

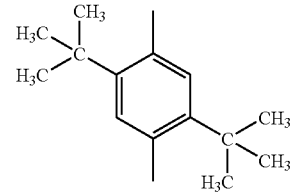

(11-8)

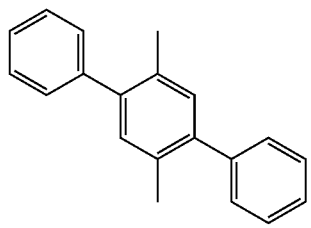

(11-9)

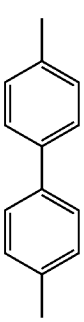

(11-10)

-continued

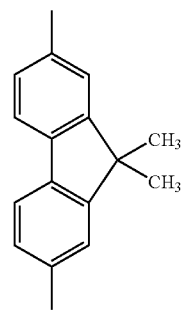
(11-11)

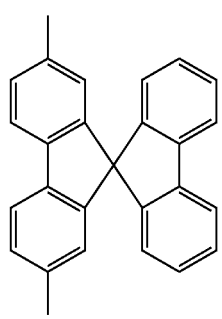
(11-12)

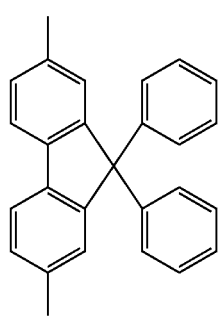
(11-13)

Note that the carbon atoms of an aryl group or an arylene group described in this specification represent carbon atoms that form a ring of the main skeleton, and carbon atoms of a substituent bound to the main skeleton are not included therein. As a substituent bound to an aryl group or an arylene group, an alkyl group having 1 to 4 carbon atoms or an aryl group having 6 to 13 carbon atoms can be given. Specifically, a methyl group, an ethyl group, a propyl group, a butyl group, a phenyl group, a naphthyl group, a fluorenyl group, or the like can be given. Further, the number of substituents included in an aryl group or an arylene group has may be either single or plural. In the case where the aryl group or the arylene group has two substituents, the substituents may be bound to each other to form a ring. For example, when the aryl group is a fluorenyl group, carbon at a 9-position may have two phenyl groups, and the two phenyl groups may be bound to each other to form a spiro ring structure. The structural formula (11-12) is an example in which a spiro ring structure is formed.

In addition, in the general formula (G1), examples of hydrogen, the alkyl group having 1 to 4 carbon atoms, the haloalkyl group having 1 to 4 carbon atoms, the substituted or unsubstituted aryl group having 6 to 13 carbon atoms, or halogen represented by $R^{11}$ to $R^{18}$ include substituents represented by structural formulae (12-1) to (12-21).

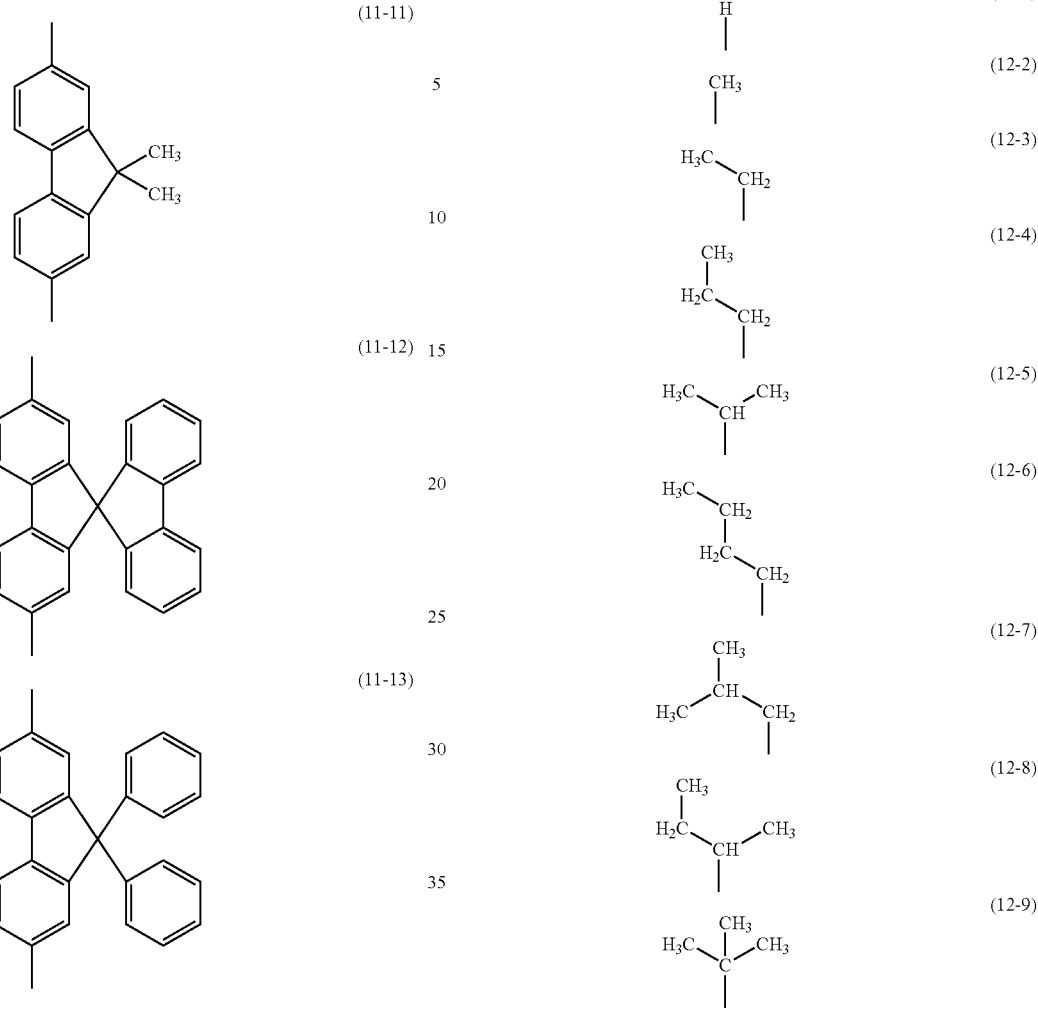

(12-14)
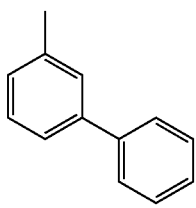
(12-15)
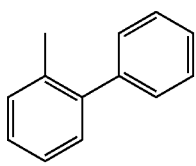
(12-16)
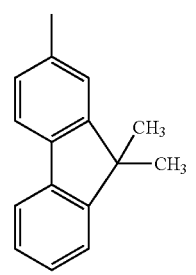
(12-17)
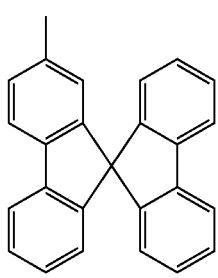
(12-18)
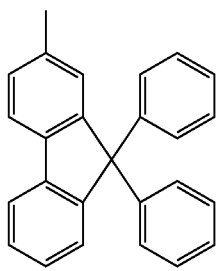
(12-19)
F—
(12-20)
Cl—
(12-21)
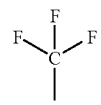
In the general formula (G1), specific examples of the heterocycle represented by Het include a pyridyl group or a pyrimidinyl group represented by structural formulae (13-1) to (13-6).
(13-1)
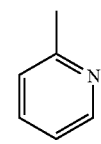
(13-2)
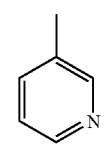
(13-3)
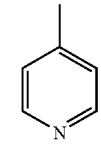
(13-4)
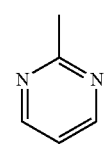
(13-5)
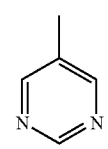
(13-6)
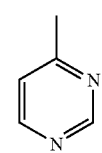
In particular, Het is preferably a substituent represented by the general formula (G1-1). In other words, Het is preferably 2-pyridyl, 4-pyridyl, pyrimidin-2-yl, or pyrimidin-4-yl.

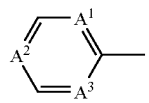
(G1-1)

In the formula, one or two of $A^1$ to $A^3$ represent(s) nitrogen, and the other(s) represent(s) carbon.

When the substitutent represented by Het is any of 2-pyridyl, 4-pyridyl, pyrimidin-2-yl, and pyrimidin-4-yl, a benzoxazole derivative having an excellent electron-injecting property and an excellent electron-transporting property can be obtained.

Further, in the benzoxazole derivative represented by the general formula (G1), the arylene groups represented by $Ar^1$ to $Ar^4$ are each preferably a phenyl group. Specifically, the arylene group is preferably any of 1,2-phenylene, 1,3-phenylene, and 1,4-phenylene. The arylene groups represented by $Ar^1$ to $Ar^4$ are each a phenylene group, so that synthesis or refinement (high purification) becomes easy.

In other words, one of the benzoxazole derivatives according to the present invention is a benzoxazole derivative represented by the general formula (G2).

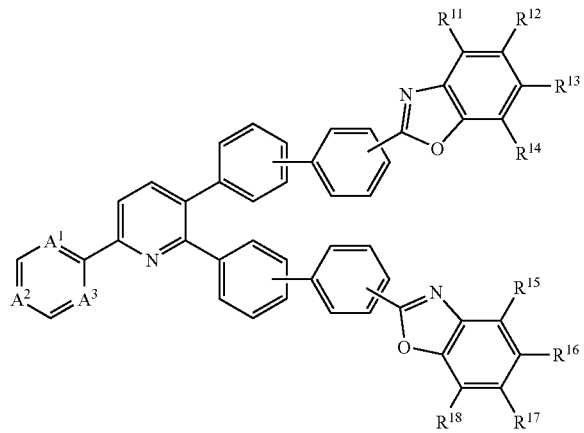
(G2)

In the formula, one or two of $A^1$ to $A^3$ represent(s) nitrogen, and the other(s) represent(s) carbon, and $R^1$ to $R^{18}$ are independently hydrogen, an alkyl group having 1 to 4 carbon atoms, a haloalkyl group having 1 to 4 carbon atoms, a substituted or unsubstituted aryl group having 6 to 13 carbon atoms, or halogen.

In addition, in the benzoxazole derivative represented by the general formula (G1), $Ar^1$ to $Ar^4$ are preferably substituted or unsubstituted 1,4-phenylens in view of easiness in synthesis or refinement (high purification).

In other words, one of the benzoxazole derivatives of the present invention is a benzoxazole derivative represented by the general formula (G3).

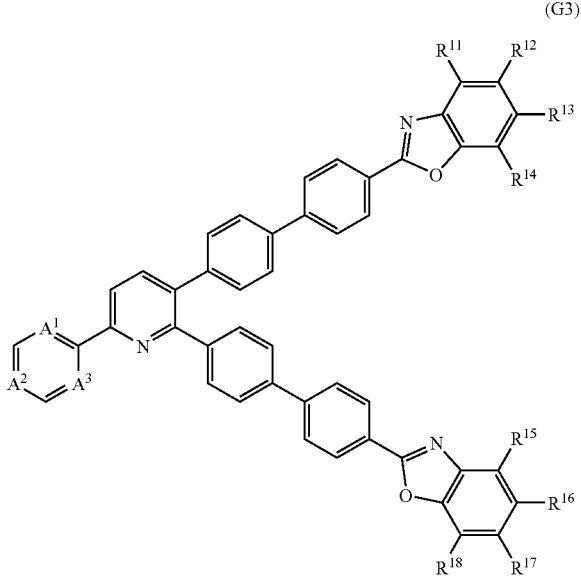
(G3)

In the formula, one or two of $A^1$ to $A^3$ represent(s) nitrogen, and the other(s) represent(s) carbon, and $R^{11}$ to $R^{18}$ are independently hydrogen, an alkyl group having 1 to 4 carbon atoms, a haloalkyl group having 1 to 4 carbon atoms, a substituted or unsubstituted aryl group having 6 to 13 carbon atoms, or halogen.

In addition, the benzoxazole derivative represented by the general formula (G1), preferably has a structure in which the same substituents are bound to a pyridine ring in view of easiness in synthesis or refinement (high purification). In other words, preferably, $Ar^1$ and $Ar^3$ have the same structure and $Ar^2$ and $Ar^4$ have the same structure. Further, preferably, $R^{11}$ and $R^{15}$ have the same structure, $R^{12}$ and $R^{16}$ have the same structure, $R^{13}$ and $R^{17}$ have the same structure, and $R^{14}$ and $R^{18}$ have the same structure.

Examples of the benzoxazole derivative represented by the general formula (G1) include benzoxazole derivatives represented by structural formulae (101) to (208). However, the present invention is not limited to the following structural formulae.

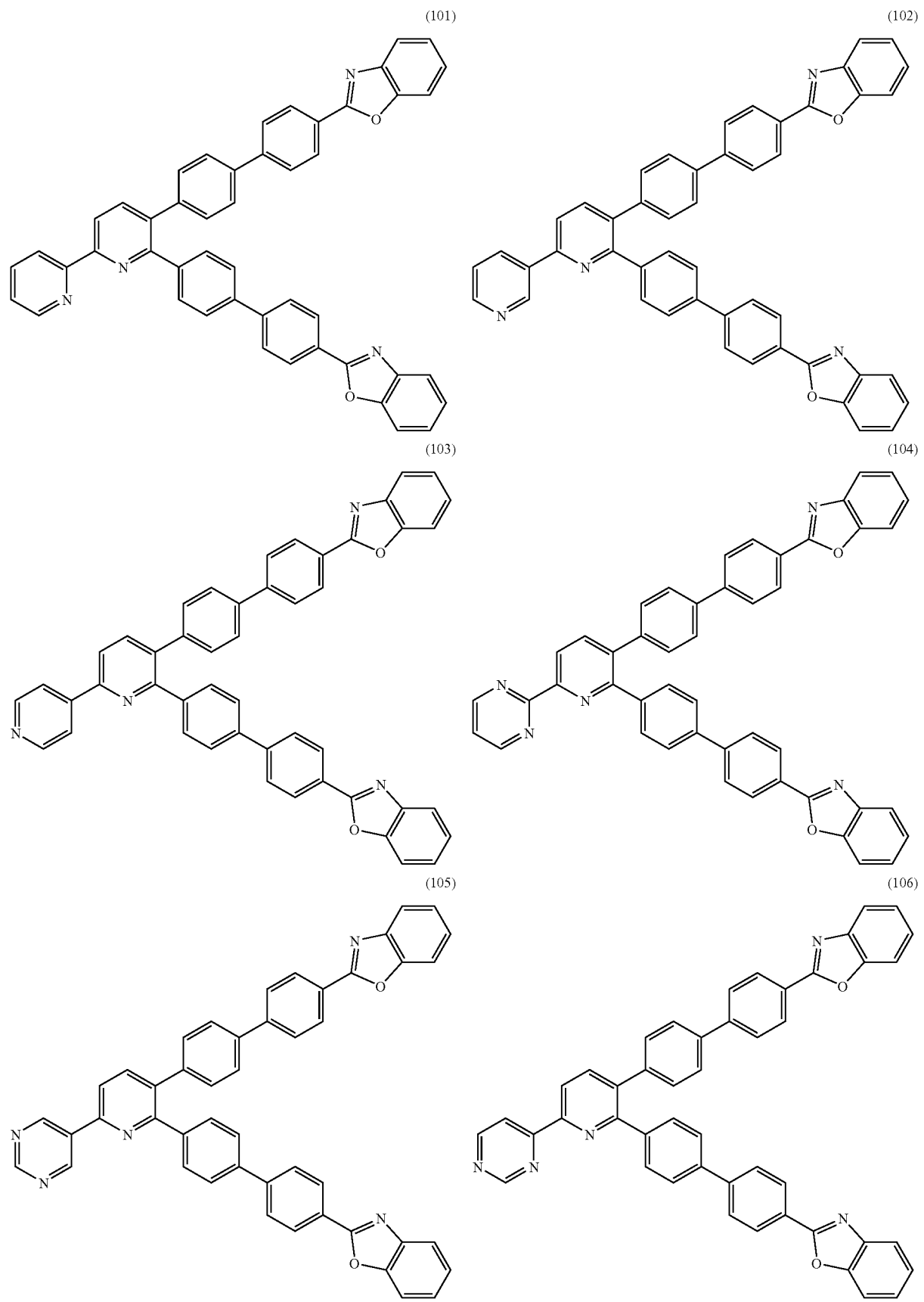

-continued
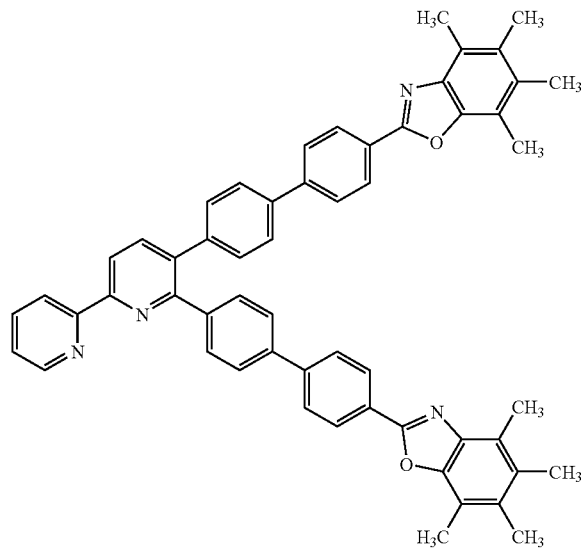
(107)
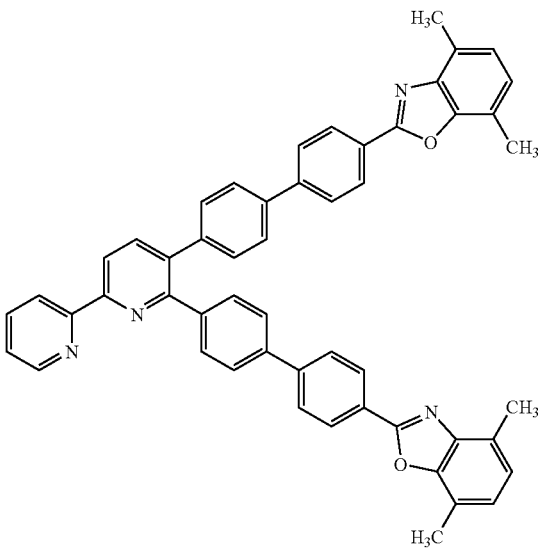
(108)
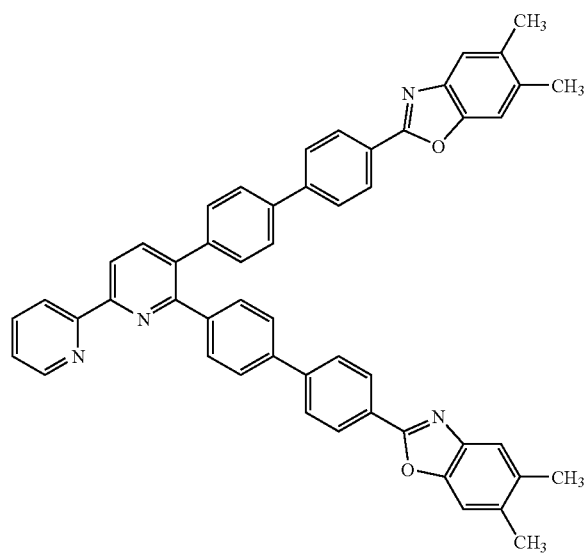
(109)
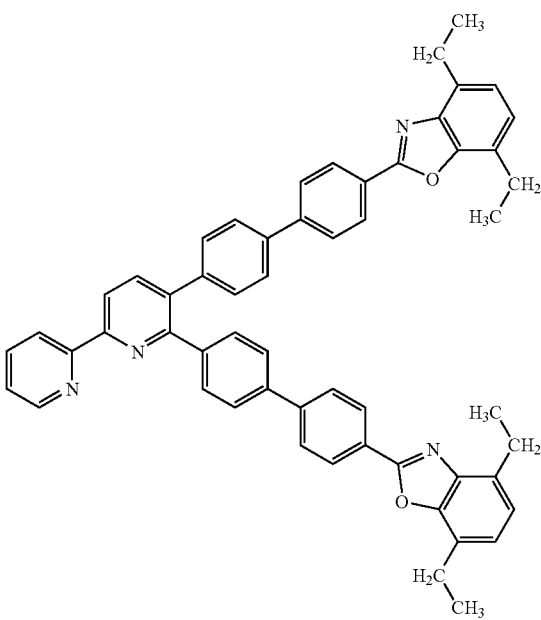
(110)

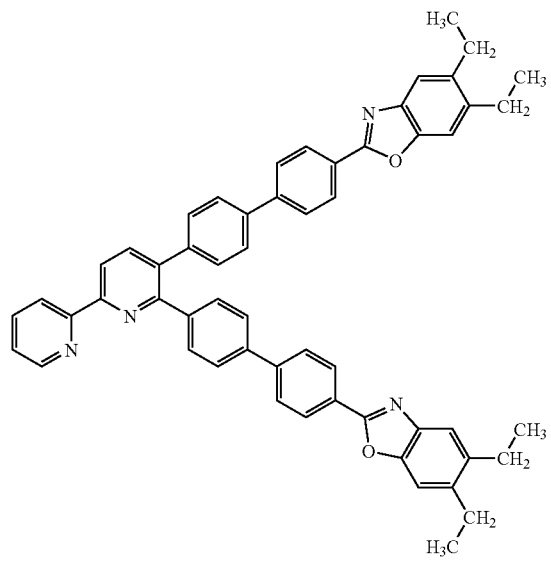
(111)
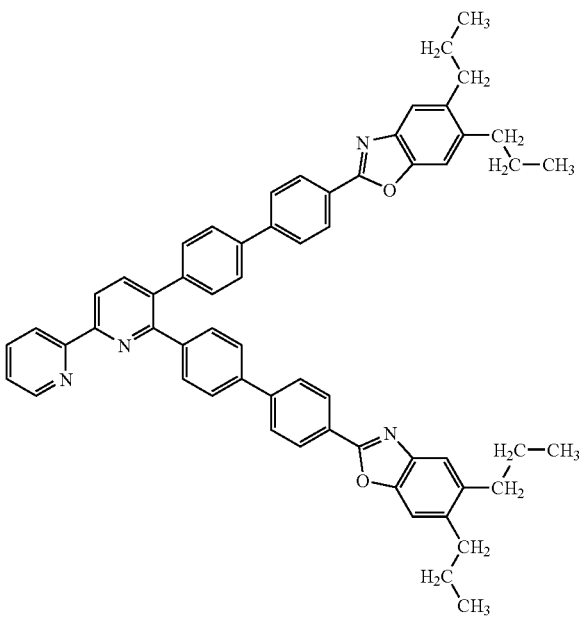
(112)
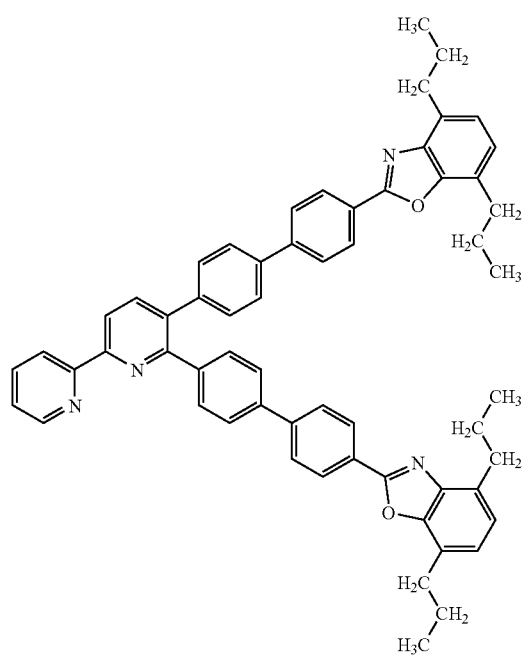
(113)
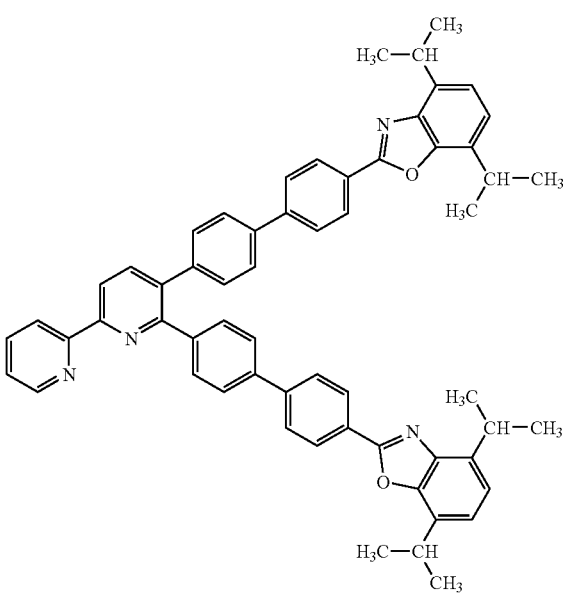
(114)

(115)
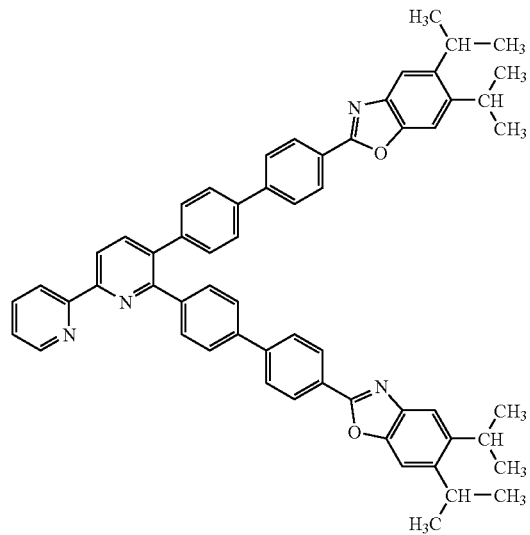
(116)
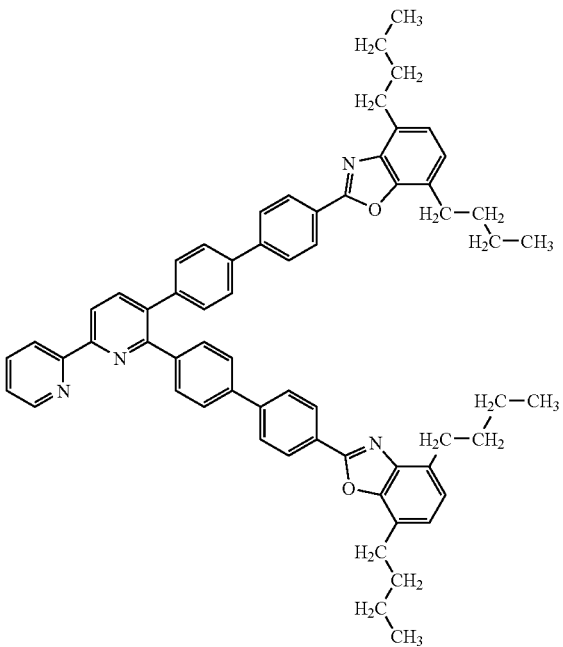
(117)
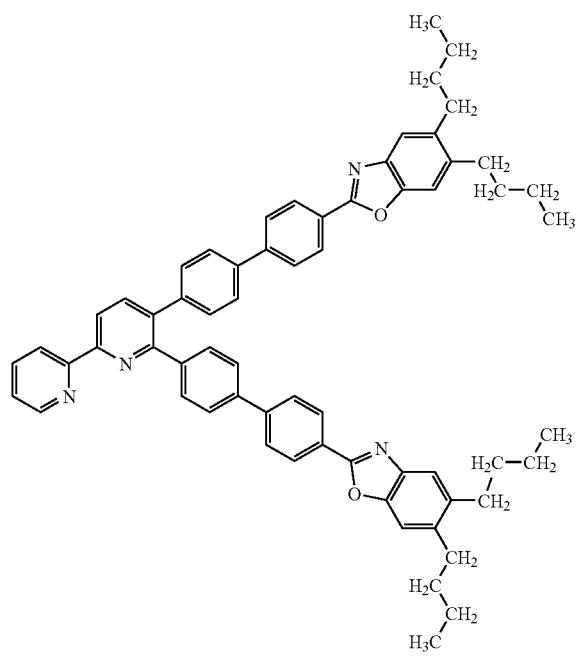
(118)
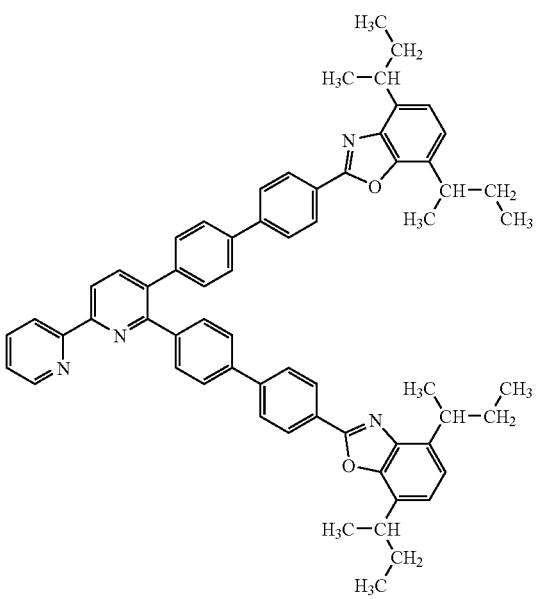

(119)
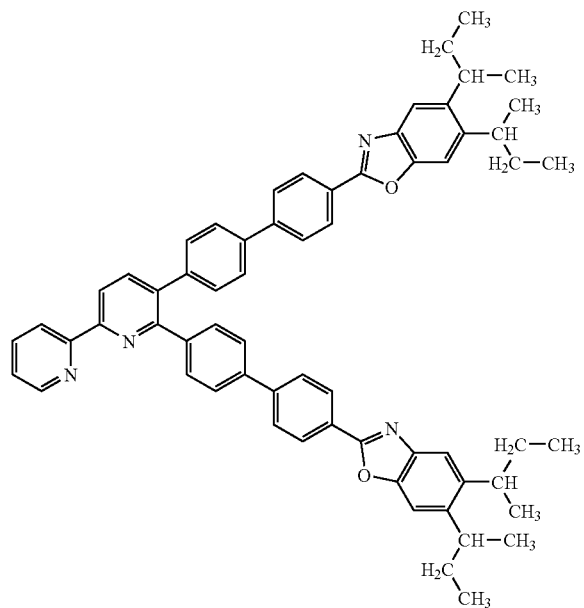
(120)
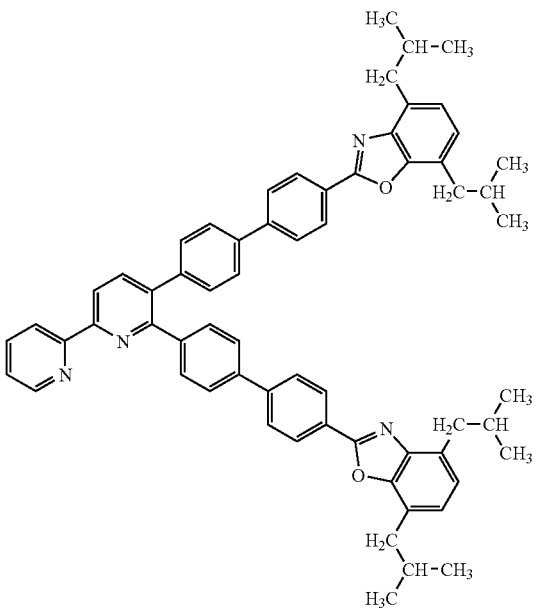
(121)
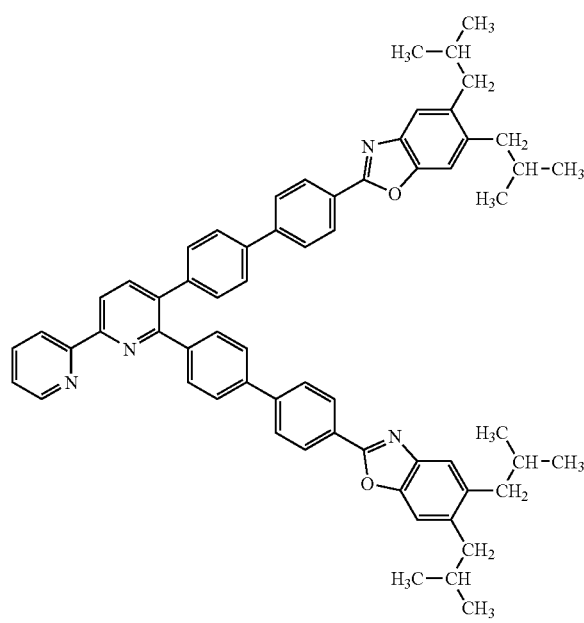
(122)
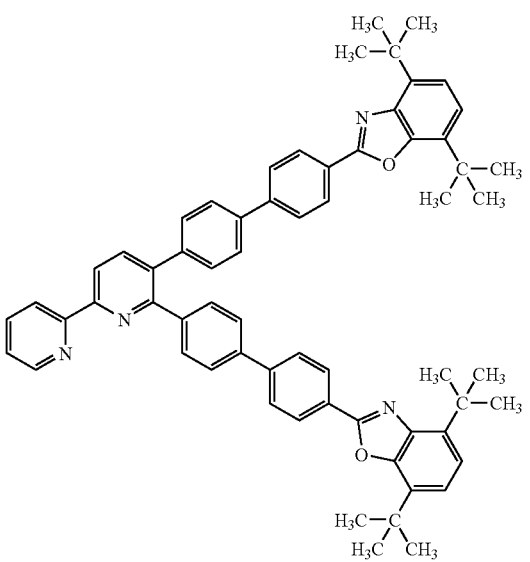

-continued
(123)
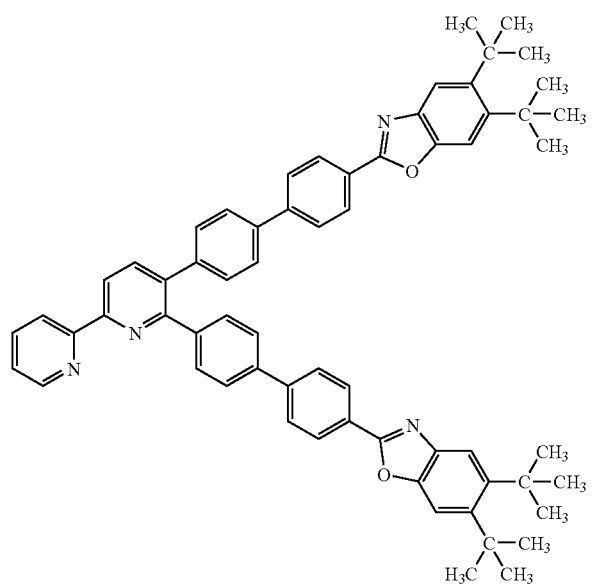
(124)
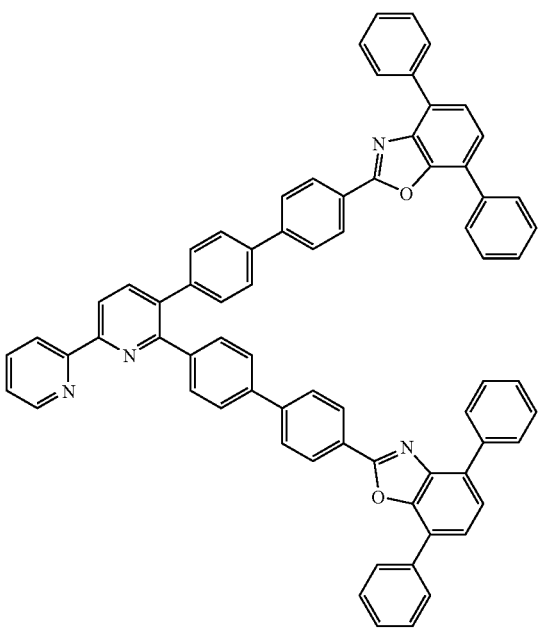
(125)
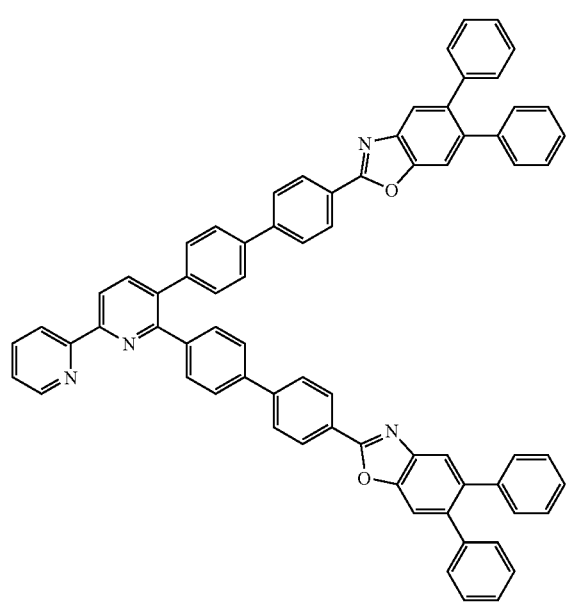
(126)
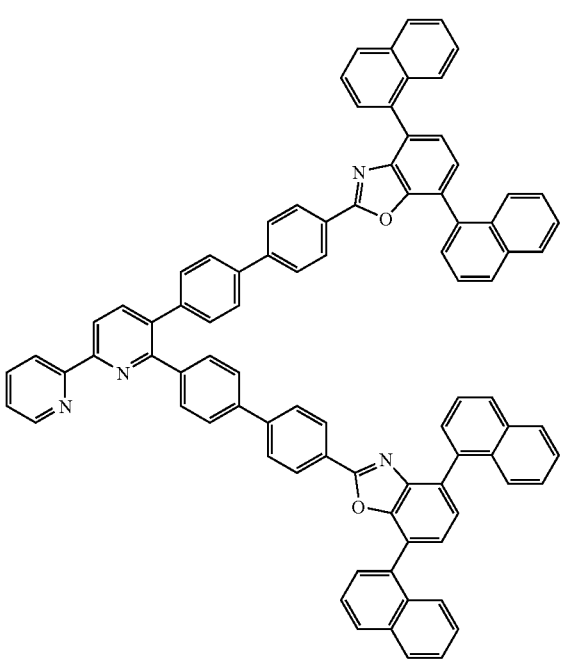

(127)
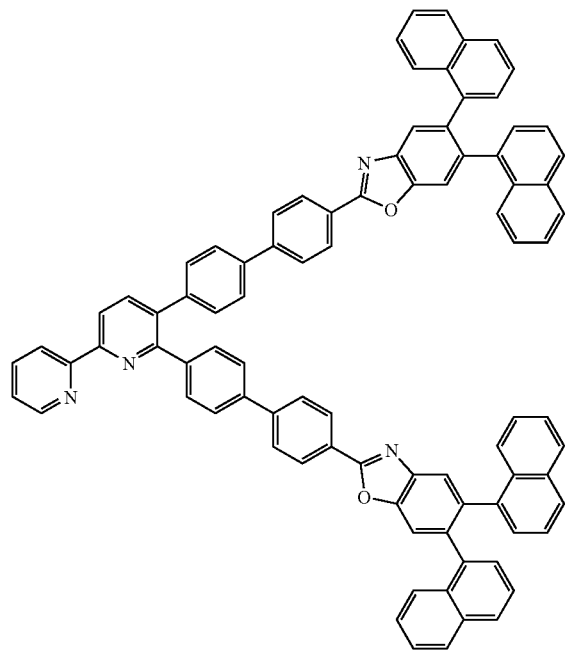
(128)
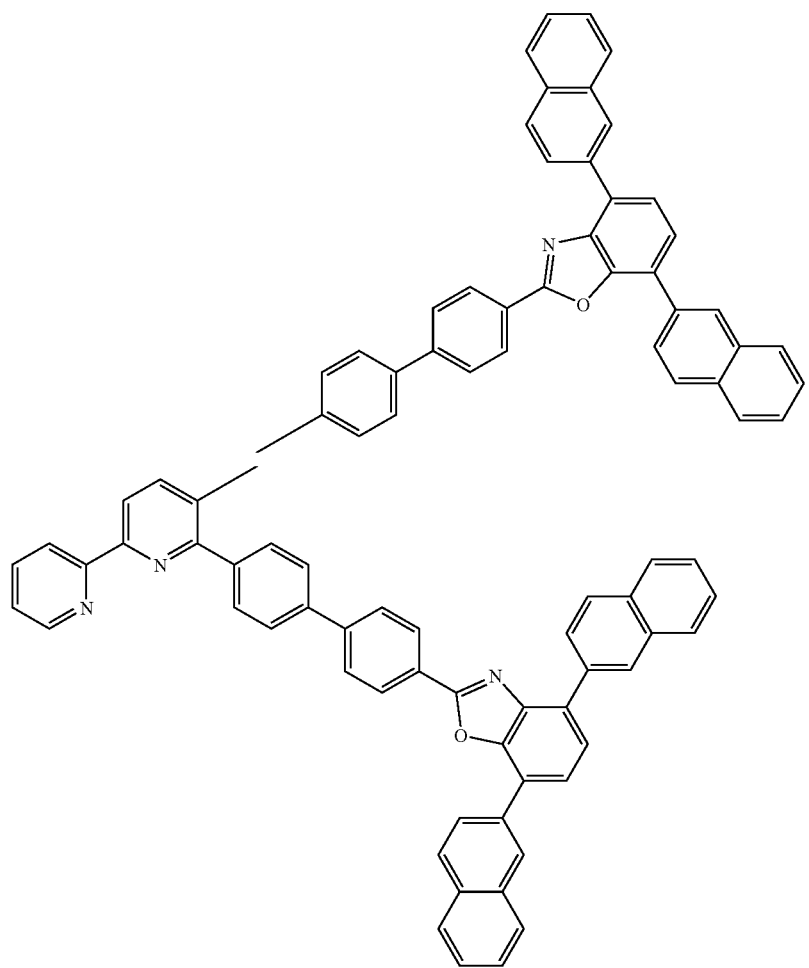

-continued
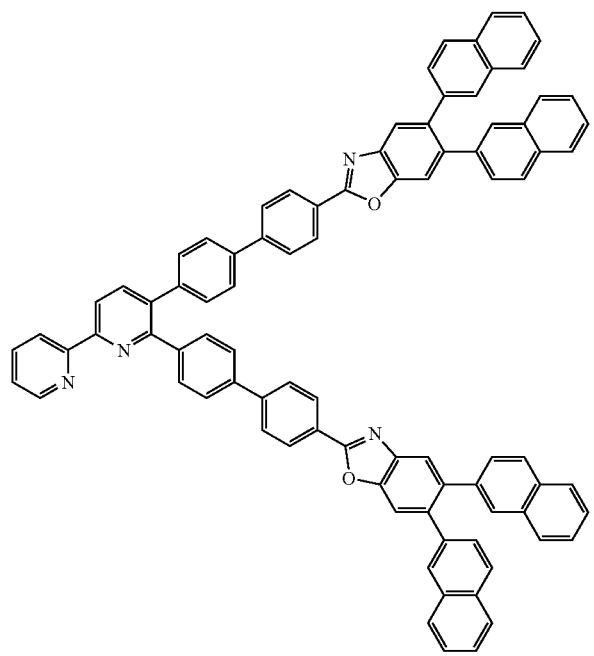
(129)
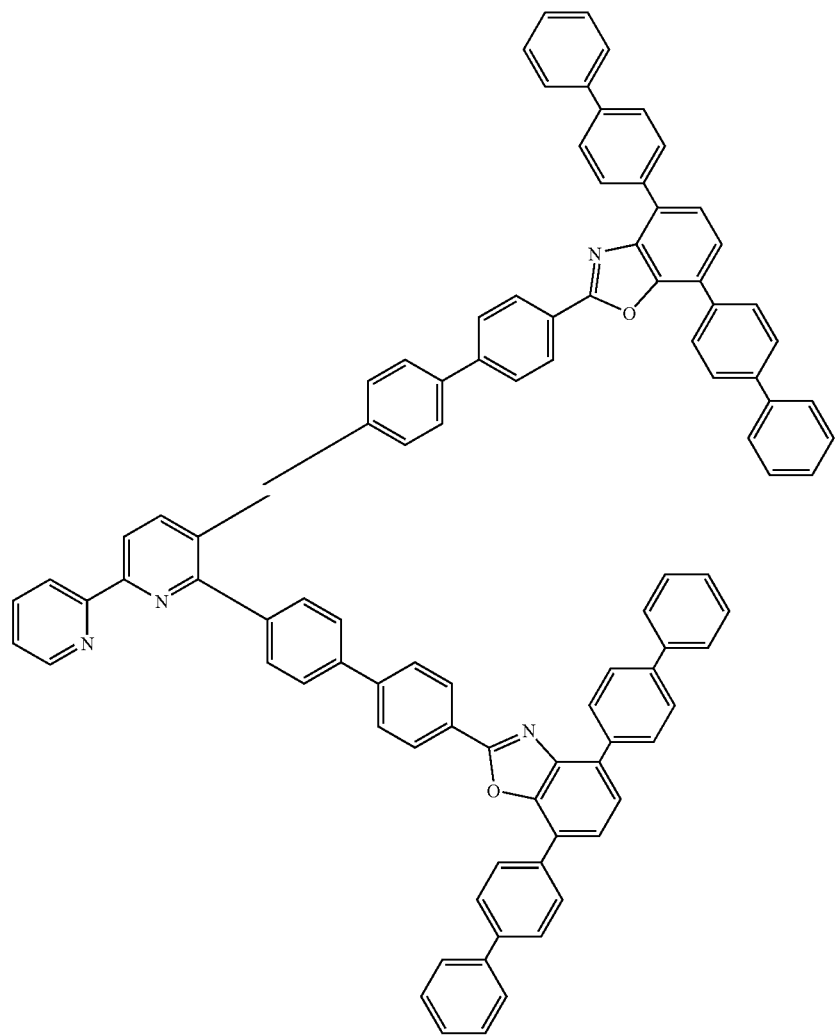
(130)

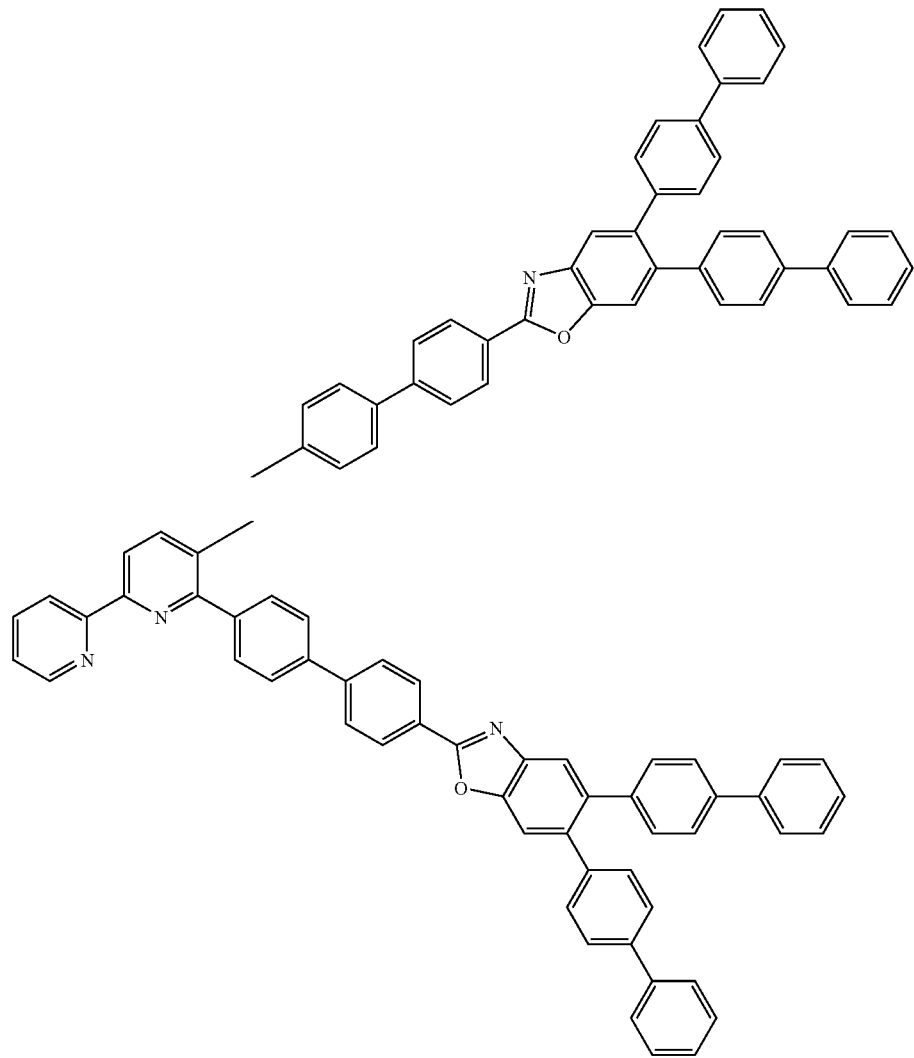
(131)
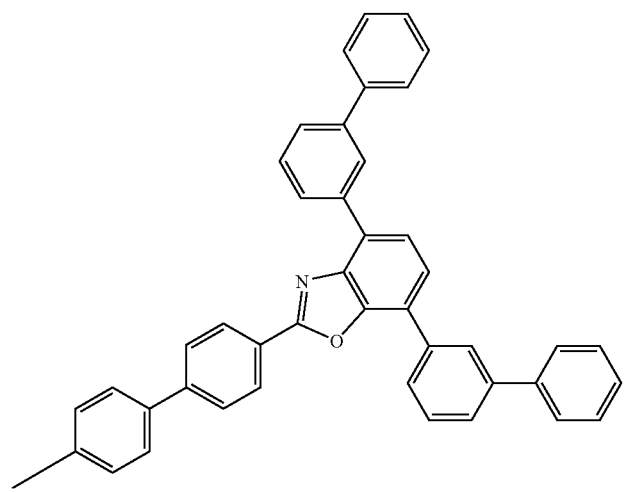
(132)

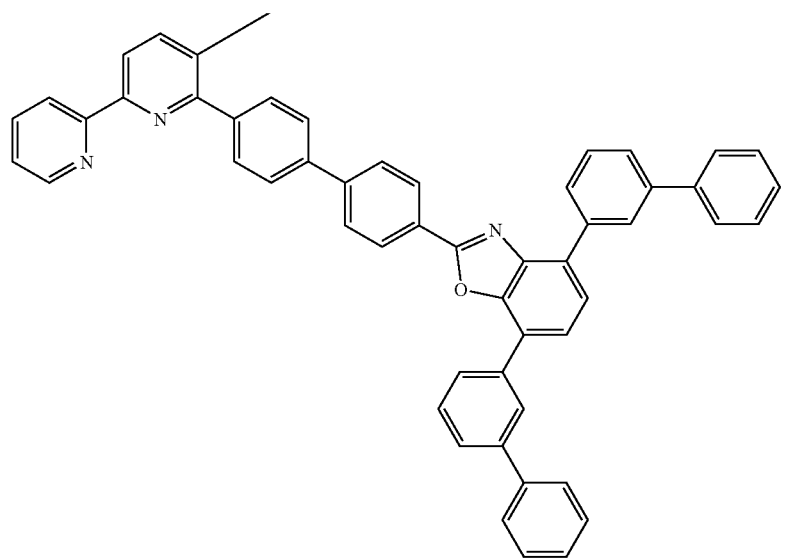
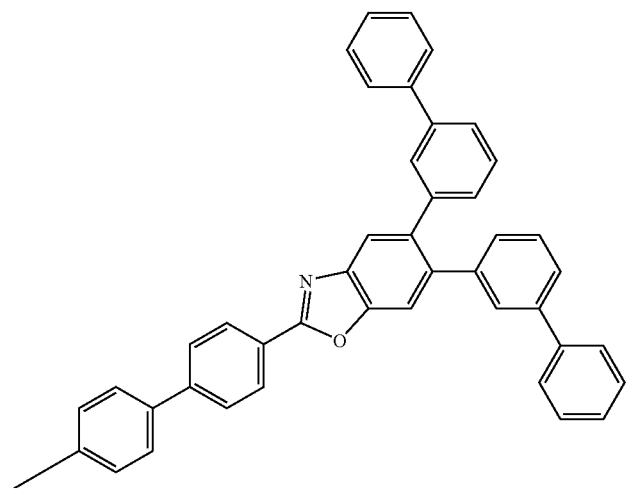
(133)
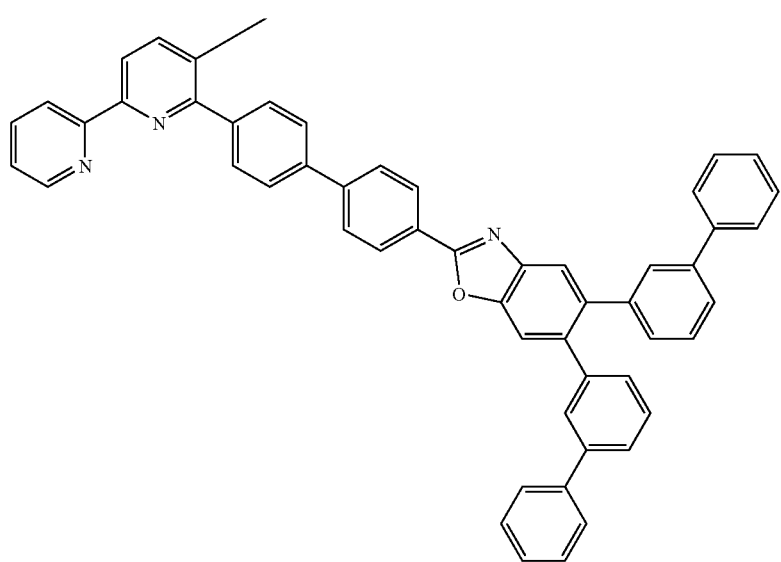

(134)
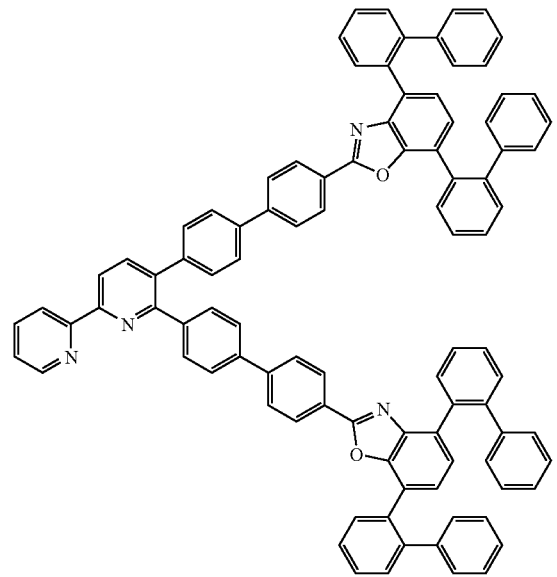
(135)
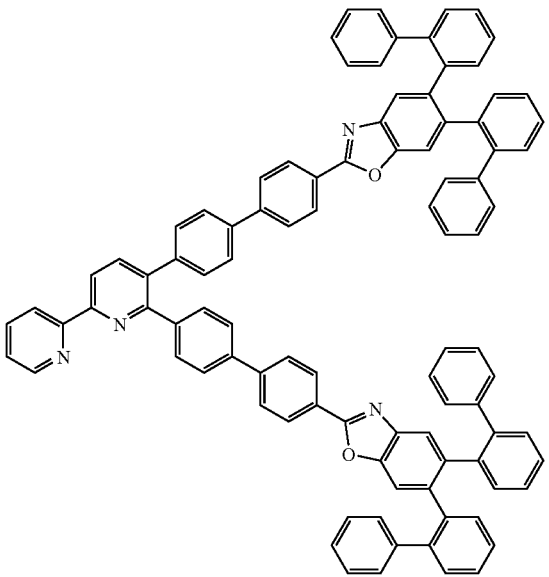
(136)
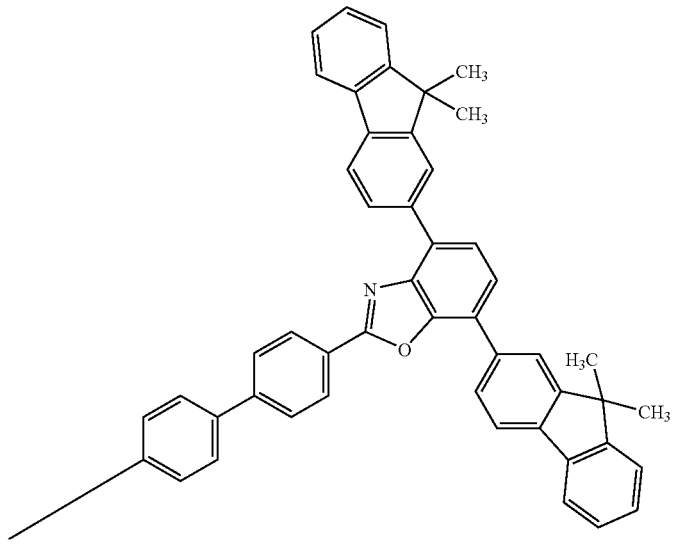

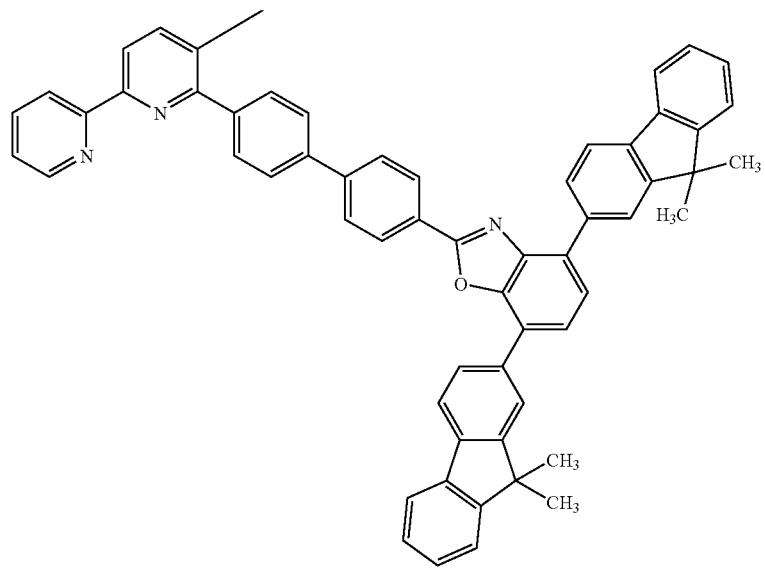
(137)
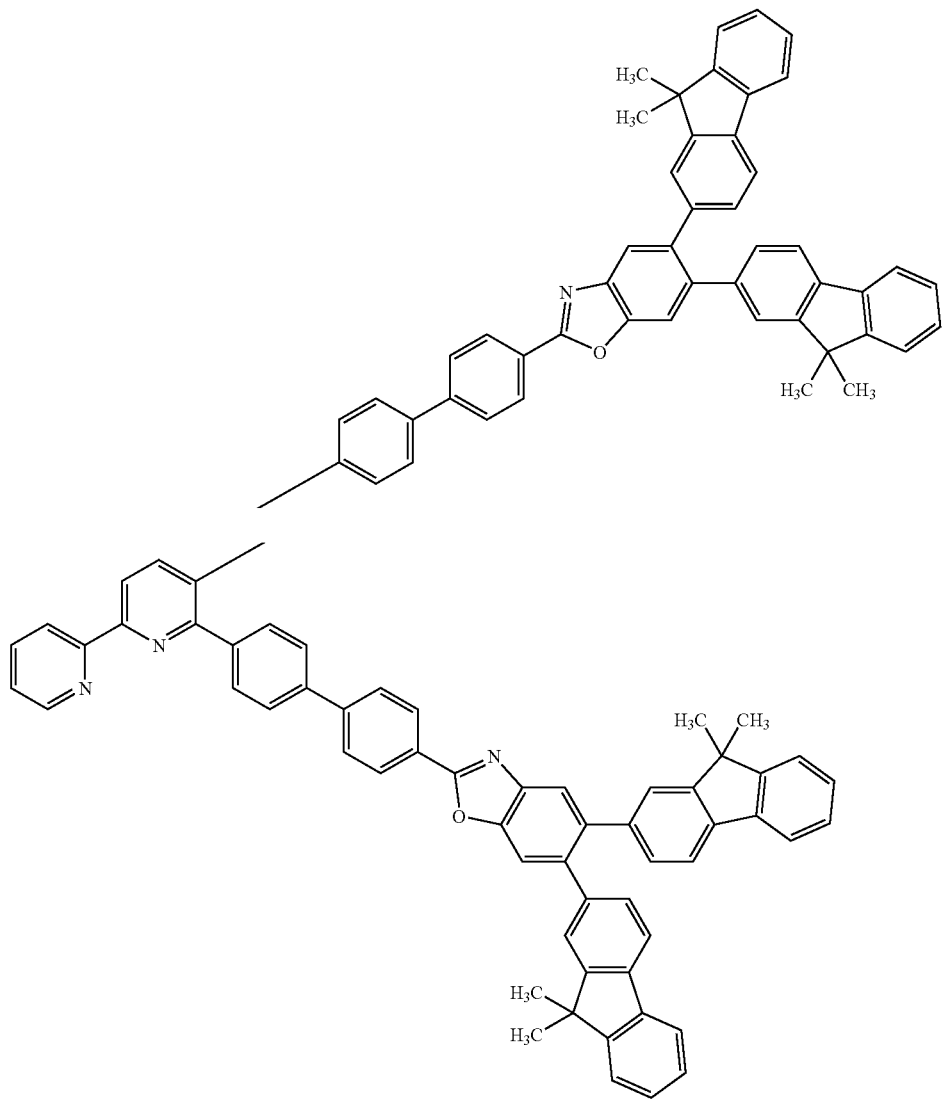

(138)
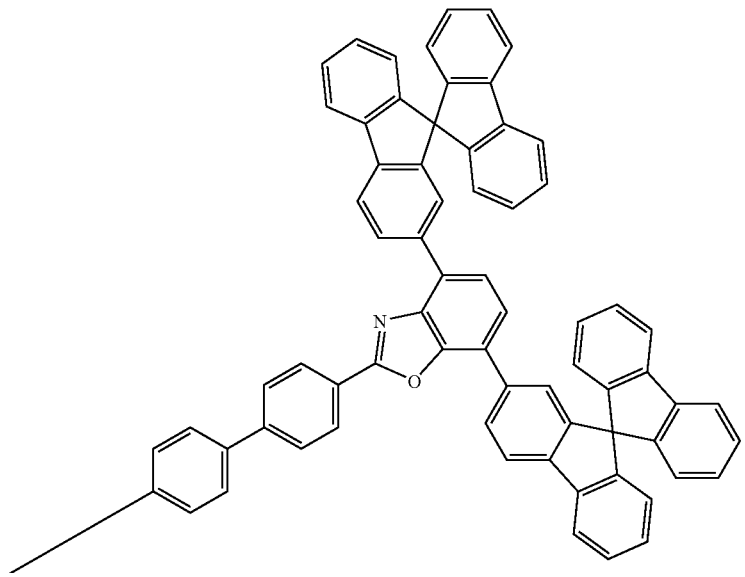
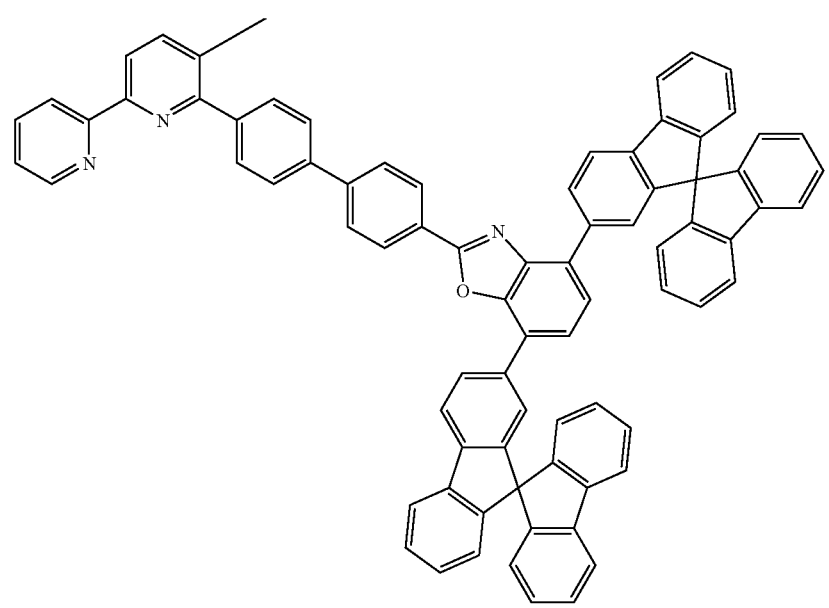

(139)
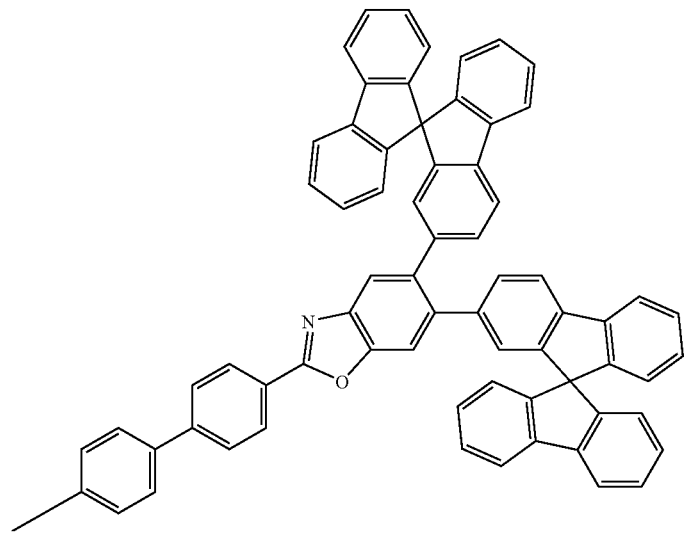
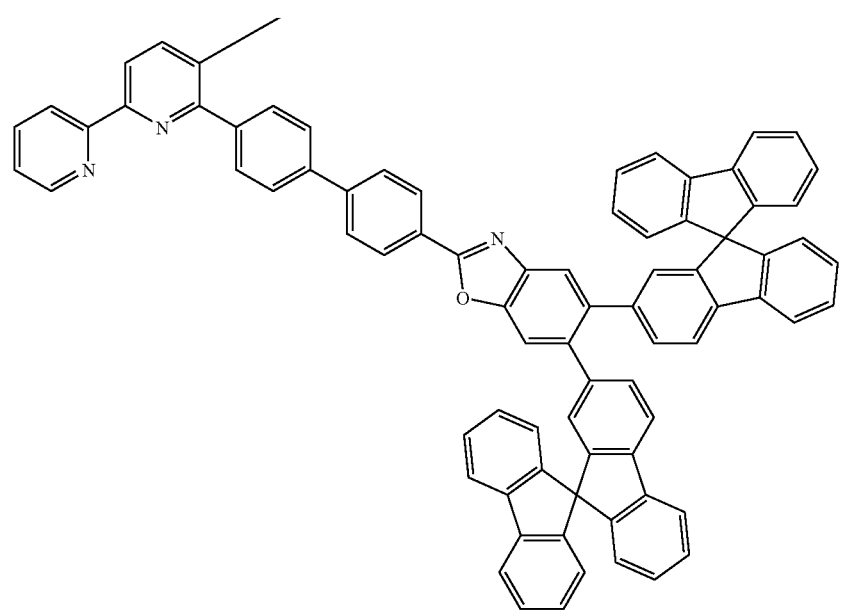

(140)
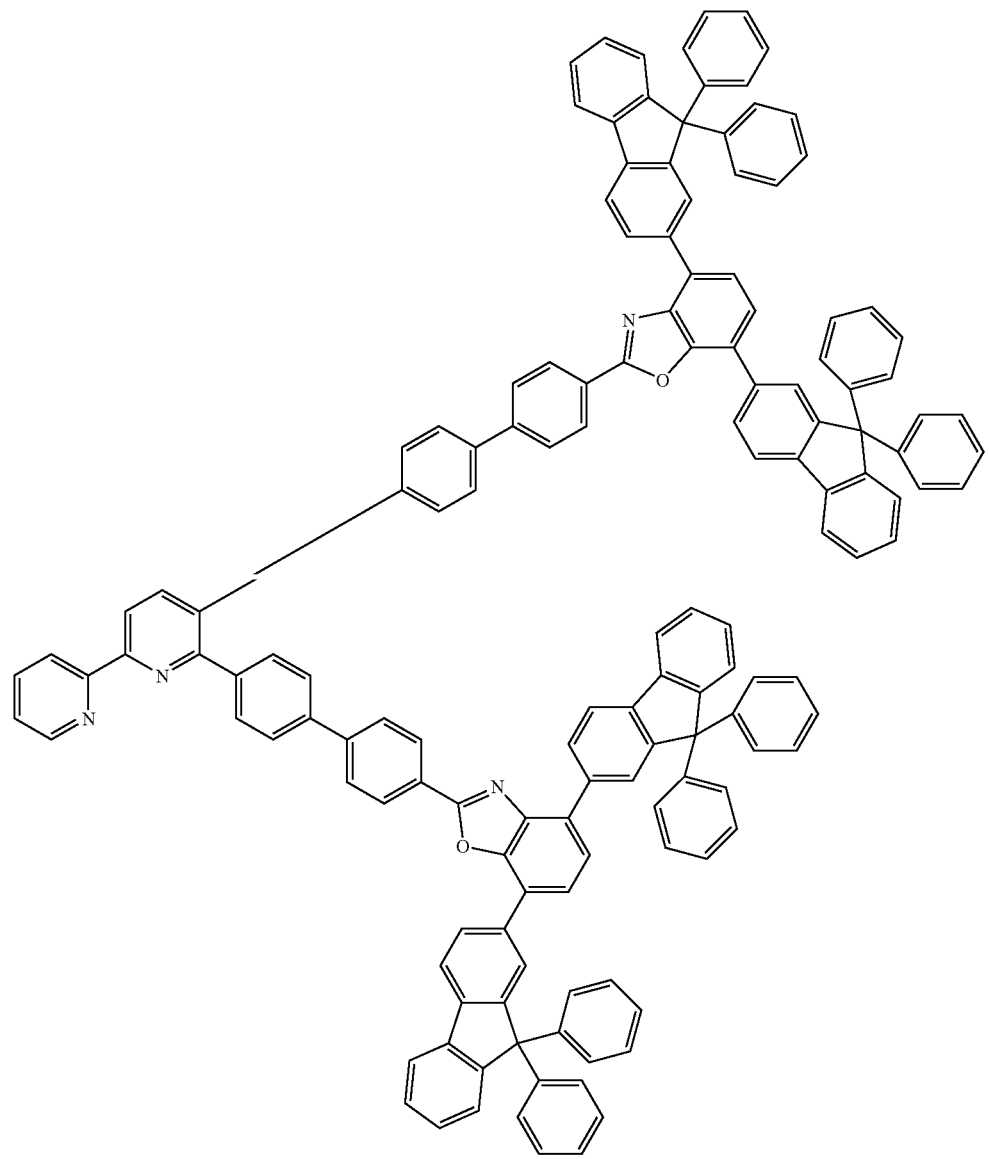
(141)
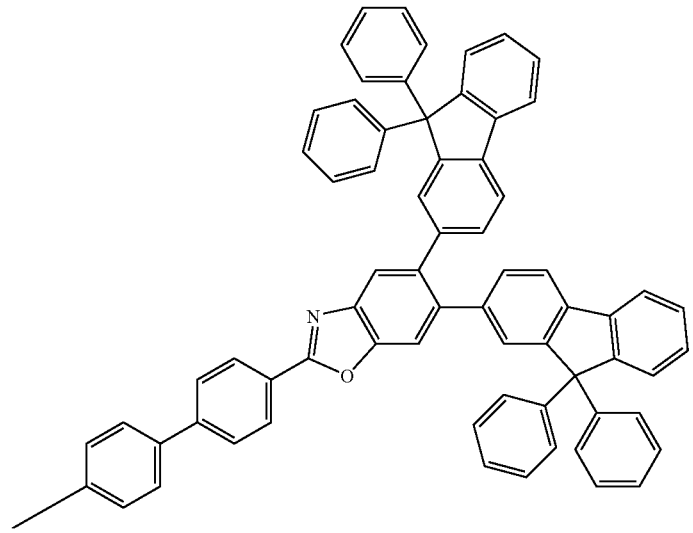

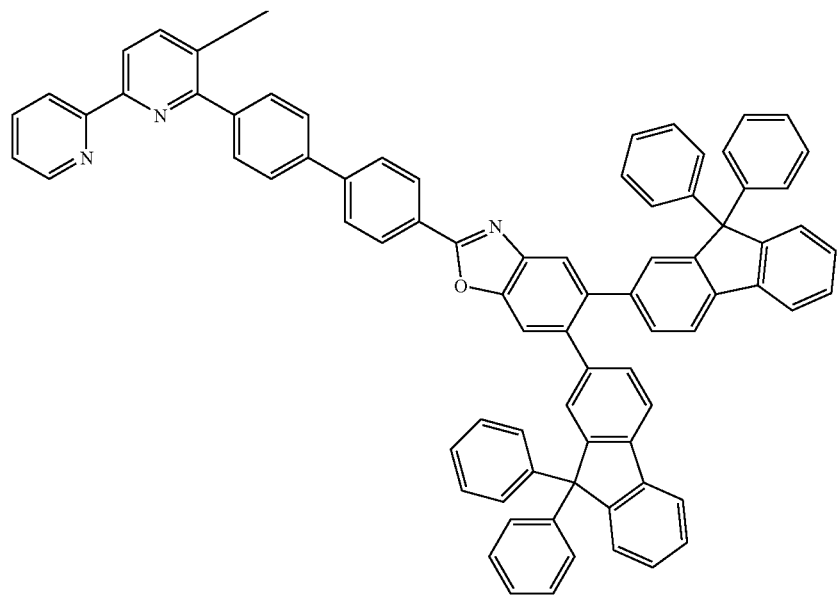
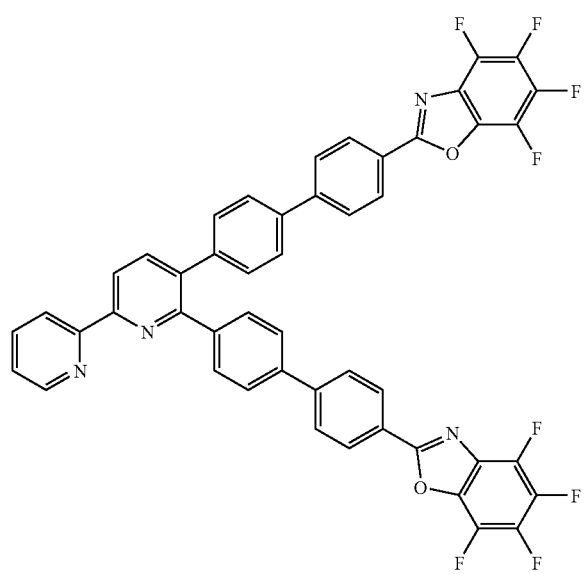
(142)
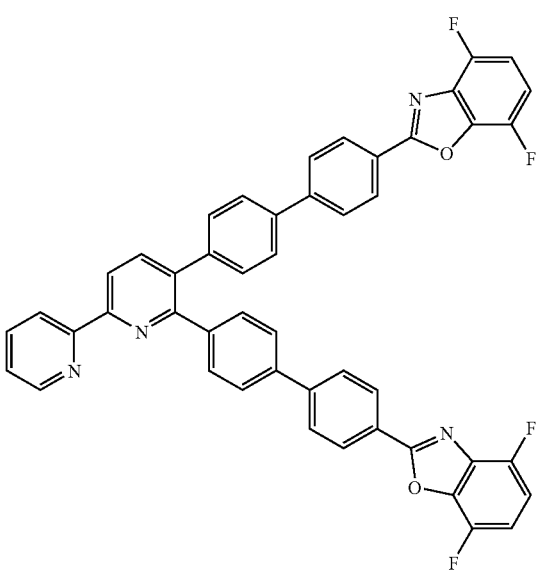
(143)

-continued
(144)
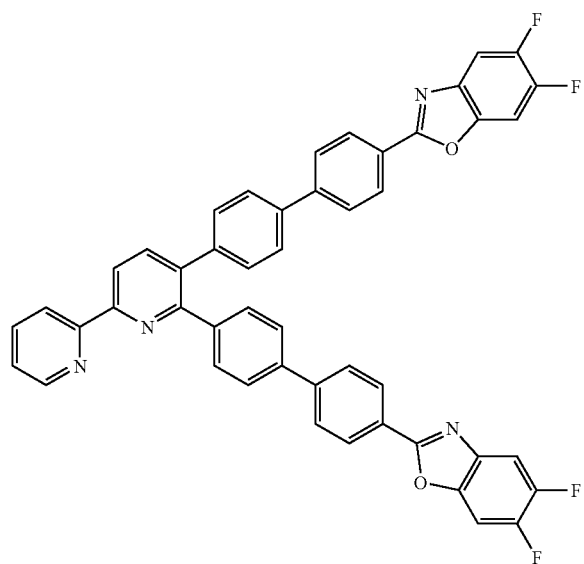
(145)
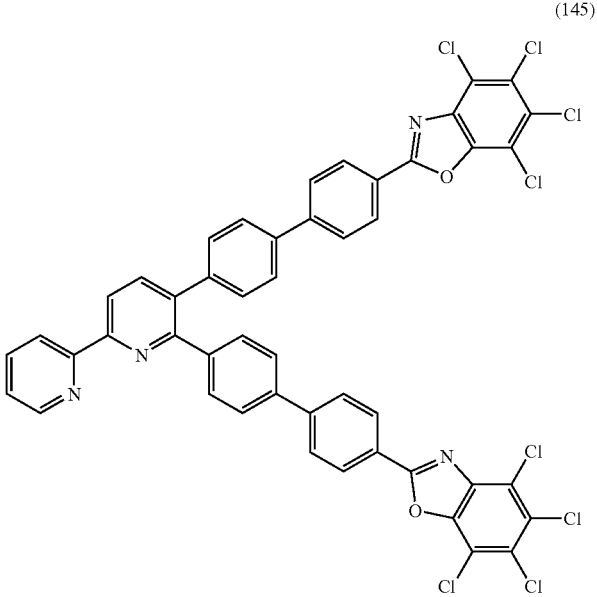
(146)
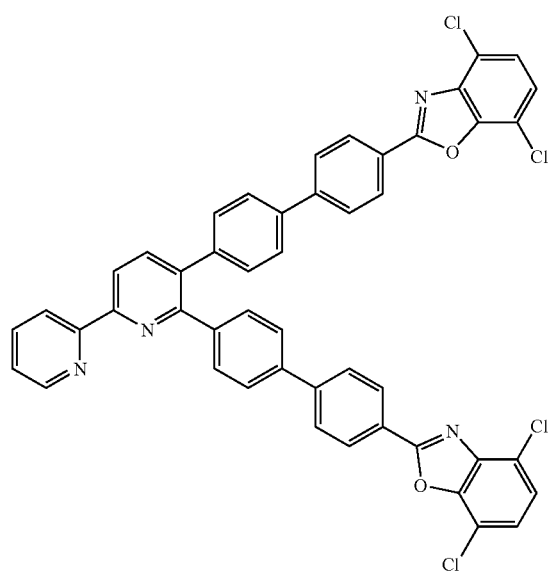
(147)
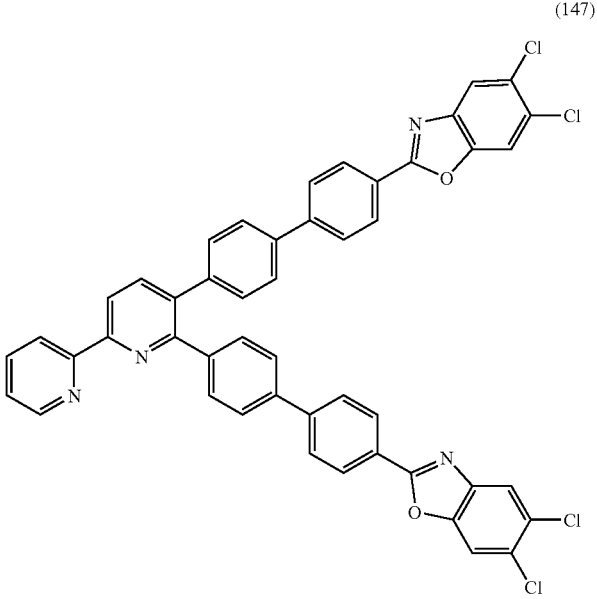

(148)
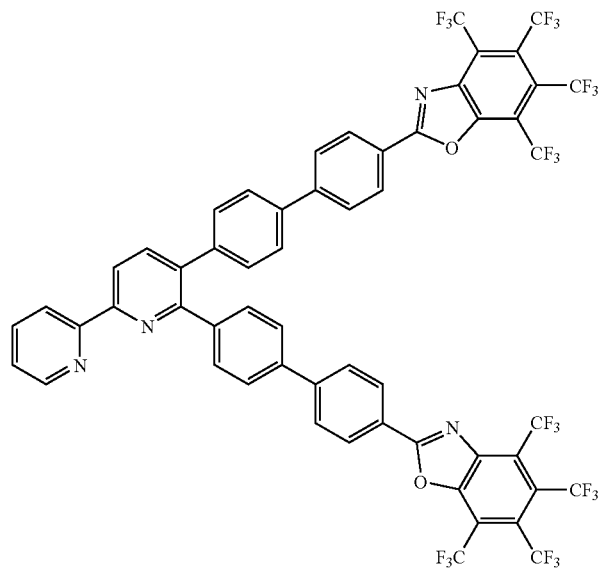
(149)
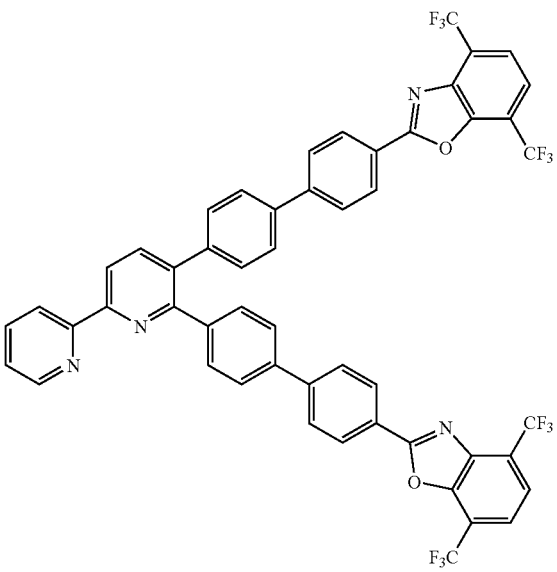
(150)
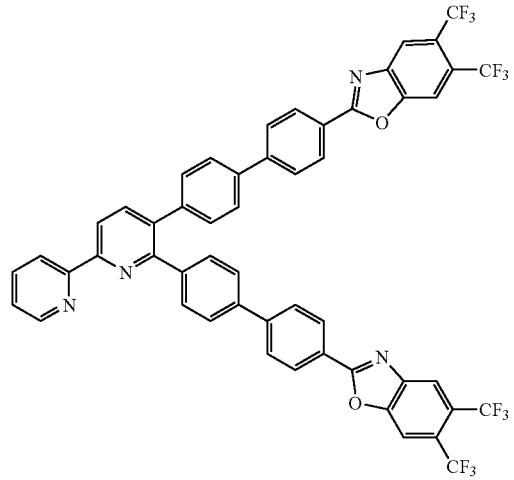
(151)
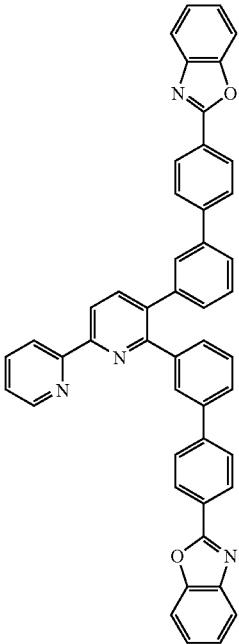

(152)
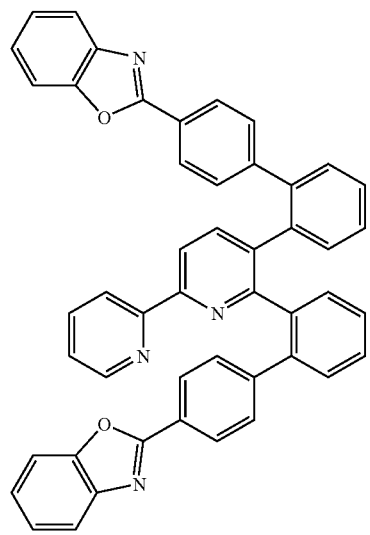
(153)
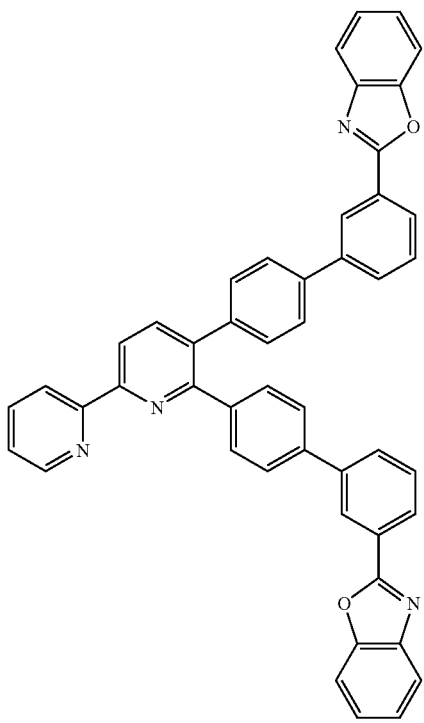
(154)
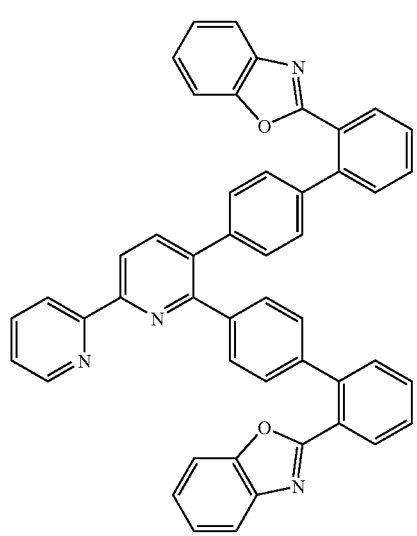
(155)
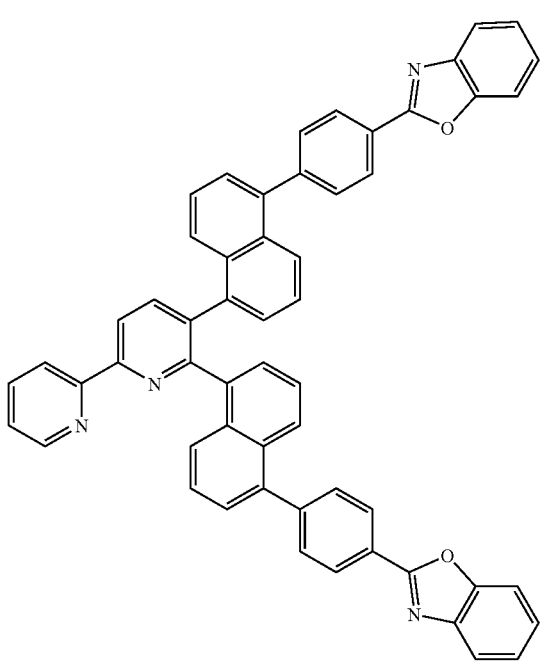

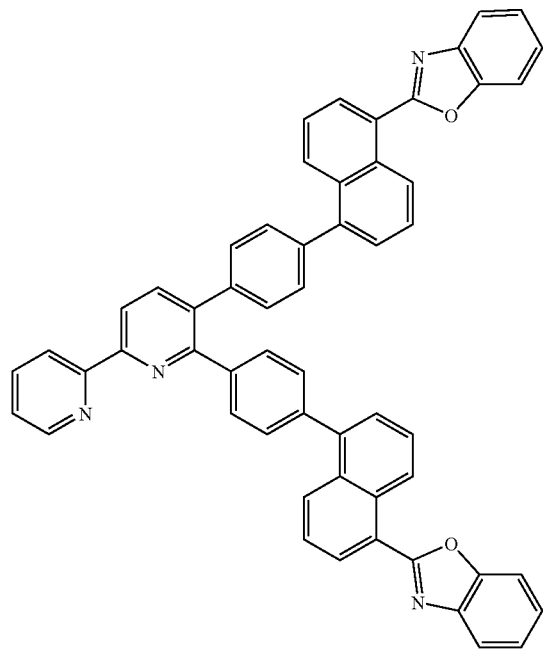
(156)
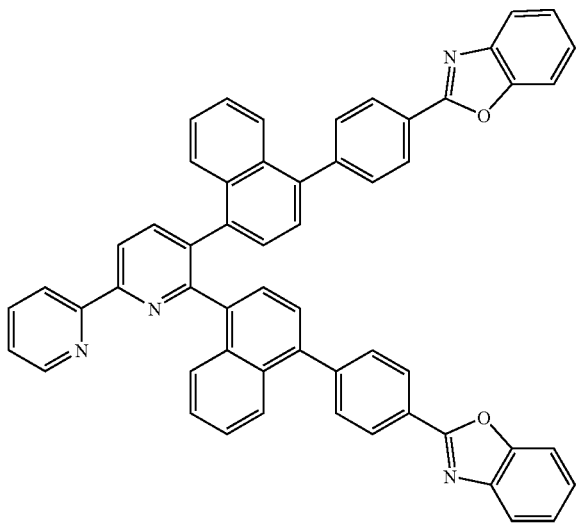
(157)
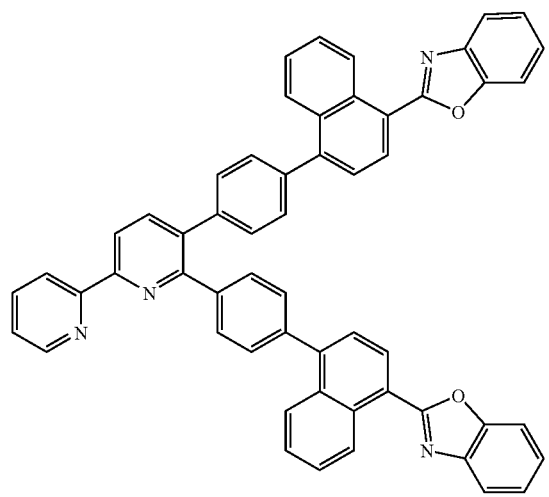
(158)
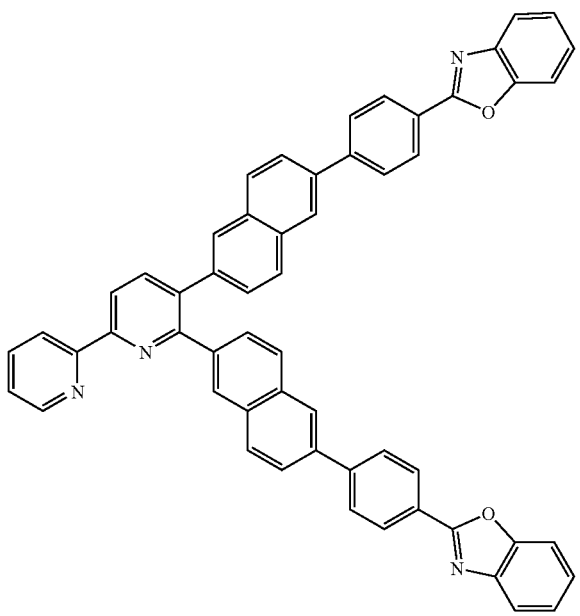
(159)

-continued
(160)
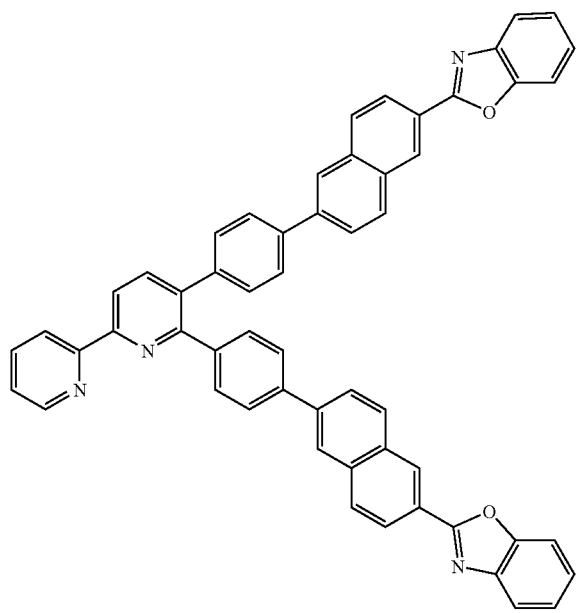
(161)
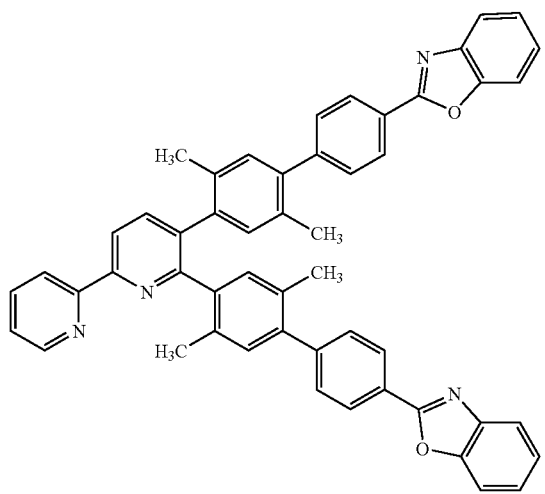
(162)
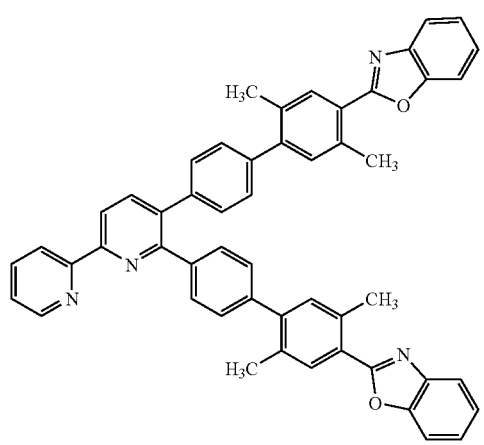
(163)
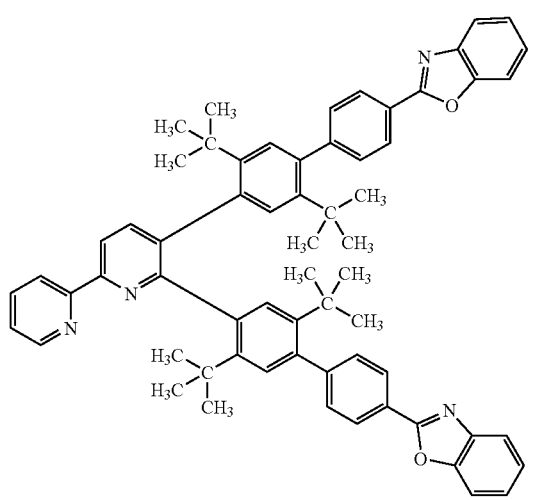
(164)
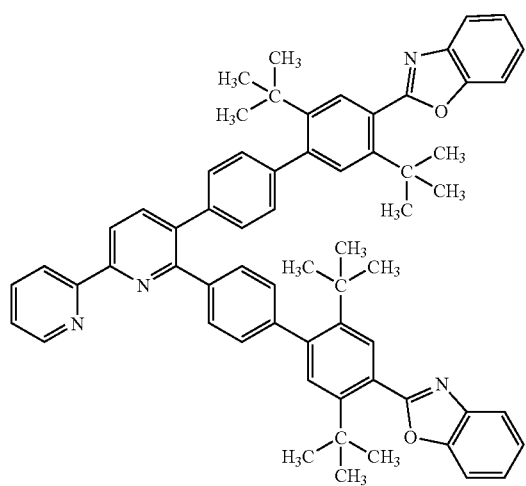
(165)
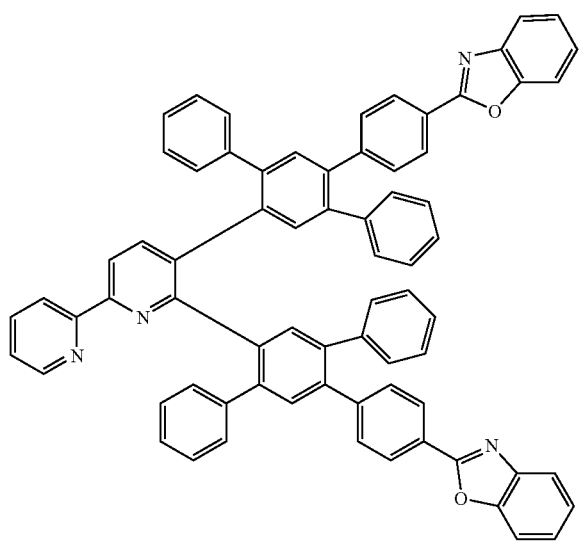

-continued
(166)
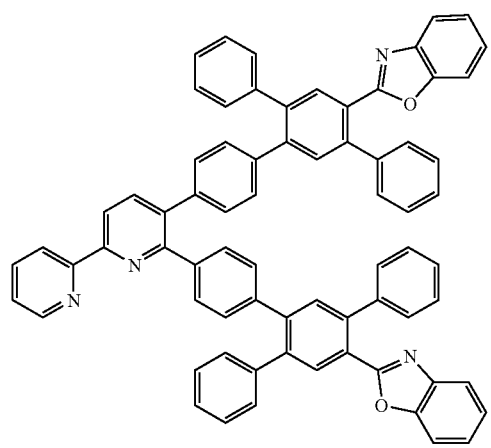
(167)
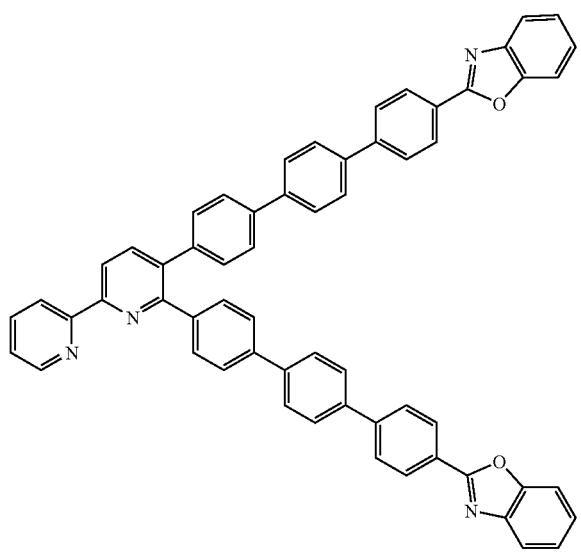
(168)
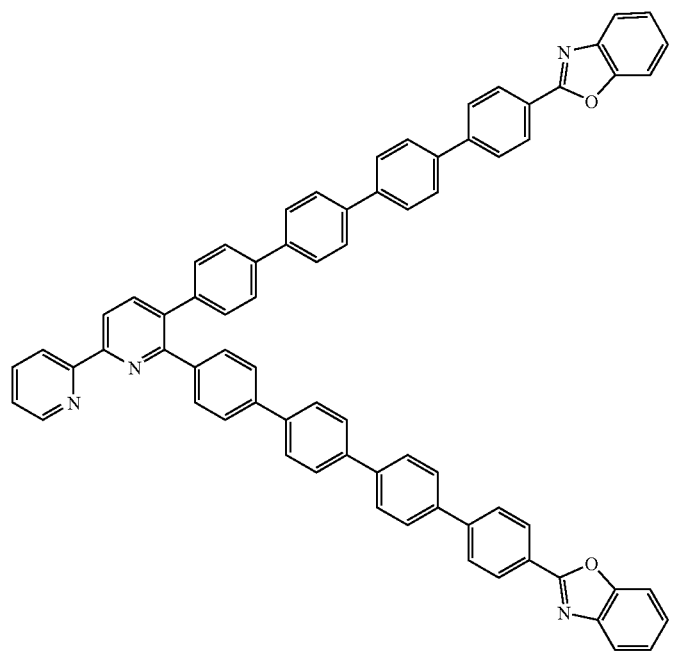
(169)
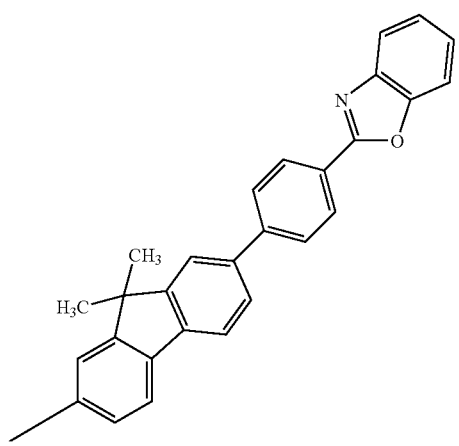

-continued
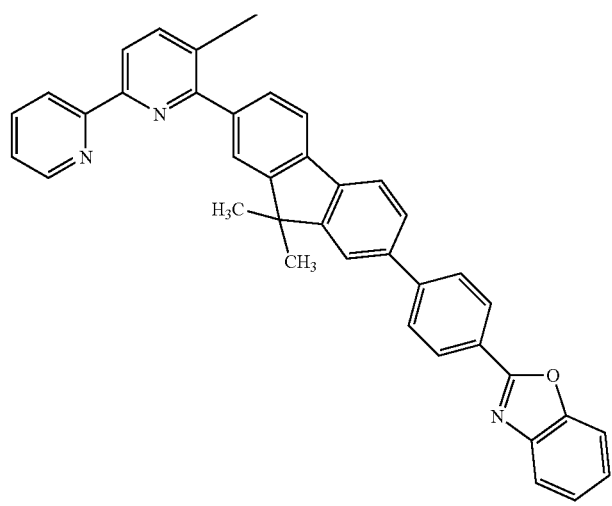
(170)
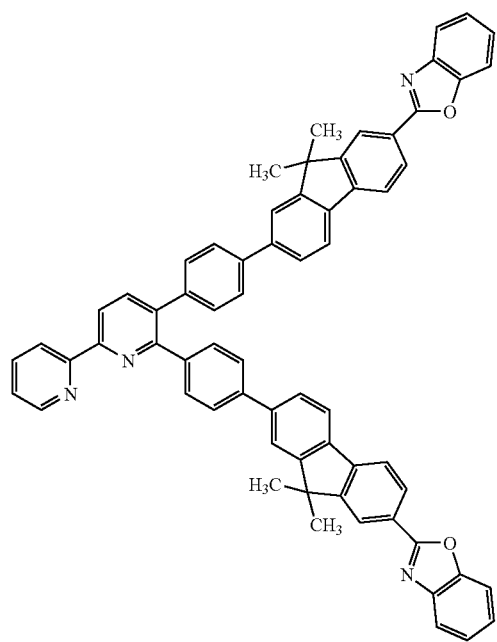
(171)
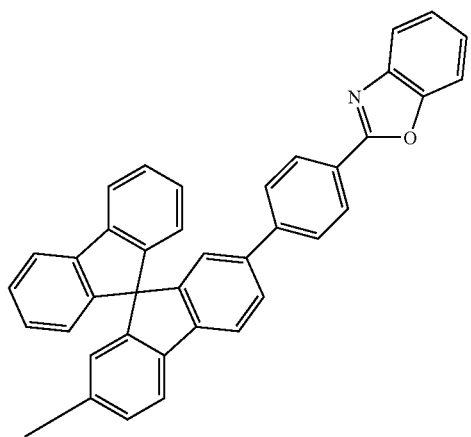

-continued
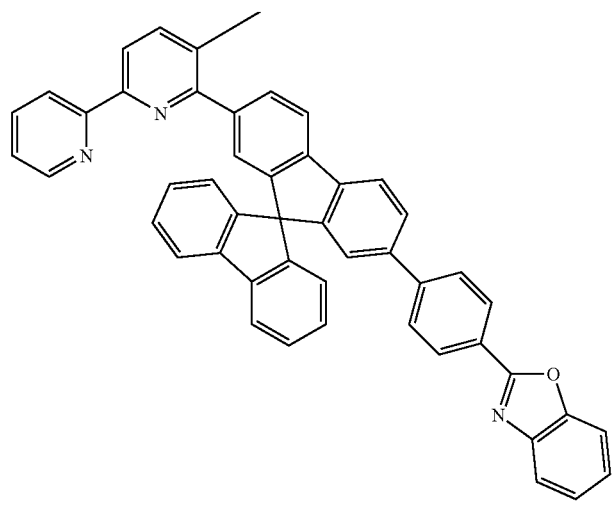
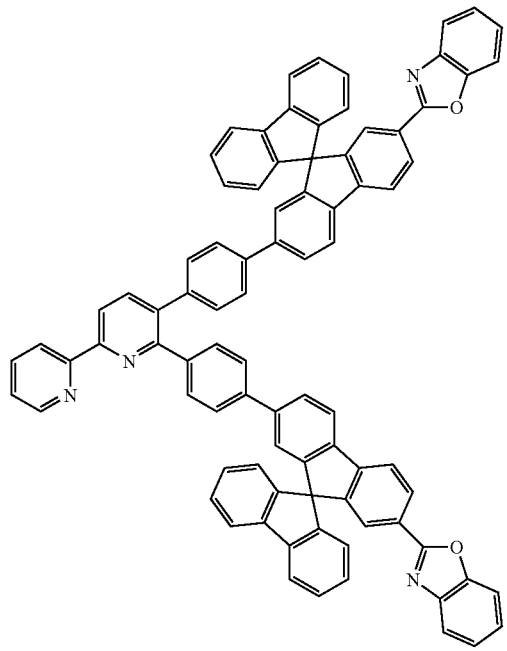
(172)
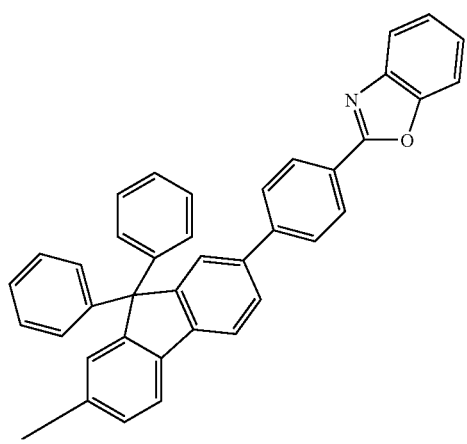
(173)

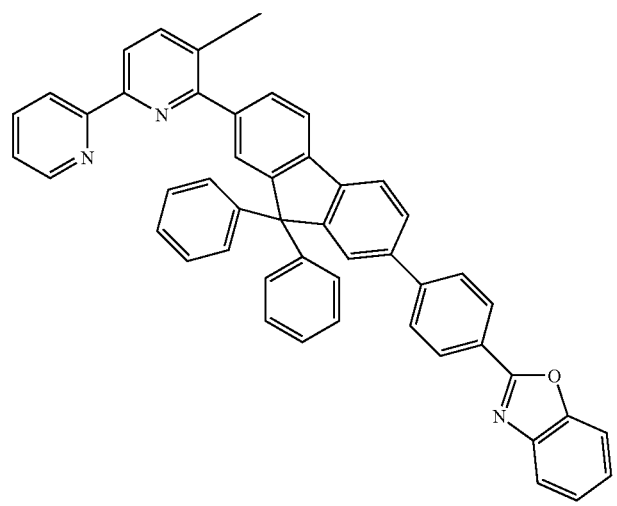
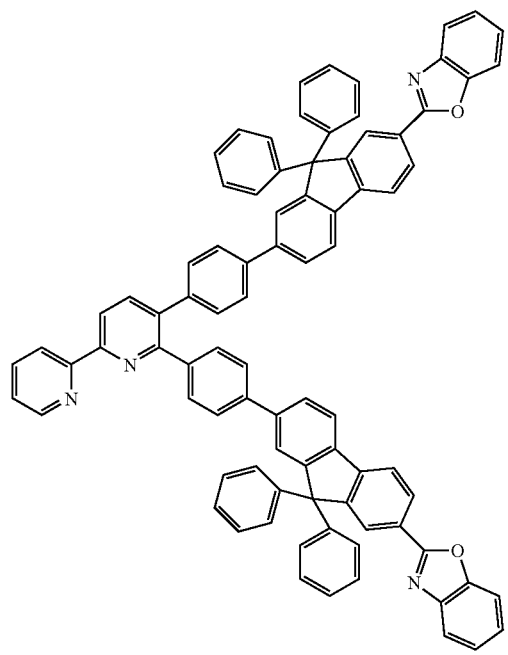
(174)

-continued
(175)
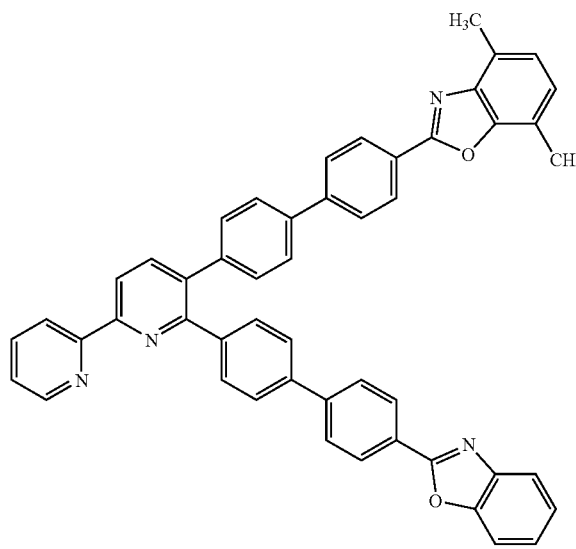
(176)
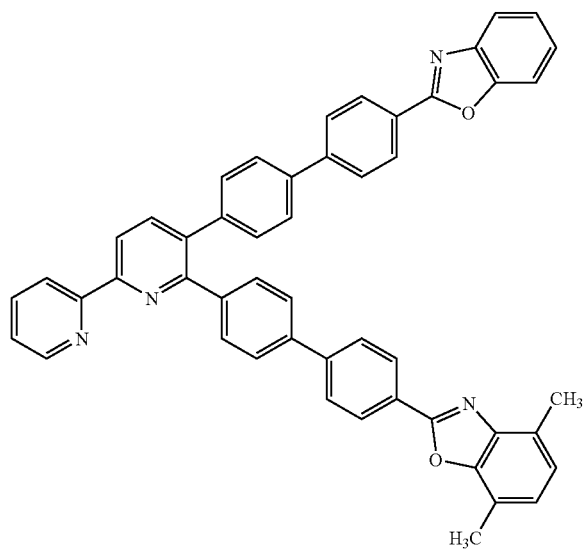
(177)
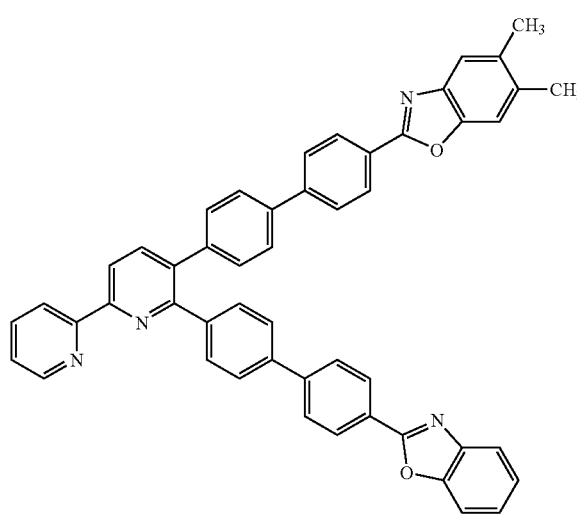
(178)
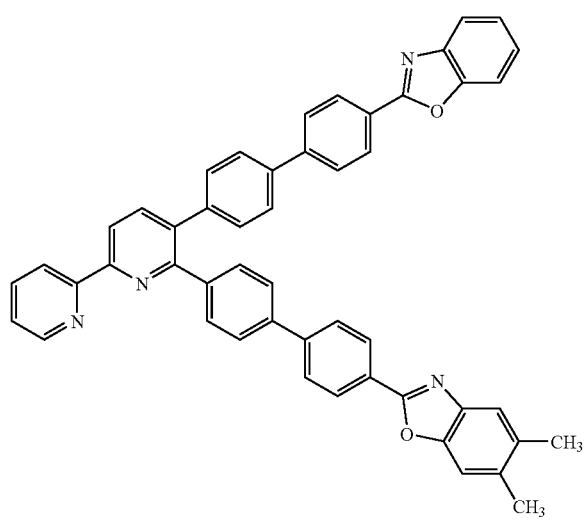
(179)
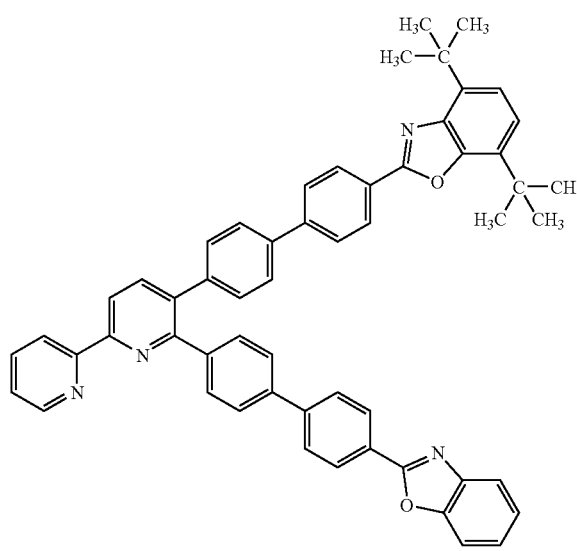
(180)
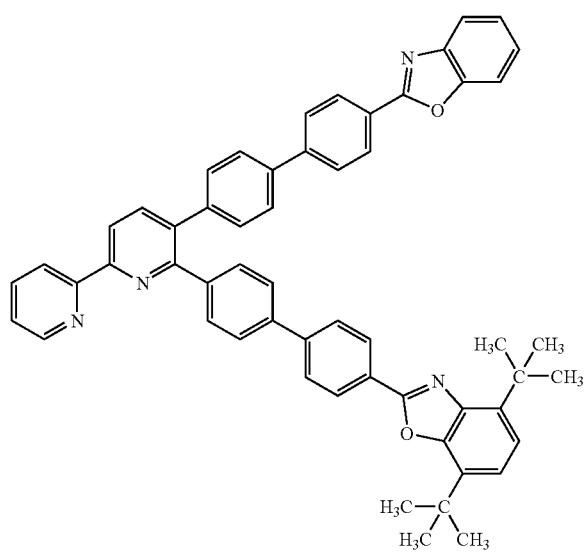

-continued
(181)
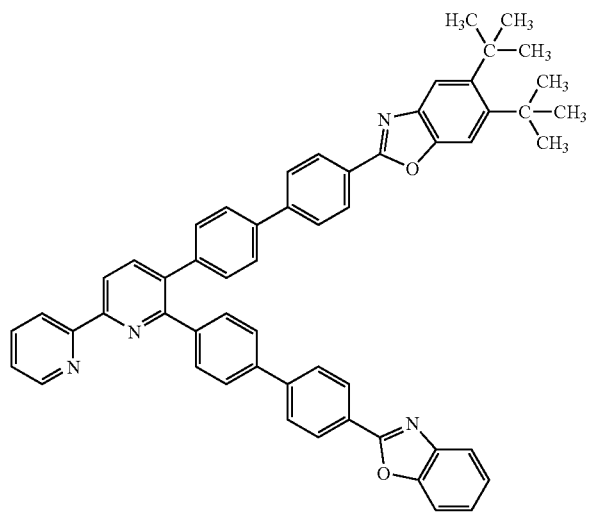
(182)
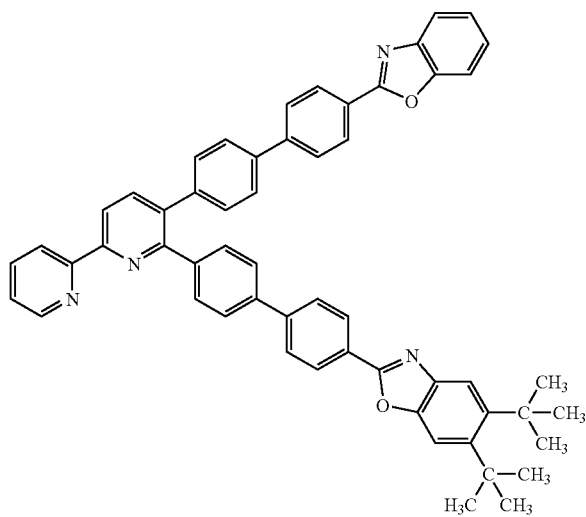
(183)
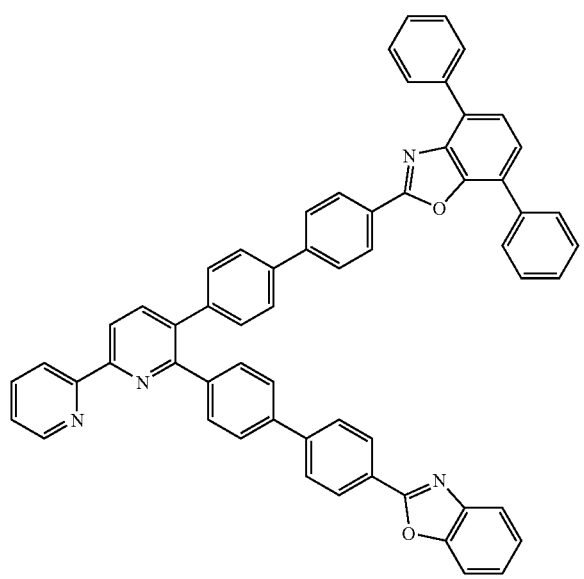
(184)
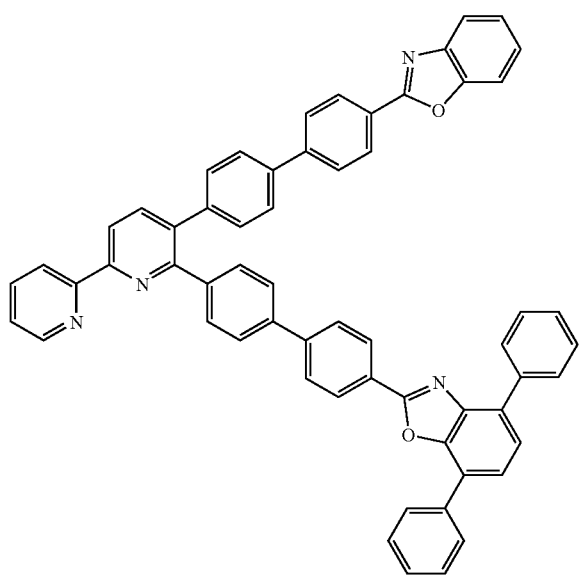
(185)
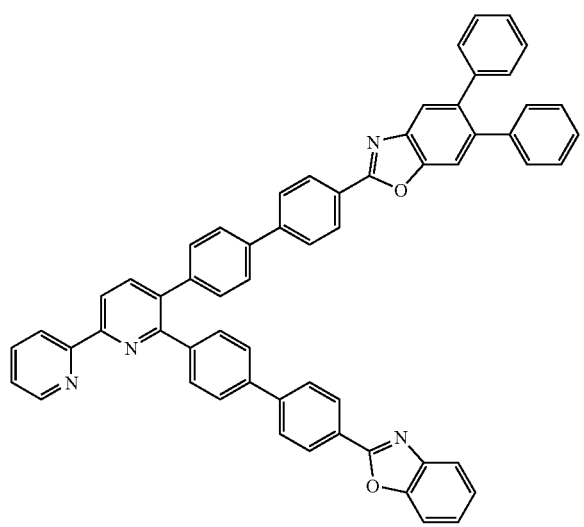
(186)
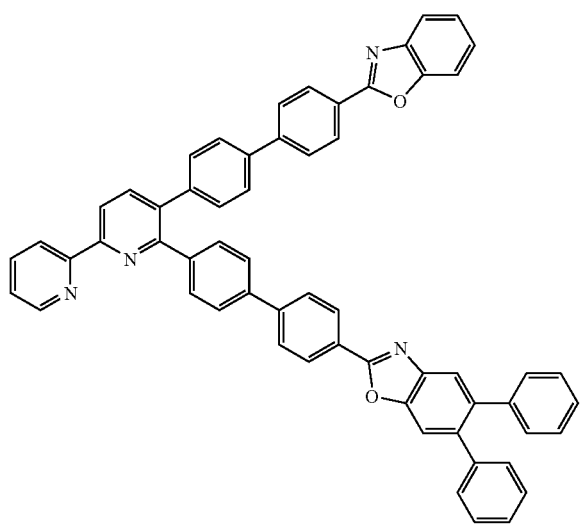

-continued
(187)
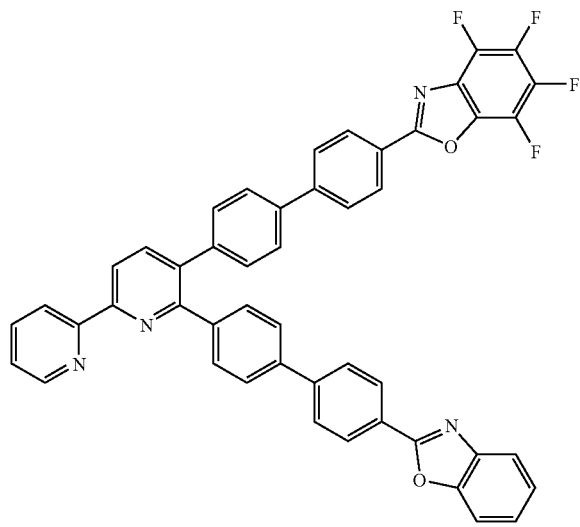
(188)
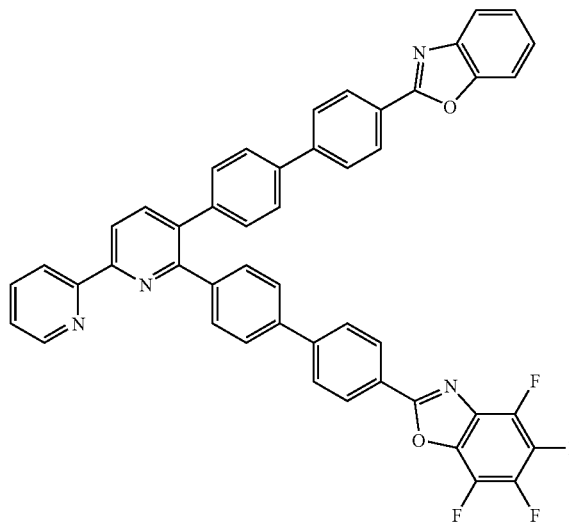
(189)
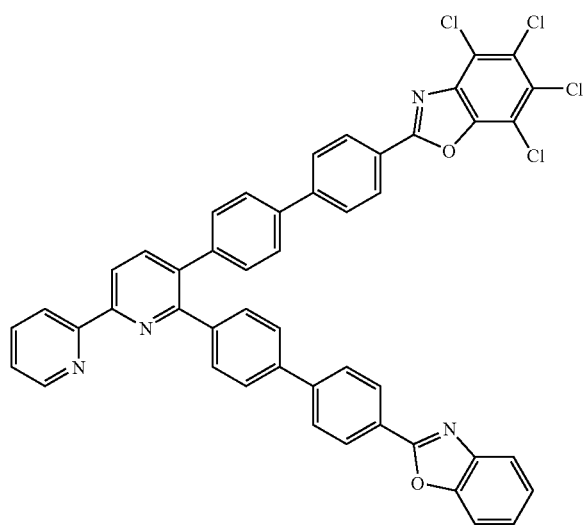
(190)
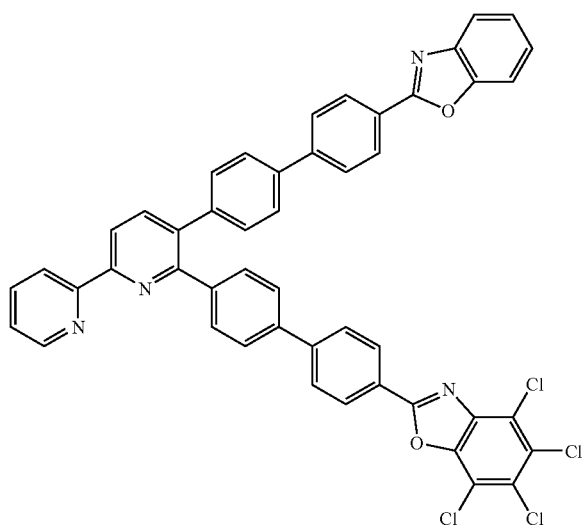
(191)
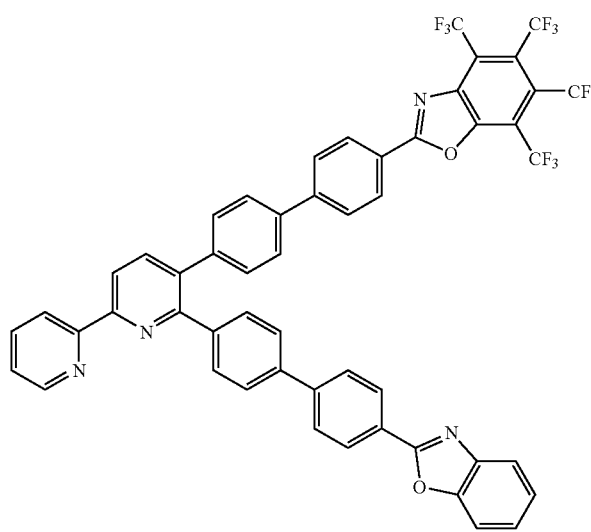
(192)
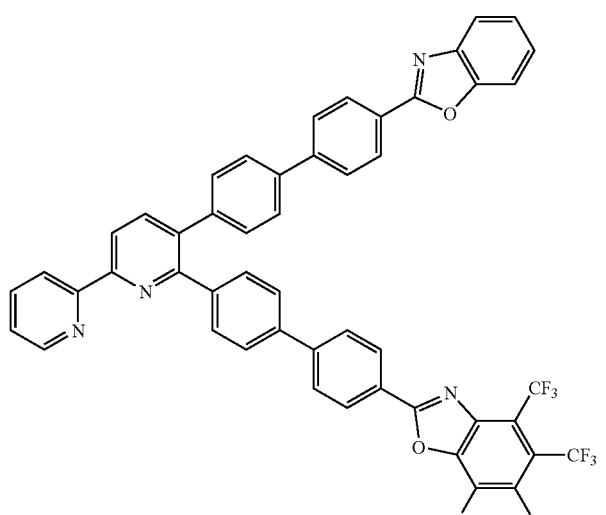

-continued
(193)
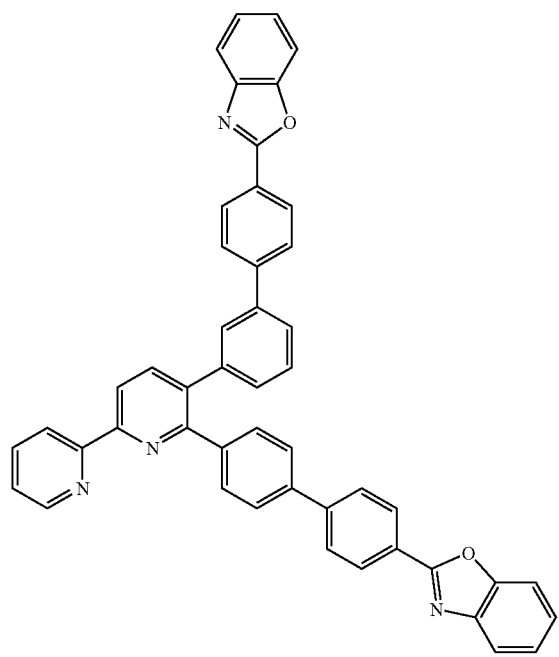
(194)
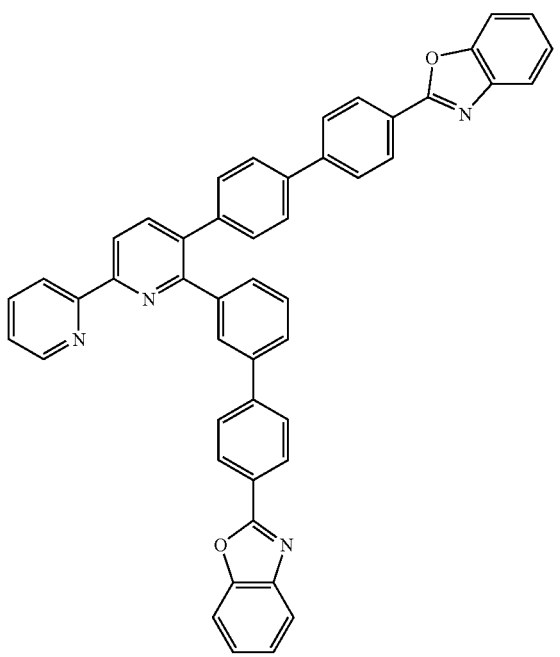
(195)
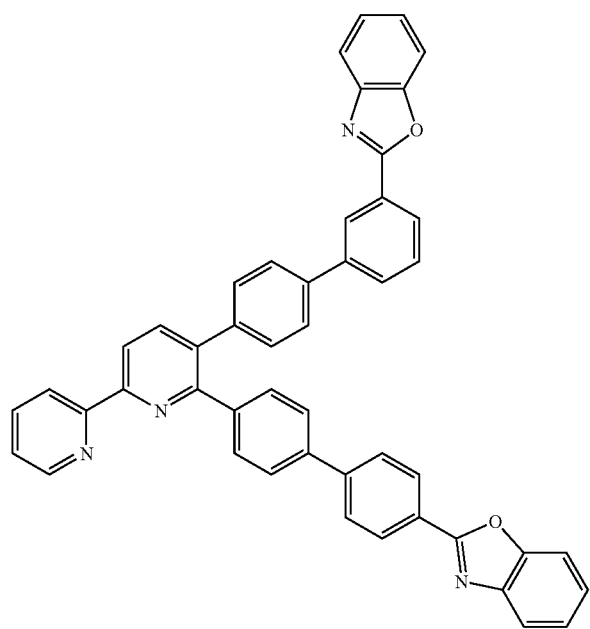
(196)
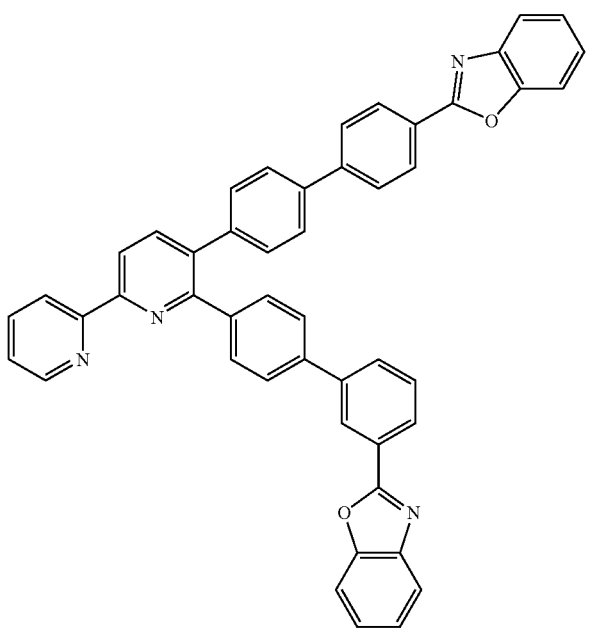

(197)
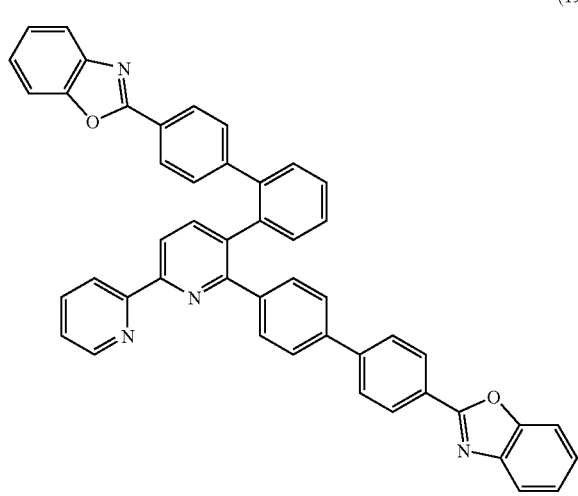
(198)
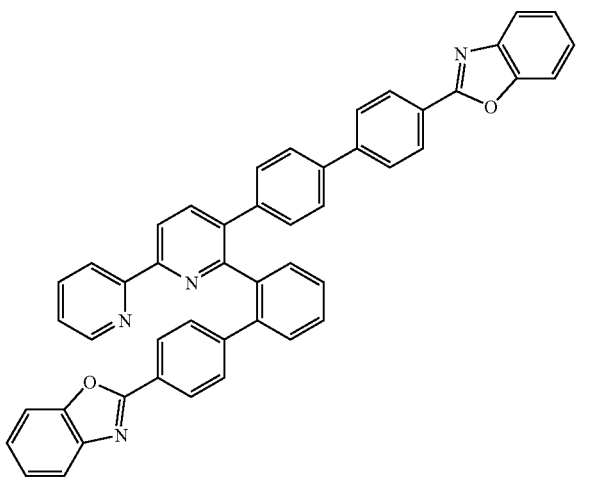
(199)
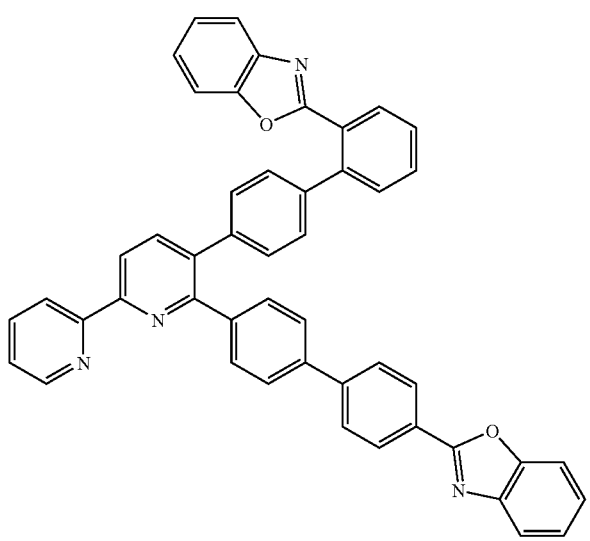
(200)
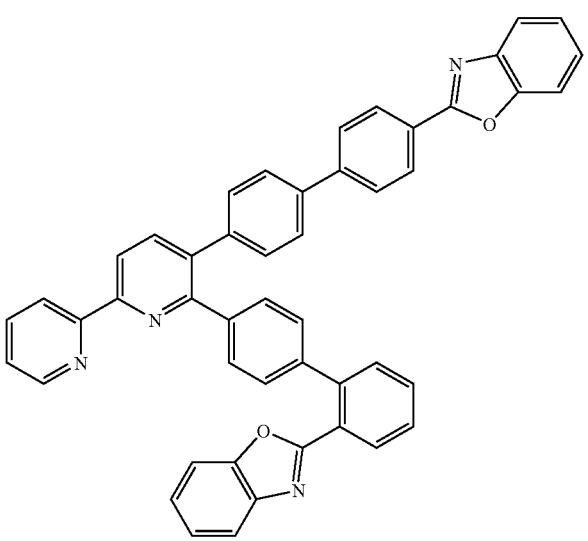

-continued
(201)
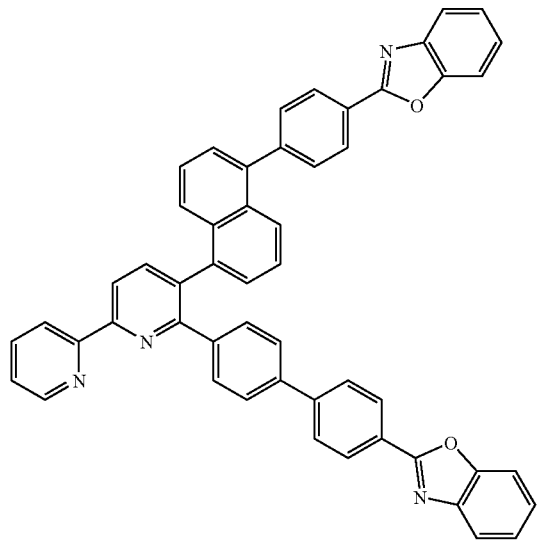
(202)
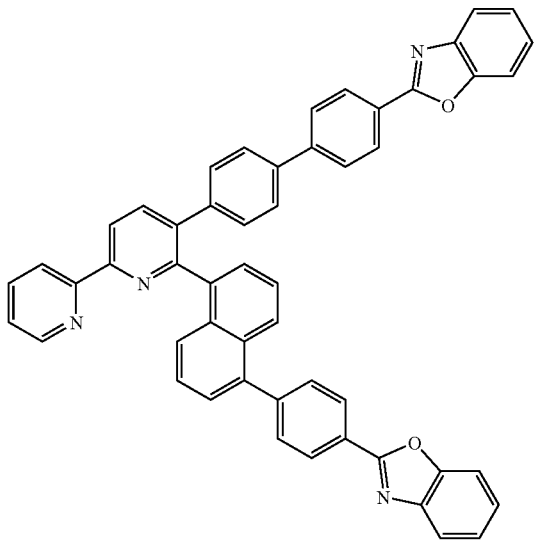
(203)
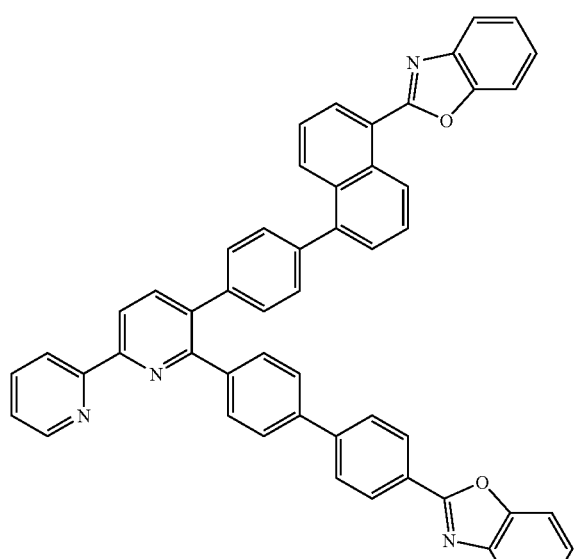
(204)
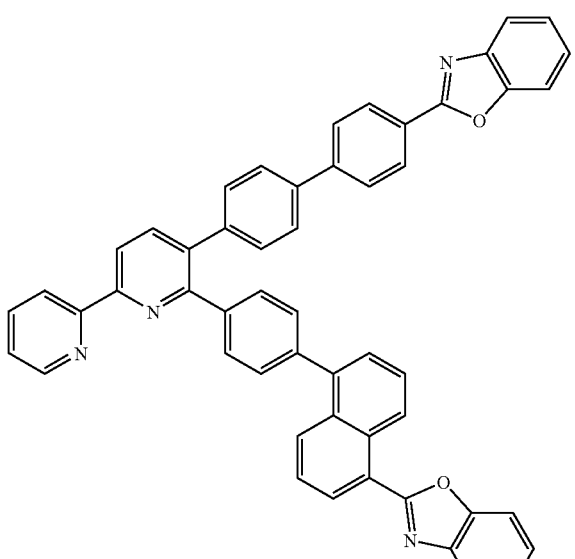
(205)
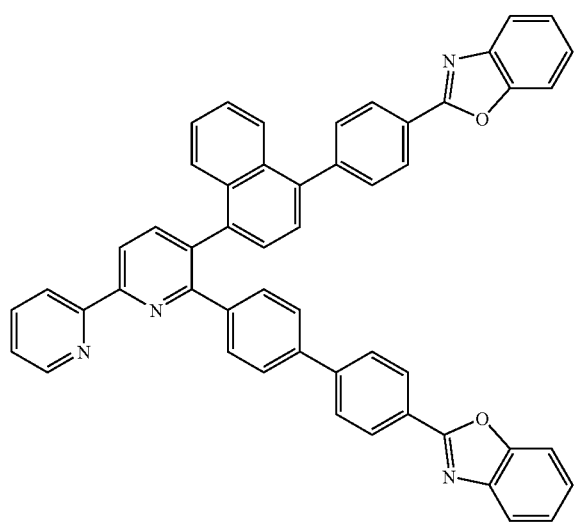
(206)
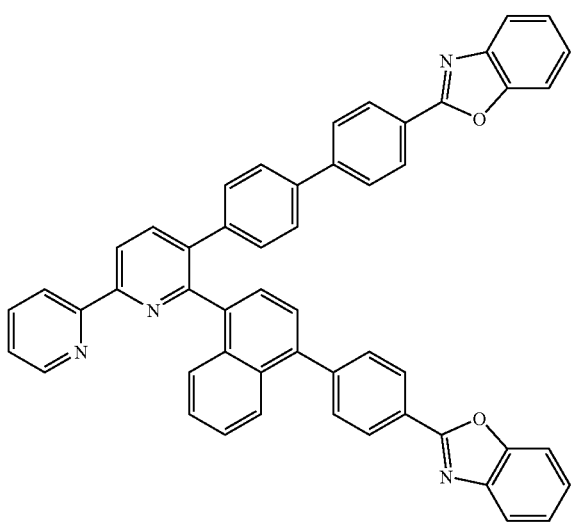

(207)

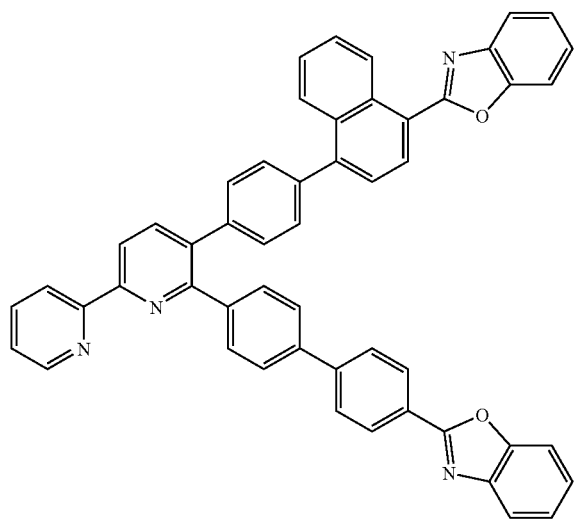

(208)

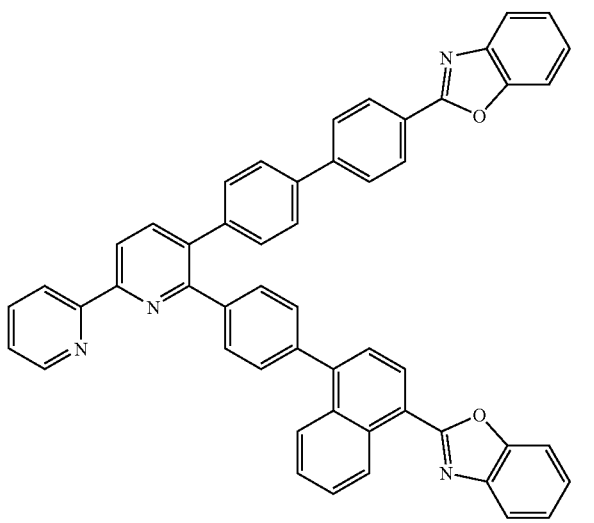

As a synthesis method of the benzoxazole derivatives of the present invention, various reactions can be applied. For example, the benzoxazole derivatives of the present invention can be synthesized by synthetic reactions shown below. Note that the synthesis method of the benzoxazole derivatives of the present invention is not limited to the following synthesis methods.

<Synthesis Method of the Compound Represented by the General Formula (G1)>

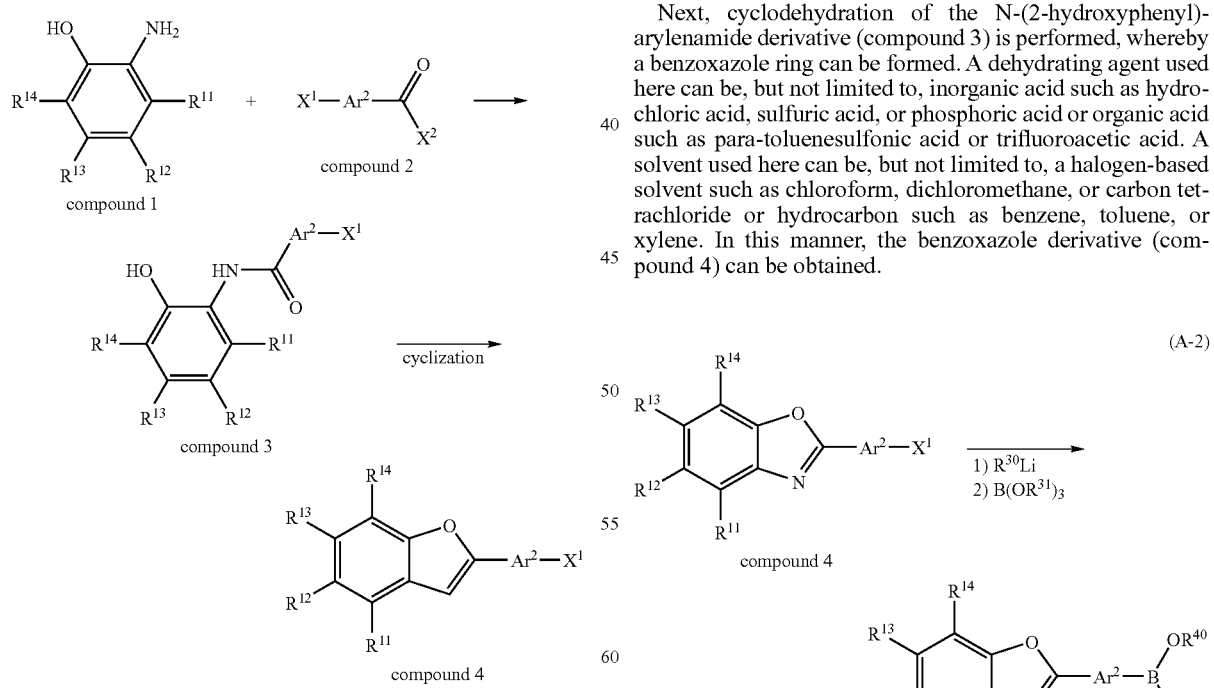

First of all, a benzoxazole derivative (compound 4) can be synthesized in accordance with a synthesis scheme (A-1). In this scheme, $R^{11}$ to $R^{14}$ are independently hydrogen, an alkyl group having 1 to 4 carbon atoms, a haloalkyl group having 1 to 4 carbon atoms, a substituted or unsubstituted aryl group having 6 to 13 carbon atoms, or halogen. $Ar^2$ is a substituted or unsubstituted arylene group having 6 to 13 carbon atoms. Further, $X^1$ is halogen, in particular, chlorine, bromine or iodine is preferable. Furthermore, $X^2$ is halogen and is preferably chlorine.

First, an ortho-aminophenol derivative (compound 1) is acylated with an acyl halide (compound 2), whereby a N-(2-hydroxyphenyl)-arylenamide derivative (compound 3) can be obtained. A solvent used here can be, but not limited to, an ether-based solvent such as diethyl ether or tetrahydrofuran or a halogen-based solvent such as chloroform, dichloromethane, or carbon tetrachloride.

Next, cyclodehydration of the N-(2-hydroxyphenyl)-arylenamide derivative (compound 3) is performed, whereby a benzoxazole ring can be formed. A dehydrating agent used here can be, but not limited to, inorganic acid such as hydrochloric acid, sulfuric acid, or phosphoric acid or organic acid such as para-toluenesulfonic acid or trifluoroacetic acid. A solvent used here can be, but not limited to, a halogen-based solvent such as chloroform, dichloromethane, or carbon tetrachloride or hydrocarbon such as benzene, toluene, or xylene. In this manner, the benzoxazole derivative (compound 4) can be obtained.

Next, boron oxidation or organoboration of the benzoxazole derivative (compound 4) is performed using an alkyllithium reagent and a boron reagent, whereby a boronic acid of the benzoxazole derivative (compound 5) or an organoboron compound of the benzoxazole derivative (compound 5) can be obtained.

In the synthesis scheme (A-2), $R^{11}$ to $R^{14}$ are independently hydrogen, an alkyl group having 1 to 4 carbon atoms, a haloalkyl group having 1 to 4 carbon atoms, a substituted or unsubstituted aryl group having 6 to 13 carbon atoms, or halogen. $Ar^2$ is a substituted or unsubstituted arylene group having 6 to 13 carbon atoms. Further, $X^1$ is halogen and is preferably, chlorine, bromine or iodine in particular. In addition, $R^{30}$ is an alkyl group having 1 to 6 carbon atoms, $R^{31}$ is an alkyl group having 1 to 6 carbon atoms, $R^{40}$ and $R^{41}$ are independently hydrogen or an alkyl group having 1 to 6 carbon atoms. In the synthesis scheme (A-2), $R^{40}$ and $R^{41}$ may be bound to each other to form a ring.

In the synthesis scheme (A-2), an ether-based solvent such as diethyl ether, tetrahydrofuran (THF), or cyclopentyl methyl ether can be used. However, the solvent that can be used is not limited to these solvents. The alkyllithium reagent may be, but not limited to, n-butyllithium in which $R^{30}$ is an n-butyl group, tert-butyllithium in which $R^{30}$ is a tert-butyl group, sec-butyllithium in which $R^{30}$ is a sec-butyl group, methyllithium in which $R^{30}$ is a methyl group, or the like. The boron reagent may be, but not limited to, trimethyl borate in which $R^{31}$ is a methyl group, triisopropyl borate in which $R^{31}$ is an isopropyl group, or the like.

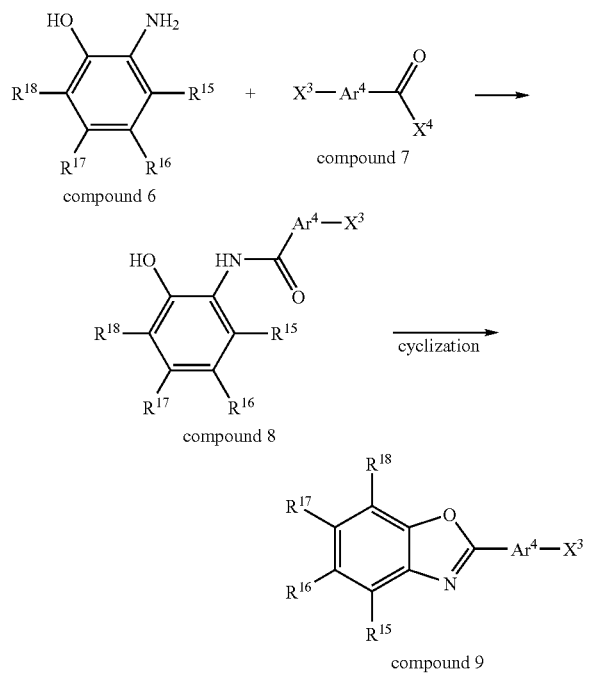

In addition, a benzoxazole derivative (compound 9) can be synthesized in accordance with a synthesis scheme (A-3). In this scheme, $R^{15}$ to $R^{18}$ are independently hydrogen, an alkyl group having 1 to 4 carbon atoms, a haloalkyl group having 1 to 4 carbon atoms, a substituted or unsubstituted aryl group having 6 to 13 carbon atoms, or halogen; and $Ar^4$ is a substituted or unsubstituted arylene group having 6 to 13 carbon atoms. Furthermore, $X^3$ is halogen, which is preferably chlorine, bromine, or iodine. Still furthermore, $X^4$ is halogen, and chloride is particularly preferable.

First, an ortho-aminophenol derivative (compound 6) is acylated with an acyl halide (compound 7), whereby a N-(2-hydroxyphenyl)-arylenamide derivative (compound 8) can be obtained. A solvent used here can be, but not limited to, an ether-based solvent such as diethyl ether or tetrahydrofuran or a halogen-based solvent such as chloroform, dichloromethane, or carbon tetrachloride.

Next, cyclodehydration of the N-(2-hydroxyphenyl)-arylenamide derivative (compound 8) is performed, whereby a benzoxazole ring is formed. A dehydrating agent used here can be, but not limited to, inorganic acid such as hydrochloric acid, sulfuric acid, or phosphoric acid or organic acid such as para-toluenesulfonic acid or trifluoroacetic acid. A solvent used here can be, but not limited to, a halogen-based solvent such as chloroform, dichloromethane, or carbon tetrachloride or hydrocarbon such as benzene, toluene, or xylene. In this manner, the benzoxazole derivative (compound 9) can be obtained.

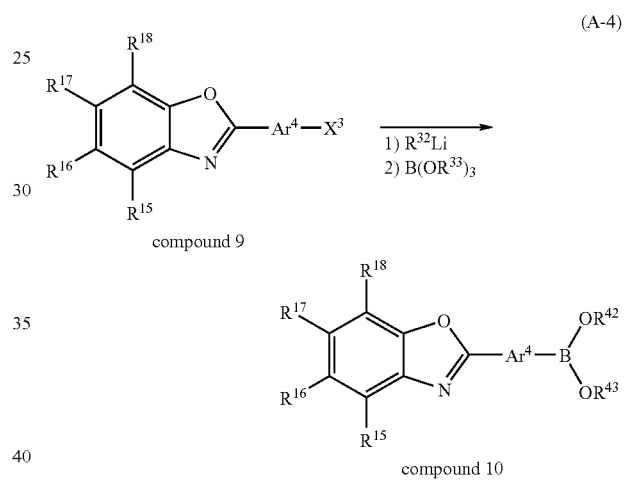

Next, in accordance with the synthesis scheme (A-4), boron oxidation or organoboration of the benzoxazole derivative (compound 9) is performed using an alkyllithium reagent and a boron reagent, whereby a boronic acid of the benzoxazole derivative (compound 10) or an organoboron compound of the benzoxazole derivative (compound 10) can be obtained.

In the synthesis scheme (A-4), $R^{15}$ to $R^{18}$ are independently hydrogen, an alkyl group having 1 to 4 carbon atoms, a haloalkyl group having 1 to 4 carbon atoms, a substituted or unsubstituted aryl group having 6 to 13 carbon atoms, or halogen. $Ar^4$ is a substituted or unsubstituted arylene group having 6 to 13 carbon atoms. Furthermore, $X^3$ is halogen, which is preferably chlorine, bromine, or iodine. In addition, $R^{32}$ is an alkyl group having 1 to 6 carbon atoms, $R^{33}$ is an alkyl group having 1 to 6 carbon atoms, and $R^{42}$ and $R^{43}$ are independently hydrogen or an alkyl group having 1 to 6 carbon atoms. In the synthesis scheme (A-4), $R^{42}$ and $R^{43}$ may be bound to each other to form a ring.

In the synthetic scheme (A-4), as a solvent that can be used, an ether-based solvent such as diethyl ether, tetrahydrofuran (THF), or cyclopentyl methyl ether can be given, without being limited thereto. As an alkyl lithium reagent, n-butyllithium in which $R^{32}$ is an n-butyl group, tert-butyllithium in which $R^{32}$ is a tert-butyl group, sec-butyllithium in which $R^{32}$ is a sec-butyl group, methyl lithium in which $R^{32}$ is a methyl group, or the like can be given, without being limited thereto. As a boron reagent, trimethyl borate in which $R^{33}$ is a methyl group, triisopropyl borate in which $R^{33}$ is an isopropyl group, or the like can be given, without being limited thereto.

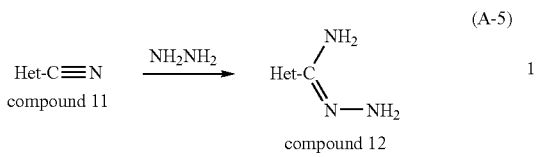

In addition, as represented by the synthesis scheme (A-5), an amidrazone derivative (compound 12) can be obtained by a reaction of a heterocyclic compound (compound 11) having a nitrile group and hydrazine. In the synthesis scheme (A-5), Het is a pyridyl group or a pyrimidinyl group.

Examples of the solvent used in the synthesis scheme (A-5) include alcohols such as ethanol, methanol, or butanol, water, and the like. Note that the solvent is not limited to these examples. In addition, in a case where hydrazine is used as the solvent, it is unnecessary to use another solvent. Further, as for the hydrazine used as a reagent, hydrazine hydrate is preferable in terms of safety, but the present invention is not limited to hydrazine hydrate.

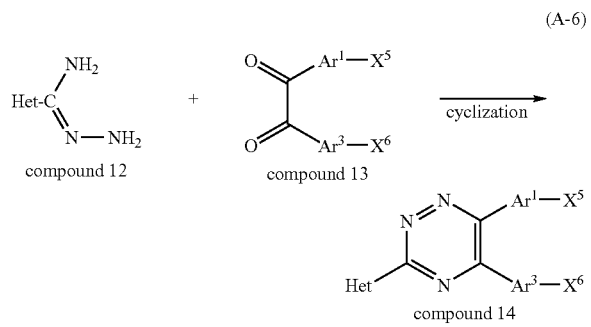

Then, as represented by the synthesis scheme (A-6), the amidrazone derivative (compound 12) and a 1,2-diketone derivative (compound 13) can be cyclized to obtain a 1,2,4-triazine derivative (compound 14). In the synthesis scheme (A-6), Het is a pyridyl group or a pyrimidinyl group. In addition, $X^5$ and $X^6$ are independently halogen or a triflate group, and when $X^5$ and $X^6$ are halogen, chlorine, bromine or iodine is preferable. In addition, $Ar^1$ and $Ar^3$ are independently a substituted or unsubstituted arylene group having 6 to 13 carbon atoms.

In the synthesis scheme (A-6), examples of solvents that can be used include halogen-based solvents such as dichloromethane, chloroform, and carbon tetrachloride; alcohols such as ethanol, methanol, or isopropanol; aromatic hydrocarbons such as benzene, toluene, or xylene; and the like, without being limited thereto. In the case where a halogen-based solvent is used, chloroform or carbon tetrachloride having high boiling point is preferably used.

In addition, in the synthesis scheme (A-6), $Ar^1$ and $Ar^3$ are preferably the same in terms of yield and refinement. However, the present invention is not limited to this.

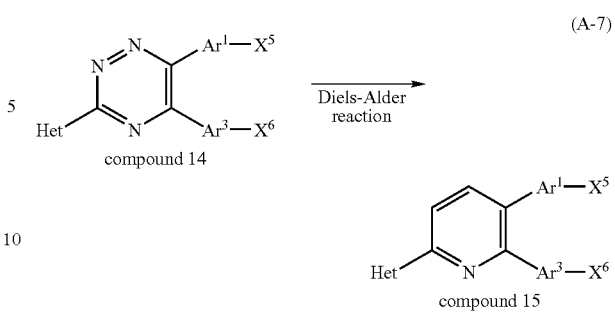

The 1,2,4-triazine derivative (compound 14) is denitrified by a compound having an alkene structure with Diels-Alder reaction, so that a pyridine derivative (compound 15) is obtained. In the synthesis scheme (A-7), Het is a pyridyl group or a pyrimidinyl group. In addition, $X^5$ and $X^6$ are independently halogen or a triflate group, and when $X^5$ and $X^6$ represent halogen, chlorine, bromine or iodine is preferable. In addition, $Ar^1$ and $Ar^3$ are independently a substituted or unsubstituted arylene group having 6 to 13 carbon atoms.

Examples of the solvent that can be used in the synthesis scheme (A-7) include, but not limited to, alcohols such as ethanol, methanol, and butanol; ethers such as diethyl ether, tetrahydrofuran (THF), cyclopentyl methyl ether, and diisopropyl ether; alkanes such as hexane, cyclohexane, heptane, and octane; aromatic hydrocarbons such as benzene, toluene, and xylene; halogen solvents such as dichloromethane, chloroform, carbon tetrachloride; 1,2-dichloroethane, 1,1,2,2-tetrachloromethane, chlorobenzene, bromobenzene, 1,2-dichlorobenzene, 1,3-dichlorobenzene, 1,4-dichlorobenzene, 1,2-dibromobenzene, 1,3-dibromobenzene, and 1,4-dibromobenzene; and the like. In addition, the solvent used is preferably a solvent having a high boiling point such as xylene or dichlorobenzene.

In addition, examples of the compound having an alkene structure include cyclopentadiene, bicyclo[2,2,1]hepta-2,5-diene, and the like. Note that the compound having an alkene structure used is not limited to these examples.

Next, the pyridine derivative (compound 15) and an organoboron compound or a boronic acid of the benzoxazole derivative represented by the compound 5 or the compound 10 are reacted with Suzuki-Miyaura coupling, so that a target benzoxazole derivative represented by the general formula (G1) can be obtained.

Examples of a paradium catalyst that can be used in the Suzuki-Miyaura coupling include, but not limited to, palladium(II) acetate, tetrakis(triphenylphosphine)palladium(0), bis(triphenylphosphine)palladium(II) dichloride, and the like. Examples of a ligand in the palladium catalyst that can be used in the Suzuki-Miyaura coupling include, but are not limited to, tri(ortho-tolyl)phosphine, triphenylphosphine, tricyclohexylphosphine, and the like. As a base that can be used in the Suzuki-Miyaura coupling, an organic base such as sodium tert-butoxide, an inorganic base such as potassium carbonate, and the like can be given, but the base which can be used is not limited thereto. Examples of a solvent that can be used in the Suzuki-Miyaura coupling include, but not limited to, a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of an ether such as ethylene glycol dimethyl ether and water; or the like can be given. Further, a mixed solvent of toluene and water; a mixed solvent of toluene, ethanol, and water; or a mixed solvent of ether such as ethylene glycol dimethyl ether and water is more preferable.

Further, in the Suzuki-Miyaura coupling, instead of using an organoboron compound or a boronic acid as represented by the compound 5 or the compound 10, cross coupling reaction using a compound of organoaluminum, organozirconium, organozinc, organotin, or the like may be used. However, the present invention is not limited thereto.

When the compound of the general formula (G1) is synthesized, it is more preferable in terms of yield and refinement (high purification) that the compound 5 and the compound 10 that are used as source materials are the same, in other words, that $R^{11}$ and $R^{15}$, $R^{12}$ and $R^{16}$, $R^{13}$ and $R^{17}$, and $R^{14}$ and $R^{18}$ are the same and 2 equivalents of the same organoboron reagent or boronic acid are used.

The benzoxazole derivatives of the present invention have an excellent electron-injecting property. In particular, when Het in the general formula (G1) is any one of 2-pyridyl, 4-pyridyl, pyrimidin-2-yl, and pyrimidin-4-yl, the benzoxazole derivatives can have both an excellent electron-injecting property and an excellent electron-transporting property. Therefore, by using the benzoxazole derivatives of the present invention for electronics device such as light-emitting elements or organic transistors, favorable electrical characteristics can be obtained.

Further, the organic compounds serving as source materials to synthesize the benzoxazole derivatives of the present invention are novel substances, and thus are included in the present invention.

An organic compound according to an embodiment of the present invention is the organic compound represented by the general formula (G11).

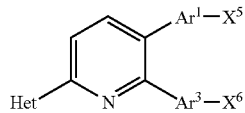

(G11)

In the formula, Het is a pyridyl group or a pyrimidinyl group, $Ar^1$ and $Ar^3$ are independently a substituted or unsubstituted arylene group having 6 to 13 carbon atoms, and $X^5$ and $X^6$ are independently halogen or a triflate group.

Specific examples of the organic compound represented by the general formula (G11) include organic compounds represented by structural formulae (301) to (360). However, the present invention is not limited to the following structural formulas.

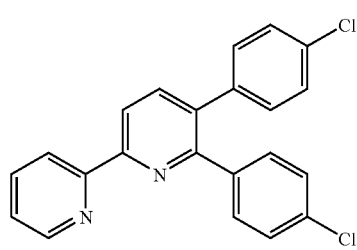

(301)

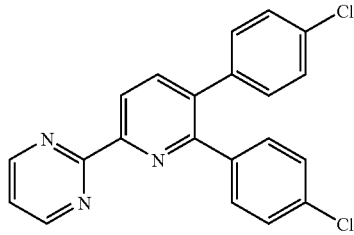

(302)

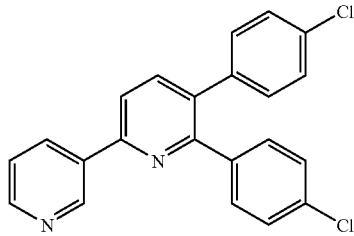

(303)

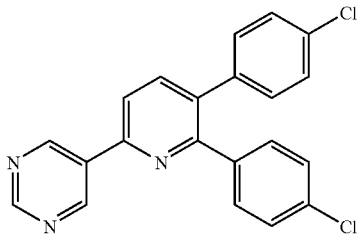

(304)

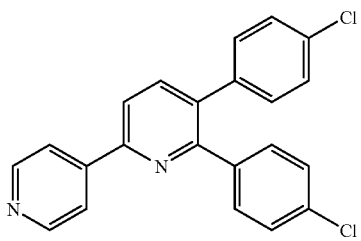

(305)

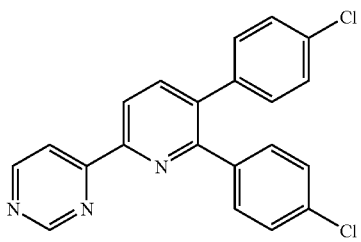

(306)

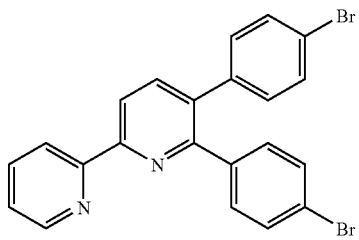

(307)

(308) 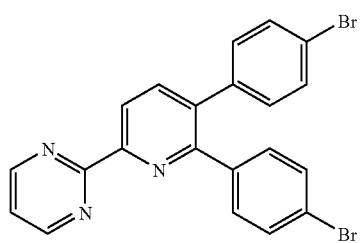
(309) 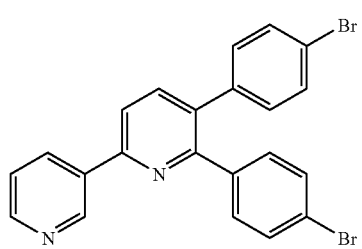
(310) 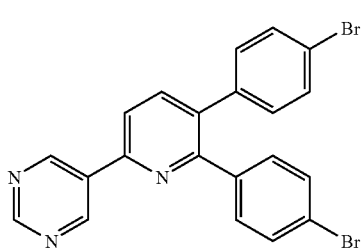
(311) 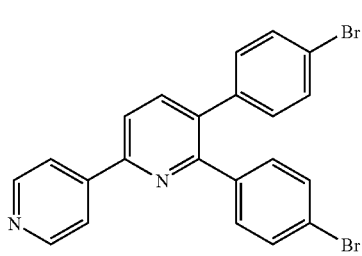
(312) 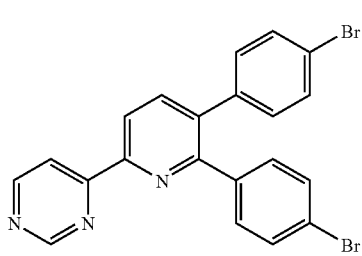
(313) 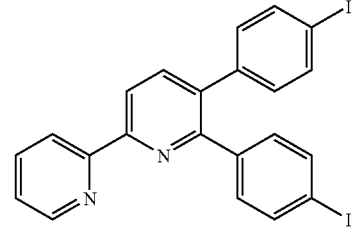
(314) 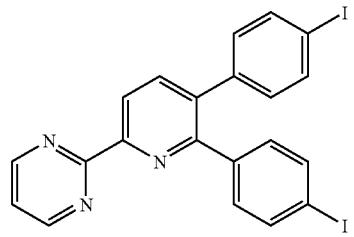
(315) 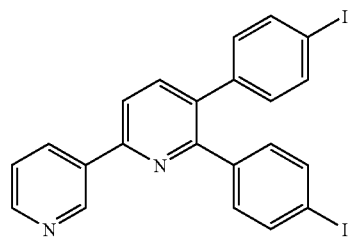
(316) 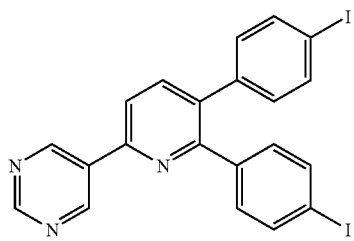
(317) 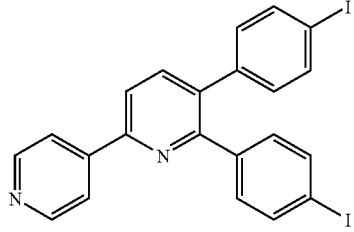
(318) 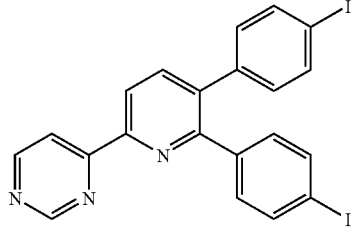
(319) 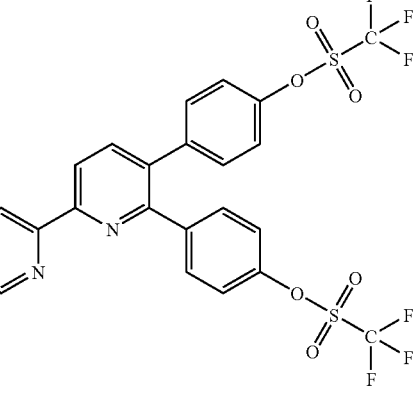

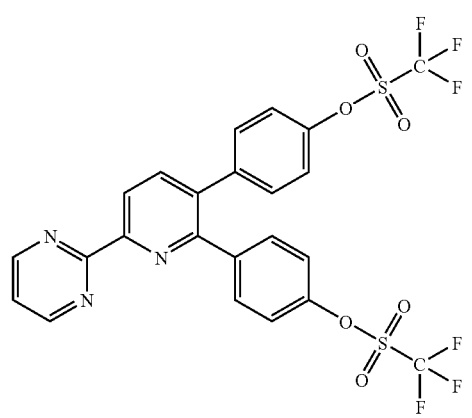
(320)
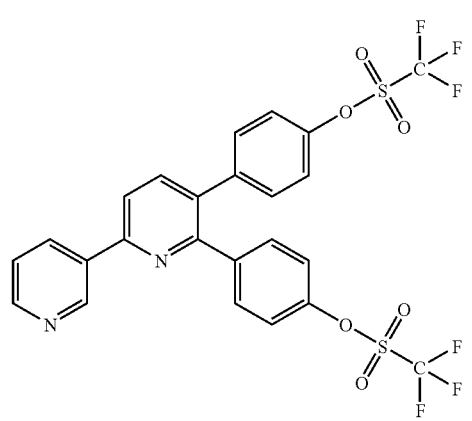
(321)
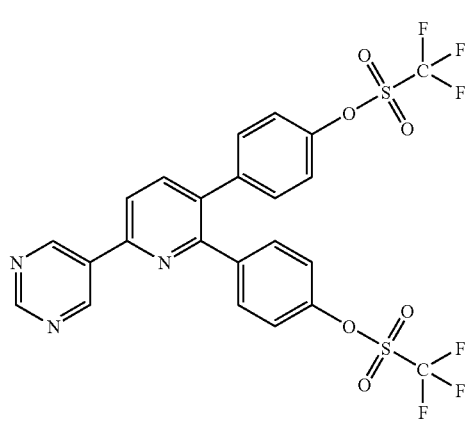
(322)
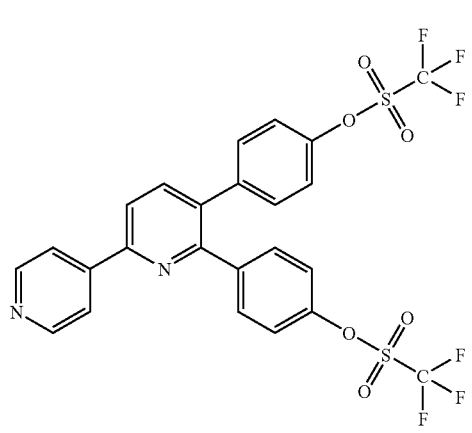
(323)
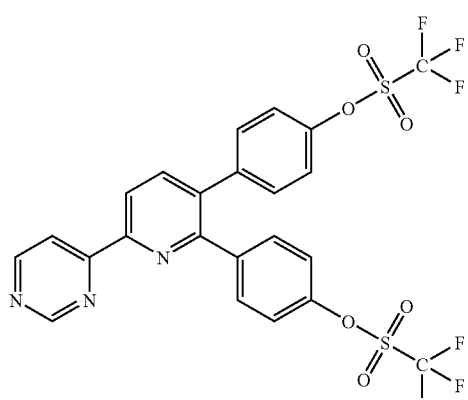
(324)
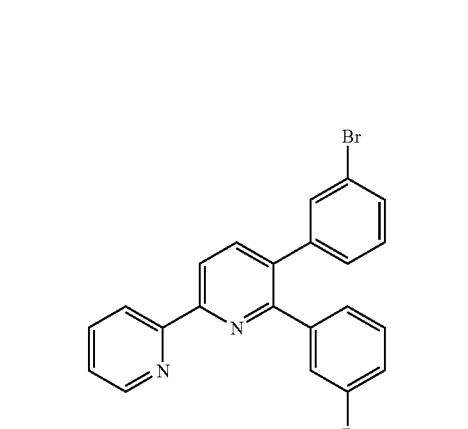
(325)
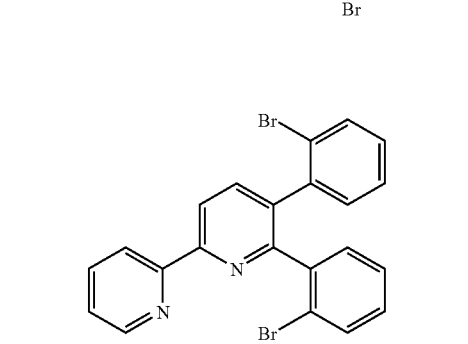
(326)
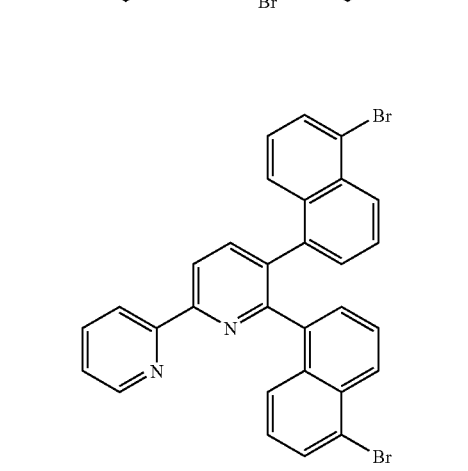
(327)

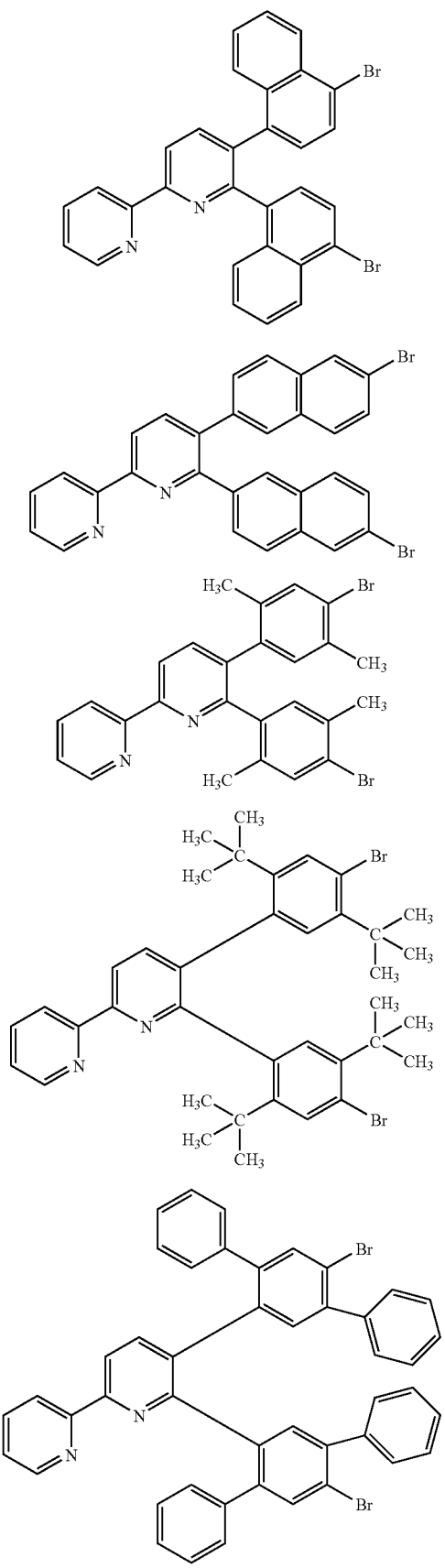
(328)
(329)
(330)
(331)
(332)
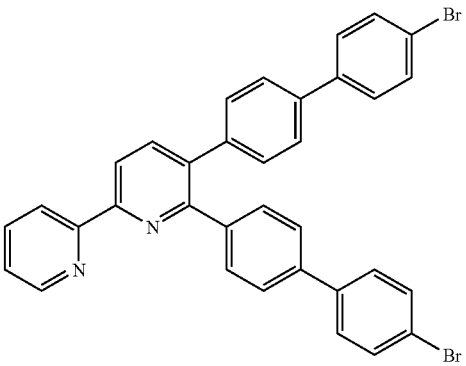
(333)
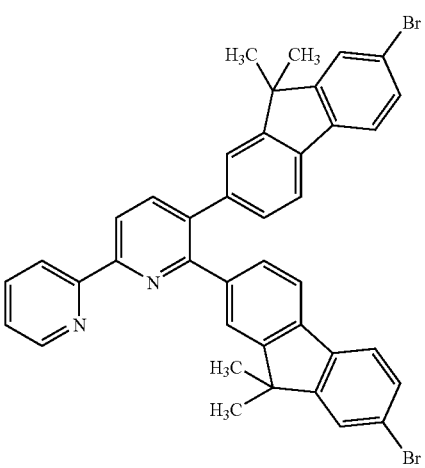
(334)
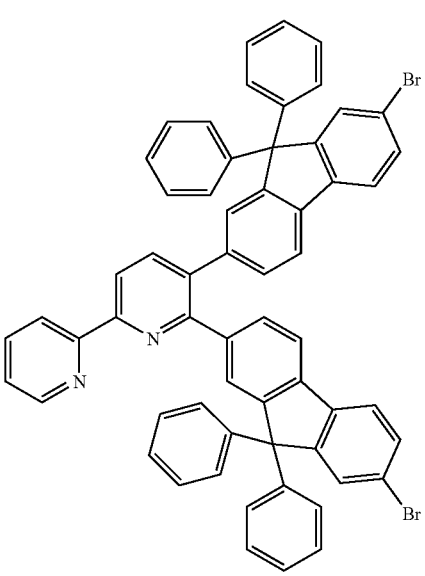
(335)

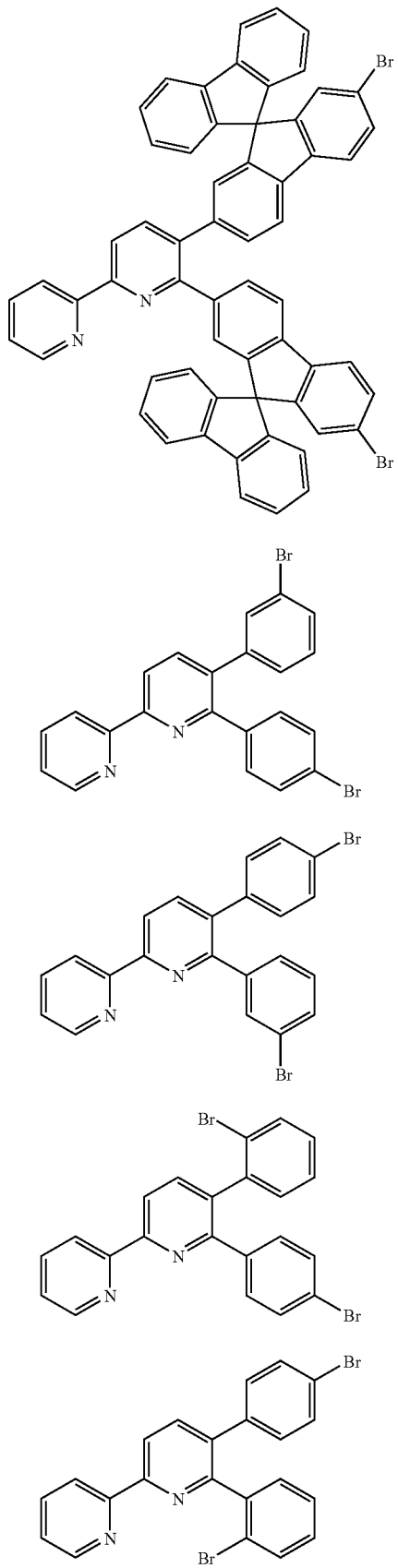
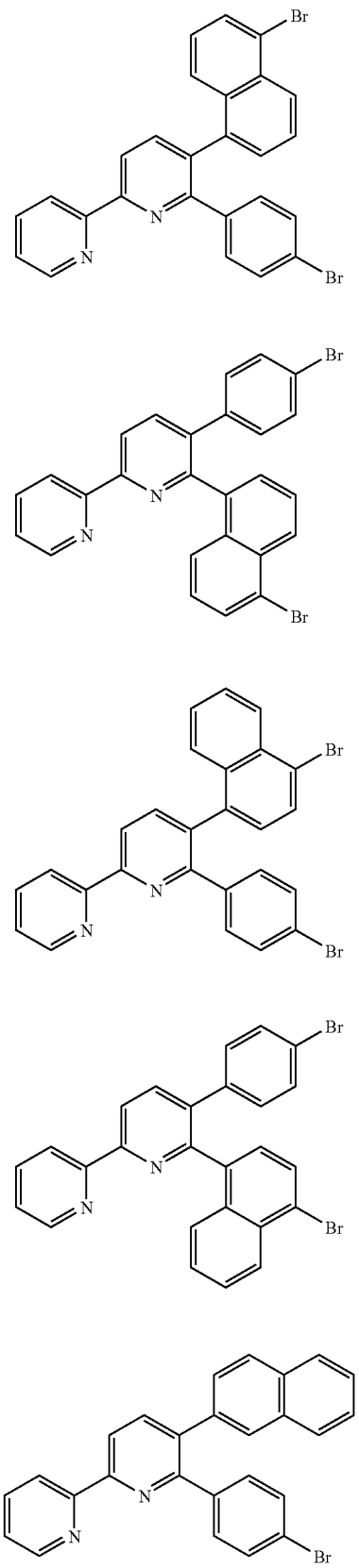

-continued
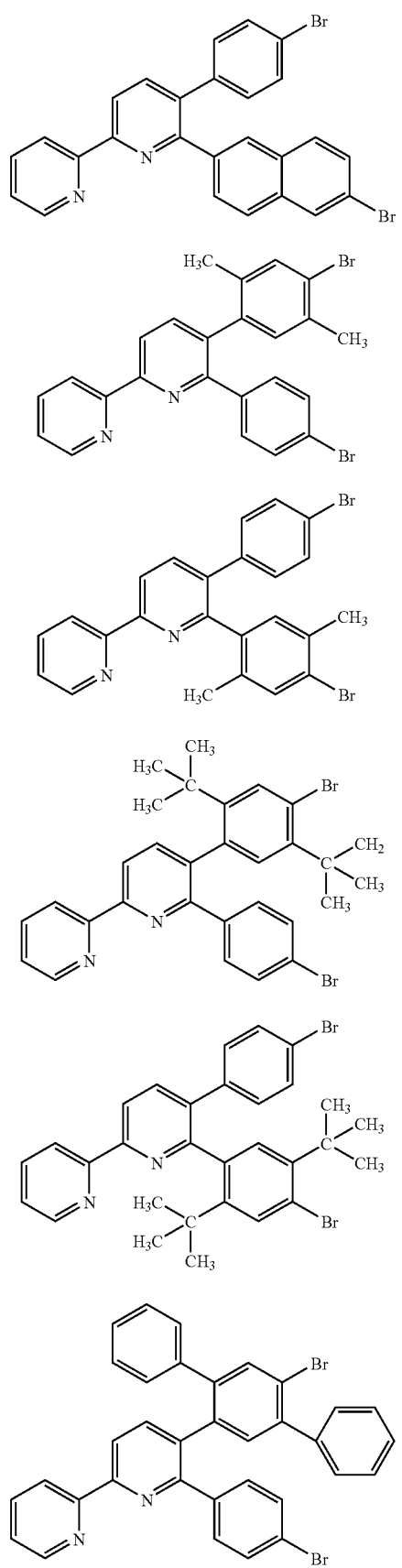
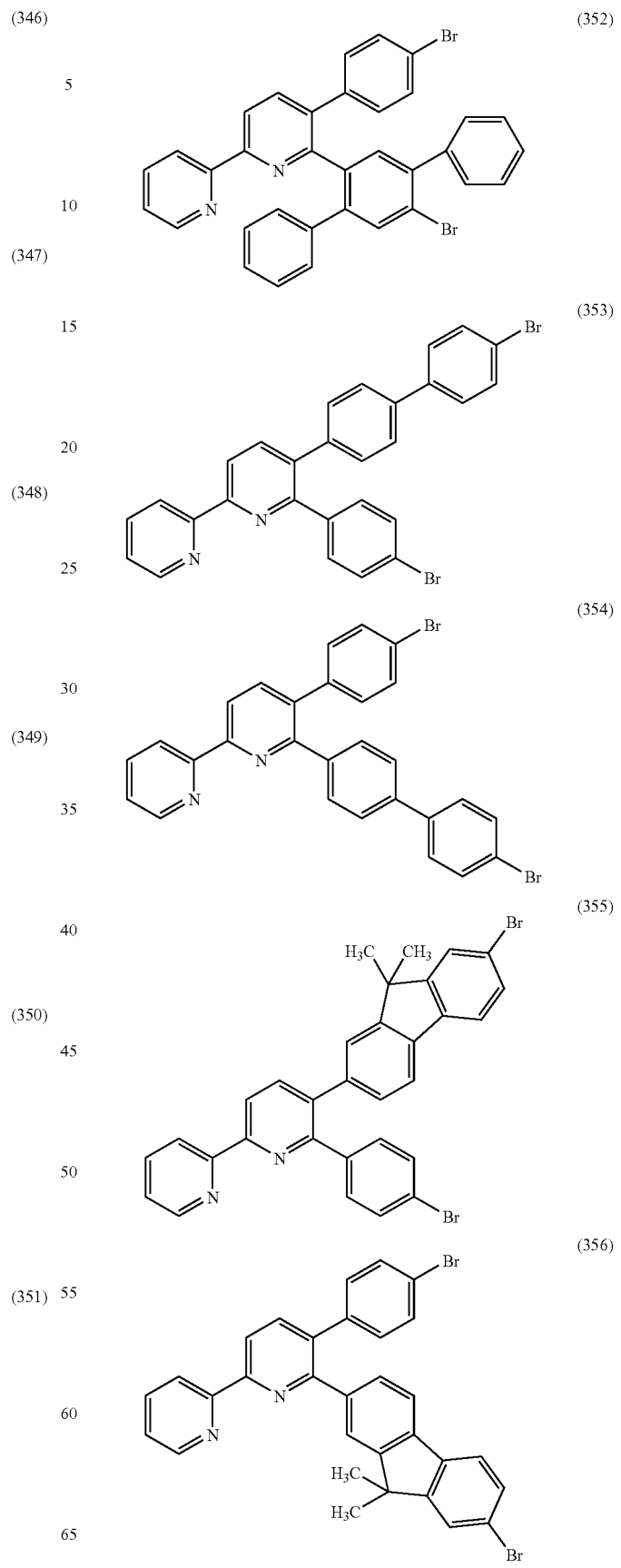

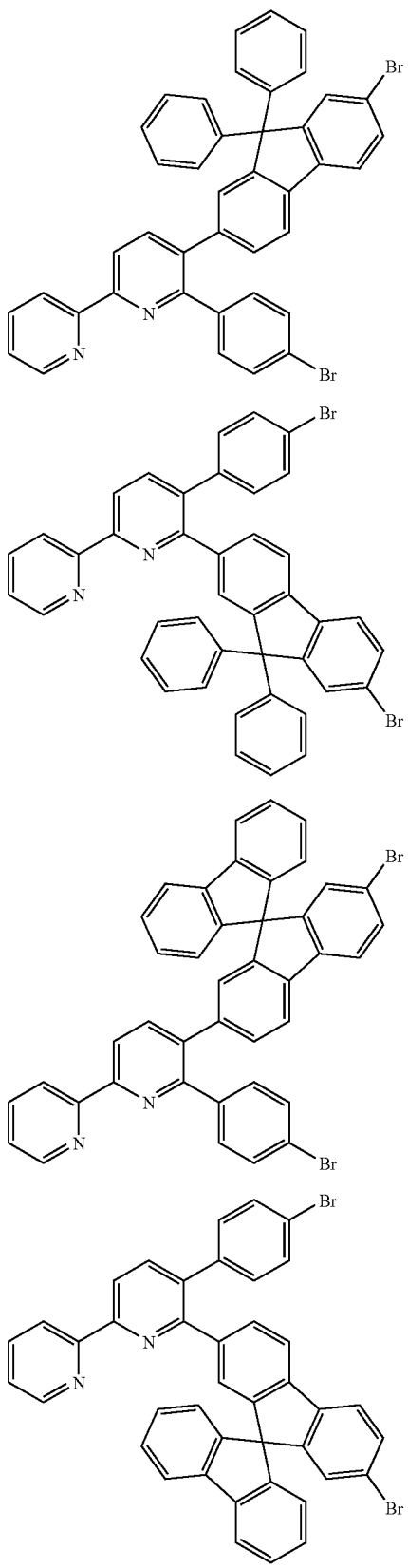

A synthesis method of the organic compound represented by the general formula (G11) can employ various types of reactions. For example, it can be synthesized by a synthesis method that is similar to that of the compound 15 described above (the synthesis scheme (A-7)).

Embodiment 2

In Embodiment 2, one mode of a light-emitting element using a benzoxazole derivative shown in Embodiment 1 will be described with reference to FIG. 1 and FIG. 2.

A light-emitting element of the present invention has a plurality of layers between a pair of electrodes. The plurality of layers are stacked by combining layers formed with a substance having a high carrier-injecting property and a substance having a high carrier-transporting property so that a light-emitting region is formed apart from the electrodes, or, so that carriers are recombined in a portion apart from the electrodes.

In this embodiment, the light-emitting element includes a first electrode 102, a second electrode 104, and an EL layer which is provided between the first electrode 102 and the second electrode 104. Note that in description of this embodiment, the first electrode 102 functions as an anode and the second electrode 104 functions as a cathode. In other words, below is described a case where light emission is obtained when a voltage is applied to the first electrode 102 and the second electrode 104 such that a potential of the first electrode 102 is higher than that of the second electrode 104.

A substrate 101 is used as a support of the light-emitting element. The substrate 101 can be formed of, for example, glass, plastic, metal, or the like. Note that materials other than these can be used as long as they can function as a support of a light-emitting element. Note that in the case where light from the light-emitting element is extracted outside through the substrate 101, the substrate 101 preferably has a light-transmitting property.

Preferably, the first electrode 102 is formed using any of metals, alloys, or conductive compounds, a mixture thereof, or the like with a high work function (specifically, a work function of 4.0 eV or higher is preferable). Specifically, for example, indium oxide-tin oxide (ITO: Indium Tin Oxide), indium oxide-tin oxide containing silicon or silicon oxide, indium oxide-zinc oxide (IZO: Indium Zinc Oxide), indium oxide containing tungsten oxide and zinc oxide (IWZO), or the like is given. Such conductive metal oxide films are usually formed by sputtering, but may also be formed by inkjet, spin coating, or the like by application of sol-gel method or the like. For example, indium oxide-zinc oxide (IZO) can be formed by a sputtering method using a target in which zinc oxide of 1 to 20 wt % is added to indium oxide. Indium oxide containing tungsten oxide and zinc oxide (IWZO) can be formed by sputtering using a target in which tungsten oxide of 0.5 to 5 wt % and zinc oxide of 0.1 to 1 wt % are mixed with indium oxide. Further, gold (Au), platinum (Pt), nickel (Ni), tungsten (W), chromium (Cr), molybdenum (Mo), iron (Fe), cobalt (Co), copper (Cu), palladium (Pd), titanium (Ti), nitrides of the metal materials (such as titanium nitride: TiN), and the like can be given.

In the case where a layer including a composite material described below is used as a layer in contact with the first electrode 102, various metals, alloys, electrically conductive compounds, or a mixture thereof can be used for the first electrode 102 regardless of the work function. For example, aluminum (Al), silver (Ag), an aluminum alloy (e.g., AlSi), or the like can be used. Besides, an element belonging to Group 1 or 2 of the periodic table which has a low work function, i.e., alkali metals such a lithium (Li) and cesium (Cs) and alkaline earth metals such as magnesium (Mg), calcium (Ca), and strontium (Sr); alloys of them (e.g., MgAg and AlLi); rare earth metals such as europium (Eu) and ytterbium (Yb); alloys of them; and the like can also be used. A film of an alkali metal, an alkaline earth metal, or an alloy including these can be formed by vacuum evaporation. Alternatively, an alloy including an alkali metal or an alkaline earth metal can be formed by a sputtering method. Further, silver paste or the like can be formed by an inkjet method.

The EL layer 103 described in this embodiment includes a hole-injecting layer 111, a hole-transporting layer 112, a light-emitting layer 113, an electron-transporting layer 114, and an electron-injecting layer 115. Note that it is acceptable as long as the EL layer 103 include a benzoxazole derivative shown in Embodiment 1. Thus, the structure of other stacked layers is not specifically limited. That is, there is no particular limitation on the stacked structure of the EL layer 103, and a benzoxazole derivative shown in Embodiment 1 may be appropriately combined with a layer formed of a substance having a high electron-transporting property, a substance having a high hole-transporting property, a substance having a high electron-injecting property, a substance having a high hole-injecting property, a bipolar substance (a substance having high electron-transporting and hole-transporting properties), a substance having a high light-emitting property, and/or the like to form the EL layer 103. For example, the EL layer 103 can be formed by an appropriate combination of a hole-injecting layer, a hole-transporting layer, a light-emitting layer, an electron-transporting layer, an electron-injecting layer, and/or the like. Specific materials to form each of the layers will be given below.

The hole-injecting layer 111 is a layer including a substance having a high hole-injecting property. As the substance having a high hole-injecting property, molybdenum oxide, vanadium oxide, ruthenium oxide, tungsten oxide, manganese oxide, or the like can be used. In addition, as a low-molecular organic compound, the following compounds are given: phthalocyanine-based compounds such as phthalocyanine (abbreviation: $H_2Pc$), copper(II) phthalocyanine (abbreviation: CuPc), and vanadyl phthalocyanine (abbreviation: VOPc); aromatic amine compounds such as 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B); 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1); and the like.

As a further alternative, a composite material formed by mixing an acceptor substance into a substance with a high hole-transporting property can also be used for the hole-injecting layer 111. It is to be noted that, by using the material with a high hole-transporting property containing an acceptor material, a material used to form an electrode may be selected regardless of its work function. In other words, besides a material with a high work function, a material with a low work function may also be used as the first electrode 102. Such composite materials can be formed by co-evaporation of a substance having a high hole-transporting property and an acceptor substance.

It is to be noted that, in this specification, the term "composition" means not only a simple mixture of two materials but also a mixture of a plurality of materials in a condition where an electric charge is given and received among the materials.

As the organic compound used for the composite material, various compounds such as an aromatic amine compound, a carbazole derivative, aromatic hydrocarbon, and a high molecular compound (oligomer, dendrimer, polymer, or the like) can be used. The organic compound used for the composite material is preferably an organic compound having a high hole-transporting property. Specifically, a substance having a hole mobility of $10^{-6}$ cm$^2$/Vs or higher is preferably used. In addition to these, any substance that has a hole-transporting property higher than an electron-transporting property can be used. The organic compound that can be used for the composite material is specifically shown below.

For example, the following organic compounds can be used for the composite material: aromatic amine compounds such as MFDATA, TDATA, DPAB, DNTPD, DPA3B, PCz-PCA1, PCzPCA2, PCzPCN1, 4,4'-bis[N-(1-naphthyl)-N-phenylamino]biphenyl (abbreviation: NPB or α-NPD), and N,N'-bis(3-methylphenyl)-N,N'-diphenyl-[1,1'-biphenyl]-4,4'-diamine (abbreviation: TPD); carbazole derivatives such as 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), and 1,4-bis[4-(N-carbazolyl)phenyl-2,3,5,6-tetraphenylbenzene; and aromatic hydrocarbon compounds such as 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butyl-anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), and 9,10-bis[4-(2,2-diphenylvinyl)phenyl]anthracene (abbreviation: DPVPA).

As an acceptor substance, organic compounds such as 7,7,8,8-tetracyano-2,3,5,6-tetrafluoroquinodimethane (abbreviation: $F_4$-TCNQ) and chloranil, or a transition metal oxide can be given. In addition, oxides of metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable because they have a high electron-accepting property. Among these, molybdenum oxide is especially preferable since it is stable in the air and is easily treated due to its hygroscopic property is low.

For the hole-injecting layer 111, a high molecular compound (e.g., an oligomer, a dendrimer, or a polymer) can be used. For example, the following high molecular compound can be used: poly(N-vinylcarbazole) (abbreviation: PVK); poly(4-vinyltriphenylamine) (abbreviation: PVTPA); poly[N-(4-{N'-[4-(4-diphenylamino)phenyl]phenyl-N'-phenylamino}phenyl)methacrylamide] (abbreviation: PTPDMA); and poly[N,N'-bis(4-butylphenyl)-N,N'-bis(phenyl)benzidine] (abbreviation: Poly-TPD). In addition, high molecular compounds doped with acid such as poly(3,4- ethylenedioxythiophene)/poly(styrenesulfonic acid) (PEDOT/PSS), and polyaniline/poly(styrenesulfonic acid) (PAni/PSS) can be used.

It is to be noted that the hole-injecting layer 111 can be formed using a composite material of the above-described high molecular compound, such as PVK, PVTPA, PTPDMA, or Poly-TPD, and the above-described acceptor substance.

The hole-transporting layer 112 is a layer that contains a substance with a high hole-transporting property. As a low molecular organic compound of a substance having a high hole-transporting property, aromatic amine compounds such as NPB (or α-NPD), TPD, 4,4'-bis[N-(9,9-dimethylfluoren-2-yl)-N-phenylamino]biphenyl (abbreviation; DFLDPBi), and 4,4'-bis[N-(spiro-9,9'-bifluoren-2-yl)-N-phenylamino]biphenyl (abbreviation: BSPB) can be used. The materials described here are mainly substances having a hole mobility of $10^{-6}$ cm$^2$/Vs or more. In addition to these, any substance that has a hole-transporting property higher than an electron-transporting property can be used. Note that the layer containing a substance with a high hole-transporting property is not limited to a single layer, and two or more layers containing the aforementioned substances may be stacked.

Furthermore, for the hole-transporting layer 112, a composite material in which an acceptor substance is contained in the above-mentioned substance having a high hole-transporting property can be used.

Alternatively, for the hole-transporting layer 112, a high molecular compound such as PVK, PVTPA, PTPDMA, or Poly-TPD can be used.

The light-emitting layer 113 is a layer including a substance having a high light-emitting property, and various materials can be used for the light-emitting layer 113. As the substance with a high light-emitting property, for example, a fluorescent compound which emits fluorescence or a phosphorescent compound which emits phosphorescence can be used.

Examples of a phosphorescent compound which is used for the light-emitting layer are organometallic complexes given below. As a material for blue light emission, bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$]iridium(III)picolinate (abbreviation: FIrpic), bis[2-(3',5'bistrifluoromethylphenyl)pyridinato-N,C$^{2'}$]iridium(III)picolinate (abbreviation: Ir(CF$_3$ppy)$_2$(pic)), bis[2-(4',6'-difluorophenyl)pyridinato-N,C$^{2'}$]iridium(III)acetylacetonate (abbreviation: FIr(acac)) or the like can be given. As a green light-emitting material, the following can be given: tris(2-phenylpyridinato-N,C$^{2'}$)iridium(III) (abbreviation: Ir(ppy)$_3$); bis(2-phenylpyridinato-N,C$^{2'}$)iridium(III)acetylacetonate (abbreviation: Ir(ppy)$_2$(acac)); bis(1,2-diphenyl-1H-benzimidazolato)iridium(III)acetylacetonate (abbreviation: Ir(pbi)$_2$(acac)); bis(benzo[h]quinolinato)iridium(II)acetylacetonate (abbreviation: Ir(bzq)$_2$(acac)); and the like. As a yellow light-emitting material, the following can be given: bis(2,4-diphenyl-1,3-oxazolato-N,C$^{2'}$)iridium(II)acetylacetonate (abbreviation: Ir(dpo)$_2$(acac)); bis[2-(4'-perfluorophenylphenyl)pyridinato]iridium(II)acetylacetonate (abbreviation: Ir(p-PF-ph)$_2$(acac)); bis(2-phenylbenzothiazolato-N,C$^{2'}$)iridium(III)acetylacetonate (abbreviation: Ir(bt)$_2$(acac)); and the like. As an orange light-emitting material, the following can be given: tris(2-phenylquinolinato-N,C$^{2'}$)iridium(III) (abbreviation: Ir(pq)$_3$); bis(2-phenylquinolinato-N,C$^{2'}$)iridium(III)acetylacetonate (abbreviation: Ir(pq)$_2$(acac)); and the like. As a red light-emitting material, bis[2-(2'-benzo[4,5-α]thienyl)pyridinato-N,C$^{3'}$)iridium(III)acetylacetonate (abbreviation: Ir(btp)$_2$(acac)); bis(1-phenylisoquinolinato-N,C$^{2'}$)iridium(III)acetylacetonate (abbreviation: Ir(piq)$_2$(acac)); (acetylacetonato)bis[2,3-bis(4-fluorophenyl)quinoxalinato]iridium(III) (abbreviation: Ir(Fdpq)$_2$(acac)); 2,3,7,8,12,13,17,18-octaethyl-21H,23H-porphyrinplatinum(II) (abbreviation: PtOEP); and the like are given. In addition, a rare-earth metal complex such as tris(acetylacetonato)(monophenanthroline)terbium(III) (abbreviation: Tb(acac)$_3$(Phen)); tris(1,3-diphenyl-1,3-propanedionato)(monophenanthroline)europium(III) (abbreviation: Eu(DBM)$_3$(Phen)); or tris[1-(2-thenoyl)-3,3,3-trifluoroacetonato](monophenanthroline)europium(III) (abbreviation: Eu(TTA)$_3$(Phen)) performs light emission (electron transition between different multiplicities) from a rare-earth metal ion; therefore, such a rare-earth metal complex can be used as the phosphorescent compound.

Examples of fluorescent compounds that can be used for the light-emitting layer are given below. Examples of materials for blue light emission are as follows: N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA); N,9-diphenyl-N-[4-(10-phenyl-9-anthryl)phenyl]-9H-carbazol-3-amine (abbreviation: PCAPA); perylene; 2,5,8,11-tetra-tert-butylperylene (abbreviation: TBP); 4-(10-phenyl-9-anthryl)-4'-(9-phenyl-9H-carbazol-3-yl)triphenylamine (abbreviation: PCBAPA); and the like. In addition, as a light-emitting material which exhibits green light emission, the following can be used: N-(9,10-diphenyl-2-anthryl)-N,9-diphenyl-9H-carbazol-3-amine (abbreviation: 2PCAPA); N-[9,10-bis(1,1'-biphenyl-2-yl)-2-anthryl]-N,9-diphenyl-9H-carbazol-3-amine (abbreviation: 2PCABPhA); N-(9,10-diphenyl-2-anthryl)-N,N',N'-triphenyl-1,4-phenylenediamine (abbreviation: 2DPAPA); N-[9,10-bis(1,1'-biphenyl-2-yl)-2-anthryl]-N,N',N'-triphenyl-1,4-phenylenediamine (abbreviation: 2DPABPhA); N-[9,10-bis(1,1'-biphenyl-2-yl)]-N-[4-(9H-carbazol-9-yl)phenyl]-N-phenylanthracen-2-amine (abbreviation: 2YGABPhA); N,N,9-triphenylanthracen-9-amine (abbreviation: DPhAPhA); and the like. As a light-emitting material emission of yellow light, rubrene, 5,12-bis(1,1'-biphenyl-4-yl)-6,11-diphenyltetracene (abbreviation: BPT), and the like are given. As a light-emitting material exhibiting emission of red light, N,N,N',N'-tetrakis(4-methylphenyl)tetracene-5,11-diamine (abbreviation: p-mPhTD), 7,13-diphenyl-N,N,N',N'-tetrakis(4-methylphenyl)acenaphtho[1,2-a]fluoranthene-3,10-diamine (abbreviation: p-mPhAFD), and the like are given.

Note that the light-emitting layer may have a structure in which any of the above substances having a high light-emitting property (guest material) is dispersed into another substance (host material). As a substance in which the substance with a light-emitting property is dispersed, various kinds of substances can be used, and it is preferable to use a substance whose lowest unoccupied molecular orbital (LUMO) level is higher than that of the substance with a light-emitting property and whose highest occupied molecular orbital (HOMO) level is lower than that of the substance with a light-emitting property.

As the substance in which the substance having a light-emitting property is dispersed, specifically, a metal complex such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation:

ZnPBO), or bis[2-(2-benzothiazolyl)phenolato]zinc(II) (abbreviation: ZnBTZ); a heterocyclic compound such as 2-(4-biphenylyl)-5-(4-tert-butylphenyl)-1,3,4-oxadiazole (abbreviation: PBD), 1,3-bis[5-[(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2"-(1,3,5-benzenetriyl)tris(1-phenyl-1H-benzimidazole) (abbreviation: TPBI), bathophenanthroline (abbreviation: BPhen), or bathocuproine (BCP); a condensed aromatic compound such as 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3"-(benzene-1,3,5-triyl)tripyrene (abbreviation: TPB3), 9,10-diphenylanthracene (abbreviation: DPAnth), or 6,12-dimethoxy-5,11-diphenylchrysene; an aromatic amine compound such as N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPHPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N-(9,10-diphenyl-2-anthryl)-N,9-diphenyl-9H-carbazol-3-amine (abbreviation: 2PCAPA), NPB (or α-NPD), TPD, DFLDPBi, or BSPB; or the like can be used.

As a substance in which the substance with a light-emitting property is dispersed, a plurality of kinds of substances can be used. For example, in order to suppress crystallization, a substance such as rubrene which suppresses crystallization, may be further added. In addition, NPB, Alq, or the like may be further added in order to transfer energy to the substance with a light-emitting property more efficiently.

When the light-emitting layer 113 has a structure in which the substance having a high light-emitting property is dispersed into another substance, crystallization of the light-emitting layer 113 can be suppressed. Further, concentration quenching due to high concentration of the substance having a high light-emitting property can be suppressed.

Note that for the light-emitting layer 113, a high molecular compound can be used. Specifically, as a light-emitting material which exhibits blue light emission, the following can be used: poly(9,9-dioctylfluorene-2,7-diyl) (abbreviation: PFO), poly[(9,9-dioctylfluorene-2,7-diyl-co-(2,5-dimethoxybenzene-1,4-diyl)] (abbreviation: PF-DMOP), poly{(9,9-dioctylfluorene-2,7-diyl)-co-[N,N'-di-(p-butylphenyl)-1,4-diaminobenzene]} (abbreviation: TAB-PFH), and the like. As a light-emitting material that exhibits emission of green light, poly(p-phenylenevinylene) (abbreviation: PPV), poly[(9,9-dihexylfluorene-2,7-diyl)-alt-co-(benzo[2,1,3]thiadiazol-4,7-diyl)] (abbreviation: PFBT), poly[(9,9-dioctyl-2,7-divinylenfluorenylene)-alt-co-(2-methoxy-5-(2-ethylhexyloxy)-1,4-phenylene)], or the like can be given. As a light-emitting material which exhibits orange to red light emission, the following can be used: poly[2-methoxy-5-(2'-ethylhexoxy)-1,4-phenylenevinylene] (abbreviation: MEH-PPV), poly(3-butylthiophene-2,5-diyl) (abbreviation: R4-PAT), poly {[9,9-dihexyl-2,7-bis(1-cyanovinylene)fluorenylene]-alt-co-[2,5-bis(N,N'-diphenyl amino)-1,4-phenylene]}, poly{[2-methoxy-5-(2-ethylhexyloxy)-1,4-bis(1-cyanovinylenephenylene)]-alt-co-[2,5-bis(N,N'-diphenylamino)-1,4-phenylene]} (abbreviation: CN-PPV-DPD), and the like.

The electron-transporting layer 114 is a layer containing a substance with a high electron-transporting property. The benzoxazole derivative described in Embodiment 1 has an excellent electron-transporting property and thus can be used for the electron-transporting layer 114. In particular, a benzoxazole derivative in which Het in the general formula (G1) is any one of 2-pyridyl, 4-pyridyl, pyrimidin-2-yl, and pyrimidin-4-yl has an excellent electron-transporting property, and thus can be suitably used for the electron-transporting layer. Note that the electron-transporting layer is not limited to a single layer, and may be a stack of two or more layers.

In a case where the electron-transporting layer has a stacked structure of two or more layers, as another material having a high electron-transporting property, for example, as a low molecular organic compound, a metal complex such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), or bis[2-(2-benzothiazolyl)phenolato]zinc(II) (abbreviation: ZnBTZ), can be used. Further, the following heterocyclic compounds can be also used: 2-(4-biphenylyl)-5-(4-tert-butylphenyl)-1,3,4-oxadiazole (abbreviation: PBD); 1,3-bis[5-(p-tert-butylphenyl)-1,3,4-oxadiazol-2-yl]benzene (abbreviation: OXD-7); 3-(4-biphenylyl)-4-phenyl-5-(4-tert-butylphenyl)-1,2,4-triazole (abbreviation: TAZ); 2,2',2"-(1,3,5-benzenetriyl)-tris(1-phenyl-1H-benzimidazole) (abbreviation: TPBI); bathophenanthroline (abbreviation: BPhen); bathocuproine (abbreviation: BCP); and the like. The materials described here are mainly materials having an electron mobility of $10^{-6}$ cm$^2$/Vs or more. In addition, other than the above substances, any substance that has an electron-transporting property higher than a hole-transporting property can be used. Further, the electron-transporting layer may be formed by not only a single layer but also a stacked structure in which two or more layers made from the above mentioned substances are stacked.

In the case where the electron-transporting layer has a stacked structure of two or more layers, an example of another substance having a high electron-transporting property is a high molecular compound. For example, poly[(9,9-dihexylfluorene-2,7-diyl)-co-(pyridine-3,5-diyl)] (abbreviation: PF-Py), poly[(9,9-dioctylfluorene-2,7-diyl)-co-(2,2'-bipyridine-6,6'-diyl)] (abbreviation: PF-BPy), and the like can be used.

The electron-injecting layer 115 is a layer including a substance having a high electron-injecting property. As the substance with a high electron-injecting property, an alkali metal, an alkaline-earth metal or a compound thereof such as lithium (Li), magnesium (g), lithium fluoride (LiF), cesium fluoride (CsF), cesium fluoride (CsF), or calcium fluoride (CaF$_2$) can be used. For example, a layer of a substance having an electron-transporting property to which an alkali metal, an alkaline earth metal, or a compound thereof is mixed, such as a layer of Alq to which magnesium (Mg) is added, may be used. With the use of a layer of a substance with an electron-transporting property to which an alkali metal or an alkaline earth metal is added, as the electron-injecting layer, electron injection from the second electrode 104 is performed efficiently, which is preferable.

As a substance for forming the second electrode 104, a metal, an alloy, an electrically conductive compound, a mixture thereof, or the like with a low work function (specifically, a work function of 3.8 eV or lower is preferable) can be used. As a specific example of such a cathode material, an element belonging to Group 1 or 2 in the periodic table, that is, an alkali metal such as lithium (Li) or cesium (Cs); an alkaline earth metal such as magnesium (Mg), calcium (Ca), or strontium (Sr); an alloy containing the element belonging to Group 1 or 2 (MgAg, AlLi); a rare-earth metal such as europium (Eu) or ytterbium (Yb); an alloy thereof; or the like can be used. A film of an alkali metal, an alkaline earth metal, or an alloy including these can be formed by vacuum evaporation. In addition, an alloy including an alkali metal or an alkaline earth metal can be formed by a sputtering method. Further, silver paste or the like can be formed by an inkjet method.

In the case where the electron-injecting layer 115 which is a layer functioning to promote electron injection is provided between the second electrode 104 and the electron-transporting layer 114, the second electrode 104 can be formed using various conductive materials such as Al, Ag, ITO, and indium tin oxide containing silicon or silicon oxide, regardless of their work functions. These conductive materials can be formed by a method such as sputtering, inkjet or spin coating.

As a formation method of the EL layer, various methods can be used regardless of a dry method or a wet method. For example, a vacuum evaporation method, an inkjet method, a spin coat method, or the like may be used. Film formation methods for the electrodes or the layers may be different.

For example, the EL layer may be formed by a wet method using a high molecular compound selected from the above-described materials. Further, the EL layer can also be formed by a wet method using a low molecular organic compound. Furthermore, the EL layer may be formed by a dry method such as vacuum evaporation using a low molecular organic compound.

The electrode may be formed by a wet method using sol-gel method, or by a wet method using a paste of a metal material. Further, the electrode may be formed by a dry method such as sputtering or vacuum evaporation.

For example, in the case where a light-emitting element of the present invention is applied to a display device and the display device is manufactured using a large-sized substrate, it is preferable to form the light-emitting layer by a wet method. When the light-emitting layer is formed by an inkjet method, it becomes easy to form the light-emitting layers separately for different colors even when a large-sized substrate is used.

The light-emitting element of the present invention that has the structure as described above emits light when a current flows due to a potential difference generated between the first electrode 102 and the second electrode 104 and holes and electrons are recombined in the EL layer 103.

The emitted light is extracted outside through one or both of the first electrode 102 and the second electrode 104. Therefore, one or both of the first electrode 102 and the second electrode 104 have a light-transmitting property. For example, when only the first electrode 102 has a light-transmitting property, light emission is extracted from the substrate side through the first electrode 102. Meanwhile, when only the second electrode 104 has a light-transmitting property, light emission is extracted from the side opposite to the substrate side through the second electrode 104. In a case where each of the first electrode 102 and the second electrode 104 has a light transmitting property, light emission is extracted from both of the substrate side and the side opposite to the substrate through the first electrode 102 and the second electrode 104.

The structure of the layers provided between the first electrode 102 and the second electrode 104 is not limited to the aforementioned one. Any structure other than the above structure can be employed as long as a light-emitting region for recombination of holes and electrons is positioned away from the first electrode 102 and the second electrode 104 so as to prevent quenching caused by proximity of the light-emitting region to metal, and any of the benzoxazole derivatives shown in Embodiment 1 is provided.

That is, there is no particular limitation on the stacked structure of the layers, and any of the benzoxazole derivatives shown in Embodiment 1 may be combined as appropriate with a layer containing a substance with a high electron-transporting property, a substance with a high hole-transporting property, a substance with a high electron-injecting property, a substance with a high hole-injecting property, a bipolar substance (a substance with a high electron and hole-transporting property), and/or the like.

Figure 2:
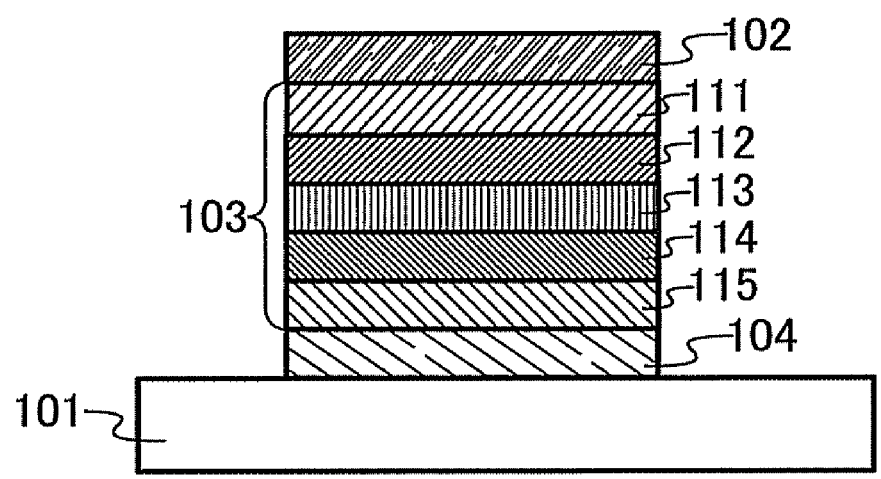
FIG. 2 illustrates a light-emitting element according to an embodiment of the present invention.

In addition, as illustrated in FIG. 2, a structure may be employed in which the second electrode 104 serving as a cathode, the EL layer 103, and the first electrode 102 serving as an anode are stacked sequentially over the substrate 101. In FIG. 2, a structure is employed in which the electron-injecting layer 115, the electron-transporting layer 114, the light-emitting layer 113, the hole-transporting layer 112, and the hole-injecting layer 111 are stacked sequentially over the second electrode 104.

In this embodiment, the light-emitting element is formed over a substrate made of glass, plastic, or the like. By forming a plurality of such light-emitting elements over a substrate, a passive matrix light-emitting device can be manufactured. Alternatively, for example, a thin film transistor (TFT) may be formed over a substrate made of glass, plastic, or the like, and a light-emitting element may be formed over an electrode that is electrically connected to the TFT. Thus, an active matrix light-emitting device which controls the driving of a light-emitting element by a TFT can be manufactured. A structure of the TFT is not particularly limited. The TFT may be either of staggered type or inverted staggered type. In addition, a driver circuit provided for a TFT substrate may include both N-type and P-type TFTs, or using either N-type or P-type TFTs. In addition, the crystallinity of a semiconductor film used for the TFT is not particularly limited. Either an amorphous semiconductor film or a crystalline semiconductor film may be used. Further, a single crystalline semiconductor film may be used. The single crystalline semiconductor film can be formed by a Smart Cut (registered trademark) method or the like.

Each of the benzoxazole derivatives described in Embodiment 1 has an electron-accepting property and thus has an excellent electron-injecting property. Thus, by using such a benzoxazole derivative as an electron-transporting material of a light-emitting element, in particular, for an electron-transporting layer, the light-emitting element can have low driving voltage. In addition, a light-emitting element with low power consumption can be obtained. In particular, a benzoxazole derivative in which Het in the general formula (G1) is any one of 2-pyridyl, 4-pyridyl, pyrimidin-2-yl, and pyrimidin-4-yl has an excellent electron-transporting property, and thus can be suitably used for the electron-transporting layer.

Many light-emitting elements that use an organic compound have excessive holes, when they are driven. Accordingly, in order to improve emission efficiency, it is important to supply more electrons by using a material having an excellent electron-transporting property. The benzoxazole derivatives described in Embodiment 1 are excellent in an electron-transporting property; accordingly, by using any of the benzoxazole derivatives for a light-emitting element, carrier balance can be improved, whereby emission efficiency can be improved.

Note that this embodiment can be combined with any of the other embodiments as appropriate.

Embodiment 3

In Embodiment 3, a structure in which any of the benzoxazole derivatives shown in Embodiment 1 is used for a light-emitting layer is described as one mode of a light-emitting element of the present invention.

Because the benzoxazole derivatives shown in Embodiment 1 have an excellent electron-transporting property, the benzoxazole derivatives can each be used as a host material in a light-emitting layer having a structure in which a substance with a high light-emitting property (guest material) is dispersed in another substance (host material).

In a case where the benzoxazole derivative shown in Embodiment 1 is used as a host material and where a guest material emits fluorescence, it is preferable to use, as a guest material, a substance whose lowest unoccupied molecular orbital (LUMO) level is lower and whose highest occupied molecular orbital (HOMO) level is higher than that of the benzoxazole derivatives shown in Embodiment 1. Examples of materials for blue light emission are as follows: N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), and the like. In addition, as a light-emitting material which exhibits green light emission, the following can be used: N-(9,10-diphenyl-2-anthryl)-N,9-diphenyl-9H-carbazol-3-amine (abbreviation: 2PCAPA); N-[9,10-bis(1,1'-biphenyl-2-yl)-2-anthryl]-N,9-diphenyl-9H-carbazol-3-amine (abbreviation: 2PCABPhA); N-(9,10-diphenyl-2-anthryl)-N,N',N'-triphenyl-1,4-phenylenediamine abbreviation: 2DPAPA); N-[9,10-bis(1,1'-biphenyl-2-yl)-2-anthryl]-N,N',N'-triphenyl-1,4-phenylenediamine (abbreviation: 2DPABPhA); N-[9,10-bis(1,1'-biphenyl-2-yl)]-N-[4-(9H-carbazol-9-yl)phenyl]-N-phenylanthracen-2-amine (abbreviation: 2YGABPhA); N,N,9-triphenylanthracen-9-amine (abbreviation: DPhAPhA); and the like. As a light-emitting material emission of yellow light, rubrene, 5,12-bis(1,1'-biphenyl-4-yl)-6,11-diphenyltetracene (abbreviation: BPT), and the like are given. As a light-emitting material exhibiting emission of red light, N,N,N',N'-tetrakis(4-methylphenyl)tetracene-5,11-diamine (abbreviation: p-mPhTD), 7,13-diphenyl-N,N,N',N'-tetrakis(4-methylphenyl)acenaphtho[1,2-a]fluoranthene-3,10-diamine (abbreviation: p-mPhAFD), and the like are given.

Alternatively, in the case where the benzoxazole derivative shown in Embodiment 1 is used as a host material and where a guest material emits phosphorescence, it is preferable to use, as a guest material, a substance having lower triplet excitation energy than the benzoxazole derivatives shown in Embodiment 1. Examples include organometallic complexes such as bis[2-(2'-benzo[4,5-α]thienyl)pyridinato-N,$C^{3'}$]iridium(III) acetylacetonate (abbreviation: Ir(btp)$_2$(acac)), bis(1-phenylisoquinolinato-N,$C^{2'}$)iridium(III) acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), and 2,3,7,8,12,13,17,18-octaethyl-21H,23H-porphyrin platinum(II) (abbreviation: PtOEP).

Because the benzoxazole derivatives shown in Embodiment 1 have an electron-transporting property, by using any of the benzoxazole derivatives for a light-emitting layer, the light-emitting layer can have a high electron-transporting property. Such a light-emitting layer can provide light emission with high efficiency when a guest material with high electron-trapping property is used.

As the substance (host material) into which the substance having a light-emitting property (guest material) is dispersed, a plurality of kinds of substances can be used. Therefore, the light-emitting layer may contain a second host material in addition to any of the benzoxazole derivatives shown in Embodiment 1. Since the benzoxazole derivative shown in Embodiment 1 has an excellent electron-transporting property, it is preferable to use a material having an excellent hole-transporting property as the second host material. With such a structure, the light-emitting layer has a hole-transporting property and an electron-transporting property, and the recombination probability of holes and electrons in the light-emitting layer is increased, so that light emission with high efficiency can be obtained. Further, a light-emitting element with low driving voltage can be obtained.

Note that this embodiment can be combined with any of the other embodiments as appropriate.

Embodiment 4

In Embodiment 4, a structure in which any of the benzoxazole derivatives shown in Embodiment 1 is used for an electron-injecting layer is described as one mode of a light-emitting element of the present invention.

Since any of the benzoxazole derivatives shown in Embodiment 1 has an excellent electron-injecting property, the benzoxazole derivatives can be used for an electron-injecting layer of a light-emitting element. In the case where any of the benzoxazole derivatives shown in Embodiment 1 is used for an electron-injecting layer, an alkali metal, an alkaline earth metal such as lithium or magnesium, or a compound thereof is preferably added, in addition to the benzoxazole derivatives shown in Embodiment 1. With such a structure, an electron-injecting property from an electrode serving as a cathode is increased, and a light-emitting element with low driving voltage can be obtained.

Note that this embodiment can be combined with any of the other embodiments as appropriate.

Embodiment 5

In Embodiment 5, an embodiment of a light-emitting element having a structure in which a plurality of light-emitting units according to the present invention is stacked (hereinafter, referred to as a stack-type element) will be described with reference to FIG. 3. This light-emitting element is a stacked-type element including a plurality of light-emitting units between a first electrode and a second electrode. The structure of each light-emitting unit can be similar to any of the structures described in Embodiments 2 to 4. In other words, the light-emitting element described in Embodiment 2 is a light-emitting element having one light-emitting unit. In this embodiment, a light-emitting element having a plurality of light-emitting units will be described.

Figure 3:
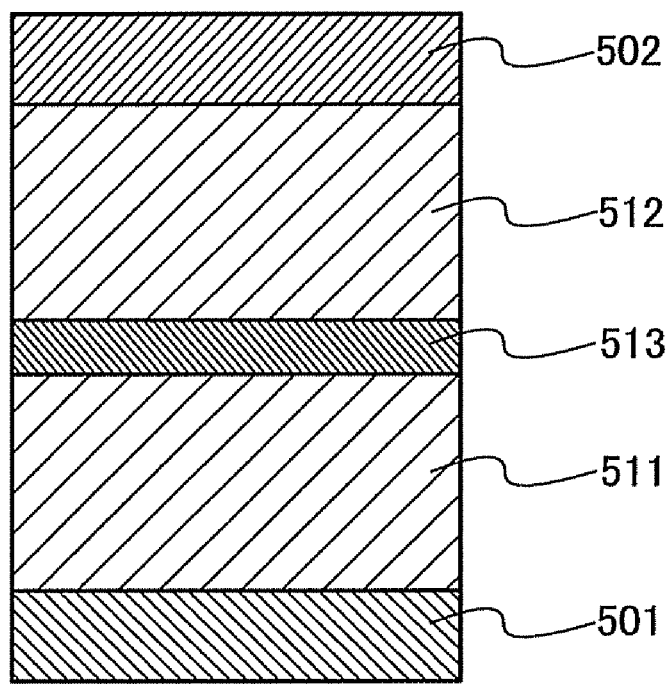
FIG. 3 illustrates a light-emitting element according to an embodiment of the present invention.

In FIG. 3, a first light-emitting unit 511 and a second light-emitting unit 512 are stacked between a first electrode 501 and a second electrode 502. The first electrode 501 and the second electrode 502 may be similar to the electrodes described in Embodiment 1. In addition, the first light-emitting unit 511 and the second light-emitting unit 512 may have the same structure or different structures. Structures of the first light-emitting unit 511 and the second light-emitting unit 512 may be similar to any of the structures described in Embodiments 2 to 4.

A charge-generating layer 513 is a layer which injects electrons into one light-emitting unit and injects holes into the other light-emitting unit when voltage is applied to the first electrode 501 and the second electrode 502, and may have either a single-layer structure or a stacked structure of plural layers. As a stacked structure of plural layers, a structure in which a hole-injecting layer and an electron-injecting layer are stacked is preferable.

As the hole-injecting layer, a semiconductor or an insulator, such as molybdenum oxide, vanadium oxide, rhenium oxide, or ruthenium oxide, can be used. Alternatively, the hole-injecting layer may have a structure in which an acceptor substance is added to a substance having a high hole-transporting property. The layer including a substance having a high hole-transporting property and an acceptor substance is formed of the composite material described in Embodiment 2 and includes, as an acceptor substance, 7,7,8,8-tetracyano-2,3,5,6-tetrafluoroquinodimethane (abbreviation: $F_4$-TCNQ) or metal oxide such as vanadium oxide, molybdenum oxide, or tungsten oxide. As the substance having a high hole-transporting property, various compounds such as an aromatic amine compound, a carbazole derivative, aromatic hydrocarbon, a high-molecular compound, oligomer, dendrimer, polymer, and the like can be used. Note that a substance having a hole mobility of $10^{-6}$ cm$^2$/Vs or higher is preferably employed as the substance having a high hole-transporting property. It is to be noted that any substance that has a higher hole-transporting property than an electron-transporting property may be used other than the above substances. Since the composite material of the substance having a high hole-transporting property and the acceptor substance is excellent in a carrier-injecting property and a carrier-transporting property, low-voltage driving and low-current driving can be realized.

As the electron-injecting layer, an insulator or a semiconductor, such as lithium oxide, lithium fluoride, or cesium carbonate, can be used. Alternatively, the electron-injecting layer may have a structure in which a donor substance is added to a substance having a high electron-transporting property. As the donor substance, an alkali metal, an alkaline-earth metal, a rare-earth metal, a metal that belongs to Group 13 of the periodic table, or an oxide or carbonate thereof may be used. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the donor substance. As the substance having a high electron-transporting property, the materials described in Embodiment 2 may be used. Note that a substance having an electron mobility of $10^{-6}$ cm$^2$/Vs or higher is preferably employed as the substance having a high electron-transporting property. It is to be noted that any substance that has a higher electron-transporting property than a hole-transporting property may be used other than the above substances. Since the composite material of the substance having a high electron-transporting property and the donor substance is excellent in a carrier-injecting property and a carrier-transporting property, low-voltage driving and low-current driving can be realized.

Further, the electrode materials described in Embodiment 2 can be used for the charge-generating layer 513. For example, the charge-generating layer 513 may be formed by combining a layer including a substance having a high hole-transporting property and metal oxide with a transparent conductive film. It is preferable that the charge-generating layer be a highly light-transmitting layer in view of light extraction efficiency.

In any cases, the charge-generating layer 513 interposed between the first light-emitting unit 511 and the second light-emitting unit 512 may have any structure as long as electrons are injected to one light-emitting unit and holes are injected to the other light-emitting unit when voltage is applied to the first electrode 501 and the second electrode 502. For example, any structure is acceptable for the charge-generating layer 513 as long as the layer 513 injects electrons and holes into the first light-emitting unit 511 and the second light-emitting unit 512, respectively, when a voltage is applied so that the potential of the first electrode is higher than the potential of the second electrode.

Although the light-emitting element having two light-emitting units is described in this embodiment, a light-emitting element in which three or more light-emitting units are stacked can be employed similarly. By arranging a plurality of light-emitting units between a pair of electrodes so as to be partitioned by a charge-generating layer as in the light-emitting element of this embodiment, the element can perform light emission in a high luminance region while keeping a current density low; whereby the element can have long life. In the case where the light-emitting element is applied to a lighting device, voltage drop due to resistance of an electrode material can be reduced. Accordingly, uniform emission in a large area is possible. Furthermore, a light-emitting device of low power consumption, which can be driven at low voltage, can be realized.

When light-emitting units have different emission colors, light emission with desired color can be obtained as a whole light-emitting element. For example, in the light-emitting element having two light-emitting units, when emission color of the first light-emitting unit and emission color of the second light-emitting unit are complementary colors, a light-emitting element emitting white light as a whole light-emitting element can be obtained. Note that the "complementary color" means a relation between colors which becomes an achromatic color when they are mixed. That is, white light emission can be obtained by mixture of light obtained from substances emitting the lights of complementary colors. Also in a light-emitting element including three light-emitting units, white light emission can be similarly obtained as a whole light-emitting element in the case where emission color of the first light-emitting unit is red, emission color of the second light-emitting unit is green, and emission color of the third light-emitting unit is blue, for example.

Note that this embodiment can be combined with any of the other embodiments as appropriate.

Embodiment 6

In Embodiment 6, an embodiment of a light-emitting device including a light-emitting element according to the present invention will be described.

Figure 4A:
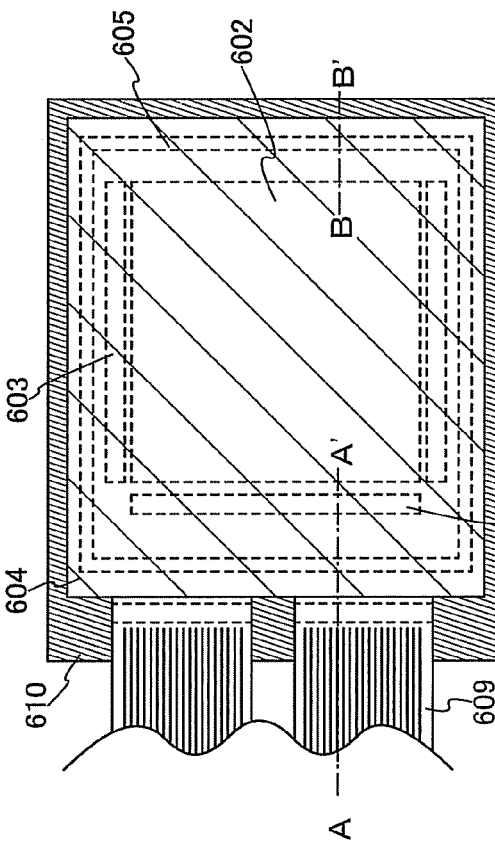
FIGS. 4A and 4B illustrate a light-emitting device according to an embodiment of the present invention.
Figure 4B:
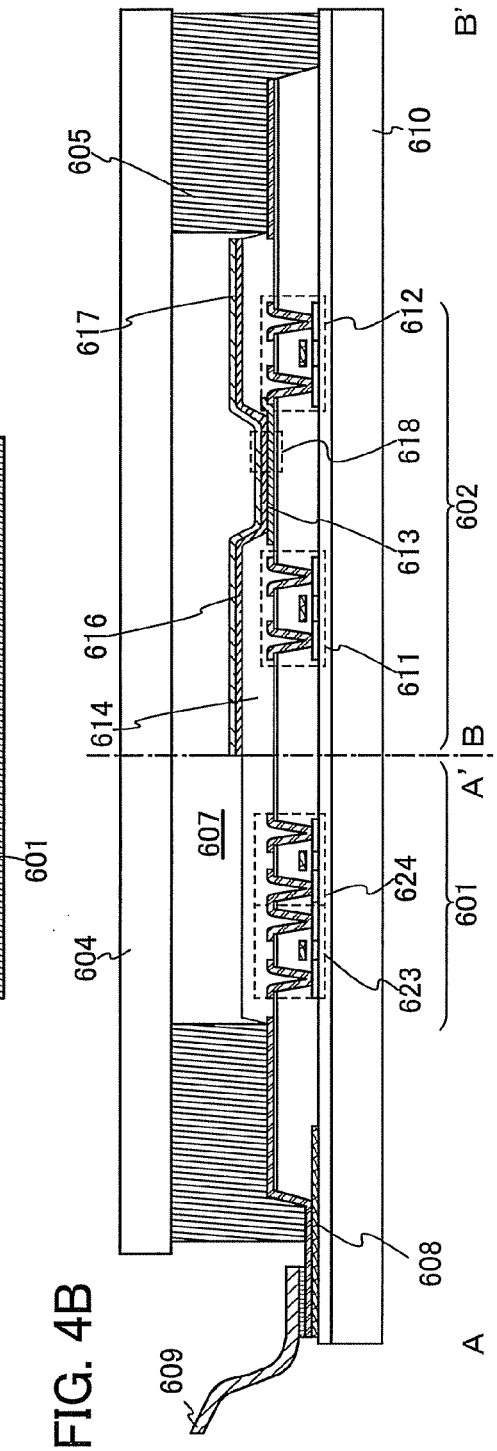

In this embodiment, a light-emitting device which has a light-emitting element according to the present invention in a pixel portion will be described with reference to FIGS. 4A and 4B. FIG. 4A is a top view of the light-emitting device, and FIG. 4B is a cross-sectional view taken along A-A' and B-B' in FIG. 4A. This light-emitting device includes a driver circuit portion (source side driver circuit) 601, a pixel portion 602, and a driver circuit portion (gate side driver circuit) 603, which are indicated by dotted lines, for controlling light emission from the light-emitting element. Also, a reference numeral 604 represents a sealing substrate, a reference numeral 605 represents a sealant, and the inside that is surrounded by the sealant 605 is a space 607.

A lead wiring 608 is used to transmit signals to be inputted to the source side driver circuit 601 and the gate side driver circuit 603 and receives a video signal, a clock signal, a start signal, a reset signal, and the like from a flexible printed circuit (FPC) 609 which is an external input terminal. Although only the FPC is illustrated here, this FPC may be provided with a printed wiring board (PWB). The light-emitting device in this specification includes not only a main body of a light-emitting device but also a light-emitting device with an FPC or a PWB attached thereto.

Next, a sectional structure of the light-emitting device will be described with reference to FIG. 4B. Although the driver circuit portion and the pixel portion are formed over an element substrate 610, FIG. 4B illustrates the source side driver circuit 601, which is one of the driver circuit portions, and one pixel in the pixel portion 602.

The source side driver circuit 601 includes a CMOS circuit formed by combining an N-channel TFT 623 and a P-channel TFT 624. Alternatively, the driver circuit may be formed with various CMOS circuits, PMOS circuits, or NMOS circuits. In this embodiment, a driver-integrated type in which a driver circuit is formed over a substrate provided with a pixel portion is described; however, the present invention is not limited to this type, and the driver circuit can be formed outside the substrate.

The pixel portion 602 is formed of a plurality of pixels each of which includes a switching TFT 611, a current control TFT 612, and a first electrode 613 which is electrically connected to a drain of the current control TFT 612. Note that an insulator 614 is formed so as to cover an end portion of the first electrode 613. Here, the insulator 614 is formed using a positive photosensitive acrylic resin film.

In order to improve the coverage, the insulator 614 is formed to have a curved surface with curvature at its upper or lower end portion. For example, in the case of using positive photosensitive acrylic as a material of the insulator 614, it is preferable that the insulator 614 be formed so as to have a curved surface with a curvature radius (0.2 µm to 3 µm) only at its upper end portion. The insulator 614 can be formed using either a negative type which becomes insoluble in an etchant by light irradiation or a positive type which becomes soluble in an etchant by light irradiation.

An EL layer 616 and a second electrode 617 are formed over the first electrode 613. Here, the first electrode 613 can be formed using any of various metals, alloys, electrically conductive compounds, and mixtures thereof. If the first electrode is used as an anode, it is preferable to use, among those materials, a metal, an alloy, an electrically conductive compound, a mixture thereof, or the like with a high work function (preferably, a work function of 4.0 eV or higher). For example, the first electrode 613 can be formed using a single-layer film of an indium tin oxide film containing silicon, an indium zinc oxide film, a titanium nitride film, a chromium film, a tungsten film, a Zn film, a Pt film, or the like; or a stacked film such as a stack of a titanium nitride film and a film containing aluminum as its main component or a three-layer structure of a titanium nitride film, a film containing aluminum as its main component, and a titanium nitride film. When the first electrode 613 has a stacked structure, the first electrode 613 can have a resistance low enough to serve as a wiring, giving a good ohmic contact, and can function as an anode.

The EL layer 616 is formed by various methods such as an evaporation method using an evaporation mask, an inkjet method, and a spin coating method. The EL layer 616 includes any of the benzoxazole derivatives described in Embodiment 1. Any of low molecular compounds, high molecular compounds, oligomers, and dendrimers may be employed as a material used for the EL layer 616. As the material for the EL layer, not only an organic compound but also an inorganic compound may be used.

As a material used for the second electrode 617, any of various metals, alloys, electrically conductive compounds, and mixtures thereof can be used. If the second electrode is used as a cathode, it is preferable that the second electrode is formed using a metal, an alloy, an electrically conductive compound, a mixture thereof, or the like with a low work function (preferably, a work function of 3.8 eV or lower) among such materials. For example, an element belonging to Group 1 or Group 2 of the periodic table, that is, an alkali metal such as lithium (Li) or cesium (Cs), an alkaline-earth metal such as magnesium (Mg), calcium (Ca), or strontium (Sr), an alloy containing these (e.g., MgAg, AlLi), and the like can be given. If light generated in the EL layer 616 is transmitted through the second electrode 617, the second electrode 617 can be formed using a stack of a metal thin film and a transparent conductive film (indium tin oxide (ITO), indium tin oxide containing silicon or silicon oxide, indium zinc oxide (IZO), indium oxide containing tungsten oxide and zinc oxide (IWZO), or the like).

The sealing substrate 604 is attached using the sealant 605 to the element substrate 610; thus, a light-emitting element 618 is provided in the space 607 surrounded by the element substrate 610, the sealing substrate 604, and the sealant 605. The space 607 is filled with a filler. There are cases where the space 607 may be filled with an inert gas (such as nitrogen or argon), or where the space 607 may be filled with the sealant 605.

An epoxy based resin is preferably used for the sealant 605. In addition, it is desirable to use a material that allows permeation of moisture or oxygen as little as possible. As the sealing substrate 604, a plastic substrate formed of FRP (fiberglass-reinforced plastics), PVF (polyvinyl fluoride), polyester, acrylic, or the like can be used other than a glass substrate or a quartz substrate.

As thus described, a light-emitting device having a light-emitting element of the present invention can be obtained.

A light-emitting device of the present invention includes any of the light-emitting elements described in Embodiments 2 to 5. The light-emitting elements described in Embodiments 2 to 5 each have low driving voltage; therefore, a light-emitting device with low power consumption can be obtained.

Figure 5A:
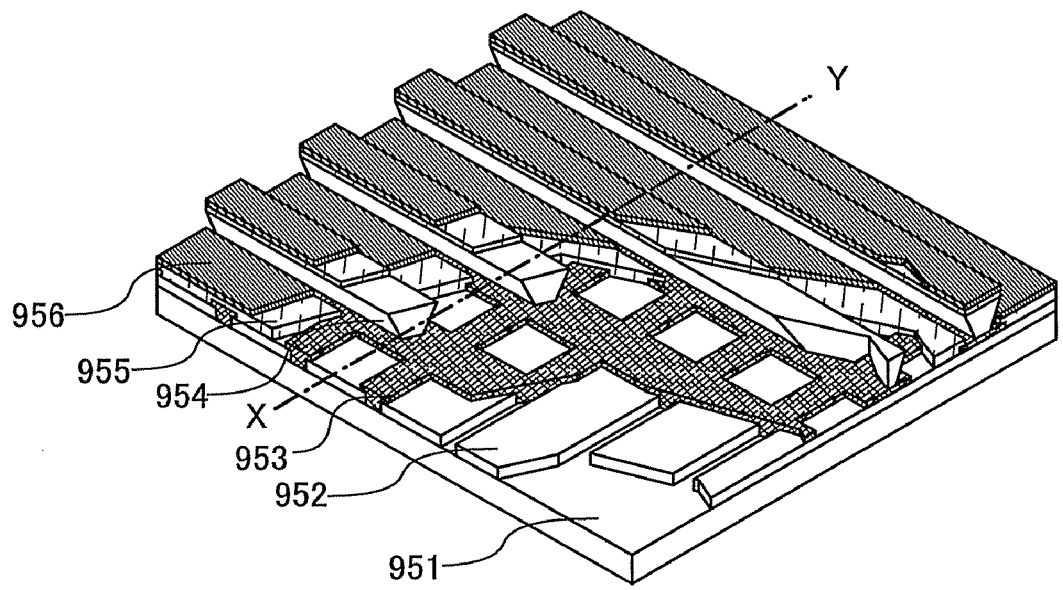
FIGS. 5A and 5B illustrate a light-emitting device according to an embodiment of the present invention.
Figure 5B:
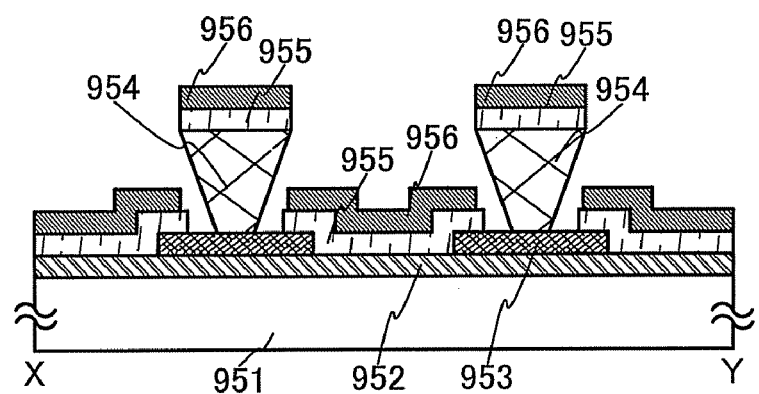

As described above, an active-matrix light-emitting device that controls driving of a light-emitting element with a transistor is described in this embodiment; however, a passive-matrix light-emitting device may be used. FIGS. 5A and 5B illustrate a passive-matrix light-emitting device which is manufactured by application of the present invention. FIG. 5A is a perspective view of the light-emitting device, and FIG. 5B is a cross-sectional view of FIG. 5A taken along the line X-Y. In FIGS. 5A and 5B, an EL layer 955 is provided between an electrode 952 and an electrode 956 over a substrate 951. An edge portion of the electrode 952 is covered with an insulating layer 953. A partition layer 954 is provided over the insulating layer 953. The sidewalls of the partition layer 954 are aslope so that a distance between both sidewalls is gradually narrowed toward the surface of the substrate. That is, a cross section in a short side direction of the partition layer 954 is a trapezoidal shape, and a lower side (the side in the same direction as the plane direction of the insulating layer 953 and touching the insulating layer 953) is shorter than an upper side (the side in the same direction as the plane direction of the insulating layer 953, and not touching the insulating layer 953). Fabrication of the partition layer 954 in this manner allows patterning of the cathode. In addition, in a passive-matrix light-emitting device, a light-emitting device with low power consumption can be obtained by including a light-emitting element with low driving voltage according to the present invention.

Note that this embodiment can be combined with any of the other embodiments as appropriate.

Embodiment 7

In Embodiment 7, embodiments of electronic devices of the present invention including the light-emitting device described in Embodiment 6 as a part will be described. Such electronic devices of the present invention each include any of the light-emitting elements described in Embodiments 2 to 5 and a display portion with low power consumption.

As electronic devices manufactured using the light-emitting device of the present invention, video cameras, digital cameras, goggle-type displays, navigation systems, audio reproducing devices (car audio set, audio component set, or the like), computers, game machines, portable information terminals (mobile computer, mobile phone, portable game machine, electronic book, or the like), and image reproducing devices provided with a recording medium (specifically, a device provided with a display device that can reproduce the content of a recording medium such as a Digital Versatile Disc (DVD) and display the image), and the like are given. Specific examples of these electronic devices are illustrated in FIGS. 6A to 6D.

Figure 6A:
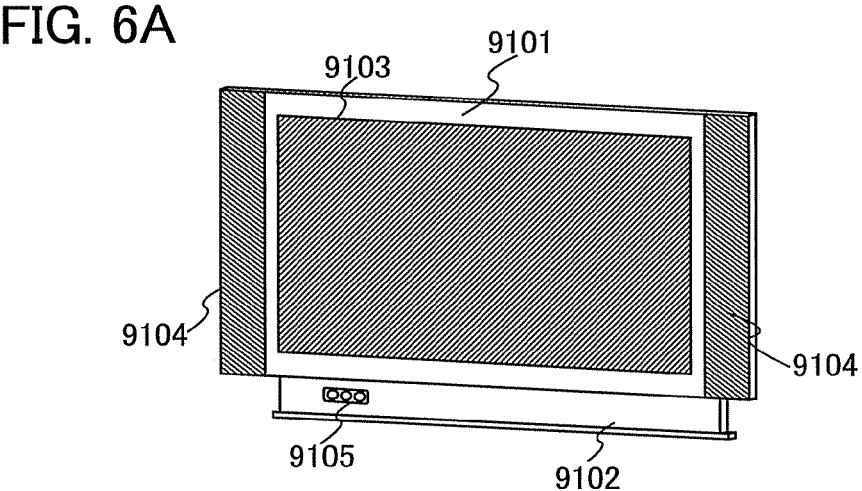
FIGS. 6A to 6D each illustrate an electronic device according to an embodiment of the present invention.

FIG. 6A illustrates a television device of this embodiment, which includes a housing 9101, a support 9102, a display portion 9103, speaker portions 9104, a video input terminal 9105, and the like. In the display portion 9103 of the television device, light-emitting elements that are similar to those described in Embodiments 2 to 5 are arranged in matrix. Features of the light-emitting elements are that driving voltage is low and power consumption is low. Since the display portion 9103 which includes such light-emitting elements has similar features, this television device consumes low power. With such features, the number or scale of power supply circuits in the television device can be drastically reduced, and therefore, the size and weight of the housing 9101 and the support 9102 can be reduced. In the television device of this embodiment, reduction in power consumption and reduction in size and weight are achieved; accordingly, a product which is suitable for living environment can be provided.

Figure 6B:
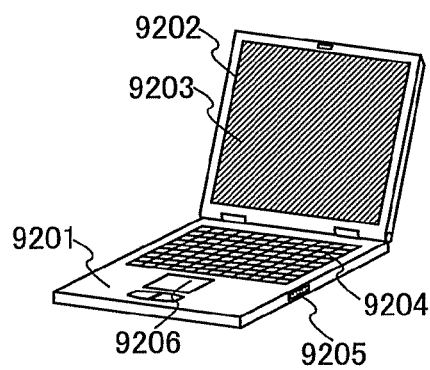

FIG. 6B illustrates a computer of this embodiment, which includes a main body 9201, a housing 9202, a display portion 9203, a keyboard 9204, an external connection port 9205, a pointing device 9206, and the like. In the display portion 9203 of this computer, light-emitting elements that are similar to those described in Embodiments 2 to 5 are arranged in matrix. Features of the light-emitting elements are that driving voltage is low and power consumption is low. Since the display portion 9203 which includes such light-emitting elements has similar features, this computer consumes low power. With such features, the number or scale of power supply circuits in the computer can be drastically reduced, and therefore, the size and weight of the main body 9201 and the housing 9202 can be reduced. In the computer of this embodiment, reduction in power consumption and reduction in size and weight are achieved; accordingly, a product which is suitable for environment can be provided.

Figure 6C:
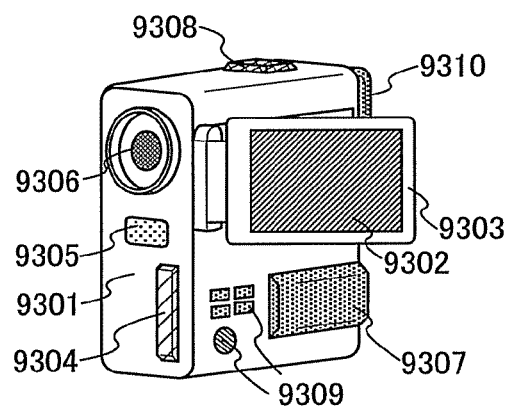

FIG. 6C illustrates a camera that includes a main body 9301, a display portion 9302, a housing 9303, an external connection port 9304, a remote control receiving portion 9305, an image receiving portion 9306, a battery 9307, an audio input portion 9308, operation keys 9309, an eyepiece portion 9310, and the like. In the display portion 9302 of this camera, light-emitting elements similar to those described in Embodiments 2 to 5 are arranged in matrix. Features of the light-emitting elements are that driving voltage is low and power consumption is low. The display portion 9302 which includes such light-emitting elements has similar features. Therefore, this camera consumes low power. With such features, the number or scale of power supply circuits in the camera can be drastically reduced, and therefore, the size and weight of the main body 9301 can be reduced. In the camera of this embodiment, reduction in power consumption and reduction in size and weight are achieved; therefore, a product which is suitable for being carried around can be provided.

Figure 6D:
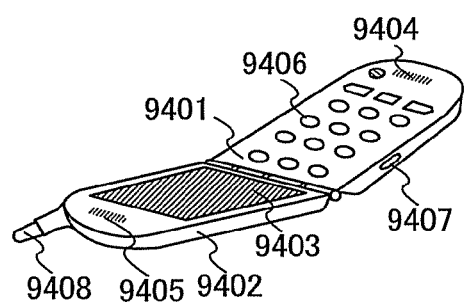

FIG. 6D illustrates a mobile phone of this embodiment, which includes a main body 9401, a housing 9402, a display portion 9403, an audio input portion 9404, an audio output portion 9405, operation keys 9406, an external connection port 9407, an antenna 9408, and the like. In the display portion 9403 of the mobile phone, light-emitting elements that are similar to those described in Embodiments 2 to 5 are arranged in matrix. Features of the light-emitting elements are that driving voltage is low and power consumption is low. Since the display portion 9403 which includes such light-emitting elements has similar features, this mobile phone consumes low power. With such features, the number or scale of power supply circuits in the mobile phone can be drastically reduced, and therefore, the size and weight of the main body 9401 and the housing 9402 can be reduced. In the mobile phone of this embodiment, reduction in power consumption and reduction in size and weight are achieved; therefore, a product which is suitable for being carried around can be provided.

Figure 12A:
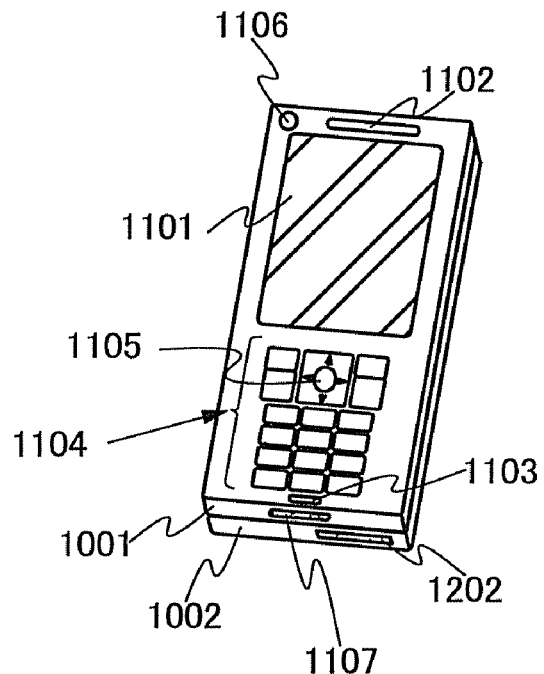
FIGS. 12A to 12C illustrate an electronic device according to an embodiment of the present invention.
Figure 12B:
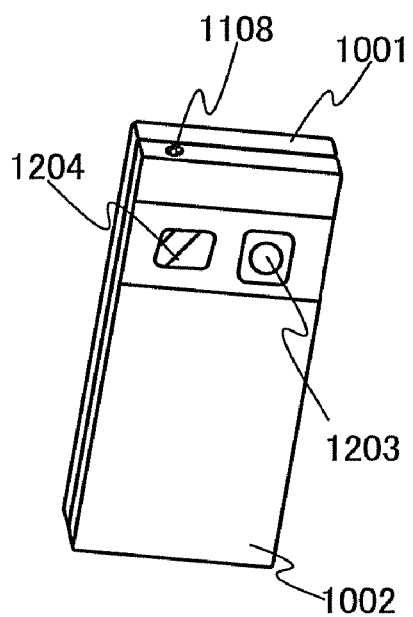
Figure 12C:
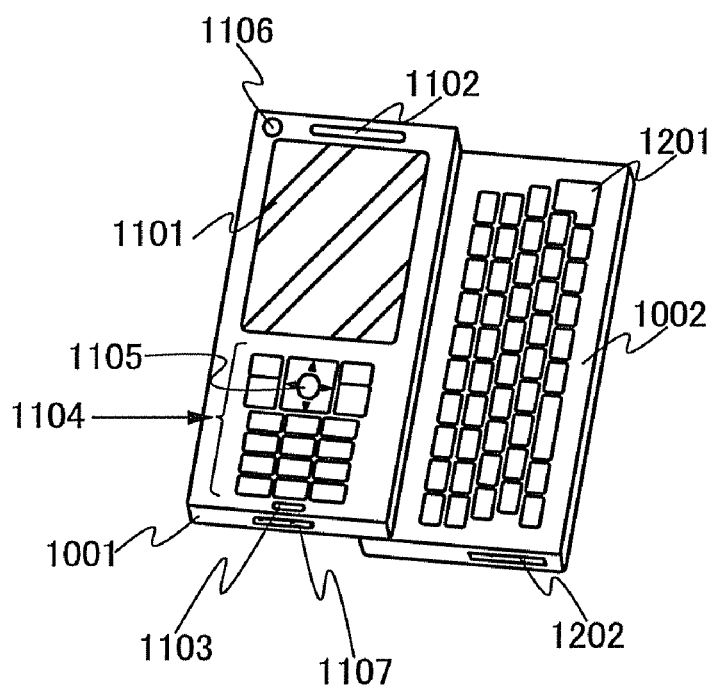

FIGS. 12A to 12C illustrate an example of a structure of a mobile phone, which is different from the structure of the mobile phone of FIG. 6D. FIG. 12A is a front view, FIG. 12B is a rear view, and FIG. 12C is a development view. The mobile phone in FIGS. 12A to 12C is a so-called smartphone which has both a function as a phone and a function as a portable information terminal, and incorporates a computer to conduct a variety of data processing in addition to voice calls.

The mobile phone illustrated in FIGS. 12A to 12C has two housings 1001 and 1002. The housing 1001 includes a display portion 1101, a speaker 1102, a microphone 1103, operation keys 1104, a pointing device 1105, a camera lens 1106, an external connection terminal 1107, and the like, while the housing 1002 includes an earphone terminal 1108, a keyboard 1201, an external memory slot 1202, a camera lens 1203, a light 1204, and the like. In addition, an antenna is incorporated in the housing 1001.

Further, in addition to the above-described structure, the smartphone may incorporate a non-contact IC chip, a small size memory device, or the like.

In the display portion 1101, the light-emitting device described in Embodiment 6 can be incorporated, and a display direction can be appropriately changed depending on the usage mode. Because the camera lens 1106 is provided in the same plane as the display portion 1101, the smartphone can be used as a videophone. Further, a still image and a moving image can be taken with the camera lens 1203 and the light 1204 by using the display portion 1101 as a viewfinder. The speaker 1102 and the microphone 1103 can be used for video calling, recording and playing sound, and the like without being limited to voice calls. With the use of the operation keys 1104, making and receiving calls, inputting simple information of e-mails or the like, scrolling of the screen, moving the cursor and the like are possible. Furthermore, the housing 1001 and the housing 1002, which are overlapped with each other (FIG. 12A), can be developed by sliding as illustrated in FIG. 12C and can be used as a portable information terminal. At this time, smooth operation can be conducted using the keyboard 1201 and the pointing device 1105. The external connection terminal 1107 can be connected to an AC adaptor and various types of cables such as a USB cable, and charging and data communication with a computer or the like are possible. Furthermore, a large amount of data can be stored and moved by inserting a recording medium into the external memory slot 1202.

In addition to the above-described functions, the smartphone may have an infrared communication function, a television receiver function, and the like.

Figure 7:
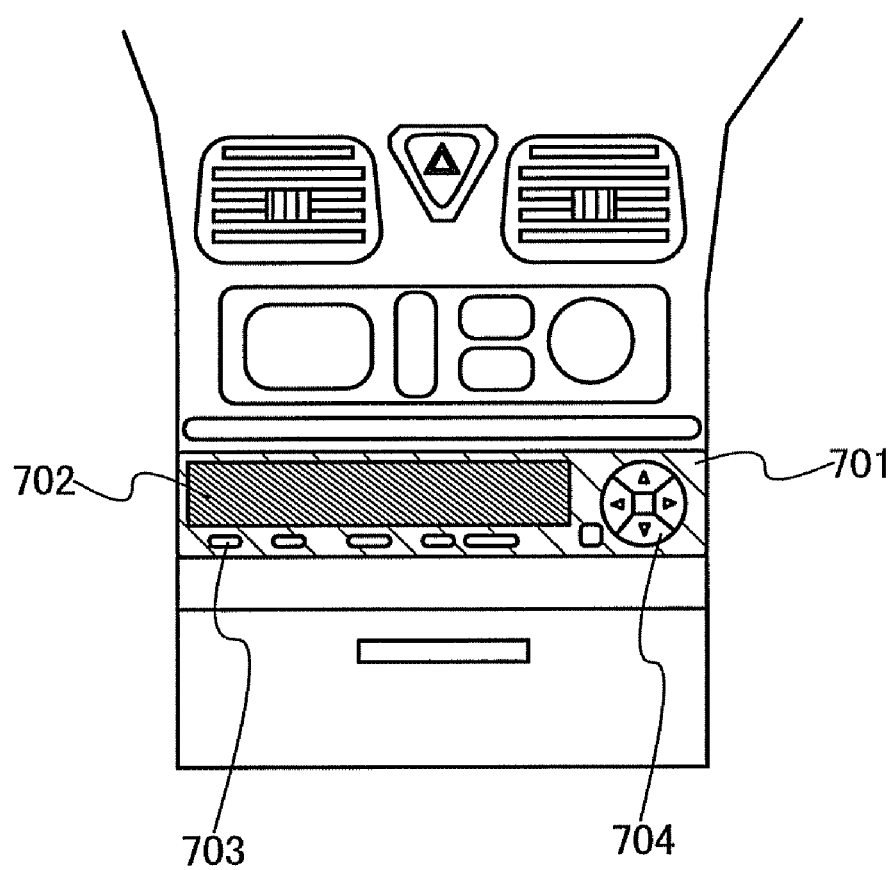
FIG. 7 illustrates an electronic device according to an embodiment of the present invention.

FIG. 7 illustrates an audio reproducing device, specifically, a car audio system, which includes a main body 701, a display portion 702, and operation switches 703 and 704. The display portion 702 can be realized using the light-emitting device (passive-matrix type or active-matrix type) described in Embodiment 6. Further, the display portion 702 may employ a segment type light-emitting device. In any case, the use of a light-emitting element of the present invention makes it possible to form a bright display portion while achieving low power consumption, with the use of a vehicle power source (12 V to 42 V). Although an in-car audio system is illustrated in this embodiment, the present invention may be used for a portable audio device or an audio device for household use.

Figure 8:
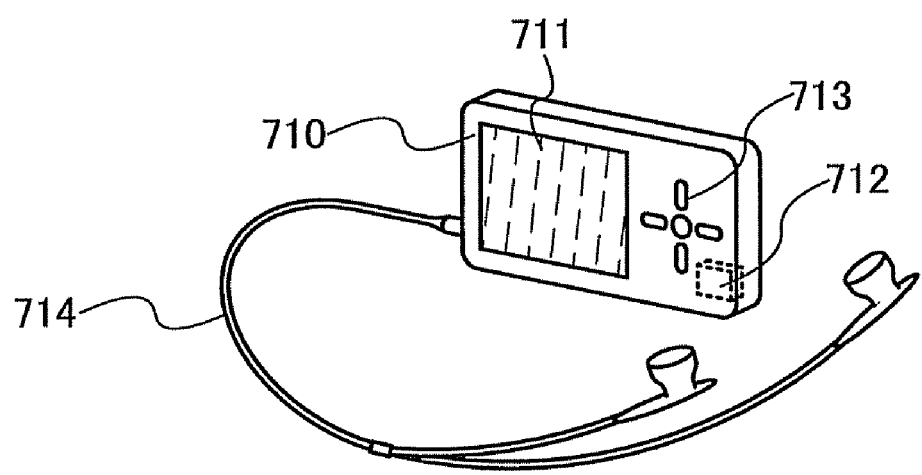
FIG. 8 illustrates an electronic device according to an embodiment of the present invention.

FIG. 8 illustrates a digital player as an example of an audio reproducing device. The digital player illustrated in FIG. 8 includes a main body 710, a display portion 711, a memory portion 712, an operation portion 713, earphones 714, and the like. Note that a pair of headphones or a wireless pair of earphones can be used instead of the pair of earphones 714. The display portion 711 can be realized using the light-emitting device (passive-matrix type or active-matrix type) described in Embodiment 6. Further, the display portion 711 may employ a segment type light-emitting device. In any case, the use of a light-emitting element of the present invention makes it possible to form a bright display portion which can display images even when using a secondary battery (a nickel-hydrogen battery or the like) while achieving low power consumption. As the memory portion 712, a hard disk or a nonvolatile memory is used. For example, a NAND type flash memory with a recording capacity of 20 to 200 gigabytes (GB) is used, and by operating the operation portion 713, an image or a sound (e.g., music) can be recorded and reproduced. Note that in the display portion 702 and the display portion 711, white characters are displayed against a black background, and thus, power consumption can be reduced. This is particularly effective for portable audio systems.

As described above, the applicable range of the light-emitting device manufactured by applying the present invention is so wide that the light-emitting device is applicable to electronic devices in various fields. By applying the present invention, an electronic device which has a display portion consuming low power can be manufactured.

The light-emitting device to which the present invention is applied has a light-emitting element with high emission efficiency, and can also be used as a lighting device. One mode of using a light-emitting element to which the present invention is applied as a lighting device is described with reference to FIG. 9.

Figure 9:
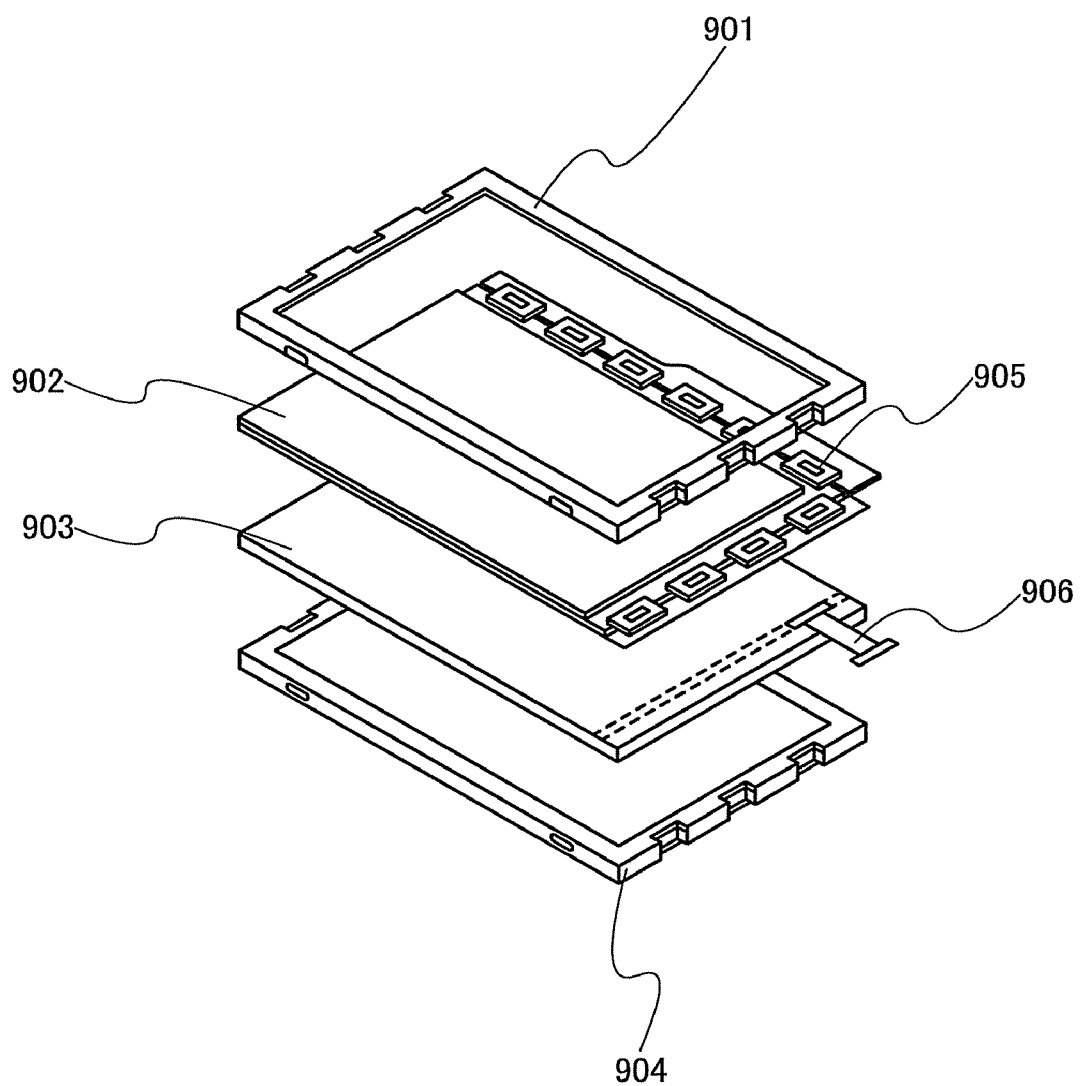
FIG. 9 illustrates an electronic device according to an embodiment of the present invention.

FIG. 9 illustrates a liquid crystal display device using the light-emitting device to which the present invention is applied as a backlight, as an example of the electronic device using a light-emitting device according to the present invention as a lighting device. The liquid crystal display device illustrated in FIG. 9 includes a housing 901, a liquid crystal layer 902, a backlight 903, and a housing 904. The liquid crystal layer 902 is connected to a driver IC 905. The light-emitting device to which the present invention is applied is used as the backlight 903, and current is supplied through a terminal 906.

Because the light-emitting device according to the present invention is thin and consumes low power, reduction in thickness and power consumption of a liquid crystal display device is possible by using a light-emitting device according to the present invention as a backlight of the liquid crystal display device. Moreover, a light-emitting device according to the present invention is a plane-emission lighting device and can have a large area. Thus, the backlight can have a large area, and a liquid crystal display device having a large area can also be obtained.

Figure 10:
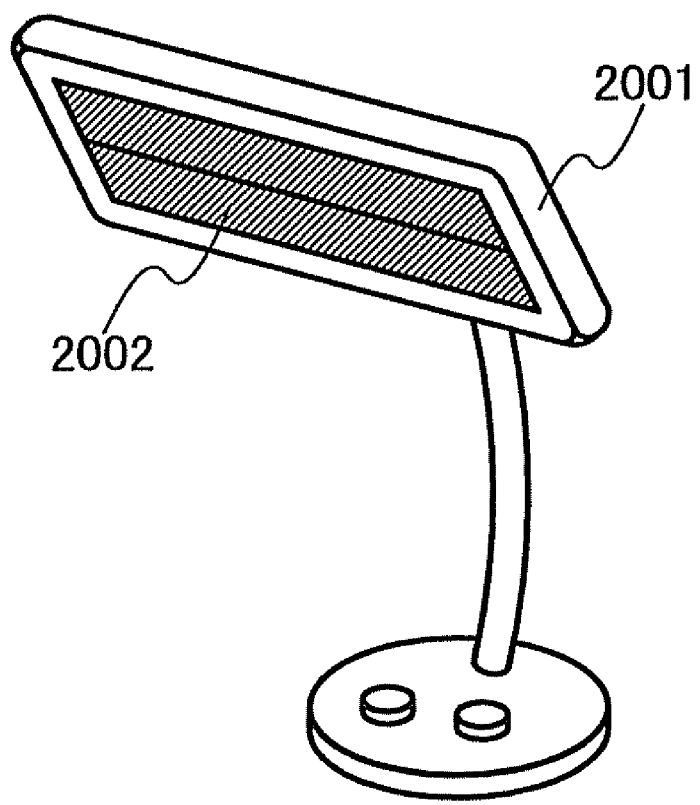
FIG. 10 illustrates a lighting device according to an embodiment of the present invention.

FIG. 10 illustrates an example in which a light-emitting device according to the present invention is used for a desk lamp, which is one of lighting devices. The desk lamp illustrated in FIG. 10 includes a housing 2001 and a light source 2002, and a light-emitting device according to the present invention is used as the light source 2002. Because a light-emitting device of the present invention consumes low power, the desk lamp also consumes low power.

Figure 11:
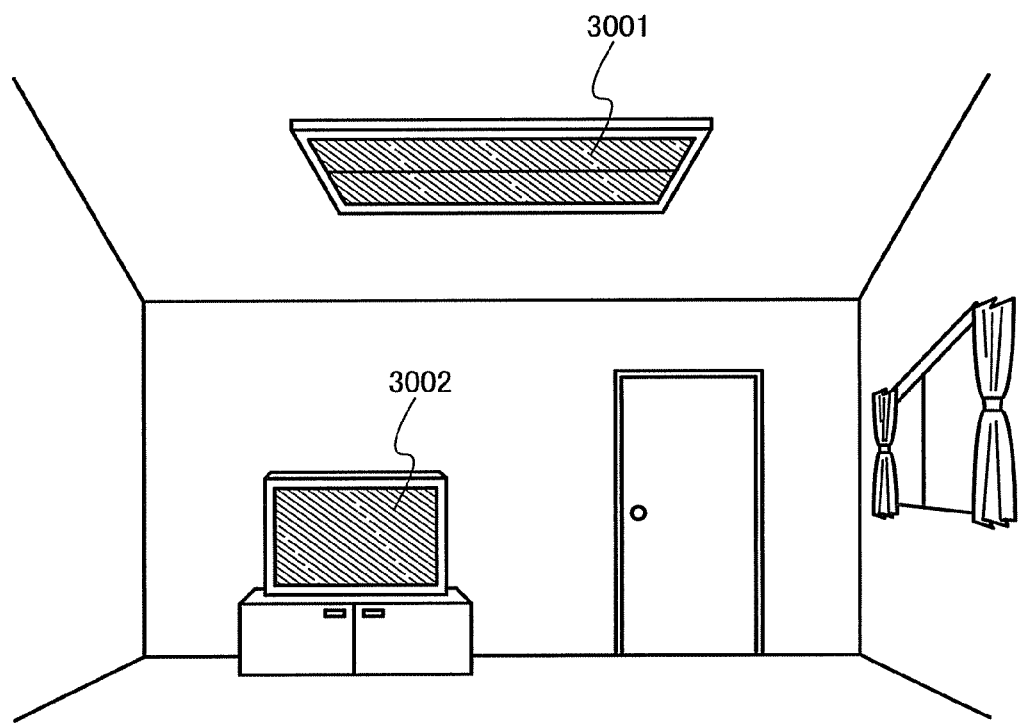
FIG. 11 illustrates a lighting device according to an embodiment of the present invention.

FIG. 11 illustrates an example in which the light-emitting device to which the present invention is applied is used for an indoor lighting device 3001. Because a light-emitting device according to the present invention can have a large area, it can be used for a lighting device having a large area. Moreover, because a light-emitting device according to the present invention consumes low power, it can be used for a lighting device which consumes low power. A television device 3002 according to the present invention as illustrated in FIG. 6A is placed in a room where the light-emitting device to which the present invention is applied is used as the indoor lighting device 3001. Thus, public broadcasting and movies can be watched. In such a case, since both devices consume low power, environmental load can be reduced.

Note that this embodiment can be combined with any of the other embodiments as appropriate.

EXAMPLE 1

In Example 1, a synthesis method of 2,2'-[2,2'-bipyridine-5,6-diylbis(biphenyl-4,4'-diyl)]bisbenzoxazole (abbreviation: BOxP2BPy) represented by the structural formula (101) is described.

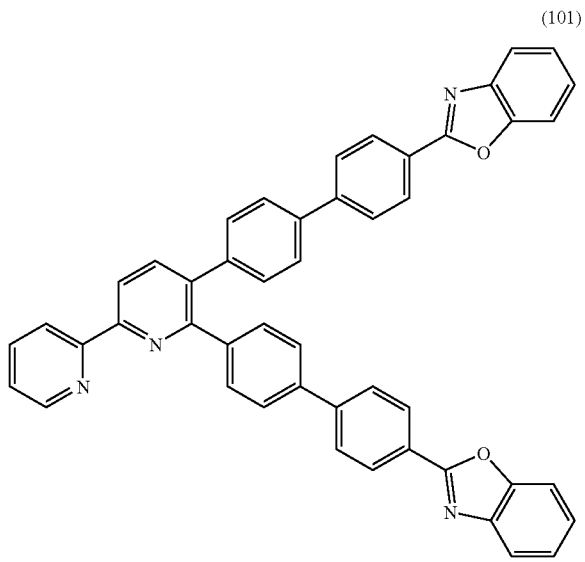

(101)

[Step 1: Synthesis of 4-(benzoxazol-2-yl)phenylboronic Acid]
(i) Synthesis of 4-bromo-N-(2-hydroxyphenyl)benzamide
A synthesis scheme of 4-bromo-N-(2-hydroxyphenyl)benzamide is shown in (B-1).

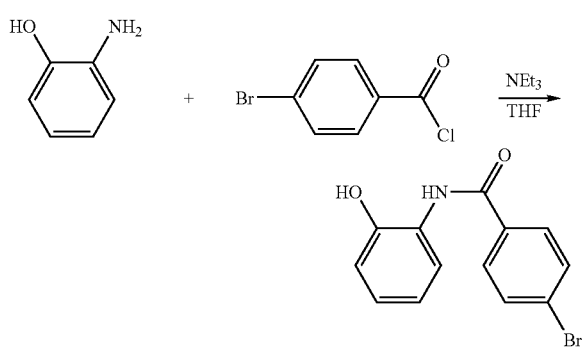

(B-1)

In a 200 mL three-necked flask were placed 2.2 g (20 mmol) of 2-aminophenol, 3.0 mL (22 mmol) of triethylamine, and 50 mL of tetrahydrofuran (THF). Then, the mixture was cooled to 0° C. After cooling, 50 mL of a THF solution containing 4.5 g (20 mmol) of 4-bromobenzoyl chloride was dripped under a nitrogen stream. This solution was stirred at 0° C. for 4 hours under a nitrogen stream. After a certain time, water was added to the solution, and an aqueous layer was extracted with ethyl acetate. The resulting extract was combined with the organic layer, and the organic layer was washed with 0.2 M hydrochloric acid and a saturated aqueous solution of sodium bicarbonate, and then dried with magnesium sulfate. The mixture was subjected to suction filtration through Celite (produced by Wako Pure Chemical Industries, Ltd., Catalog No. 531-16855), and the filtrate was condensed to give a solid. The obtained solid was recrystallized with ethyl acetate/hexane, so that 5.3 g of target white powder was obtained in a yield of 88%.
(ii) Synthesis of 2-(4-bromophenyl)benzoxazole
A synthesis scheme of 2-(4-bromophenyl)benzoxazole is shown in (B-2).

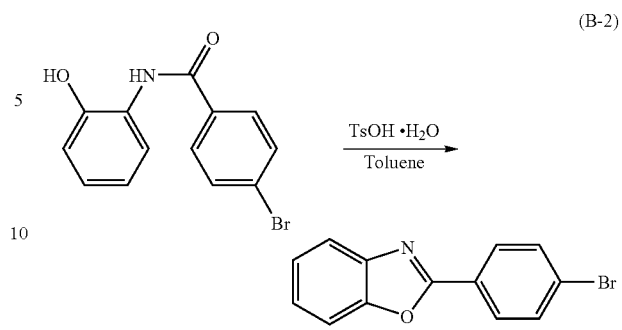

(B-2)

5.3 g (18 mmol) of 4-bromo-N-(2-hydroxyphenyl)benzamide, 8.0 g (46 mmol) of para-toluenesulfonic acid monohydrate, and 200 mL of toluene were put in a 300 mL three-neck flask. The mixture was refluxed for 4 hours under a nitrogen stream. After a certain time, water was added to the mixture, and an organic layer and an aqueous layer was extracted with ethyl acetate. The resulting extract was combined with the organic layer, and the organic layer was washed with a saturated aqueous solution of sodium bicarbonate and then a saturated saline, and dried with magnesium sulfate. The obtained mixture was subjected to suction filtration through Celite (produced by Wako Pure Chemical Industries, Ltd., Catalog No. 531-16855), and the filtrate was condensed to obtain a solid. The obtained solid was recrystallized with ethyl acetate/hexane, so that 3.1 g of target white powder was obtained with a yield of 61%.
(iii) Synthesis of 4-(benzoxazol-2-yl)phenylboronic Acid
A synthesis scheme of 4-(benzoxazol-2-yl)phenylboronic acid is shown in (B-3).

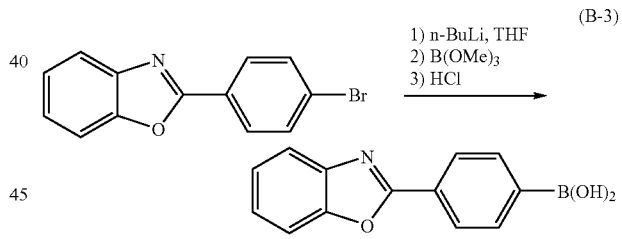

(B-3)

First, 5.5 g (20 mmol) of 2-(4-bromophenyl)benzoxazole was put into a 300 mL three-neck flask and the atmosphere in the flask was substituted by nitrogen. 120 mL of THF was added and cooled to −78° C. under a nitrogen stream. After cooling, 13 mL (22 mmol) of 1.6 M n-butyllithium was dripped to this solution, and the mixture was stirred at the same temperature for 2 hours. After a certain time, 4.4 mL (40 mmol) of trimethyl borate was added to this solution, and the temperature of the solution was raised to room temperature, and then, the solution was stirred for 16 hours. After a certain time, 100 mL of 1M hydrochloric acid was added and stirred for 1 hour. An aqueous layer of the obtained mixture was extracted with ethyl acetate. The obtained extract was washed with a saturated saline together with the organic layer and then dried over magnesium sulfate. The obtained mixture was subjected to gravity filtration, and the obtained filtrate was concentrated to give a solid. The obtained solid was recrystallized with ethyl acetate/hexane, so that 3.3 g of target white powder was obtained with a yield of 69%.

[Step 2: Synthesis of 5,6-bis(4-bromophenyl)-2,2'-bipyridine]
(i) Synthesis of pyridine-2-carboxyamidorazone
A synthesis scheme of pyridine-2-carboxyamidorazone is shown in (B-4).

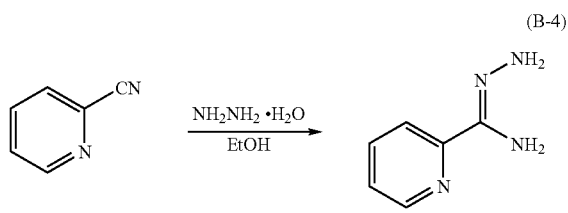

(B-4)

In a 500 mL recovery flask were put 21 g (0.20 mol) of 2-cyanopyridine, 200 mL of ethanol, 33 mL (0.68 mol) of hydrazine monohydrate. This solution was stirred at room temperature for 44 hours under a nitrogen stream. After a certain time, water was added to the solution. This solution was subjected to extraction with chloroform, and the extract was cleaned with a saturated saline, then the organic layer and then dried with magnesium sulfate. The mixture was subjected to gravity filtration, and the obtained filtrate was concentrated to give a solid. A suspension in which hexane was added to this solid was irradiated with ultrasonic waves, and subjected to suction filtration to recover the solid, so that 21 g of a target white powder was recovered in a yield of 75%.

(ii) Synthesis of 5,6-bis(4-bromophenyl)-3-(2-pyridyl)-1,2,4-triazine
A synthesis scheme of 5,6-bis(4-bromophenyl)-3-(2-pyridyl)-1,2,4-triazine is shown in (B-5).

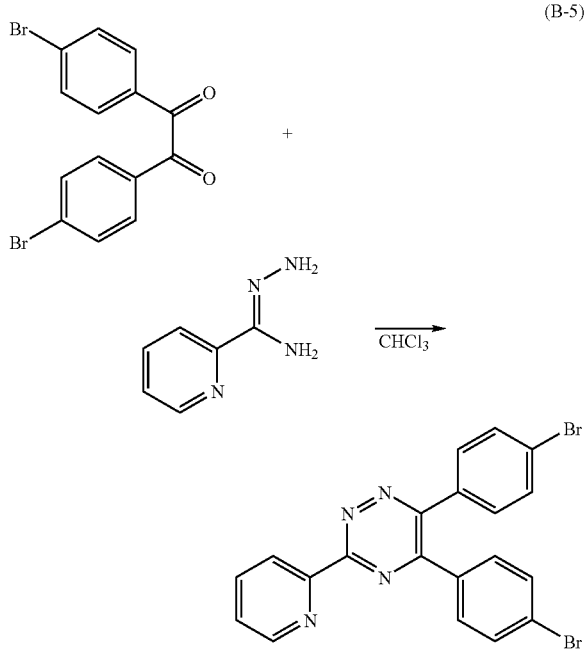

(B-5)

10 g (28 mmol) of 4-4'-dibromobenzil, 4.3 g (31 mmol) of pyridine-2-carboxyamidrazone, and 100 mL of chloroform were put into a 300 mL three-neck flask. The mixture was refluxed for 6 hours under a nitrogen stream. After a certain time, water was added to the mixture, and an aqueous layer was extracted with chloroform. The obtained extract combined with the organic layer was washed with 1.0M hydrochloric acid, a saturated aqueous solution of sodium bicarbonate and saturated saline in that order, and the organic layer was dried with magnesium sulfate. The mixture was filtered, and the obtained filtrate was concentrated to give a solid. A suspension in which ethanol/hexane was added to this solid was irradiated with ultrasonic wave, and subjected to suction filtration to recover a solid, so that 12 g of a target yellow powder was obtained in a yield of 91%.

(iii) Synthesis of 5,6-bis(4-bromophenyl)-2,2'-bipyridine
A synthesis scheme of 5,6-bis(4-bromophenyl)-2,2'-bipyridine is shown in (B-6).

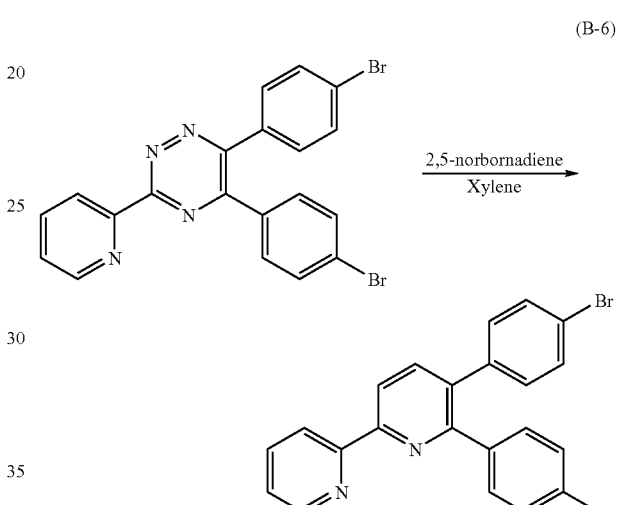

(B-6)

In a 500 mL three-neck flask were put 13 g (27 mmol) of 5,6-bis(4-bromophenyl)-3-(2-pyridyl)-1,2,4-triazine, 9.0 mL (83 mmol) of 2,5-Norbornadiene, and 150 mL of xylene. This mixture was refluxed at 140° C. for 5 hours under a nitrogen stream. After a certain time, water was added to the mixture, and an aqueous layer was extracted with toluene. The extract was washed with a saturated saline together with the organic layer, and the organic layer was then dried with magnesium sulfate. The mixture was subjected to gravity filtration, and the obtained filtrate was concentrated to give a solid. The solid was refined with silica gel column chromatography (toluene), so that a target substance, 7.5 g of light-yellow powder was obtained in a yield of 59%.

The compound was measured with a nuclear magnetic resonance (NMR) measurement, and the measurement showed that the obtained compound was 5,6-bis(4-bromophenyl)-2,2'-bipyridine.

The $^1$H NMR data is shown below.

$^1$H NMR (300 MHz, CDCl$_3$): δ(ppm)=7.10 (d, J=8.4 Hz, 2H), 7.31-7.47 (m, 7H), 7.80-7.86 (m, 2H), 8.46 (d, J=8.4 Hz, 1H), 8.54 (d, J=7.8 Hz, 1H), 8.71 (d, J=4.8 Hz, 1H).

Figure 13A:
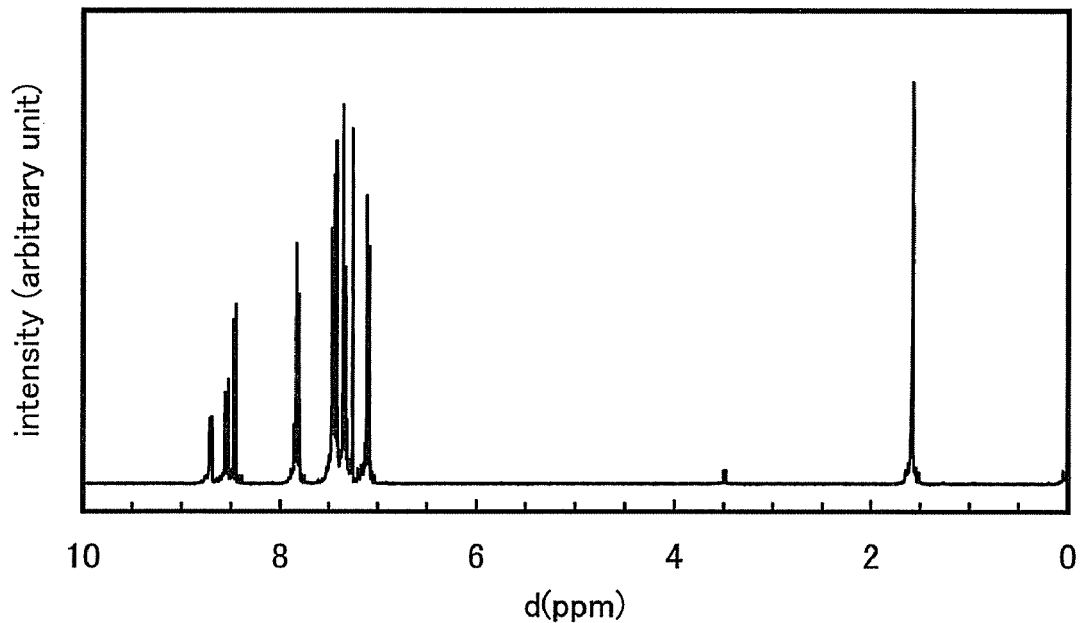
FIGS. 13A and 13B are $^1$H NMR charts of 5,6-bis(4-bromophenyl)-2,2'-bipyridine.
Figure 13B:
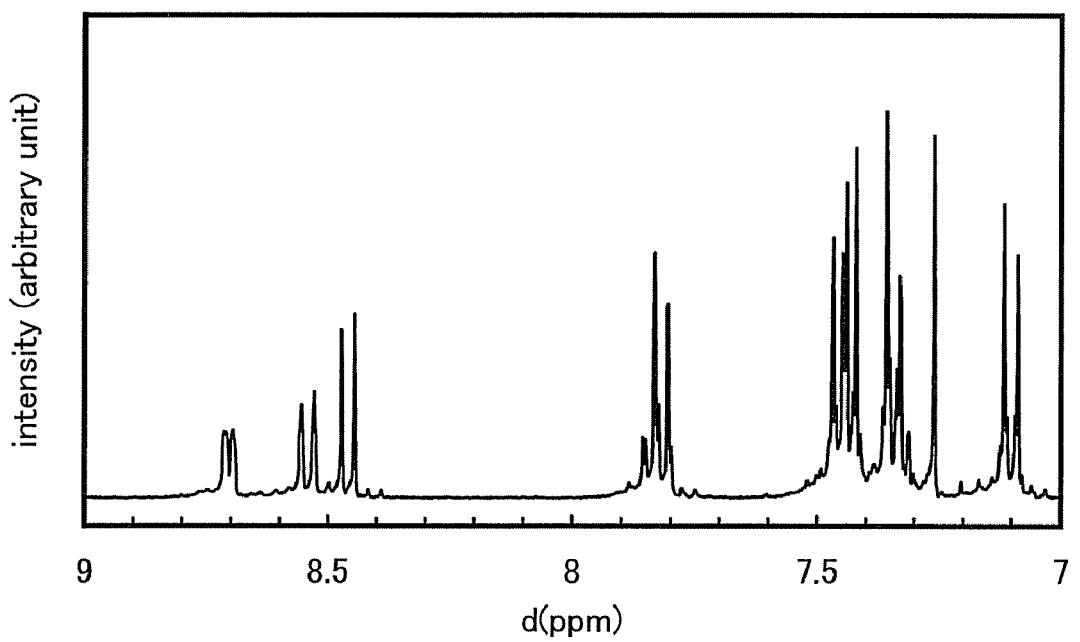

In addition, FIGS. 13A and 13B show a $^1$H NMR chart. Note that FIG. 13B shows an enlarged part of the range from 7.0 ppm to 9.0 ppm in FIG. 13A.

[Step 3: Synthesis of 2,2'-[2,2'-bipyridine-5,6-diylbis(biphenyl-4,4'-diyl)]bisbenzoxazole (Abbreviation: BOxP2BPy)]

A synthesis scheme of BOxP2BPy is shown in (B-7).

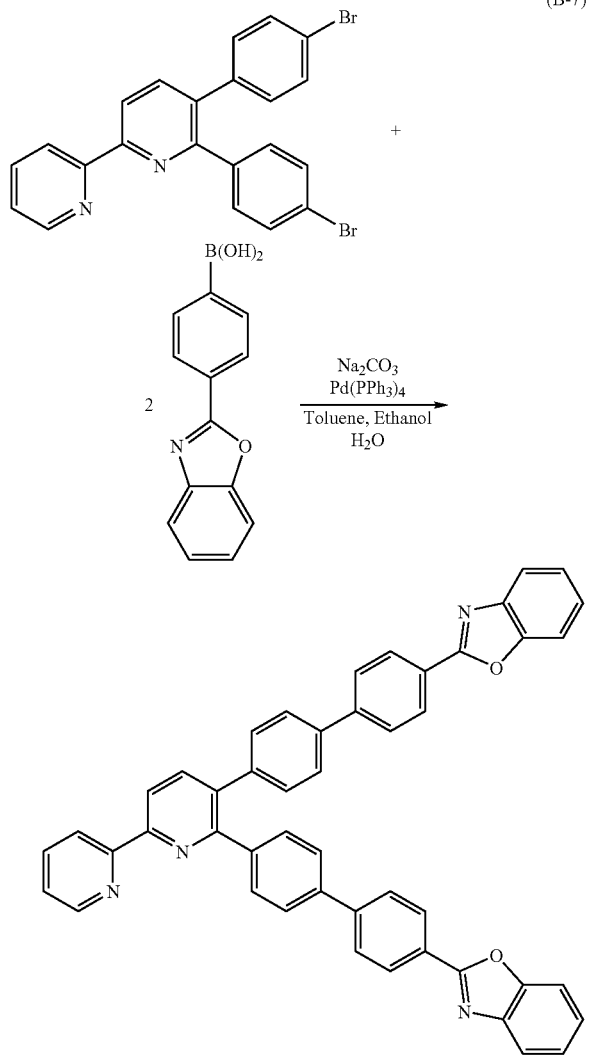

Into a 100 mL three-neck flask were put 1.4 g (3.0 mmol) of 5,6-bis(4-bromophenyl)-2,2'-bipyridine, 1.3 g (12 mmol) of sodium carbonate, 1.6 g (6.6 mmol) of 4-(benzoxazol-2-yl)phenylboronic acid, 25 ml of toluene, 6 ml of ethanol, 6 ml of water. The mixture was degassed by being stirred under reduced pressure, and the atmosphere in the flask was substituted by nitrogen. 0.14 g (0.12 mmol) of tetrakis(triphenylphosphine)palladium(0) was added, and the mixture was stirred at 80° C. for 11 hours under a nitrogen stream. After a certain time, the mixture was cooled to room temperature, and the precipitated solid was recovered by suction filtration. The obtained solid was dissolved in chloroform, and washed with water and saturated saline, then the organic layer was dried over magnesium sulfate. The obtained mixture was subjected to gravity filtration, and the obtained filtrate was concentrated to give a solid. A toluene solution of the obtained solid was subjected to suction filtration through Celite (produced by Wako Pure Chemical Industries, Ltd., Catalog No. 531-16855). The filtrate was condensed to give a solid. A suspension in which methanol was added to this solid was irradiated with ultrasonic waves, and subjected to suction filtration to recover the solid. Then, the solid was recrystallized with toluene, so that 1.1 g of a target substance, white powder was recovered in a yield of 54%.

Then, 1.4 g of the obtained target substance was subjected to sublimation purification at 330° C. under argon stream (flow rate: 3.0 mL/min) at a pressure of 10 Pa for 17 hours; thus, 0.85 g of the target substance was recovered in a yield of 59%. The compound was measured with a nuclear magnetic resonance (NMR) measurement, and the measurement showed that the obtained compound was 2,2'-[2,2'-bipyridine-5,6-diylbis(biphenyl-4,4'-diyl)]bisbenzoxazole (abbreviation: BOxP2BPy).

The $^1$H NMR data is shown below.
$^1$H NMR (300 MHz, CDCl$_3$): δ(ppm)=7.33-7.43 (m, 7H), 7.58-7.69 (m, 8H), 7.77-7.89 (m, 7H), 7.95 (d, J=8.4 Hz, 1H), 8.30-8.35 (m, 4H), 8.51 (d, J=7.8 Hz, 1H), 8.64 (d, J=7.8 Hz, 1H), 8.73 (d, J=3.9 Hz, 1H).

Figure 14A:
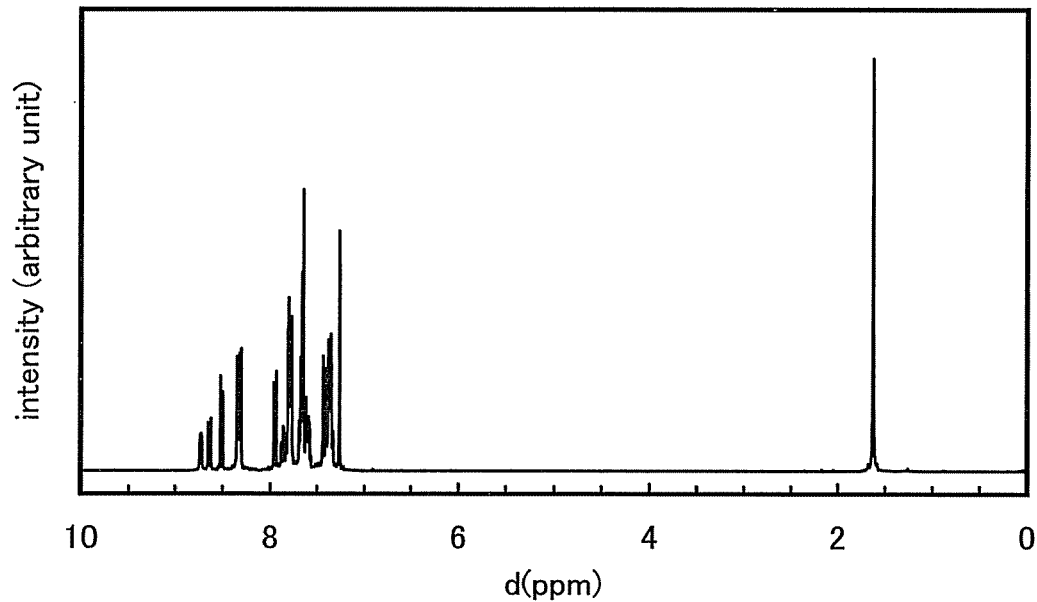
FIGS. 14A and 14B are $^1$H NMR charts of 2,2'-[2,2'-bipyridine-5,6-diylbis(biphenyl-4,4'-diyl)]bisbenzoxazole (abbreviation: BOxP2BPy)
Figure 14B:
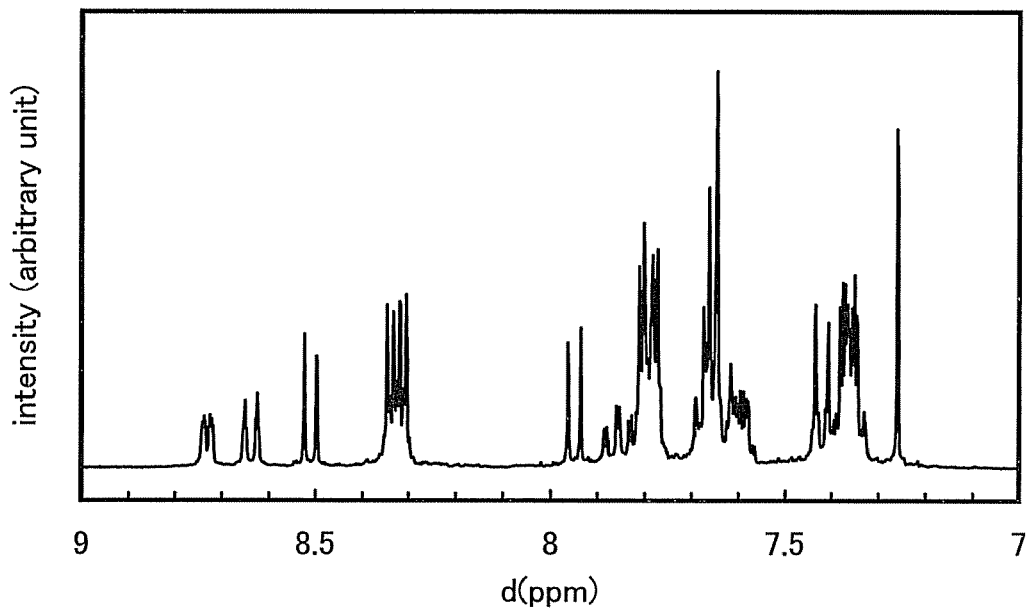

FIGS. 14A and 14B show $^1$H NMR charts. Note that FIG. 14B is a chart showing an enlarged part of FIG. 14A in the range of 7.0 ppm to 9.0 ppm.

Figure 15:
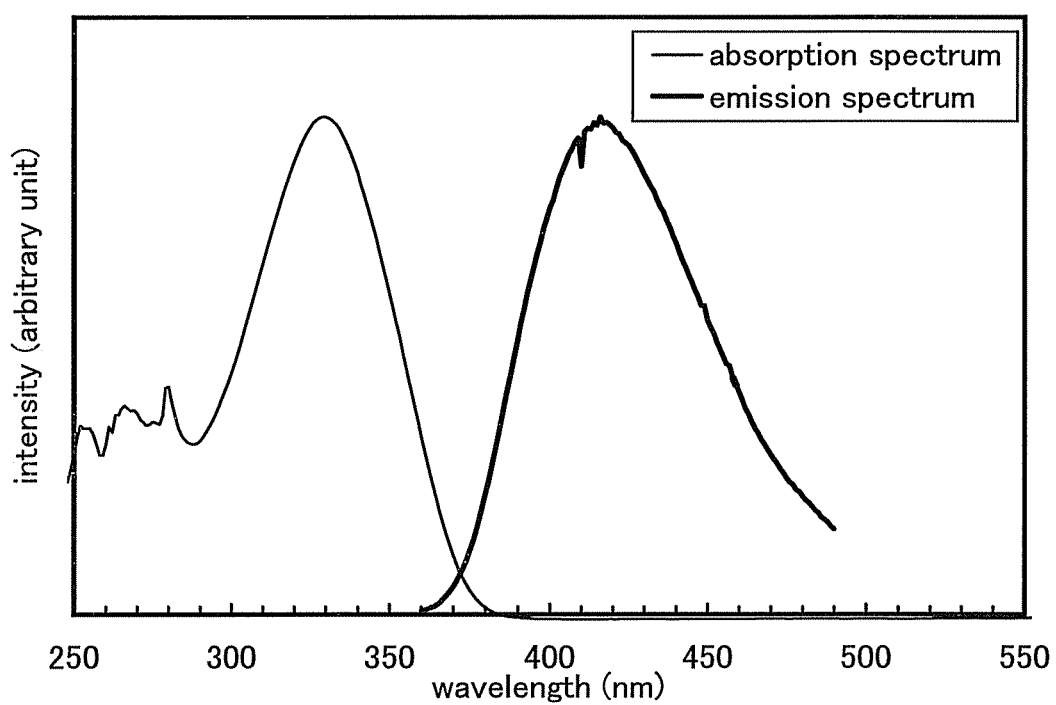
FIG. 15 is a graph showing an absorption spectrum and an emission spectrum of 2,2'-[2,2'-bipyridine-5,6-diylbis(biphenyl-4,4'-diyl)]bisbenzoxazole (abbreviation: BOxP2BPy) in a toluene solution.

FIG. 15 shows an absorption spectrum and an emission spectrum in a toluene solution of BOxP2BPy. An ultraviolet-visible spectrophotometer (V-550, manufactured by JASCO Corporation) was used for the measurement. The solution was put into a quartz cell, and the absorption spectrum from which the absorption spectrum of the quartz cell was subtracted is shown. In FIG. 15, a horizontal axis represents a wavelength (nm) and a vertical axis represents intensity (arbitrary unit). Absorption was observed around 329 nm in the case of the toluene solution. In addition, the maximum emission wavelength was 418 nm (excitation wavelength: 332 nm) in the case of the toluene solution.

Figure 16:
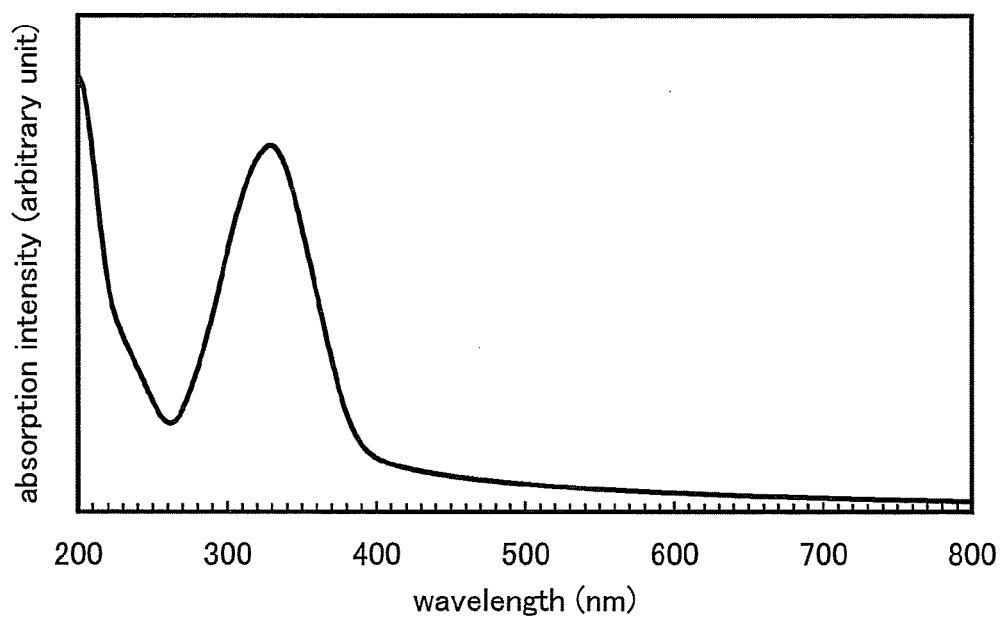
FIG. 16 is a graph showing an absorption spectrum of 2,2'-[2,2'-bipyridine-5,6-diylbis(biphenyl-4,4'-diyl)]bisbenzoxazole (abbreviation: BOxP2BPy) in a thin film state.
Figure 17:
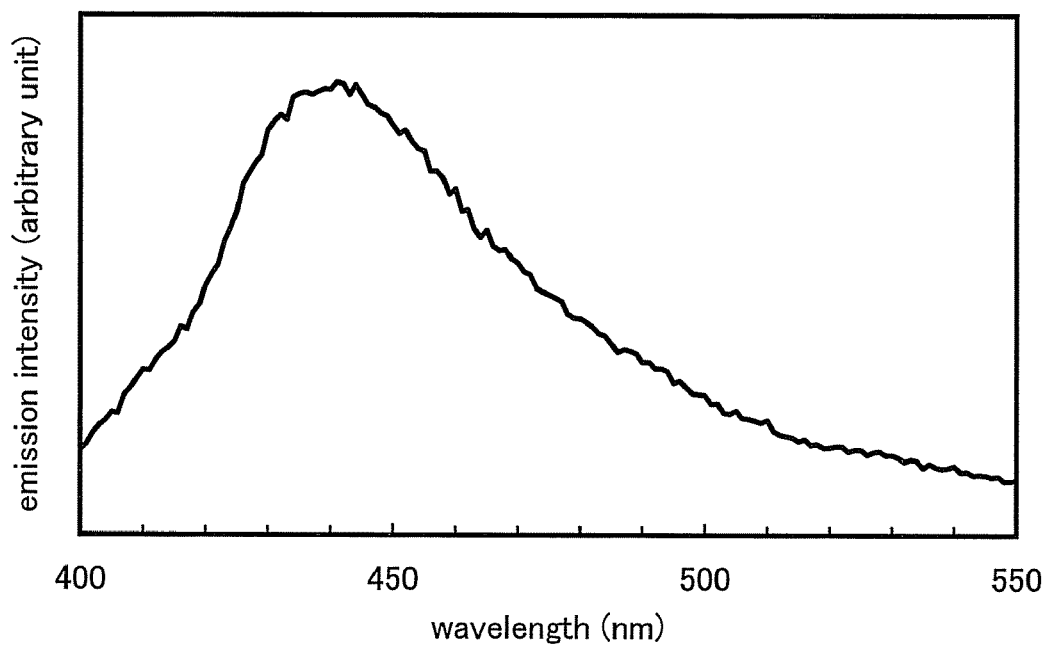
FIG. 17 is a graph showing an emission spectrum of 2,2'-[2,2'-bipyridine-5,6-diylbis(biphenyl-4,4'-diyl)]bisbenzoxazole (abbreviation: BOxP2BPy) in a thin film state.

FIG. 16 shows an absorption spectrum of a thin film of BOxP2BPy and FIG. 17 shows an emission spectrum of the thin film of BOxP2BPy. An ultraviolet-visible spectrophotometer (V-550, manufactured by JASCO Corporation) was used for the measurement. A thin film sample was formed by evaporation on a quartz substrate, and the absorption spectrum from which the absorption spectrum of the quartz substrate was subtracted is shown. In FIG. 16, the horizontal axis indicates a wavelength (nm) and the vertical axis indicates absorption intensity (arbitrary unit). In FIG. 17, the horizontal axis indicates a wavelength (nm) and the vertical axis indicates an emission intensity (arbitrary unit). Absorption was observed around 329 nm in the case of the thin film state. In addition, in the case of the thin film, the maximum emission wavelength was 441 nm (excitation wavelength: 370 nm).

In addition, when the ionizing potential of BOxP2BPy in the thin film state was measured with a photoelectron spectrometer (AC-2, by RIKEN KEIKI CO., LTD.) in the air, the ionizing potential was 6.04 eV. As a result, the HOMO level was found to be −6.04 eV. The absorption edge was obtained from tauc plot assuming direct transition with the absorption spectrum data of a thin film of BOxP2BPy. When the absorption edge was estimated as an optical energy gap, the energy gap was 3.32 eV. The LUMO level was calculated from the obtained value of the energy gap and the HOMO level, which was −2.72 eV.

Further, the oxidation-reduction reaction characteristics of BOxP2BPy were measured. The oxidation-reduction characteristics were measured by cyclic voltammetry (CV) measurement. An electrochemical analyzer (ALS model 600A, manufactured by BAS Inc.) was used for the measurement.

The solution for the CV measurement is prepared as follows: tetra-n-butylammonium perchlorate (n-Bu$_4$NClO$_4$) (produced by Tokyo Chemical Industry Co., Ltd., Catalog No. T0836) used as a supporting electrolyte is dissolved at a concentration of 100 mmol/L in dehydrated dimethylformamide (DMF) (produced by Sigma-Aldrich Corp., 99.8%, Catalog No. 22705-6) used as a solvent. Further, BOxP2BPy that was the measurement object was further dissolved at a concentration of 2 mmol/L therein. A platinum electrode (manufactured by BAS Inc., PTE platinum electrode) was used as a working electrode, a platinum electrode (manufactured by BAS Inc., Pt counter electrode for VC-3, (5 cm)) was used as an auxiliary electrode, and an Ag/Ag+ electrode (manufactured by BAS Inc., RE-5 reference electrode for nonaqueous solvent) was used as a reference electrode. The measurement was carried out at room temperature.

The oxidation reaction characteristic of BOxP2BPy was measured as follows. A scan, in which a potential of the working electrode with respect to the reference electrode was varied from 0.02 V to 1.50 V and then from 1.50 V to 0.02 V was set to as one cycle, and measurement was performed 100 cycles. The reduction reaction characteristics of BOxP2BPy were examined as follows. A scan, in which a potential of the work electrode with respect to the reference electrode was varied from −1.28 V to −2.55 V, and then from −2.55 V to −1.28 V was set to one cycle, and measurement was performed 100 cycles. Further, the scanning speed of the CV measurement was set to be 0.1 V/s.

Figure 18:
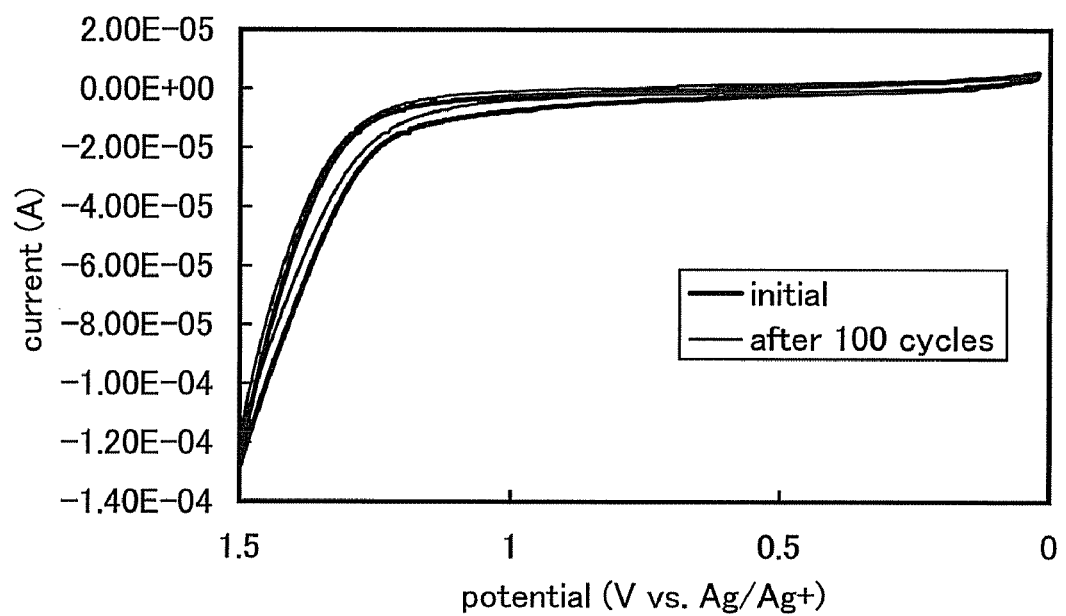
FIG. 18 is a graph showing CV measurement results of 2,2'-[2,2'-bipyridine-5,6-diylbis(biphenyl-4,4'-diyl)]bisbenzoxazole (abbreviation: BOxP2BPy)
Figure 19:
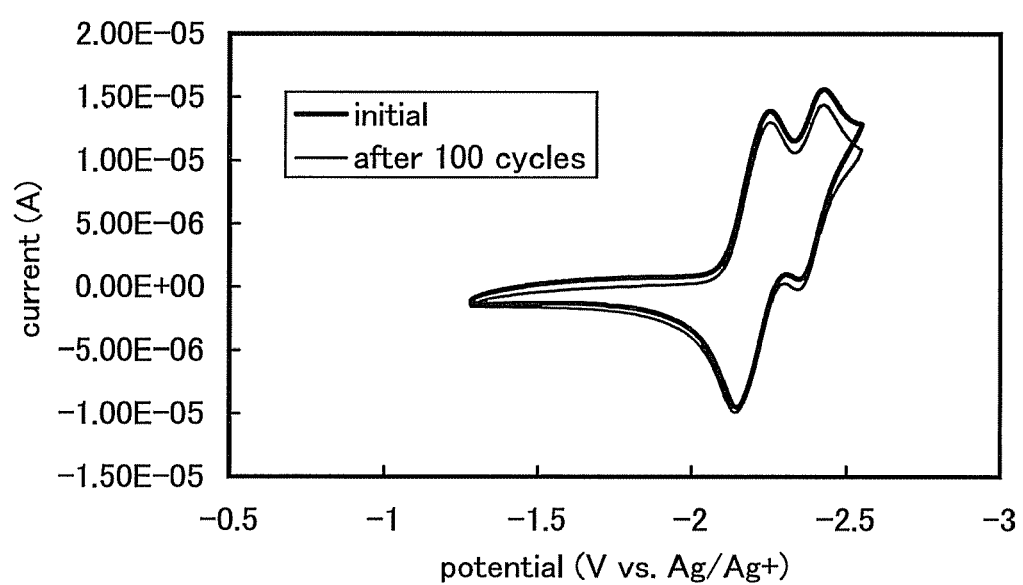
FIG. 19 is a graph showing CV measurement results of 2,2'-[2,2'-bipyridine-5,6-diylbis(biphenyl-4,4'-diyl)]bisbenzoxazole (abbreviation: BOxP2BPy)

FIG. 18 shows results of the CV measurement of BOxP2BPy on the oxidation side, and FIG. 19 shows results of the CV measurement of BOxP2BPy on the reduction side. In each of FIGS. 18 and 19, the horizontal axis indicates a potential (V) of the working electrode with respect to the reference electrode, and the vertical axis indicates a current value (μA) flowing between the working electrode and the auxiliary electrode. A current for oxidation was not observed in FIG. 18, but a current for reduction was observed at around −2.25 V (vs. Ag/Ag+ electrode) in FIG. 19.

In spite of the fact that 100 cycles of scanning were conducted repeatedly, a peak position and a peak intensity at the CV curve scarcely changed in the reduction, which reveals that BOxP2BPy which is a benzoxazole derivative of the present invention is extremely stable against repetition of the reduction.

EXAMPLE 2

In Example 2, a synthesis method of 2,2'-[2,3'-bipyridine-5,6-diylbis(biphenyl-4,4'-diyl)]bisbenzoxazole (abbreviation: BOxP2BPy(3)) represented by the structural formula (102) is described.

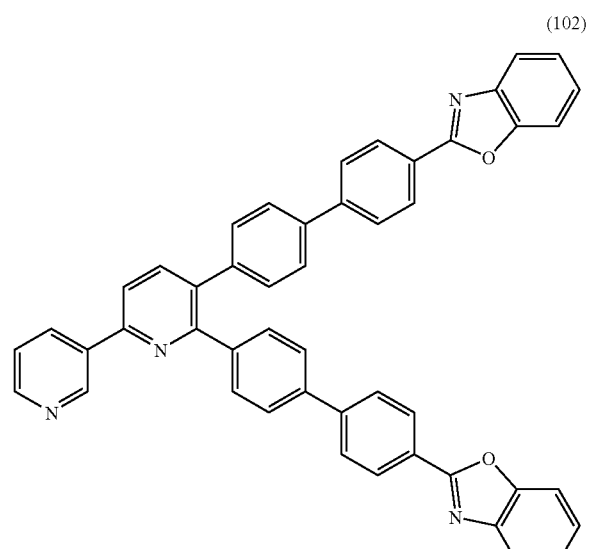
(102)

[Step 1: Synthesis of 5,6-bis(4-bromophenyl)-2,3'-bipyridine]
(i) Synthesis of pyridine-3-carboxyamidrazone
A synthesis scheme of pyridine-3-carboxyamidrazone is shown in (C-1).

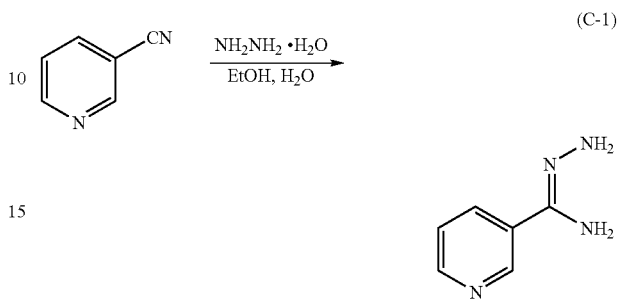
(C-1)

Into a 100 mL recovery flask, 2.6 g (25 mmol) of 3-cyanopyridine, 10 mL of ethanol, 5.0 mL of water, and 7.0 mL (0.14 mol) of hydrazine monohydrate were added. This solution was stirred at room temperature for 6 days under a nitrogen stream. After a certain time, 30 mL of saturated saline was added to the solution. This solution was extracted with chloroform, and the extract was dried with magnesium sulfate. The mixture was subjected to gravity filtration, and the obtained filtrate was concentrated to give a solid. The obtained solid was recrystallized with chloroform/hexane, so that 1.1 g of a target substance, white powder was obtained in a yield of 33%.
(ii) Synthesis of 5,6-bis(4-bromophenyl)-3-(3-pyridyl)-1,2,4-triazine
A synthesis scheme of 5,6-bis(4-bromophenyl)-3-(3-pyridyl)-1,2,4-triazine is shown in (C-2).

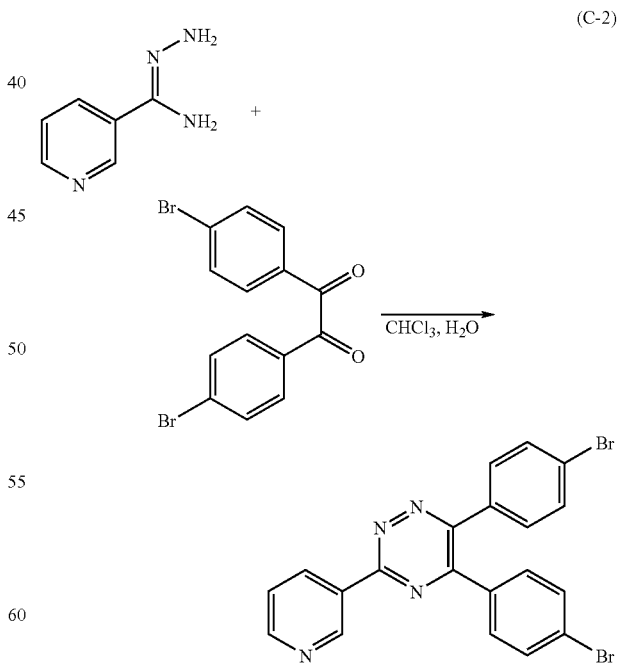
(C-2)

1.1 g (8.2 mmol) of pyridine-3-carboxyamidrazone, 80 mL of chloroform, 10 mL of water, and 3.2 g (8.8 mmol) of 4,4'-dibromobenzil were put in a 200 mL three-neck flask. The mixture was refluxed for 14 hours under a nitrogen stream. After a certain time, water was added to the mixture, and an aqueous layer was extracted with chloroform. The extract was washed with a saturated saline together with the organic layer, and the organic layer was then dried over magnesium sulfate. The mixture was subjected to gravity filtration, and the obtained filtrate was concentrated to give a solid. The obtained solid was refined with silica gel column chromatography (chloroform:ethyl acetate=2:1), so that 2.8 g of a target substance, yellow powder was obtained in a yield of 71%.

(iii) Synthesis of 5,6-bis(4-bromophenyl)-2,3'-bipyridine

A synthetic scheme of 5,6-bis(4-bromophenyl)-2,3'-bipyridine is shown in (C-3).

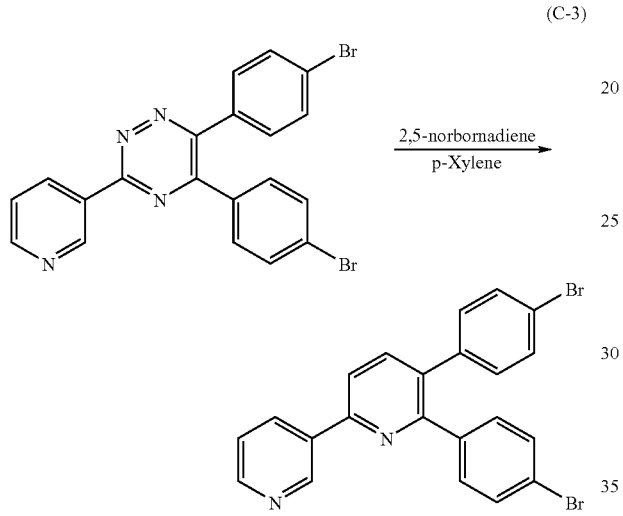

Into a 200 mL three-neck recovery flask, 2.4 g (5.0 mmol) of 5,6-bis(4-bromophenyl)-3-(3-pyridyl)-1,2,4-triazine, 60 mL of para-xylene, and 2.5 mL (23 mmol) of 2,5-Norbornadiene were put. This solution was refluxed at 150° C. for 20 hours under a nitrogen stream. After a certain time, water was added to the mixture, and an aqueous layer was extracted with toluene. The obtained extract was washed with a saturated saline together with an organic layer and the organic layer was dried over magnesium sulfate. The mixture was subjected to gravity filtration, and the obtained filtrate was concentrated to give a solid. The obtained solid was refined with silica gel column chromatography (hexane:ethyl acetate=1:1) and recrystallized with chloroform/hexane, so that an objective substance, 0.68 g of yellow powder was obtained in a yield of 28%.

This compound was measured with a nuclear magnetic resonance (NMR) measurement, and the measurement showed that the obtained compound was 5,6-bis(4-bromophenyl)-2,3'-bipyridine The $^1$H NMR data is shown below.

$^1$H NMR (300 MHz, CDCl$_3$): δ(ppm)=7.10 (d, J=8.1 Hz, 2H), 7.31-7.48 (m, 7H), 7.81 (d, J=1.8 Hz, 2H), 8.45 (d, J=7.8 Hz, 1H), 8.68 (dd, J=5.1, 2.1 Hz, 1H), 9.31 (d, J=2.1 Hz, 1H).

Figure 20A:
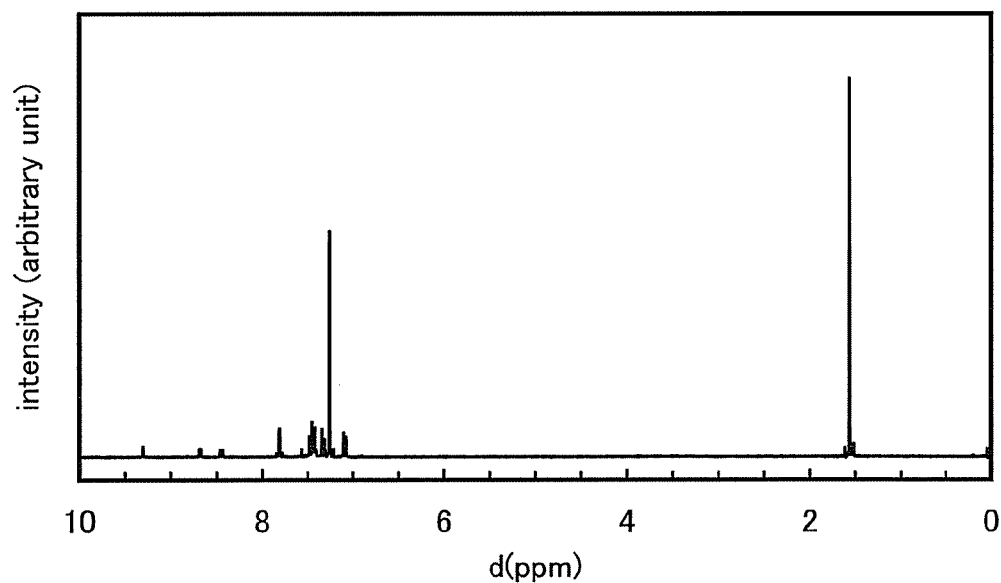
FIGS. 20A and 20B are $^1$H NMR charts of 5,6-bis(4-bromophenyl)-2,3'-bipyridine.
Figure 20B:
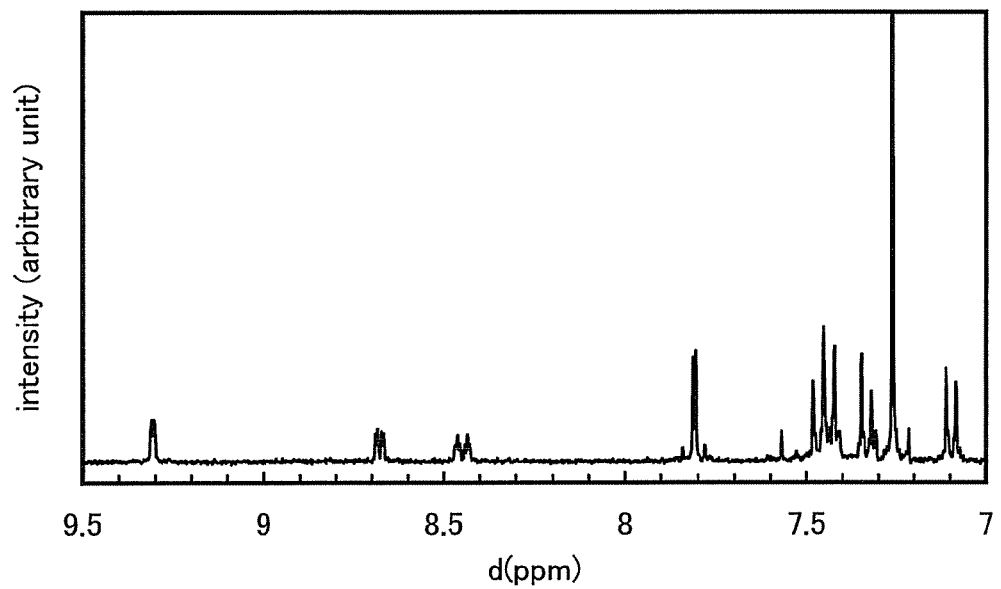

In addition, FIGS. 20A and 20B show a $^1$H NMR chart. Note that FIG. 20B is a chart showing an enlarged part of FIG. 20A in the range of 7.0 ppm to 9.5 ppm.

[Step 2: Synthesis of 2,2'-[2,3'-bipyridine-5,6-diylbis(biphenyl-4,4'-diyl)]bisbenzoxazole (abbreviation: BOxP2BPy (3))]

A synthesis scheme of BOxP2BPy(3) is shown in (C-4).

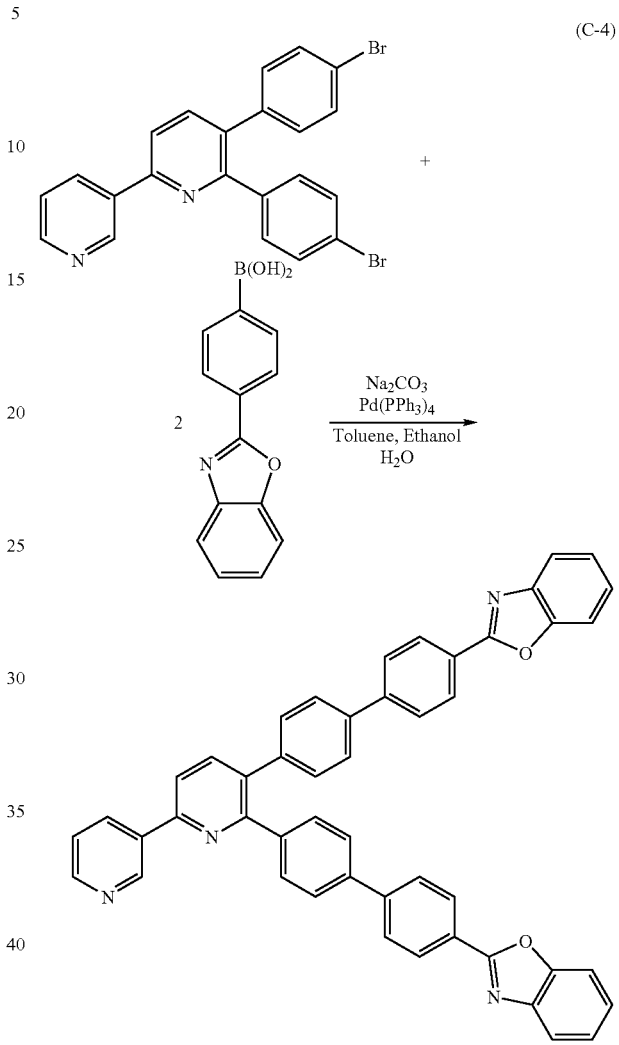

In a 100 mL three-neck flask, 0.80 g (1.7 mmol) of 5,6-bis (4-bromophenyl)-2,3'-bipyridine, 0.84 g (7.9 mmol) of sodium carbonate, 0.77 g (3.3 mmol) of 4-(benzoxazol-2-yl) phenylboronic acid, 20 mL of toluene, 4.0 mL of ethanol, and 5.0 mL of water were put. The mixture was degassed by being stirred under reduced pressure, and the atmosphere in the flask was substituted by nitrogen. After that, 78 mg (0.067 mmol) of tetrakis(triphenylphosphine)palladium(0) was added. This reaction mixture was stirred at 80° C. for 4 hours under a nitrogen stream. After a certain time, water was added to the mixture, and an aqueous layer was extracted with chloroform. The obtained extract was washed with a saturated saline together with an organic layer and the organic layer was dried over magnesium sulfate. The resulting mixture was subjected to gravity filtration, and the obtained filtrate was concentrated to give a solid. The obtained solid was refined with silica gel column chromatography (ethyl acetate:toluene=2:1) and recrystallized with toluene/hexane, so that 0.44 g of a target substance, white powder was obtained in a yield of 36%.

Then, 0.45 g of the obtained product was subjected to sublimation purification at 370° C. under an argon stream (flow rate: 3.0 mL/min) at a pressure of 10 Pa for 17 hours; thus, 0.17 g of a target compound was recovered in a yield of 37%. This compound was measured with a nuclear magnetic resonance (NMR) measurement, and the measurement showed that the obtained compound was 2,2'-[2,3'-bipyridine-5,6-diylbis(biphenyl-4,4'-diyl)]bisbenzoxazole (abbreviation: BOxP2BPy(3)).

The $^1$H NMR data is shown below.

$^1$H NMR (300 MHz, CDCl$_3$): δ(ppm)=7.35-7.45 (m, 7H), 7.59-7.69 (m, 8H), 7.78-7.92 (m, 8H), 8.31-8.36 (m, 4H), 8.52 (d, J=8.4 Hz, 1H), 8.70 (dd, J=4.8, 1.5 Hz, 1H), 9.37 (d, J=2.4 Hz, 1H).

Figure 21A:
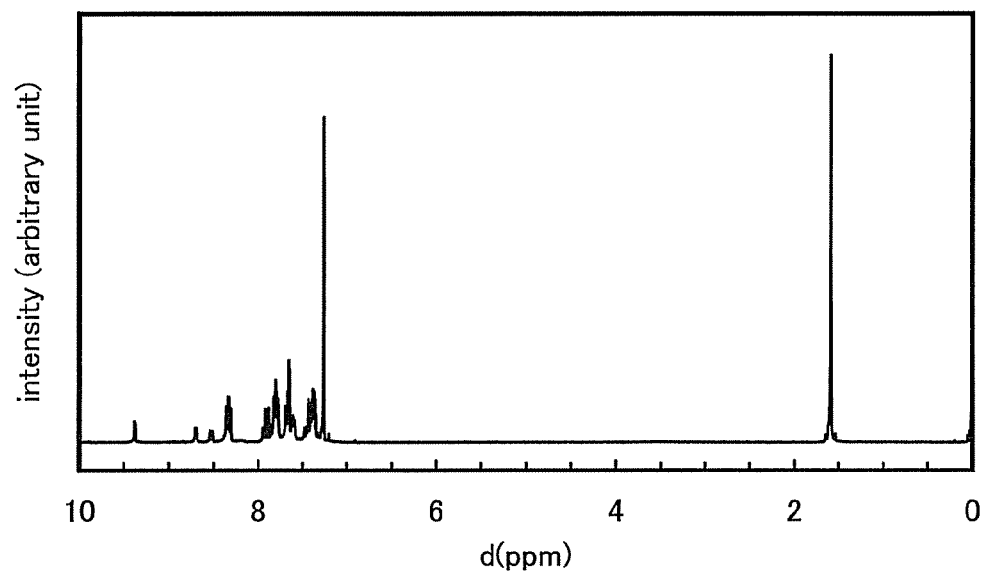
FIGS. 21A and 21B are $^1$H NMR charts of 2,2'-[2,3'-bipyridine-5,6-diylbis(biphenyl-4,4'-diyl)]bisbenzoxazole (abbreviation: BOxP2BPy(3))
Figure 21B:
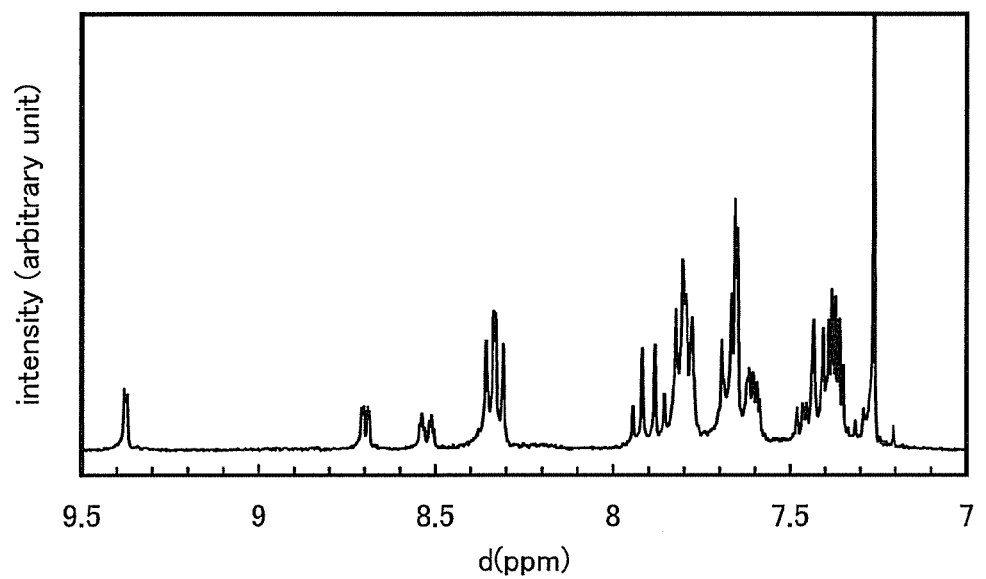

$^1$H NMR charts are shown in FIGS. 21A and 21B. Note that FIG. 21B is a chart of an enlarged part of the range of 7.0 ppm to 9.5 ppm in FIG. 21A.

Figure 22:
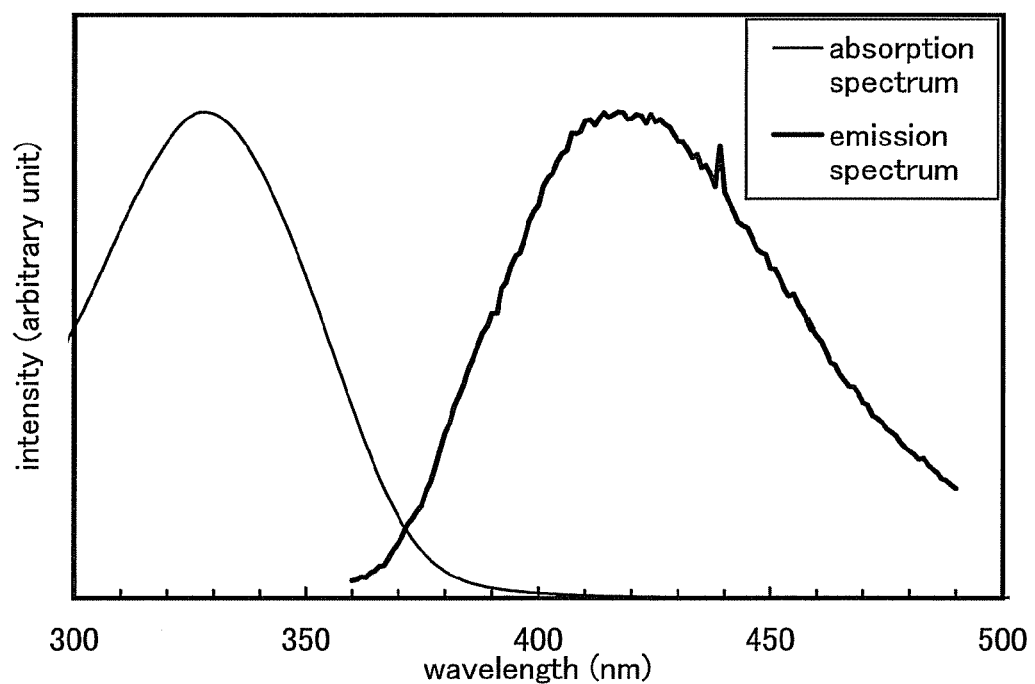
FIG. 22 is a graph showing an absorption spectrum and an emission spectrum of 2,2'-[2,3'-bipyridine-5,6-diylbis(biphenyl-4,4'-diyl)]bisbenzoxazole (abbreviation: BOxP2BPy(3)) in a toluene solution.

FIG. 22 shows an absorption spectrum and an emission spectrum of a toluene solution of BOxP2BPy(3). An ultraviolet-visible spectrophotometer (V-550, manufactured by JASCO Corporation) was used for the measurement. The solution was put into a quartz cell, and the absorption spectrum from which the absorption spectrum of the quartz cell was subtracted is shown. In FIG. 22, the horizontal axis represents a wavelength (nm) and the vertical axis represents intensity (arbitrary unit). Absorption was observed around 328 nm in the case of toluene solution. In addition, in the case of the toluene solution, the maximum emission wavelength was 417 nm (excitation wavelength: 334 nm).

Figure 23:
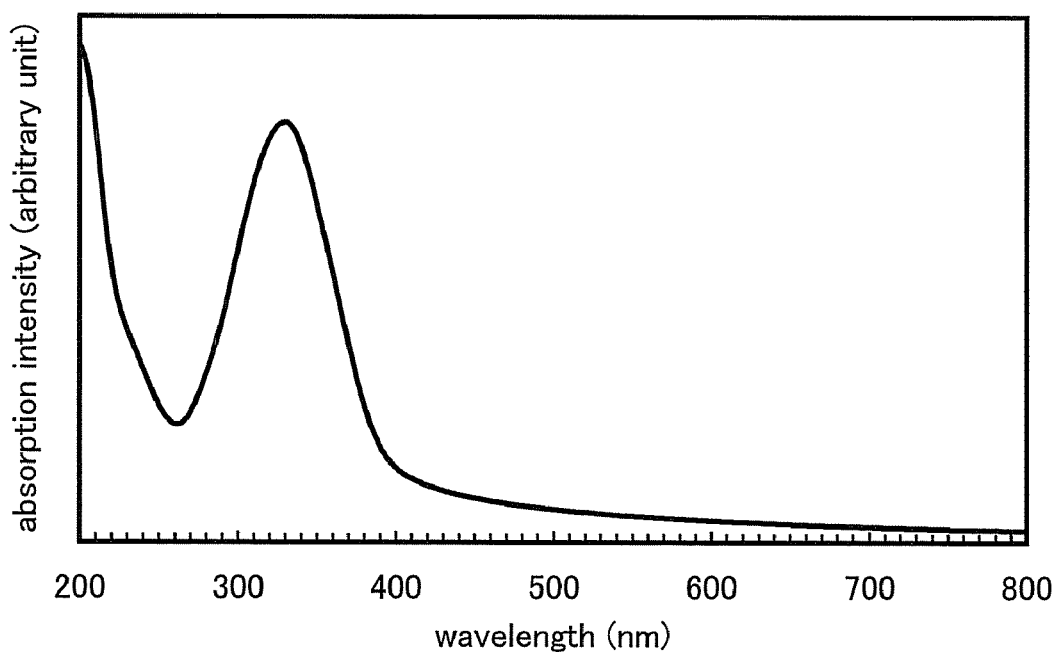
FIG. 23 is a graph showing an absorption spectrum of 2,2'-[2,3'-bipyridine-5,6-diylbis(biphenyl-4,4'-diyl)]bisbenzoxazole (abbreviation: BOxP2BPy(3)) in a thin film state.
Figure 24:
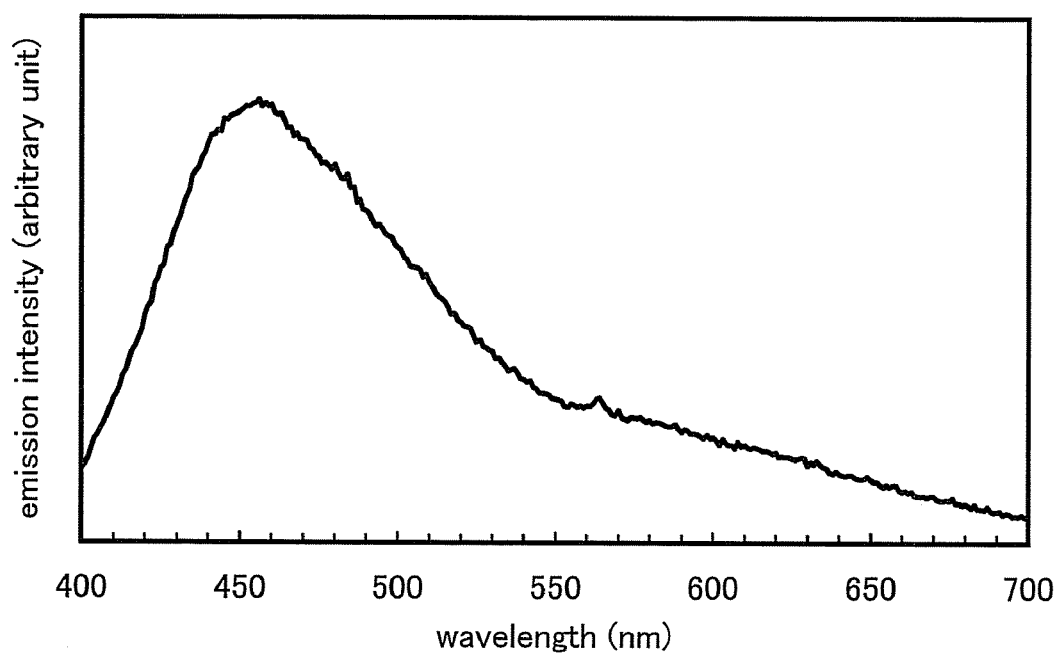
FIG. 24 is a graph showing an emission spectrum of 2,2'-[2,3'-bipyridine-5,6-diylbis(biphenyl-4,4'-diyl)]bisbenzoxazole (abbreviation: BOxP2BPy(3)) in a thin film state.

FIG. 23 shows an absorption spectrum of a thin film of BOxP2BPy(3) and FIG. 24 shows an emission spectrum of the thin film of BOxP2BPy(3). An ultraviolet-visible spectrophotometer (V-550, manufactured by JASCO Corporation) was used for the measurement. A thin film sample was formed by evaporation on a quartz substrate, and the absorption spectrum from which the absorption spectrum of the quartz substrate was subtracted is shown. In FIG. 23, the horizontal axis represents wavelength (nm) and the vertical axis represents absorption intensity (arbitrary Unit). In FIG. 24, the horizontal axis represents a wavelength (nm) and the vertical axis represents an emission intensity (arbitrary Unit). Absorption was observed around 329 nm in the case of the thin film. In addition, in the case of the thin film, the maximum emission wavelength was 454 nm (excitation wavelength: 336 nm).

Moreover, the result for the ionized potential of a thin film form of BOxP2BPy(3) measured by a photoelectron spectrometer (AC-2 photoelectron spectrometer manufactured by Riken Keiki, Co., Ltd.) in the air was 5.85 eV. As a result, the HOMO level was found to be −5.85 eV. Furthermore, with the use of the absorption spectrum data of the thin film of BOxP2BPy(3), the absorption edge was obtained by a Tauc plot assuming direct transition. The absorption edge was estimated as an optical energy gap, whereby the energy gap was 3.31 eV The LUMO level was calculated from the obtained value of the energy gap and the HOMO level, which was −2.54V.

Further, the oxidation-reduction reaction characteristics of BOxP2BPy(3) were measured. The oxidation-reduction characteristics were measured by cyclic voltammetry (CV) measurement. Further, an electrochemical analyzer (ALS model 600A, BAS Inc.) was used for the measurement.

The solution for the CV measurement was prepared as follows: tetra-n-butylammonium perchlorate (n-Bu$_4$NClO$_4$) (produced by Tokyo Chemical Industry Co., Ltd., Catalog No. T0836) used as a supporting electrolyte is dissolved at a concentration of 100 mmol/L in dehydrated dimethylformamide (DMF) (produced by Sigma-Aldrich Corp., 99.8%, Catalog No. 22705-6) used as a solvent. BOxP2BPy(3) that was a measurement object was further dissolved at a concentration of 0.6 mmol/L therein. A platinum electrode (manufactured by BAS Inc., PTE platinum electrode) was used as a working electrode, a platinum electrode (manufactured by BAS Inc., Pt counter electrode for VC-3, (5 cm)) was used as an auxiliary electrode, and an Ag/Ag+ electrode (manufactured by BAS Inc., RE-5 reference electrode for nonaqueous solvent) was used as a reference electrode. The measurement was carried out at room temperature.

Oxidation reaction characteristics of BOxP2BPy(3) were examined as follows. A scan, in which a potential of the working electrode with respect to the reference electrode was varied from −0.16 V to 1.50 V and then from 1.50 V to −0.16 V, was set to one cycle, and measurement was performed 100 cycles. Reduction reaction characteristics of BOxP2BPy(3) were examined as follows. A scan, in which a potential of the working electrode with respect to the reference electrode was varied from −0.69 V to −2.70 V and then from −2.70 V to −0.69 V, was set to one cycle, and measurement was performed 100 cycles. Further, the scanning speed of the CV measurement was set to be 0.1 V/s.

Figure 25:
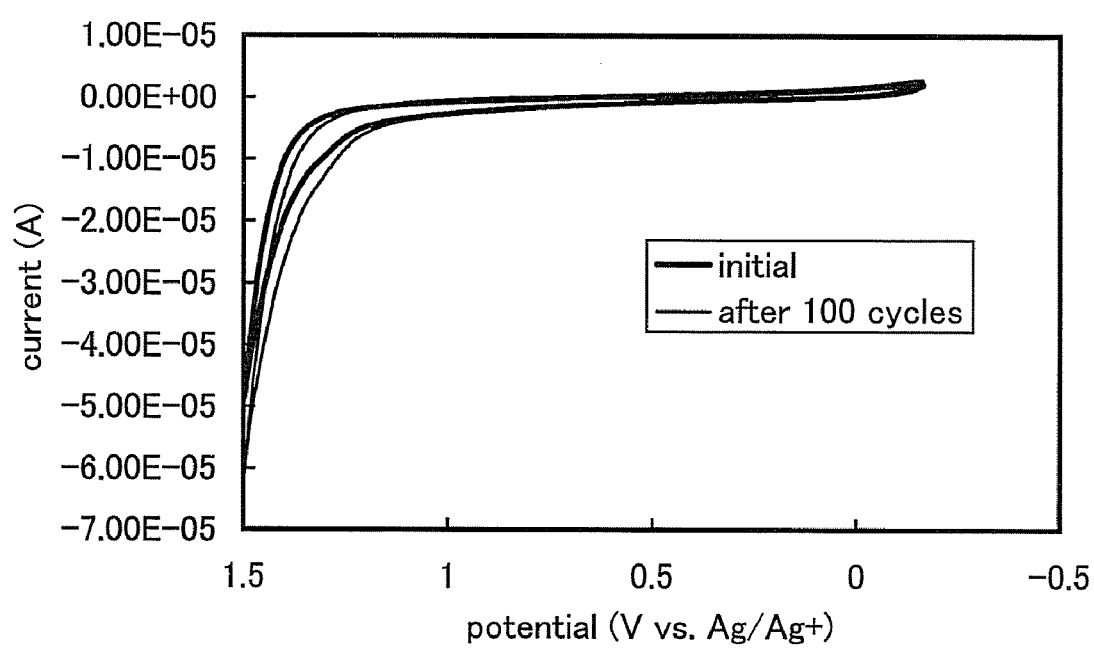
FIG. 25 is a graph showing CV measurement results of 2,2'-[2,3'-bipyridine-5,6-diylbis(biphenyl-4,4'-diyl)]bisbenzoxazole (abbreviation: BOxP2BPy(3))
Figure 26:
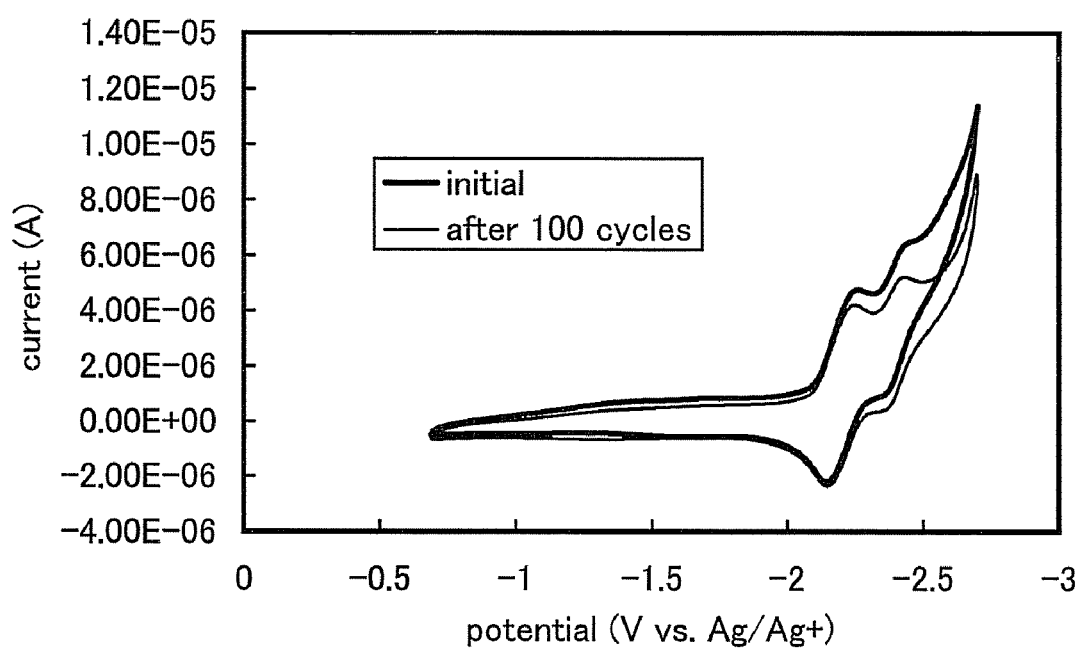
FIG. 26 is a graph showing CV measurement results of 2,2'-[2,3'-bipyridine-5,6-diylbis(biphenyl-4,4'-diyl)]bisbenzoxazole (abbreviation: BOxP2BPy(3))

FIGS. 25 and 26 show CV measurement results of oxidation characteristics and reduction characteristics of BOxP2BPy(3), respectively. In each of FIGS. 25 and 26, the horizontal axis indicates a potential (V) of the working electrode with respect to the reference electrode, and the vertical axis indicates a current value (A) flowing between the working electrode and the auxiliary electrode. A current for oxidation was not observed in FIG. 25, but a current for reduction was observed at around −2.26 V (vs. Ag/Ag$^+$ electrode) in FIG. 26.

In spite of the fact that 100 cycles of scanning were conducted repeatedly, a peak position and a peak intensity at the CV curve scarcely changed in the reduction. This elucidates BOxP2BPy(3) that is a benzoxazole derivative of the present invention is extremely stable in repetition of reduction reaction.

EXAMPLE 3

Example 3 will describe a synthesis method of 2,2'-[2,4'-bipyridine-5,6-diylbis(biphenyl-4,4'-diyl)]bisbenzoxazole (abbreviation: BOxP2BPy(4)) represented by the structural formula (103).

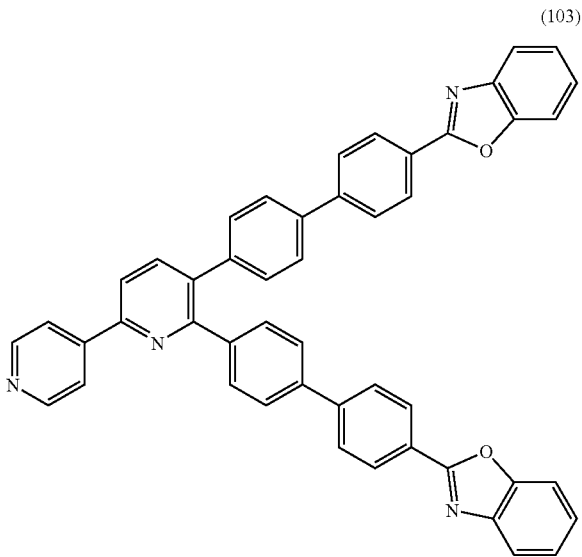

[Step 1: Synthesis of 5,6-bis(4-bromophenyl)-2,4'-bipyridine]

(i) Synthesis of pyridine-4-carboxyamidrazone

A synthesis scheme of pyridine-4-carboxyamidrazone is shown in (D-1).

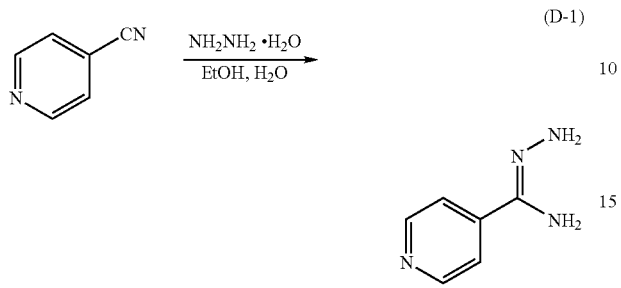

In a 50 mL recovery flask, 1.0 g (9.9 mmol) of 4-cyanopyridine, 2.0 mL of ethanol, 7.0 mL of water, and 5.5 mL (0.11 mol) of hydrazine monohydrate were put. This solution was stirred at room temperature for 26 hours under a nitrogen stream. After a certain time, water was added to the solution. This solution was extracted with chloroform, and the extract was dried with magnesium sulfate. The mixture was subjected to gravity filtration, and the obtained filtrate was concentrated to give 0.67 g of a target substance, yellow powder in a yield of 50%.

(ii) Synthesis of 5,6-bis(4-bromophenyl)-3-(4-pyridyl)-1,2,4-triazine

A synthesis scheme of 5,6-bis(4-bromophenyl)-3-(4-pyridyl)-1,2,4-triazine is shown in (D-2).

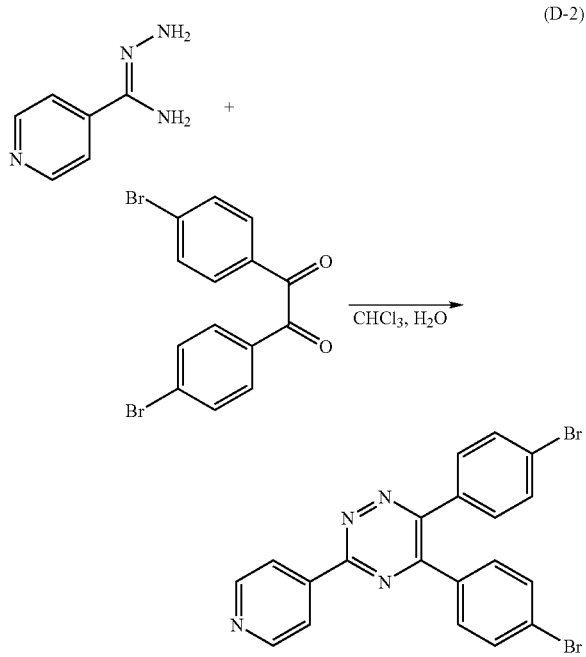

Into a 300 mL three-neck flask were put 1.2 g (8.5 mmol) of pyridine-4-carboxyamidrazone, 3.2 g (8.8 mmol) of 4,4'-dibromobenzil, 100 mL of chloroform and 10 mL of water. The mixture was stirred for 4 hours under a nitrogen stream. After a certain time, water was added to the obtained mixture, and an aqueous layer was extracted with chloroform. The obtained extract combined with the organic layer was washed with a saturated saline, and the organic layer was dried with magnesium sulfate. The mixture was subjected to gravity filtration, and the obtained filtrate was concentrated to give a solid. The obtained solid was refined with silica gel column chromatography (chloroform: ethyl acetate=10:1), so that 2.2 g of a target substance, yellow powder was obtained in a yield of 52%.

(iii) Synthesis of 5,6-bis(4-bromophenyl)-2,4'-bipyridine

A synthesis scheme of 5,6-bis(4-bromophenyl)-2,4'-bipyridine is shown in (D-3).

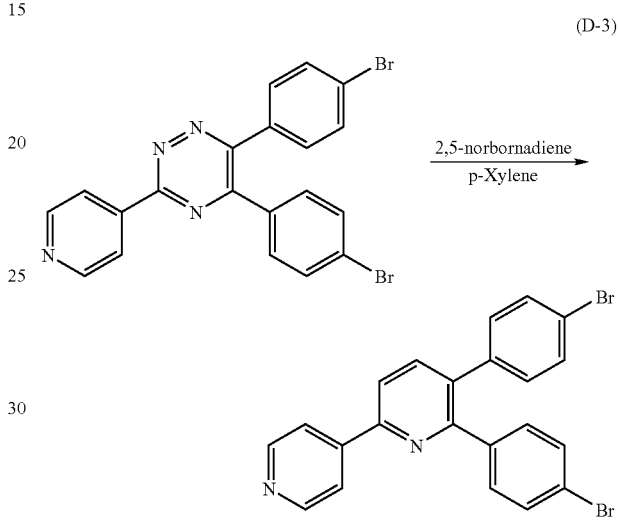

Into a 100 mL three-neck flask, 2.2 g (4.7 mmol) of 5,6-bis(4-bromophenyl)-3-(4-pyridyl)-1,2,4-triazine, 45 mL of para-xylene, 2.5 mL (23 mmol) of 2,5-Norbornadiene were put, and the solution was stirred at 140° C. for 14 hours under a nitrogen stream. After a certain time, water was added to the solution, and an aqueous layer was extracted with chloroform. The obtained extract was washed with a saturated saline together with the organic layer and then dried over magnesium sulfate. The obtained mixture was subjected to gravity filtration, and the obtained filtrate was concentrated to give a solid. The obtained solid was refined with silica gel column chromatography (hexane:ethyl acetate=2:1), so that 1.7 g of a target substance, yellow powder was obtained in a yield of 78%.

This compound was measured with a nuclear magnetic resonance (NMR) measurement, and the measurement showed that the obtained compound was 5,6-bis(4-bromophenyl)-2,4'-bipyridine.

$^1$H NMR data and $^{13}$C NMR data are shown below.

$^1$H NMR (300 MHz, CDCl$_3$): δ(ppm)=7.09 (d, J=8.7 Hz, 2H), 7.33 (d, J=8.4 Hz, 2H), 7.43-7.48 (m, 4H), 7.80-7.88 (m, 2H), 8.01 (d, J=6.3 Hz, 2H), 8.75 (d, J=5.7 Hz, 2H).

$^{13}$C NMR (75 MHz, CDCl$_3$): δ(ppm)=119.21, 120.97, 122.14, 122.85, 130.97, 131.30, 131.64, 131.87, 134.91, 138.01, 138.43, 139.60, 145.63, 150.48, 153.29, 155.86

Figure 27A:
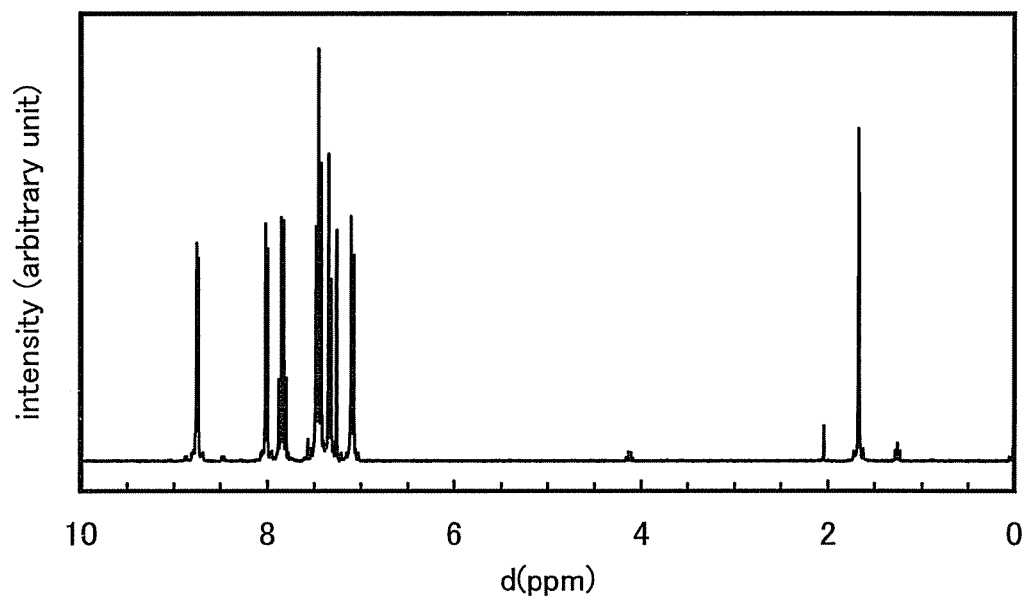
FIGS. 27A and 27B are $^1$H NMR charts of 5,6-bis(4-bromophenyl)-2,4'-bipyridine.
Figure 27B:
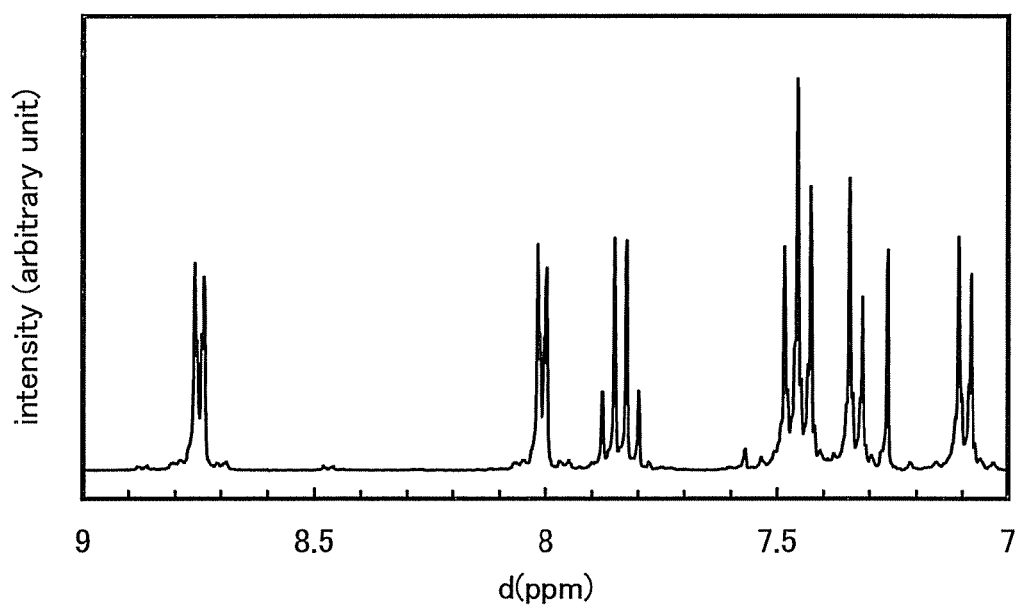
Figure 28A:
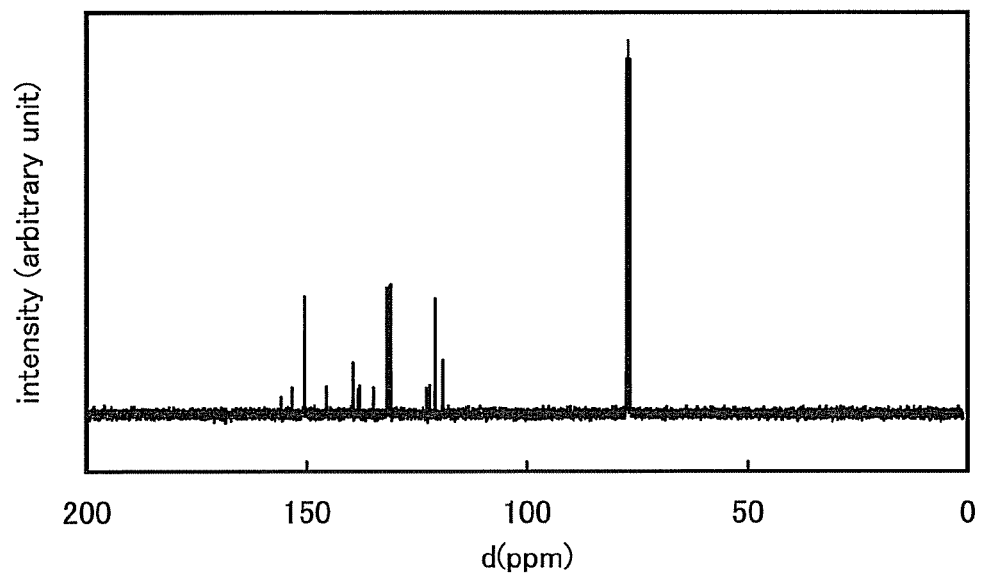
FIGS. 28A and 28B are $^{13}$C NMR charts of 5,6-bis(4-bromophenyl)-2,4'-bipyridine.
Figure 28B:
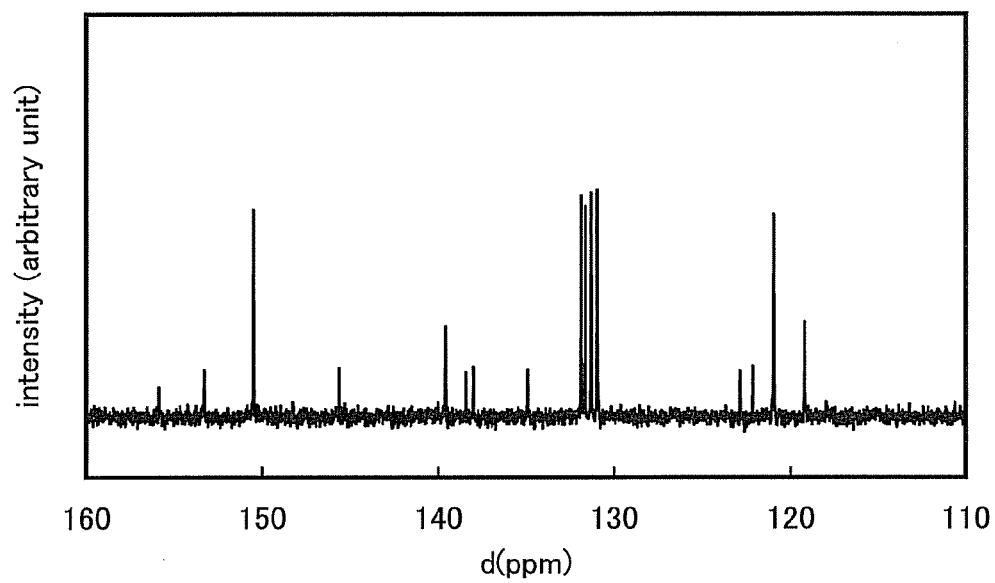

FIGS. 27A and 27B show $^1$H NMR chart. Note that FIG. 27B is a chart showing an enlarged part of FIG. 27A in the range of 7.0 ppm to 9.0 ppm. FIGS. 28A and 28B show a $^{13}$C NMR chart. Further, FIG. 28B is a chart showing an enlarged part in the range of 110 ppm to 160 ppm of FIG. 28A.

[Step 2: Synthesis of 2,2'-[2,4'-bipyridine-5,6-diylbis(biphenyl-4,4'-diyl)]bisbenzoxazole (Abbreviation: BOxP2BPy (4))]

A synthesis scheme of BOxP2BPy(4) is shown in (D-4).

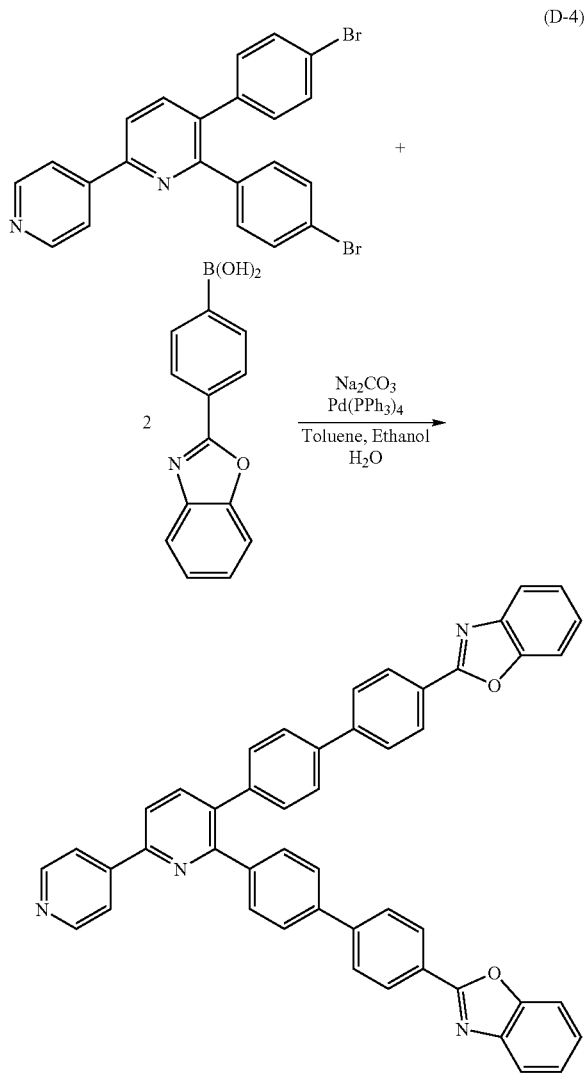

Into a 100 mL three-neck flask, 0.83 g (1.8 mmol) of 5,6-bis(4-bromophenyl)-2,4'-bipyridine, 0.82 g (7.7 mmol) of carbonate sodium, 0.81 g (3.4 mmol) of phenylboronic acid, 20 mL of toluene, 4.0 mL of ethanol, and 10 mL of water were put. The mixture was degassed by being stirred under reduced pressure, and the atmosphere in the flask was substituted by nitrogen. 82 mg (0.071 mmol) of tetrakis(triphenylphosphine)palladium(0) was added to this mixture, and stirred at 80 C.° for 12 hours under a nitrogen stream. After a certain time, the mixture was cooled to room temperature, and the precipitated solid was recovered by suction filtration. The obtained solid was dissolved in chloroform, and washed with water and a saturated saline, and the organic layer was dried over magnesium sulfate. The obtained mixture was subjected to gravity filtration, and the obtained filtrate was concentrated to give a solid. A toluene solution containing the obtained solid was dissolved in ethyl acetate, and the solution was subjected to suction filtration through Celite (produced by Wako Pure Chemical Industries, Ltd., Catalog No. 531-16855). The filtrate was condensed to give a solid. The obtained solid was recrystallized with toluene/hexane, so that an objective substance, 0.69 g of white powder was obtained in a yield of 55%.

Then, 0.66 g of the obtained product was subjected to sublimation purification at 360° C. under an argon stream (flow rate: 3.0 mL/min) at a pressure of 10 Pa for 7 hours; thus, 0.36 g of a target compound was recovered in a yield of 54%. This compound was measured with a nuclear magnetic resonance (NMR) measurement, and the measurement showed that the obtained compound was 2,2'-[2,4'-bipyridine-5,6-diylbis(biphenyl-4,4'-diyl)]bisbenzoxazole (Abbreviation: BOxP2BPy(4)).

The $^1$H NMR data is shown below.

$^1$H NMR (300 MHz, CDCl$_3$): δ(ppm)=7.35-7.43 (m, 6H), 7.59-7.69 (m, 8H), 7.77-7.82 (m, 6H), 7.93 (d, J=4.5 Hz, 2H), 8.08 (d, J=4.2 Hz, 2H), 8.31-8.35 (m, 4H), 8.78 (d, J=4.2 Hz, 2H).

Figure 29A:
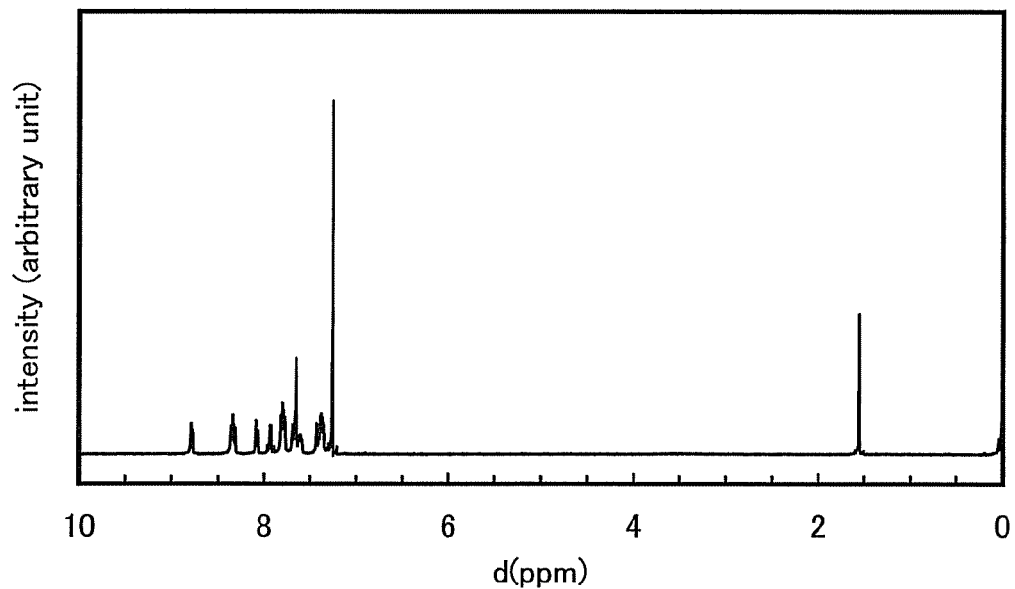
FIGS. 29A and 29B are $^1$H NMR charts of 2,2v-[2,4'-bipyridine-5,6-diylbis(biphenyl-4,4-v-diyl)]bisbenzoxazole (abbreviation: BOxP2BPy(4))
Figure 29B:
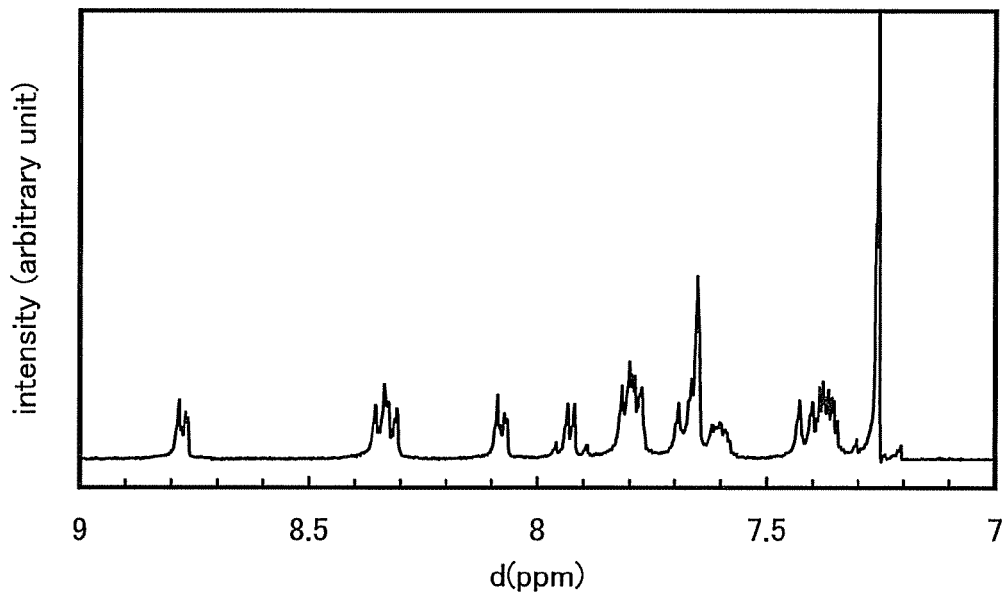

FIGS. 29A and 29B show $^1$H NMR charts. Note that FIG. 29B is a chart of an enlarged part of the range of 7.0 ppm to 9.0 ppm in FIG. 29A.

Figure 30:
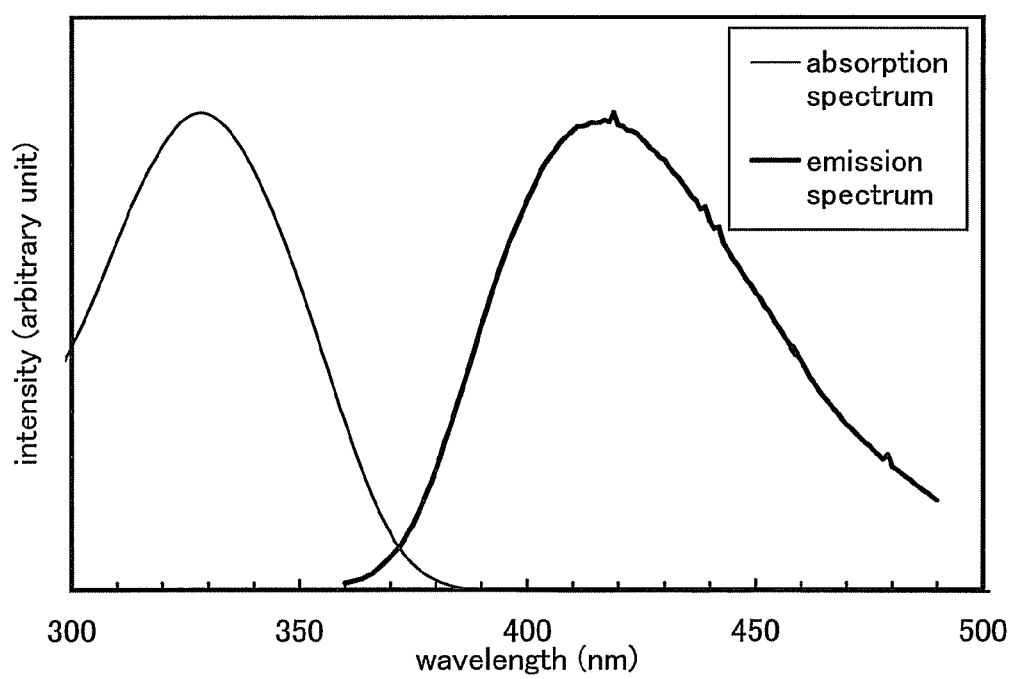
FIG. 30 is a graph showing an absorption spectrum and an emission spectrum of 2,2'-[2,4'-bipyridine-5,6-diylbis(biphenyl-4,4'-diyl)]bisbenzoxazole (abbreviation: BOxP2BPy(4)) in a toluene solution.

FIG. 30 shows an absorption spectrum and an emission spectrum in a toluene solution of BOxP2BPy(4). An ultraviolet-visible spectrophotometer (V-550, manufactured by JASCO Corporation) was used for the measurement. The solution was put into a quartz cell, and the absorption spectrum from which the absorption spectrum of the quartz cell was subtracted is shown. In FIG. 30, the horizontal axis represents a wavelength (nm) and the longitudinal axis represents an intensity (arbitrary unit). In addition, in the case of the toluene solution, absorption was observed around 328 nm, and the maximum emission wavelength was 418 nm (excitation wavelength: 330 nm).

Figure 31:
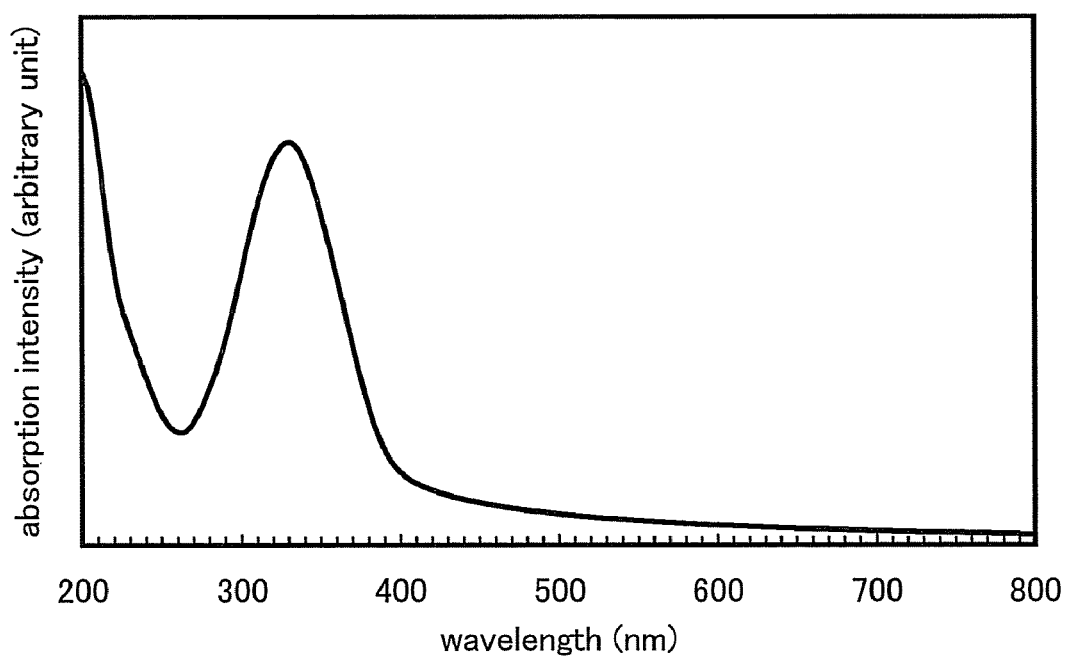
FIG. 31 is a graph showing an absorption spectrum of 2,2'-[2,4'-bipyridine-5,6-diylbis(biphenyl-4,4'-diyl)]bisbenzoxazole (abbreviation: BOxP2BPy(4)) in a thin film state.
Figure 32:
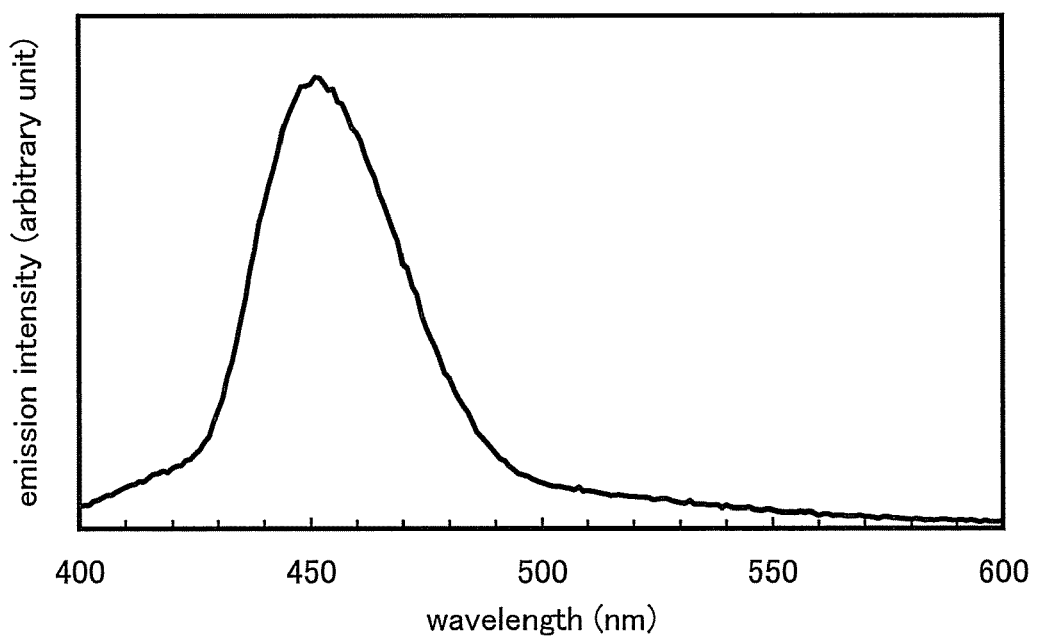
FIG. 32 is a graph showing an emission spectrum of 2,2'-[2,4'-bipyridine-5,6-diylbis(biphenyl-4,4'-diyl)]bisbenzoxazole (abbreviation: BOxP2BPy(4)) in a thin film state.

FIGS. 31 and 32 show an absorption spectrum in a thin film state and an emission spectrum in a thin film state of BOxP2BPy(4). An ultraviolet-visible spectrophotometer (V-550, manufactured by JASCO Corporation) was used for the measurement. Thin film samples were each formed by evaporation on a quartz substrate, and the absorption spectrum from which the absorption spectrum of the quartz substrate was subtracted is shown. In FIG. 31, the horizontal axis indicates a wavelength (nm) and the vertical axis indicates an absorption intensity (arbitrary unit). In FIG. 32, the horizontal axis indicates a wavelength (nm) and the vertical axis indicates an emission intensity (arbitrary unit). In the case of the thin film, absorption was observed around 330 nm. In addition, in the case of the thin film, the maximum emission wavelength was 451 nm (excitation wavelength: 332 nm).

The ionizing potential of the thin film of BOxP2BPy(4) was measured using a photoelectron spectrometer (AC-2, manufactured by Riken Keiki Co., Ltd) in the air and accordingly found to be 5.92 eV. As a result, it was found that the HOMO level was −5.92 eV. The absorption edge was obtained by tauc plot assuming direct transition with the absorption spectrum data of a thin film of BOxP2BPy(4). When the absorption edge was estimated as an optical energy gap, the energy gap was 3.29 eV. Therefore, a LUMO level of −2.63 eV was obtained from the obtained values of the energy gap value and HOMO level.

EXAMPLE 4

Example 4 will describe a synthesis method of 2,2'-[2-(bipyridin-2-yl)pyridine-5,6-diylbis(biphenyl-4,4'-diyl)]bisbenzoxazole represented by a structural formula (104) (abbreviation: BOxP2PyPm).

(104)

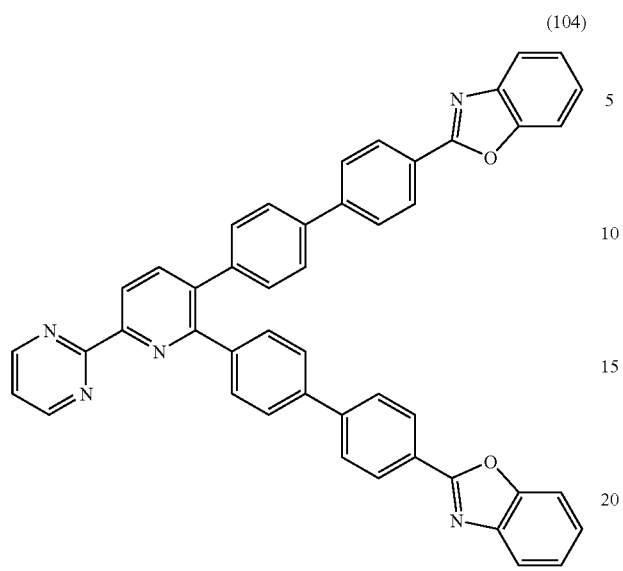

[Step 1: Synthesis of 2-[5,6-bis(4-bromophenyl)-2-pyridyl]pyrimidine]

(i) Synthesis of pyridine-2-carboxyamidrazone

A synthesis scheme of pyridine-2-carboxyamidrazone is shown in (E-1).

(E-1)

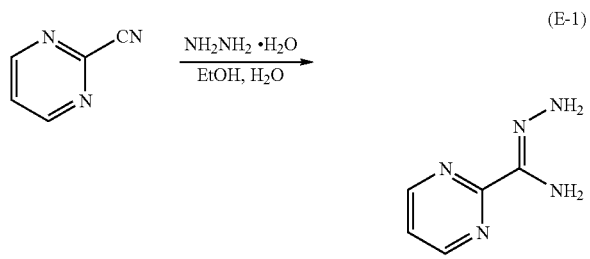

In a 50 mL recovery flask were placed 3.2 g (3.0 mmol) of 2-cyanopyridine, 15 mL of ethanol, 5.0 mL of water, and 2.0 mL (41 mmol) of hydrazine monohydrate. This solution was stirred at room temperature for 26 hours under a nitrogen stream. After a certain time, a saturated saline was added to the solution. This solution was extracted with chloroform, and the extract was dried with magnesium sulfate. The mixture was subjected to gravity filtration, and the obtained filtrate was concentrated to give 1.7 g of a target substance, yellow oily substance in a yield of 40%.

(ii) Synthesis of 5,6-bis(4-bromophenyl)-3-(pyrimidin-2-yl)-1,2,4-triazine

A synthesis scheme of 5,6-bis(4-bromophenyl)-3-(pyrimidin-2-yl)-1,2,4-triazine is shown in (E-2).

(E-2)

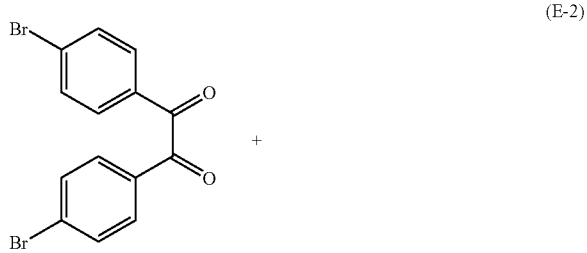

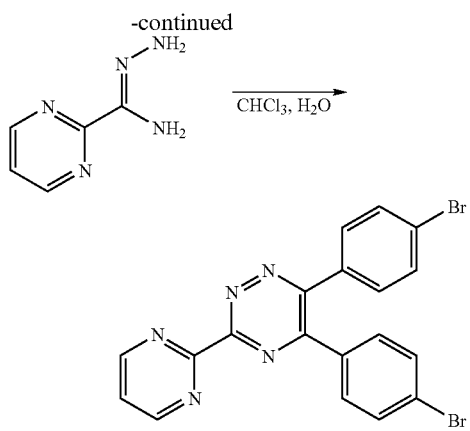

In a 200 mL three-neck flask were put 4.4 g (12 mmol) of 4,4-dibromobenzil, 1.7 g (12 mmol) of pyrimidine-2-carboxyamidrazone, 100 mL of chloroform and 5.0 mL of water. This solution was refluxed at room temperature for 14 hours under a nitrogen stream. After a certain time, water was added to the mixture, and an aqueous layer was extracted with chloroform. The obtained extract combined with the organic layer was washed with a saturated saline, and the organic layer was dried with magnesium sulfate. The mixture was subjected to gravity filtration, and the obtained filtrate was concentrated to give a solid. The obtained solid was refined with silica gel column chromatography (chloroform:ethyl acetate=1:1), so that 4.1 g of a target substance, yellow powder was obtained in a yield of 73%.

(iii) Synthesis of 2-[5,6-bis(4-bromophenyl)-2-pyridyl]pyrimidine

A synthesis scheme of 2-[5,6-bis(4-bromophenyl)-2-pyridyl]pyrimidine is shown in (E-3).

(E-3)

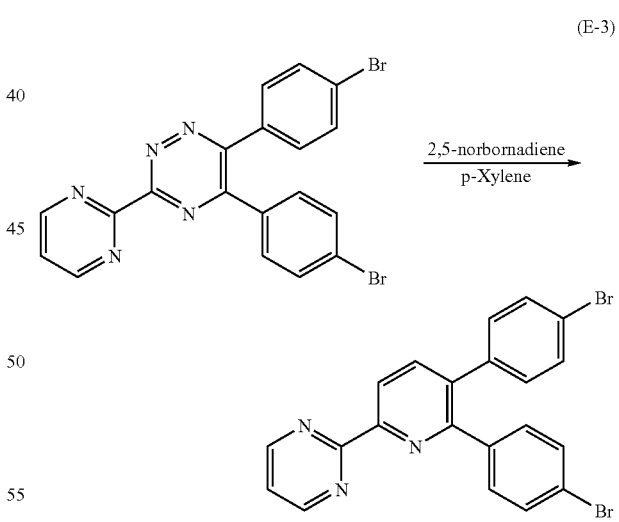

In a 200 mL three-neck flask were put 2.4 g (5.0 mmol) of 5,6-bis(4-bromophenyl)-3-(pyrimidin-2-yl)-1,2,4-triazine, 60 mL of para-xylene, 2.1 mL (19 mmol) of 2,5-Norbornadiene, and the mixture was refluxed under a nitrogen gas stream at 150° C. for 12 hours. After a certain time, water was added to the mixture, and an aqueous layer was extracted with toluene. The extract was washed with a saturated saline together with the organic layer, and the organic layer was then dried over magnesium sulfate. The mixture was subjected to gravity filtration, and the obtained filtrate was concentrated to give a solid. The obtained solid was recrystallized with chloroform/hexane, so that 1.6 g of a target substance, light-yellow solid was obtained in a yield of 67%.

This compound was measured with a nuclear magnetic resonance (NMR) measurement, and the measurement showed that the obtained compound was 2-[5,6-bis(4-bromophenyl)-2-pyridyl]pyrimidine.

The $^1$H NMR data is shown below.

$^1$H NMR (300 MHz, CDCl$_3$): δ(ppm)=7.10 (d, J=8.4 Hz, 2H), 7.27-7.47 (m, 7H), 7.87 (d, J=8.1 Hz, 1H), 8.53 (d, J=7.8 Hz, 1H), 8.95 (d, J=4.5 Hz, 2H)

Figure 33A:
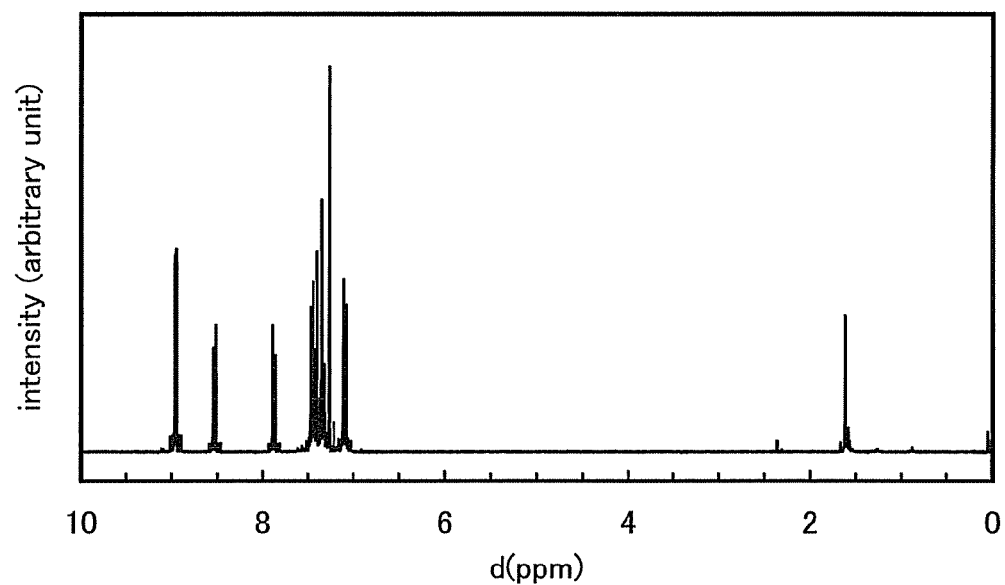
FIGS. 33A and 33B are $^1$H NMR charts of 2-[5,6-bis(4-bromophenyl)-2-pyridyl]pyrimidine.
Figure 33B:
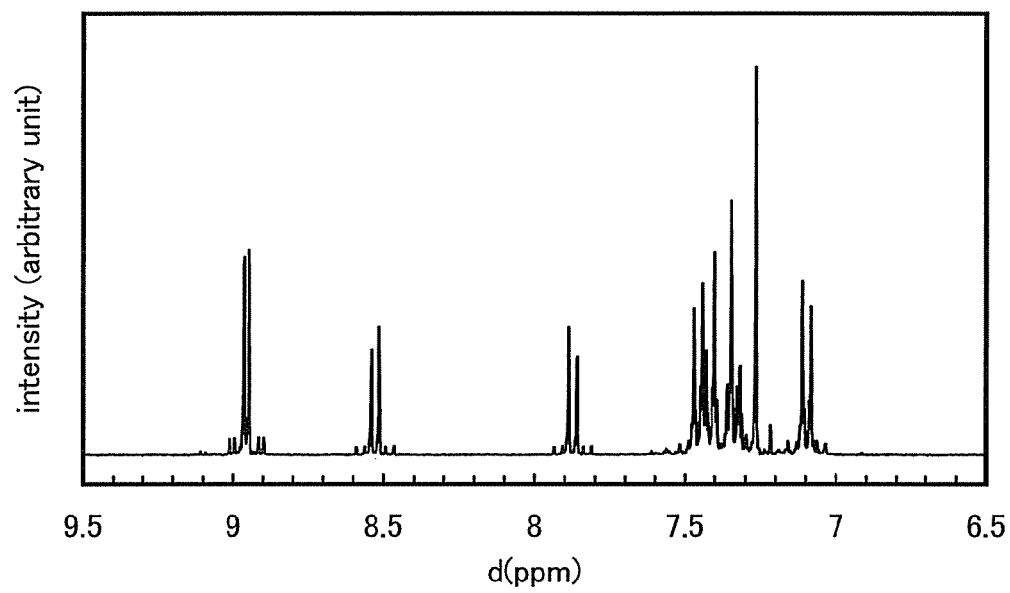

FIGS. 33A and 33B show $^1$H NMR charts. Note that FIG. 33B is a chart of an enlarged part of FIG. 33A showing the range from 6.5 ppm to 9.5 ppm.

[Step 2: 2,2'-[2-bipyridin-2-yl]pyridine-5,6-diylbis(biphenyl-4,4'-diyl)]bisbenzoxazole (Abbreviation: BOxP2PyPm)]

A synthesis scheme of BOxP2PyPm is shown in (E-4).

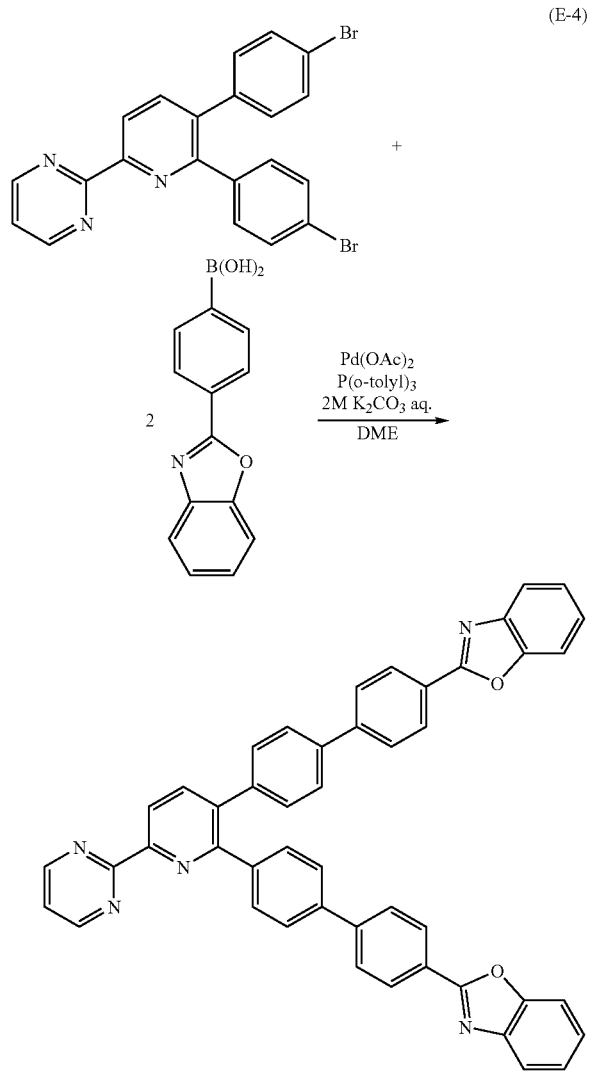

Into a 200 mL three-neck flask were put 0.80 g (1.7 mmol) of 2-[5,6-bis(4-bromophenyl)-2-pyridyl]pyrimidine, 0.11 g (0.36 mmol) of tri(ortho-tolyl)phosphine, 0.89 g (3.7 mmol) of 4-(benzoxazol-2-yl)phenylboronic acid, 70 mL of ethylene glycol dimethyl ether (DME), 4.0 mL of 2.0 M potassium carbonate aqueous solution. The mixture was degassed by being stirred under reduced pressure, and the atmosphere in the flask was substituted by nitrogen. To the mixture was added 26 mg (0.12 mmol) of palladium(II) acetate, which was stirred under a nitrogen stream at 80° C. for 13 hours. After a certain time, water was added to the mixture, and an aqueous layer was extracted with chloroform. The obtained extract combined with the organic layer was washed with a saturated sodium hydrogen carbonate aqueous solution and brine in that order, and the organic layer was dried with magnesium sulfate. The mixture was subjected to gravity filtration, and the obtained filtrate was concentrated to give a solid. After drying, a toluene solution containing the solid was subjected to suction filtration through Celite (produced by Wako Pure Chemical Industries, Ltd., Catalog No. 531-16855), and the obtained filtrate was concentrated to give a solid. This solid was recrystallized with toluene so that 0.51 g of a target substance, white powder was obtained in a yield of 42%.

Then, 0.45 g of the obtained target substance was subjected to sublimation purification at 370° C. under an argon stream (flow rate: 3.0 mL/min) and a pressure of 10 Pa for 17 hours; thus, 0.38 g of a target compound was recovered in a yield of 84%. This compound was measured with a nuclear magnetic resonance (NMR) measurement, and the measurement showed that the obtained compound was 2,2'-[2-bipyridin-2-yl]pyridine-5,6-diylbis(biphenyl-4,4'-diyl)]bisbenzoxazole (abbreviation: BOxP2PyPm).

The $^1$H NMR data is shown below $^1$H NMR (300 MHz, CDCl$_3$): δ (ppm)=7.33-7.43 (m, 7H), 7.57-7.68 (m, 8H), 7.76-7.81 (m, 6H), 8.00 (d, J=7.8 Hz, 1H), 8.29-8.35 (m, 4H), 8.57 (d, J=7.8 Hz, 1H), 8.98 (d, J=5.1 Hz, 2H).

Figure 34A:
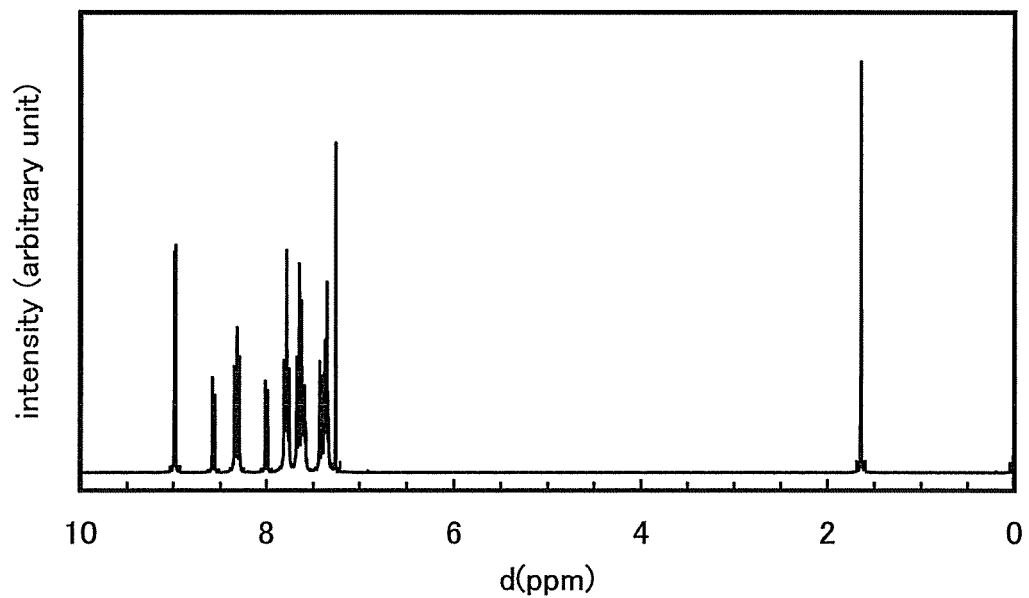
FIGS. 34A and 34B are $^1$H NMR charts of 2,2'-[2-(bipyridin-2-yl)pyridine-5,6-diylbis(biphenyl-4,4'-diyl)]bisbenzoxazole (abbreviation: BOxP2PyPm)
Figure 34B:
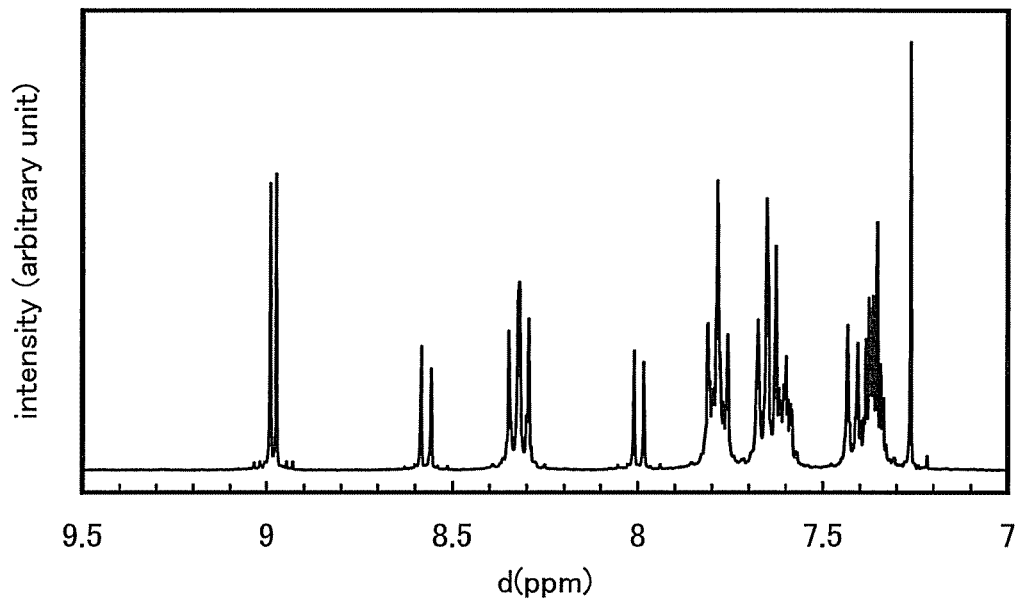

In addition, charts of $^1$H NMR are shown in FIGS. 34A and 34B. Note that FIG. 34B is a chart showing an enlarged part of FIG. 34A in a range of from 7.0 to 9.5 ppm.

Figure 35:
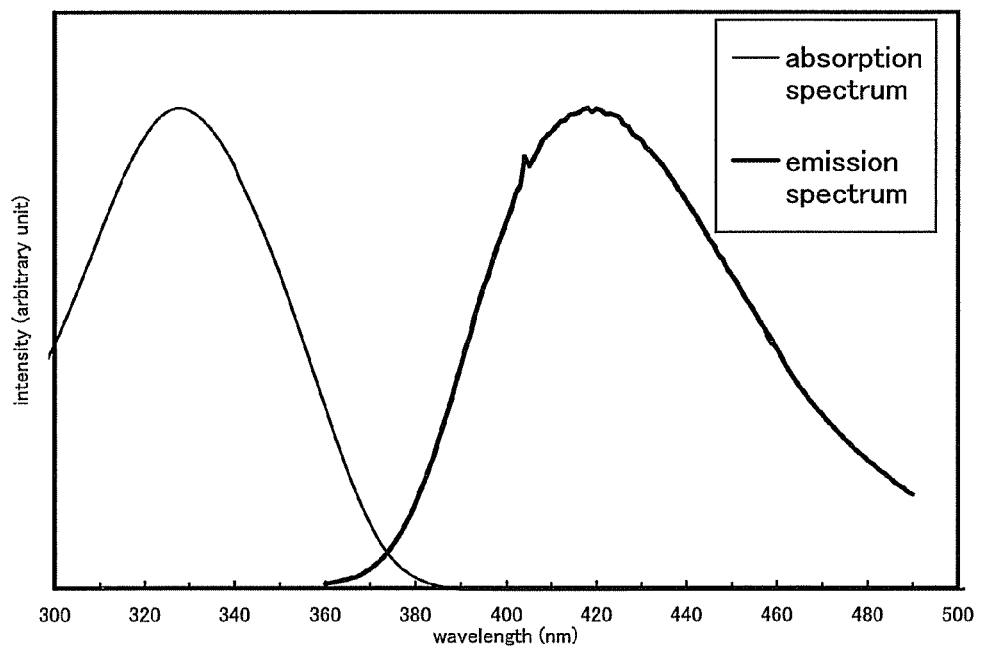
FIG. 35 is a graph showing an absorption spectrum and an emission spectrum of 2,2'-[2-(bipyridin-2-yl)pyridine-5,6-diylbis(biphenyl-4,4'-diyl)]bisbenzoxazole (abbreviation: BOxP2PyPm) in a toluene solution.

FIG. 35 shows an absorption spectrum and an emission spectrum of a toluene solution of BOxP2PyPm. An ultraviolet-visible spectrophotometer (V-550, manufactured by JASCO Corporation) was used for the measurement. The solution was put into a quartz cell, and the absorption spectrum from which the absorption spectrum of the quartz cell was subtracted is shown. In FIG. 35, the horizontal axis represents a wavelength (nm), whereas the vertical axis represents intensity (arbitrary unit). Absorption was observed around 328 nm in the case of toluene solution. In the case of the toluene solution, the maximum emission wavelength was 418 nm (excitation wavelength of 333 nm).

Figure 36:
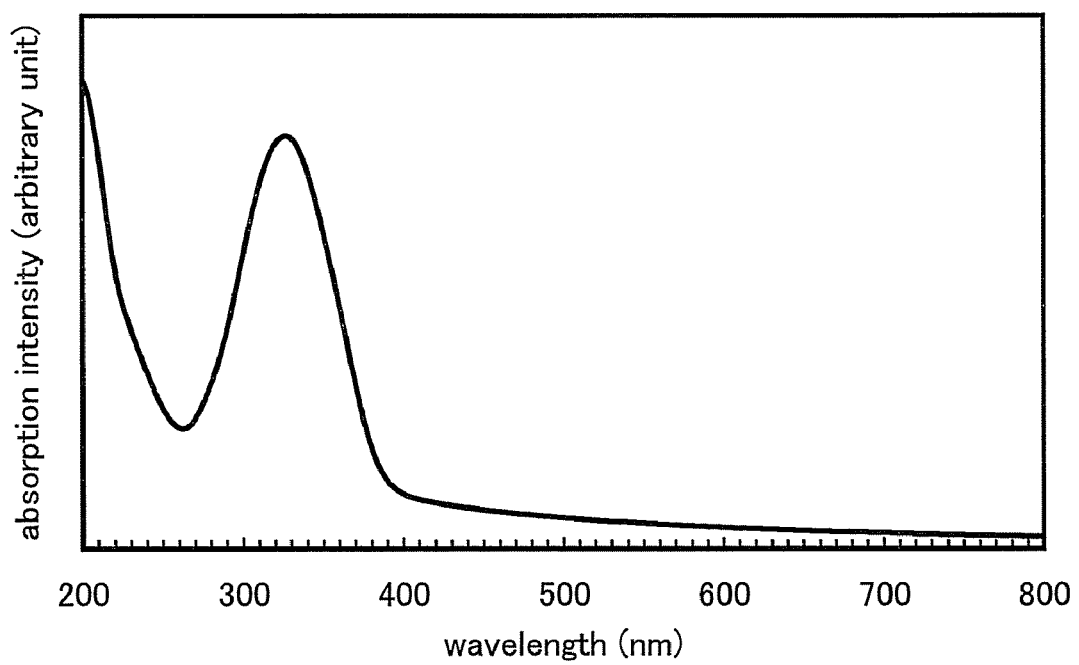
FIG. 36 is a graph showing an absorption spectrum of 2,2'-[2-(bipyridin-2-yl)pyridine-5,6-diylbis(biphenyl-4,4'-diyl)]bisbenzoxazole (abbreviation: BOxP2PyPm) in a thin film state.
Figure 37:
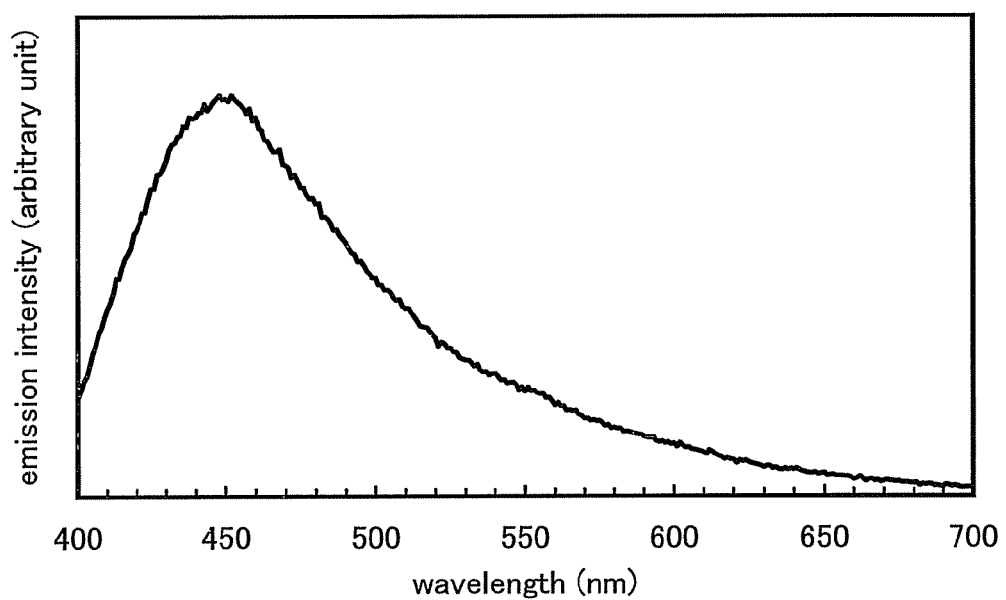
FIG. 37 is a graph showing an emission spectrum of 2,2'-[2-(bipyridin-2-yl)pyridine-5,6-diylbis(biphenyl-4,4'-diyl)]bisbenzoxazole (abbreviation: BOxP2PyPm) in a thin film state.

FIG. 36 shows an absorption spectrum of a thin film of BOxP2PyPm and FIG. 37 shows an emission spectrum of the thin film of BOxP2PyPm. An ultraviolet-visible spectrophotometer (V-550, manufactured by JASCO Corporation) was used for the measurement. A thin film sample was formed by evaporation on a quartz substrate, and the absorption spectrum from which the absorption spectrum of the quartz substrate was subtracted is shown. In FIG. 36, the horizontal axis indicates a wavelength (nm) and the vertical axis indicates an absorption intensity (arbitrary unit). In FIG. 37, the horizontal axis represents wavelength (nm) and the vertical axis represents an emission intensity (arbitrary unit). Absorption was observed around 327 nm in the case of the thin film. In addition, in the case of the thin film, the maximum emission wavelength was 450 nm (excitation wavelength: 363 nm).

In addition, when the ionizing potential of BOxP2PyPm in a thin film state was measured with a photoelectron spectrometer (AC-2, by RIKEN KEIKI CO., LTD.) in the air, the ionizing potential was 5.94 eV Accordingly, the HOMO level was found to be −5.94 eV. Furthermore, an absorption edge was obtained from a Tauc plot assuming direct transition based on the absorption spectrum data of the thin film of BOxP2PyPm, and the absorption edge was estimated as an optical energy gap. As a result, the energy gap was 3.16 eV. The LUMO level was found to be −2.78 eV by calculation from the value of the energy gap and the HOMO level.

Further, the oxidation-reduction reaction characteristics of BOxP2PyPm were measured. The oxidation-reduction characteristics were measured by cyclic voltammetry (CV) measurement. Further, an electrochemical analyzer (ALS model 600A, BAS Inc.) was used for the measurement.

The solution for the CV measurement was prepared as follows: tetra-n-butylammonium perchlorate (n-Bu$_4$NClO$_4$) (produced by Tokyo Chemical Industry Co., Ltd., Catalog No. T0836) used as a supporting electrolyte is dissolved at a concentration of 100 mmol/L in dehydrated dimethylformamide (DMF) (produced by Sigma-Aldrich Corp., 99.8%, Catalog No. 22705-6) used as a solvent. BOxP2PyPm that was a measurement object was further dissolved at a concentration of 1.0 mmol/L therein. A platinum electrode (manufactured by BAS Inc., PTE platinum electrode) was used as a working electrode, a platinum electrode (manufactured by BAS Inc., Pt counter electrode for VC-3, (5 cm)) was used as an auxiliary electrode, and an Ag/Ag+ electrode (manufactured by BAS Inc., RE-5 reference electrode for nonaqueous solvent) was used as a reference electrode. The measurement was carried out at room temperature.

The oxidation reaction characteristic of BOxP2PyPm was measured as follows. A scan, in which a potential of the working electrode with respect to the reference electrode was varied from −0.27 V to 1.50 V and then from 1.50 V to −0.27 V, was set to one cycle, and measurement was performed 100 cycles. Reduction reaction characteristics of BOxP2PyPm were examined as follows. A scan, in which a potential of the working electrode with respect to the reference electrode was varied from −0.93 V to −2.70 V and then from −2.70 V to −0.93 V, was set to one cycle, and measurement was performed 100 cycles. Further, the scanning speed of the CV measurement was set to be 0.1 V/s.

Figure 38:
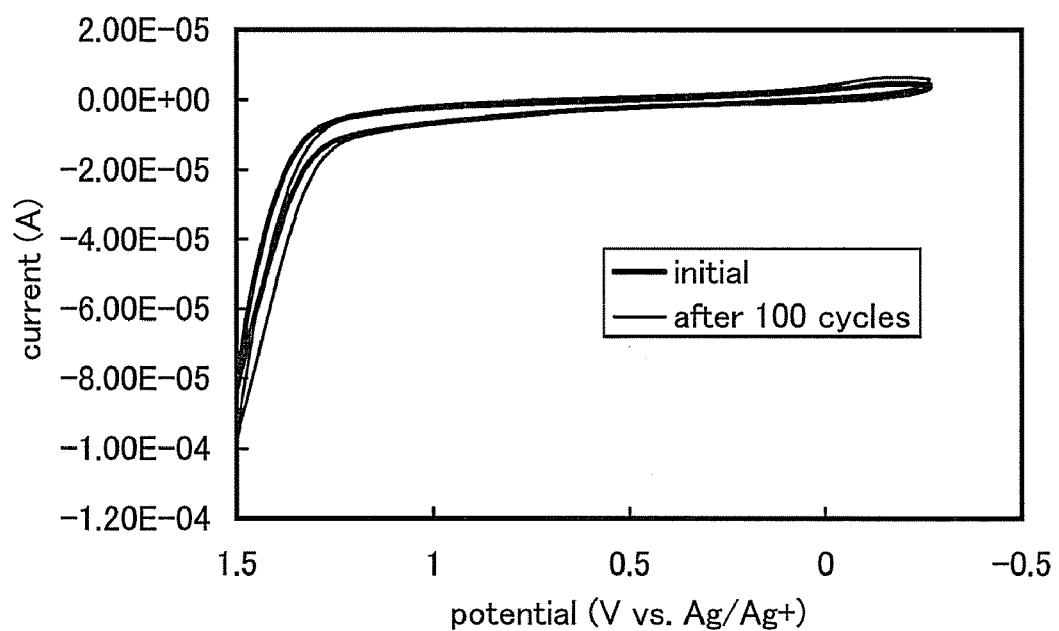
FIG. 38 is a graph showing CV measurement results of 2,2'-[2-(bipyridin-2-yl)pyridine-5,6-diylbis(biphenyl-4,4'-diyl)]bisbenzoxazole (abbreviation: BOxP2PyPm)
Figure 39:
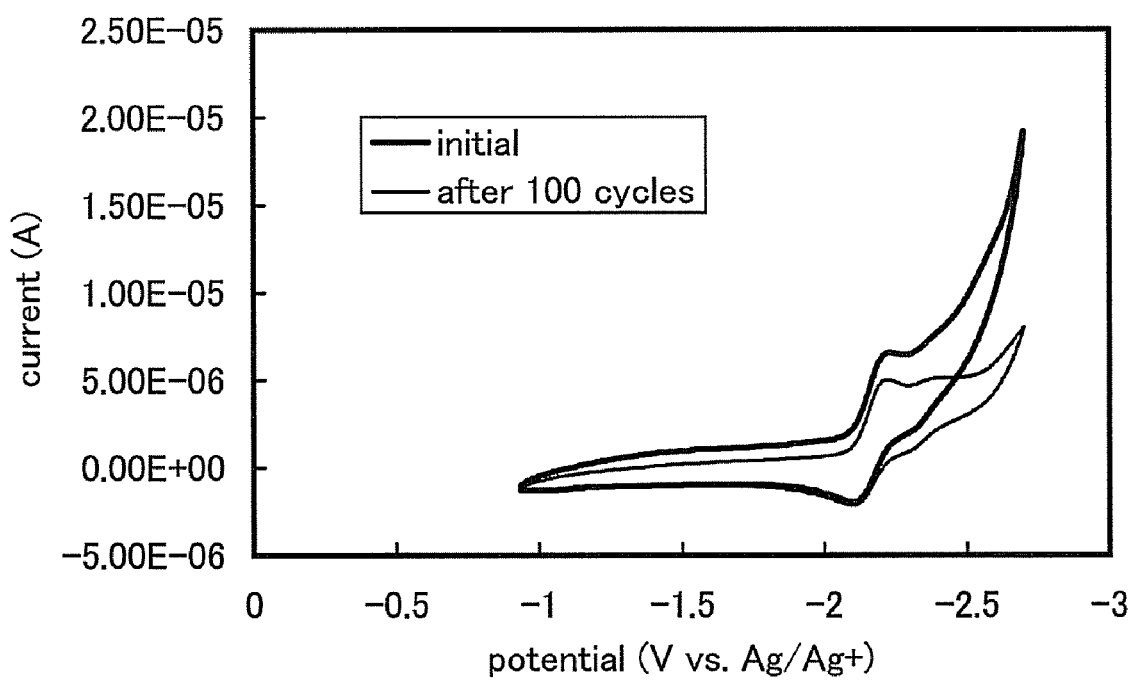
FIG. 39 is a graph showing CV measurement results of 2,2'-[2-(bipyridin-2-yl)pyridine-5,6-diylbis(biphenyl-4,4'-diyl)]bisbenzoxazole (abbreviation: BOxP2PyPm)

FIGS. 38 and 39 show CV measurement results of oxidation characteristics and reduction characteristics of BOxP2PyPm, respectively. In each of FIGS. 38 and 39, the horizontal axis indicates a potential (V) of the working electrode with respect to the reference electrode, and the vertical axis indicates a current value (A) flowing between the working electrode and the auxiliary electrode. A current for oxidation was not observed in FIG. 38, but a current for reduction was observed at around −2.23 V (vs. Ag/Ag$^+$ electrode) in FIG. 39.

In spite of the fact that 100 cycles of scanning were conducted repeatedly, a peak position and a peak intensity at the CV curve scarcely changed in the reduction, which reveals that the benzoxazole derivative of the present invention, BOxP2PyPm, is extremely stable against repetition of the reduction.

EXAMPLE 5

Figure 40:
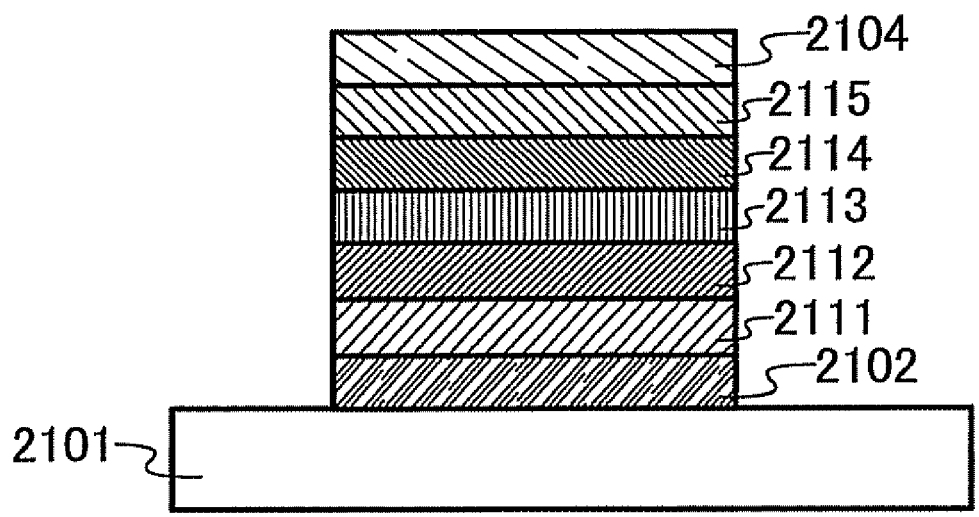
FIG. 40 is an explanatory view of light-emitting elements used in Example.
Figure 41:
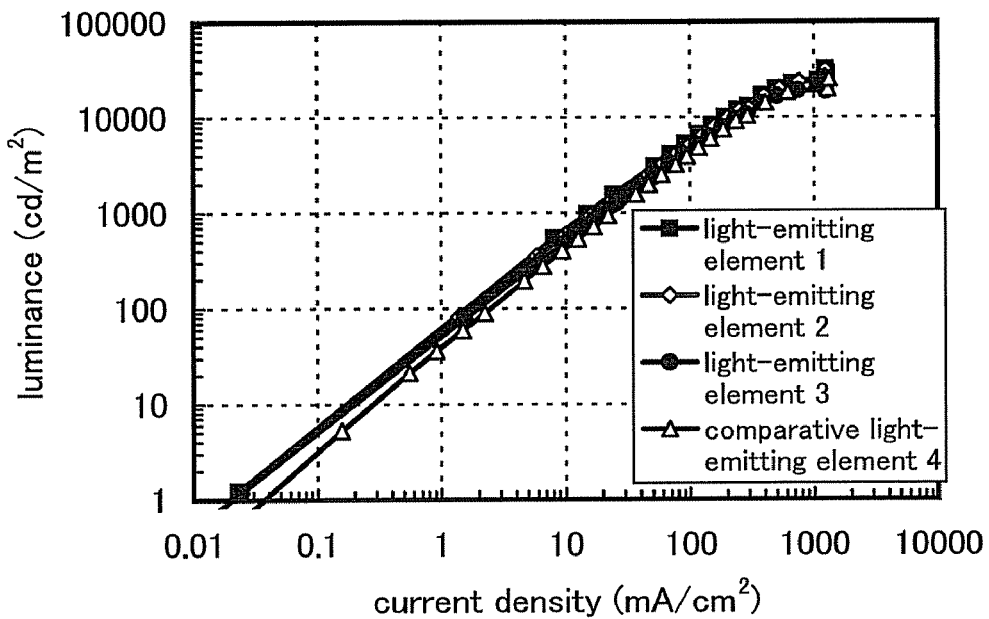
FIG. 41 is a graph showing current density vs. luminance characteristics of the light-emitting elements fabricated in Example 5.

Example 5 will describe a light-emitting element according to an embodiment of the present invention with reference to FIG. 40. Structural formulae of materials used in this example are shown below. The materials of which the structural formulae have already been shown is omitted.

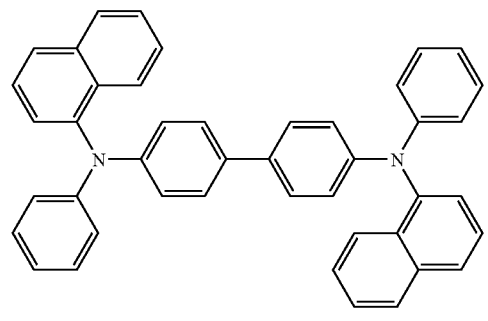

NPB

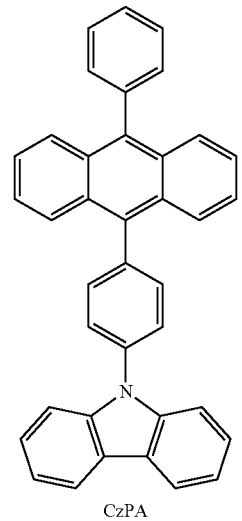

CzPA

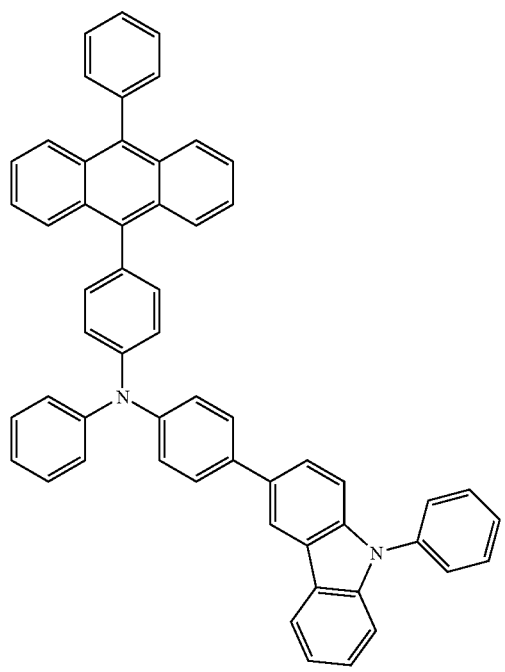

PCBAPA

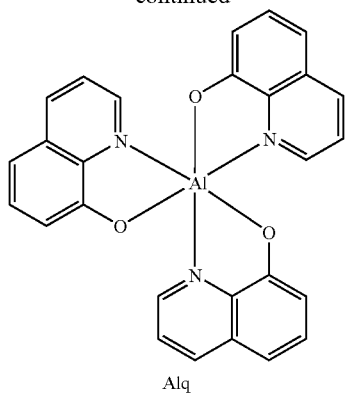

Alq

A fabrication method of the light-emitting element of this embodiment is described below.

(Light-emitting Element 1)

First, a film of indium tin oxide containing silicon oxide (ITSO) was formed by sputtering over a glass substrate 2101 to form a first electrode 2102. The thickness of the first electrode 2102 was 110 m and the area of the first electrode 2102 was 2 mm×2 mm.

Next, the substrate provided with the first electrode 2102 was fixed to a substrate holder provided in a vacuum evaporation apparatus such that the side on which the first electrode was formed faced downward. After the pressure in a film formation chamber was lowered to approximately $10^{-4}$ Pa, a layer 2111 containing a composite material of an organic compound and an inorganic compound was formed on the first electrode 2102 by co-evaporation of 4,4'-bis[N-(1-naphthyl)-N-phenylamino]biphenyl (abbreviation: NPB) and molybdenum(VI) oxide. The film thickness is 50 nm and the weight ratio between NPB and molybdenum(VI) oxide is adjusted to be 4:1 (=NPB:molybdenum oxide). Further, the co-evaporation is an evaporation method by which evaporation is performed simultaneously from a plurality of evaporation sources in one chamber.

Next, a film of 4,4'-bis[N-(1-naphthyl)-N-phenylamino] biphenyl (abbreviation: NPB) was formed to a thickness of 10 nm on the layer 2111 containing a composite material by an evaporation method using resistance heating to form a hole-transporting layer 2112.

Then, a light-emitting layer 2113 was formed to a thickness of 30 nm on the hole-transporting layer 2112 by co-evaporation of 9-[4-(10-phenyl-9-anthryl)phenyl]-9H-carbazole (abbreviation: CzPA) and 4-(10-phenyl-9-anthryl)-4'-(9-phenyl-9H-carbazol-3-yl)triphenylamine (abbreviation: PCBAPA). The weight ratio of CzPA and PCBAPA was adjusted so as to be 1:0.1 (=CzPA:PCBAPA).

Then, a film of 2,2'-[2,2'-bipyridine-5,6-diylbis(biphenyl-4,4'-diyl)]bisbenzoxazole (abbreviation: BOxP2BPy) represented by the structural formula (101) was formed to a thickness of 30 nm by an evaporation method using resistance heating to form the electron-transporting layer 2114 over the light-emitting layer 2113.

Furthermore, a film of lithium fluoride was formed to a thickness of 1 nm on the electron-transporting layer 2114 to form an electron-injecting layer 2115.

Lastly, a film of aluminum was formed to a thickness of 200 nm on the electron-injecting layer 2115 by an evaporation method using resistance heating to form a second electrode 2104. Accordingly, a light-emitting element 1 was manufactured.

(Light-emitting Element 2)

The same substrate as that of the light-emitting element 1 was used for the light-emitting element 2. In addition, 2,2'-[2-(bipyridin-2-yl)pyridine-5,6-diylbis(biphenyl-4,4'-diyl)] bisbenzoxazole (abbreviation: BOxP2PyPm) represented by the structural formula (104) was used instead of BOxP2BPy, and the light-emitting element 2 was formed similarly to the light-emitting element 1. In other words, a 30-nm-thick film of 2,2'-[2-(bipyridin-2-yl)pyridine-5,6-diylbis(biphenyl-4,4'-diyl)]bisbenzoxazole (abbreviation: BOxP2PyPm) represented by the structural formula (104) was formed as an electron-transporting layer 2114. Except for the electron-transporting layer 2114, the light-emitting element 2 was formed like the light-emitting element 1.

(Light-emitting Element 3)

The same substrate as that of the light-emitting element 1 was used for the light-emitting element 3. 2,2'-[2,4'-bipyridine-5,6-diylbis(biphenyl-4,4'-diyl)]bisbenzoxazole (abbreviation: BOxP2BPy(4)) represented by the structural formula (103) was used instead of BOxP2BPy, and the light-emitting element 3 was formed similarly to the light-emitting element 1. In other words, a 30-nm-thick film of 2,2'-[2,4'-bipyridine-5,6-diylbis(biphenyl-4,4'-diyl)]bisbenzoxazole (abbreviation: BOxP2BPy(4)) represented by the structural formula (103) was formed as an electron-transporting layer 2114. Except for the electron-transporting layer 2114, the light-emitting element 3 was formed like the light-emitting element 1.

(Comparative Light-emitting Element 4)

A comparative light-emitting element 4 was formed like the light-emitting element 1 by using the same substrate as the light-emitting element 1 and using tris(8-quinolinolato)aluminum (III) (abbreviation: Alq) instead of BOxP2BPy. That is, a film of tris(8-quinolinolato)aluminum(III) (abbreviation: Alq) was formed to a thickness of 30 nm to form the electron-transporting layer 2114. Except for the electron-transporting layer 2114, the comparative light-emitting element 4 was formed like the light-emitting element 1.

The light-emitting elements 1 to 3 and the comparative light-emitting element 4 obtained in the above-described manner were put in a glove box with a nitrogen atmosphere and sealing was conducted so that the light-emitting elements were not exposed to air. Then, the operating characteristics of the light-emitting elements were measured. The measurement was carried out at a room temperature (in the atmosphere kept at 25° C.).

FIG. 41, FIG. 42, FIG. 43 and FIG. 44 show current density vs. luminance characteristics, voltage vs. luminance characteristics, luminance vs. current efficiency characteristics, and voltage-current characteristics of the light-emitting elements 1 to 3 and the comparative light-emitting element 4.

Figure 45:
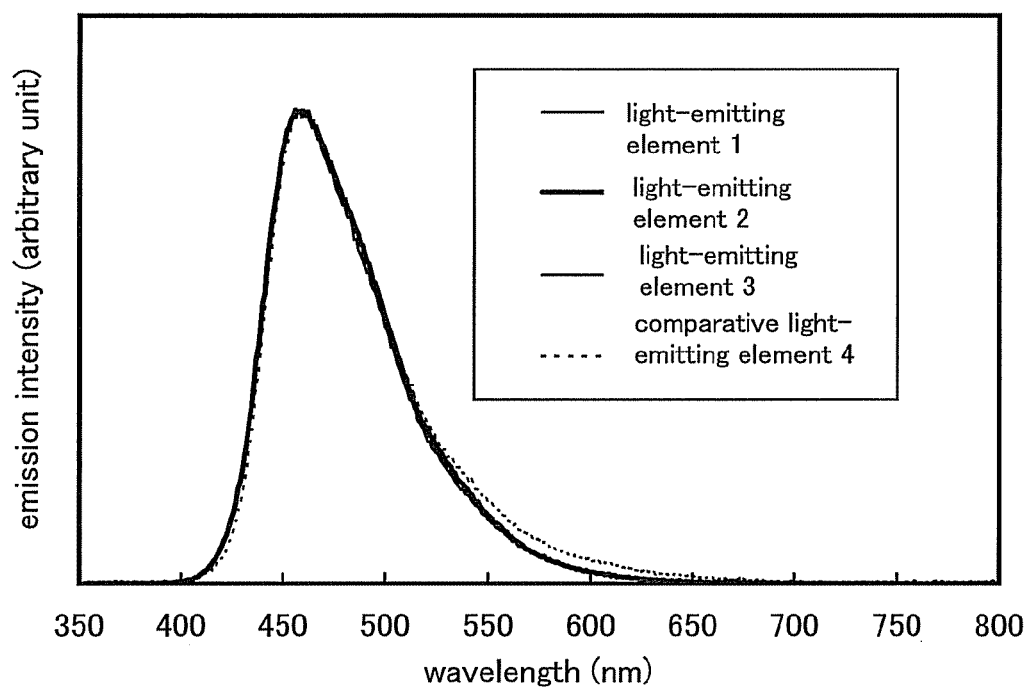
FIG. 45 is a graph showing emission spectra of the light-emitting elements fabricated in Example 5.

Also, the emission spectrum which was obtained at a current of 1 mA is illustrated in FIG. 45. As apparent from FIG. 45, light emission of the light-emitting elements 1 to 3 and the comparative light-emitting element 4 is light emission derived from PCBAPA.

The comparative light-emitting element 4 exhibited blue light emission where the CIE chromaticity coordinates are (x=0.17, y=0.19) at the luminance of 940 cd/m². The current efficiency and external quantum efficiency of the comparative light-emitting element 4 at the luminance of 940 cd/m² were 4.3 cd/A and 2.9%, respectively. Furthermore, the voltage, current density, and power efficiency of the comparative light-emitting element 4 at the luminance of 940 cd/m² were 5.8 V, 22.0 mA/cm², and 2.3 lm/W, respectively.

On the other hand, the light-emitting element 1 exhibited blue light emission where the CIE chromaticity coordinates were (x=0.15, y=0.18) at a luminance of 990 cd/m². At the luminance of 990 cd/m², the current efficiency was 6.6 cd/A and the external quantum efficiency was 4.9%, which means that high emission efficiency was exhibited. The voltage at the luminance of 990 cd/m² was 3.4 V, which showed that the driving voltage was reduced as compared with the comparative light-emitting element 4. In addition, the current density was 14.9 mA/cm², and the power efficiency was 6.1 lm/W, which showed high power efficiency.

The light-emitting element 2 exhibited blue light emission where the CIE chromaticity coordinates are (x=0.15, y=0.17) at a luminance of 930 cd/m². At the luminance of 930 cd/m², the current efficiency was 5.9 cd/A and the external quantum efficiency was 4.4%, which means that high emission efficiency was exhibited. The voltage at the luminance of 930 cd/m² was 3.8 V, which showed that the driving voltage of the light-emitting element 2 was reduced as compared with that of the comparative light-emitting element 4. In addition, the current density was 15.9 mA/cm², and the power efficiency was 4.9 lm/W, which showed high power efficiency.

The emission color of the light-emitting element 3 was located at the CIE chromaticity coordinates of (x=0.15, y=0.17) at a luminance of 850 cd/m², and blue emission was obtained. At the luminance of 850 cd/m², the current efficiency was 5.0 cd/A and the external quantum efficiency was 3.8%, which means that high emission efficiency was exhibited. The voltage at the luminance of 850 cd/m² was 4.2 V, which showed that the driving voltage of the light-emitting element 3 was reduced as compared with that of the comparative light-emitting element 4. In addition, the current density was 17.2 mA/cm², and the power efficiency was 3.7 lm/W, which showed high power efficiency.

Figure 42:
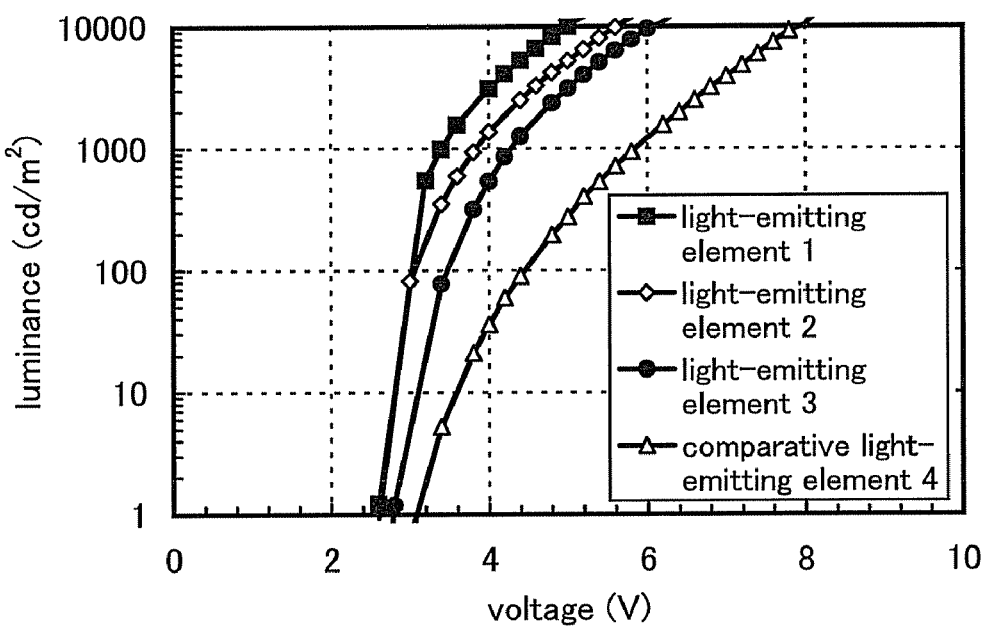
FIG. 42 is a graph showing voltage vs. luminance characteristics of the light-emitting elements fabricated in Example 5.
Figure 43:
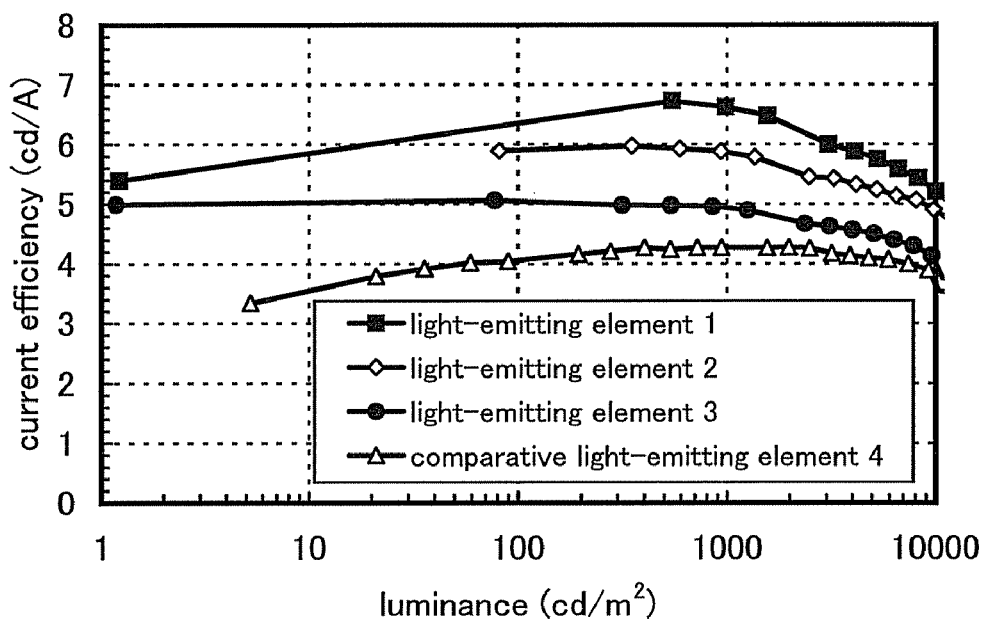
FIG. 43 is a graph showing luminance vs. current efficiency characteristics of the light-emitting elements fabricated in Example 5.
Figure 44:
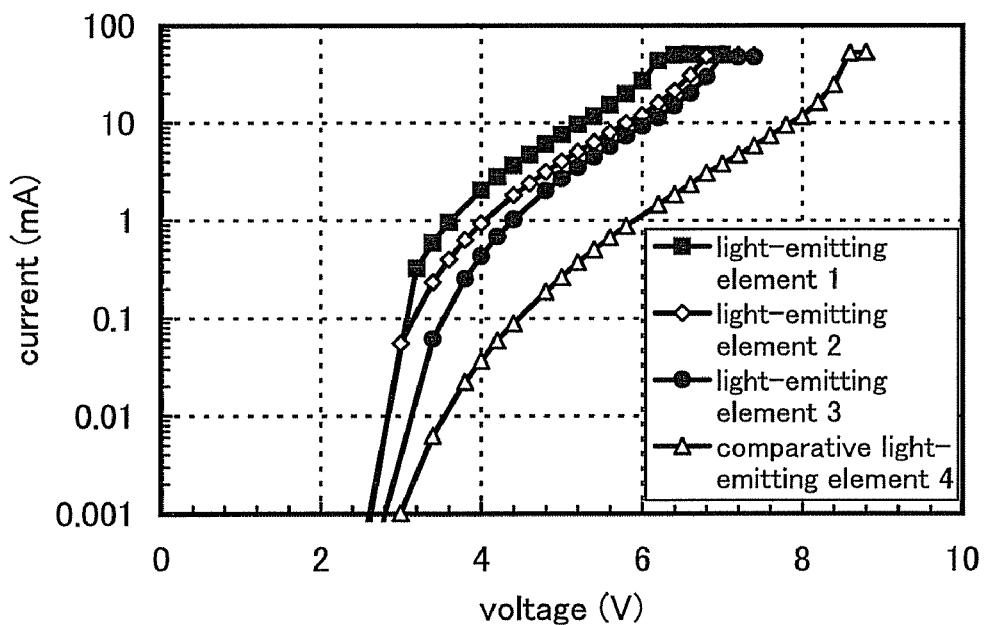
FIG. 44 is a graph showing voltage-current characteristics of the light-emitting elements fabricated in Example 5.

FIG. 44 shows that the light-emitting elements 1 to 3 use lower voltage than the comparative light-emitting element 4 to allow the same amount of electric current to flow. FIG. 43 shows that the light-emitting elements 1 to 3 have current efficiency higher than the comparative light-emitting element 4. Thus, as shown in FIG. 42, the voltage necessary for the light-emitting elements 1 to 3 to obtain the same luminance is low and thus consumption voltage can be reduced.

Therefore, by using a benzoxazole derivative of the present invention in a light-emitting element, a light-emitting element with low driving voltage can be provided. In addition, a light-emitting element with low power consumption can be obtained.

EXAMPLE 6

Figure 46:
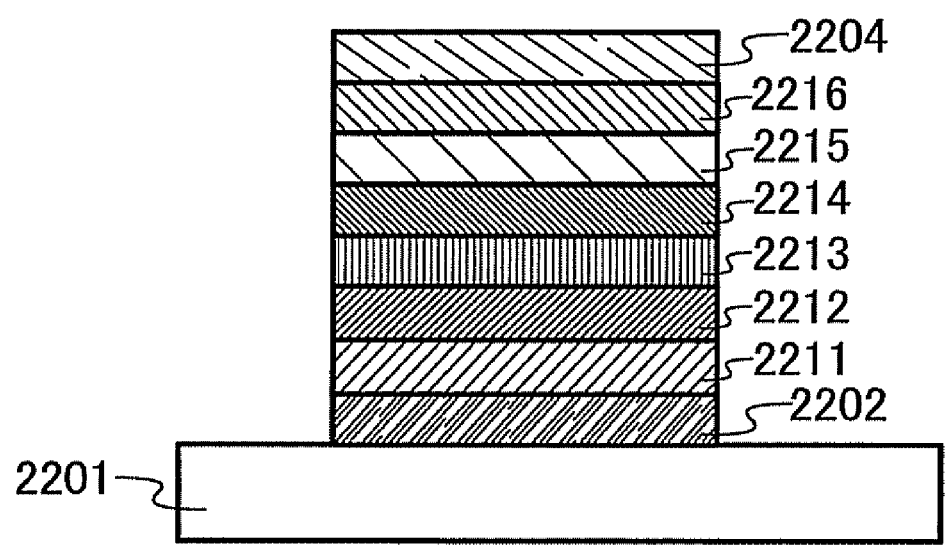
FIG. 46 is an explanatory view of light-emitting elements used in Example.
Figure 47:
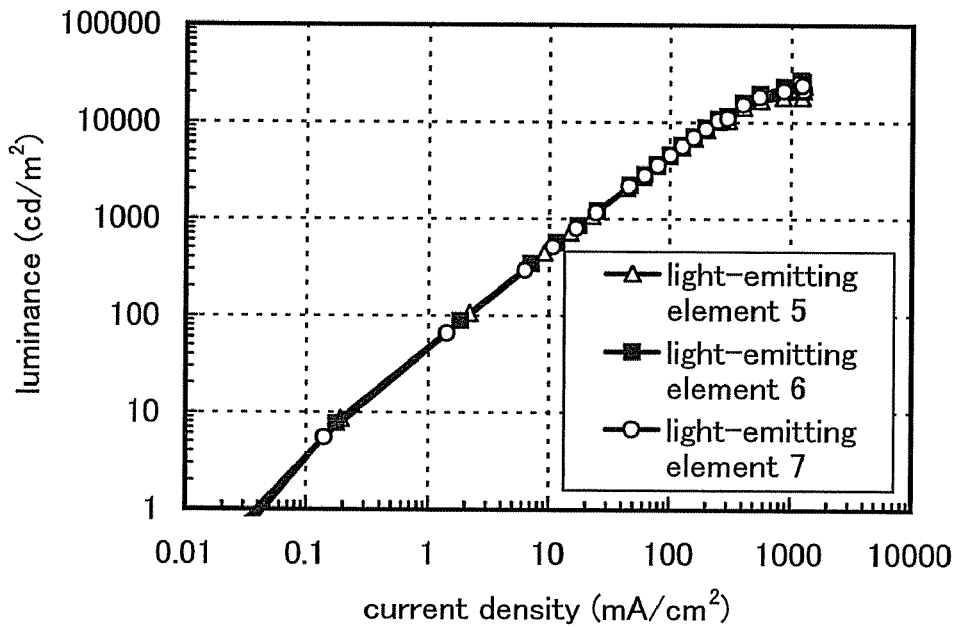
FIG. 47 is a graph showing current density vs. luminance characteristics of the light-emitting elements fabricated in Example 6.
Figure 48:
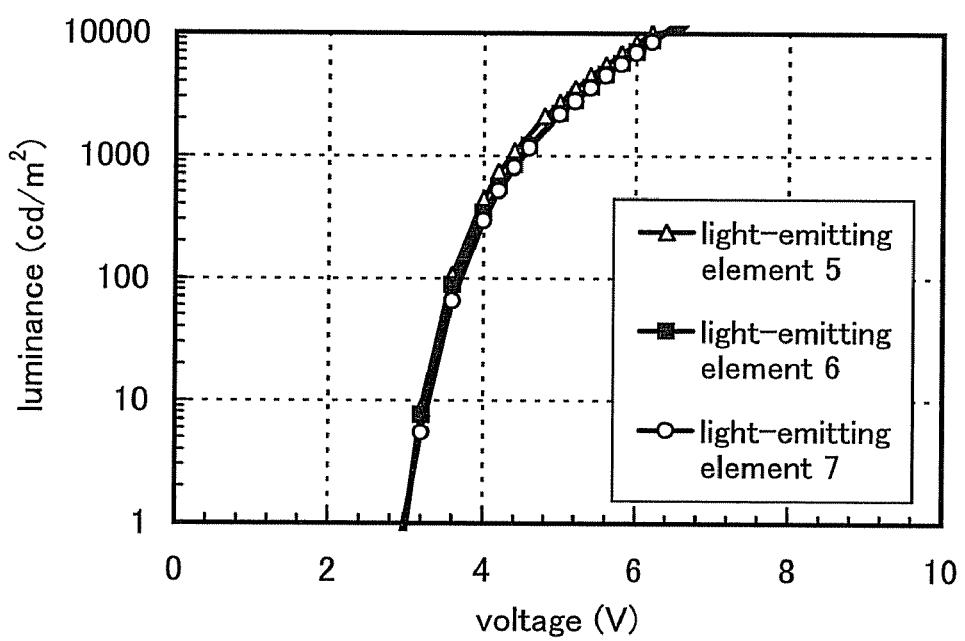
FIG. 48 is a graph showing voltage vs. luminance characteristics of the light-emitting elements fabricated in Example 6.
Figure 49:
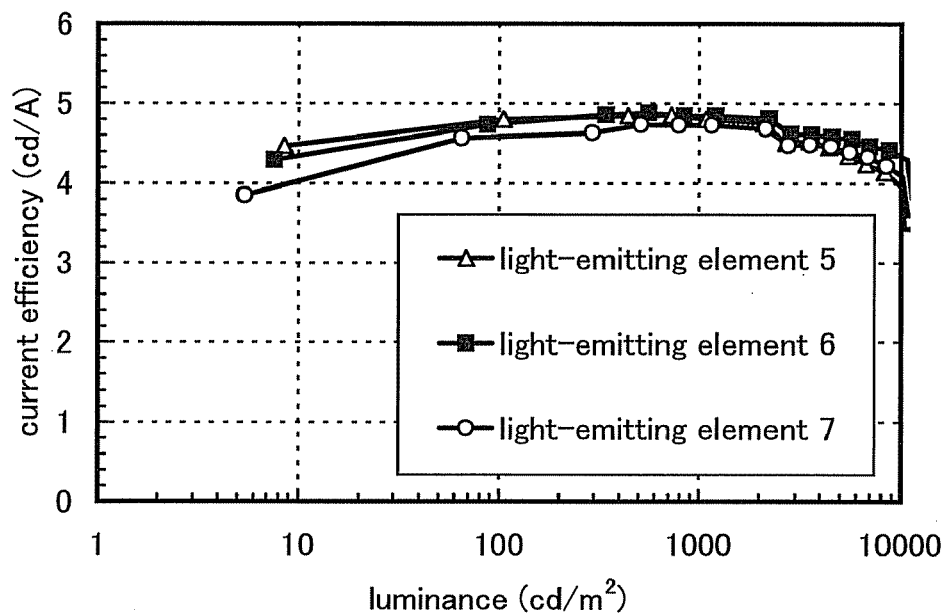
FIG. 49 is a graph showing luminance vs. current efficiency characteristics of the light-emitting elements fabricated in Example 6.
Figure 50:
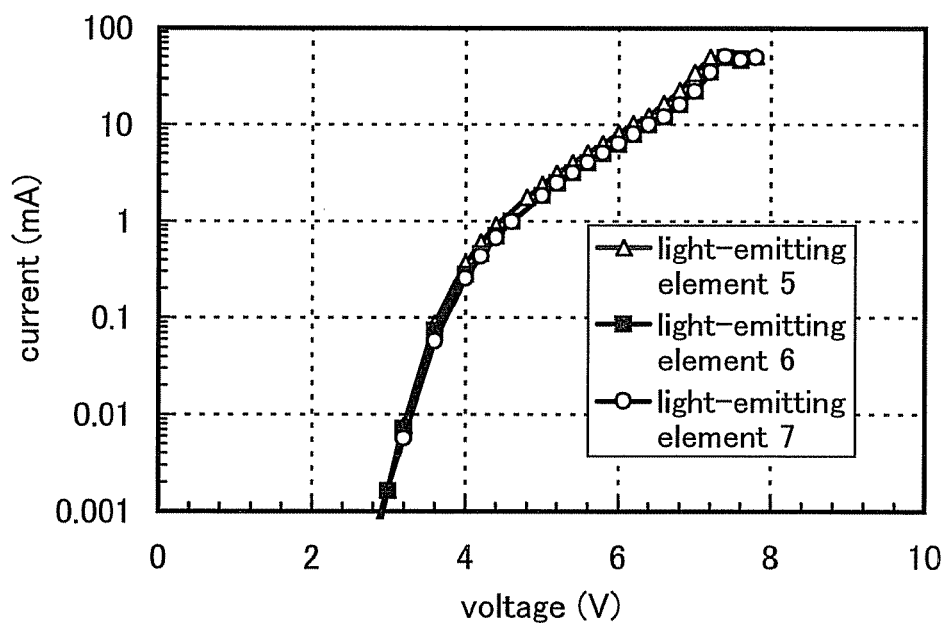
FIG. 50 is a graph showing voltage-current characteristics of the light-emitting elements fabricated in Example 6.

Example 6 describes a light-emitting element of the present invention with reference to FIG. 46. A fabrication method of the light-emitting element of this example is described below.

(Light-emitting Element 5)

First, a film of indium tin oxide containing silicon oxide (ITSO) was formed by a sputtering method over a glass substrate 2201 to form a first electrode 2202. The thickness and the area of the first electrode 2202 were 110 nm and 2 mm×2 mm respectively.

Next, the substrate provided with the first electrode 2202 was fixed to a substrate holder provided in a vacuum evaporation apparatus such that the side on which the first electrode was formed faced downward. After the pressure in a film formation chamber was lowered to approximately 104 Pa, a layer 2211 containing a composite material of an organic compound and an inorganic compound was formed on the first electrode 2202 by co-evaporation of 4,4'-bis[N-(1-naphthyl)-N-phenylamino]biphenyl (abbreviation: NPB) and molybdenum(VI) oxide. The film thickness is 50 nm and the weight ratio between NPB and molybdenum(VI) oxide is adjusted to be 4:1 (=NPB:molybdenum oxide). Further, the co-evaporation is an evaporation method by which evaporation is performed simultaneously from a plurality of evaporation sources in one chamber.

Next, a film of 4,4'-bis[N-(1-naphthyl)-N-phenylamino]biphenyl (abbreviation: NPB) was formed to a thickness of 10 nm on the layer 2211 containing a composite material by an evaporation method using resistance heating to form a hole-transporting layer 2212.

Then, a light-emitting layer 2213 was formed to a thickness of 30 nm on the hole-transporting layer 2212 by co-evaporation of 9-[4-(10-phenyl-9-anthryl)phenyl]-9H-carbazole (abbreviation: CzPA) and 4-(10-phenyl-9-anthryl)-4'-(9-phenyl-9H-carbazol-3-yl)triphenylamine (abbreviation: PCBAPA). The weight ratio of CzPA and PCBAPA was adjusted so as to be 1:0.1 (=CzPA:PCBAPA).

After that, an electron-transporting layer(A) 2214 was formed by depositing tris(8-quinolinolato)aluminum(III) (abbreviation: Alq) to a thickness of 10 nm on the light-emitting layer 2213. Further, 2,2'-[2,2'-bipyridine-5,6-diylbis(biphenyl-4,4'-diyl)]bisbenzoxazole (abbreviation: BOxP2BPy) represented by the structural formula (101) was deposited on the electron-transporting layer (A) 2214 to a thickness of 20 m as an electron-transporting layer (B) 2215. Thus, the light-emitting element of this example has a structure in which two electron-transporting layers are stacked.

Furthermore, a film of lithium fluoride was formed to a thickness of 1 nm on the electron-transporting layer (B) 2215 to form an electron-injecting layer 2216.

Lastly, a film of aluminum was formed to a thickness of 200 nm on the electron-injecting layer 2216 by an evaporation method using resistance heating to form a second electrode 2204. In this manner, a light-emitting element 5 was fabricated.

(Light-emitting Element 6)

The same substrate as that of the light-emitting element 5 was used for the light-emitting element 6. 2,2'-[2-bipyridin-2-yl]pyridine-5,6-diylbis(biphenyl-4,4'-diyl)]bisbenzoxazole represented by the structural formula (104) (abbreviation: BOxP2PyPm) was used instead of BOxP2BPy, and the light-emitting element 6 was formed similarly to the light-emitting element 5. In other words, a 20-nm-thick film of 2,2'-[2-bipyridin-2-yl]pyridine-5,6-diylbis(biphenyl-4,4'-diyl)]bisbenzoxazole (abbreviation: BOxP2PyPm) represented by the structural formula (104) was formed as an electron-transporting layer(B) 2115. Except for the electron-transporting layer(B) 2215, the light-emitting element 6 was formed like the light-emitting element 5.

(Light-emitting Element 7)

The same substrate as that of the light-emitting element 5 was used for the light-emitting element 7. 2,2'-[2,4'-bipyridine-5,6-diylbis(biphenyl-4,4'-diyl)]bisbenzoxazole (abbreviation: BOxP2BPy(4)) represented by the structural formula (103) was used instead of BOxP2BPy, and the light-emitting element 7 was formed similarly to the light-emitting element 5. In other words, a 20-nm-thick film of 2,2'-bipyridine-5,6-diylbis(biphenyl-4,4-diyl)]bisbenzoxazole (abbreviation: BOxP2BPy(4)) represented by the structural formula (103) was formed as an electron-transporting layer (B) 2215. Except for the electron-transporting layer (B) 2215, the light-emitting element 7 was formed like the light-emitting element 5.

The light-emitting elements 5 to 7 thus obtained were sealed in a glove box under a nitrogen atmosphere without being exposed to the air. Then, the operating characteristics of the light-emitting elements were measured. The measurement is carried out at a room temperature (in the atmosphere kept at 25° C.).

FIG. 47, FIG. 48, FIG. 49 and FIG. 50 show current density vs. luminance characteristics, voltage vs. luminance characteristics, luminance vs. current efficiency characteristics, and voltage-current characteristics of the light-emitting elements 5 to 7.

Figure 51:
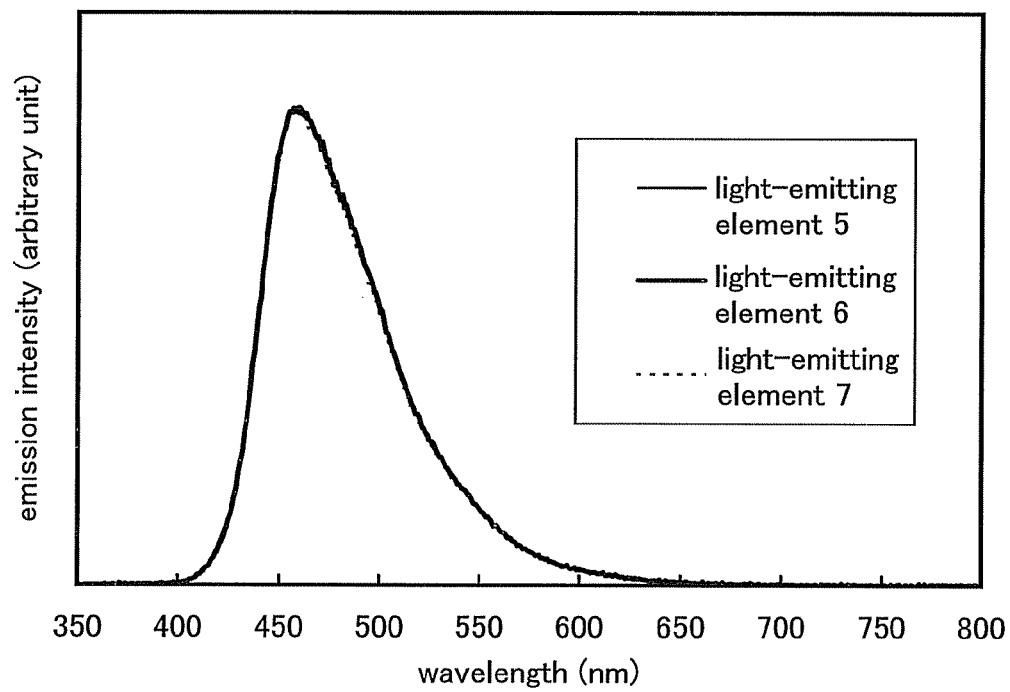
FIG. 51 is a graph showing emission spectra of the light-emitting elements fabricated in Example 6.

Also, the emission spectrum which was obtained at a current of 1 mA is shown in FIG. 51. FIG. 51 shows that emission from the light-emitting elements 5 to 7 were emission derived from PCBAPA.

On the other hand, the light-emitting element 5 exhibited blue light emission where the CIE chromaticity coordinates are (x=0.16, y=0.18) at a luminance of 1080 cd/m$^2$. In addition, the current efficiency and the external quantum efficiency at the luminance of 1080 cd/m$^2$ were 4.8 cd/A, and 3.5% respectively. The voltage at the luminance of 1080 cd/m$^2$ was 4.4 V, which showed low driving voltage. In addition, the current density was 22.5 mA/cm$^2$, and the power efficiency was 3.4 lm/W, which showed high power efficiency.

The light-emitting element 6 exhibited blue light emission where the CIE chromaticity coordinates are (x=0.16, y=0.18) at a luminance of 840 cd/m$^2$. In addition, the current efficiency and the external quantum efficiency at the luminance of 840 cd/m$^2$ were 4.8 cd/A, and 3.5% respectively. The voltage at the luminance of 840 cd/m$^2$ was 4.4 V, which showed low driving voltage. In addition, the current density was 17.4 mA/cm$^2$, and the power efficiency was 3.5 lm/W, which showed high power efficiency.

The light-emitting element 7 exhibited blue light emission where the CIE chromaticity coordinates are (x=0.16, y=0.18) at a luminance of 1160 cd/m$^2$. The current efficiency and the external quantum efficiency at luminance of 1160 cd/m$^2$ were 4.7 cd/A and 3.4%, respectively. The voltage at the luminance of 1160 cd/m$^2$ was 4.6 V, which showed low driving voltage. In addition, the current density was 24.5 mA/cm$^2$, and the power efficiency was 3.2 lm/W, which showed high power efficiency.

Figure 52:
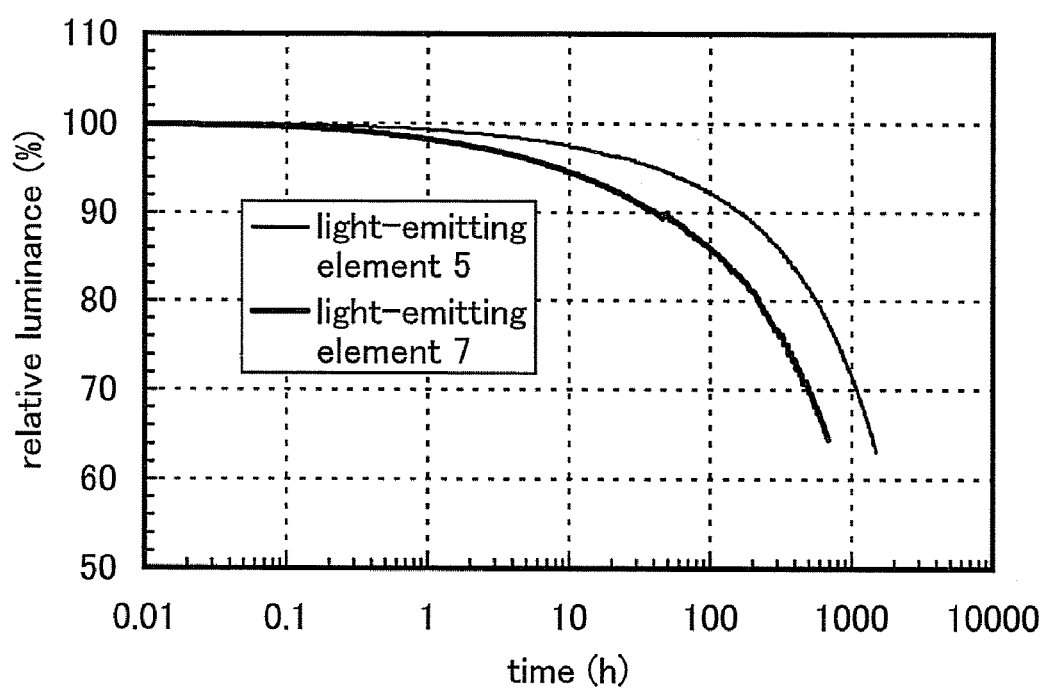
FIG. 52 is a graph showing a change in luminance with respect to driving time of light-emitting elements fabricated in Example 6.

FIG. 52 shows results of a continuous lighting test in which the light-emitting elements 5 and 7 were continuously lit by constant current driving with the initial luminance set at 1000 cd/m$^2$ (the vertical axis indicates the relative luminance on the assumption that 1000 cd/m$^2$ is 100%). As shown in FIG. 52, the luminance of the light-emitting element 5 was 63% of the initial luminance, after 1500 hours, and the luminance of the light-emitting element 7 was 64% of the initial luminance, after 690 hours.

It is found that although Alq was used as the electron-transporting layers (A) of the light-emitting elements 5 to 7, benzoxazole derivatives of the present invention, BOxP2BPy, BOxP2PyPm, and BOxP2BPy(4) were used as the second electron-transporting layers (electron-transporting layers (B)), whereby the driving voltage was able to be greatly reduced as compared with that of the comparative light-emitting element 4 described in Example 5 in which the electron-transporting layer was formed only of Alq. Further, it is found that power consumption was able to be reduced.

Therefore, by using a benzoxazole derivative of the present invention in a light-emitting element, a light-emitting element with low driving voltage can be provided. In addition, a light-emitting element with low power consumption can be obtained.

The present application is based on Japanese Patent Application serial No. 2008-129723 filed with Japan Patent Office on May 16, 2008, the entire contents of which are hereby incorporated by reference.

What is claimed is:

1. A benzoxazole derivative represented by a general formula (G1)

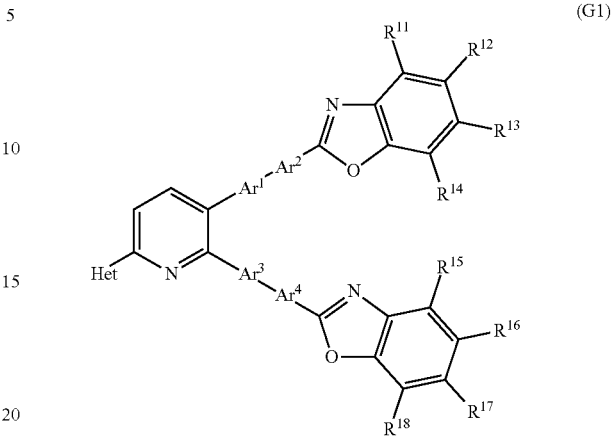

(G1)

wherein Het represents a pyridyl group or a pyrimidinyl group, Ar$^1$ to Ar$^4$ are independently a substituted or unsubstituted arylene group having 6 to 13 carbon atoms, and R$^{11}$ to R$^{18}$ are independently hydrogen, an alkyl group having 1 to 4 carbon atoms, a haloalkyl group having 1 to 4 carbon atoms, a substituted or unsubstituted aryl group having 6 to 13 carbon atoms, or halogen.

2. The benzoxazole derivative according to claim 1, wherein Het is a substituent represented by a general formula (G1-1),

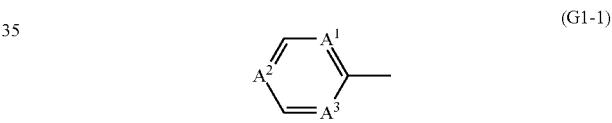

(G1-1)

wherein one or two of A$^1$ to A$^3$ is/are nitrogen, and the other(s) is/are carbon.

3. The benzoxazole derivative according to claim 1, wherein the benzoxazole derivative is represented by a general formula (G2)

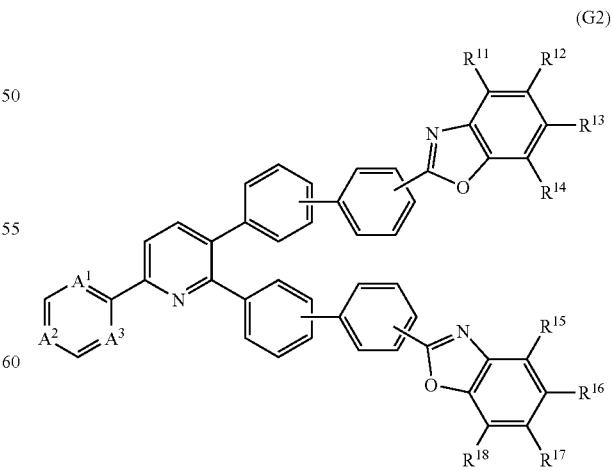

(G2)

wherein, one or two of A$^1$ to A$^3$ is/are nitrogen, and the other(s) is/are carbon.

4. The benzoxazole derivative according to claim 1, wherein the benzoxazole derivative is represented by a general formula (G3)

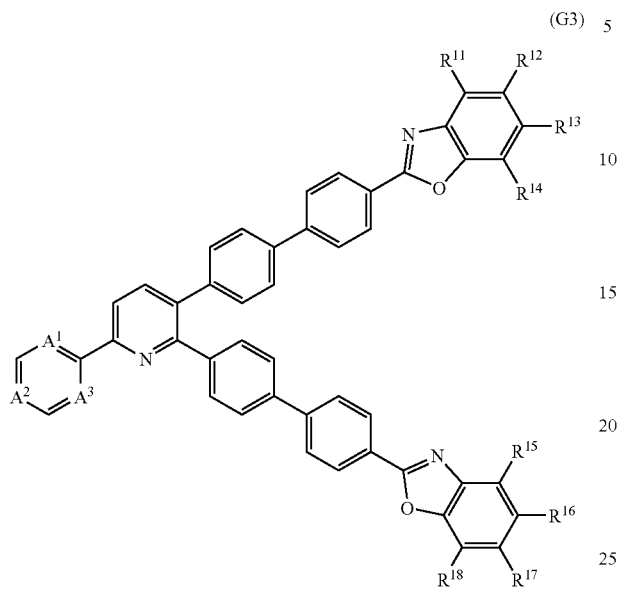

(G3)

wherein one or two of $A^1$ to $A^3$ is/are nitrogen, and the other(s) is/are carbon.

5. The benzoxazole derivative according to claim 1, wherein $Ar^1$ and $Ar^3$ have the same structure, and $Ar^2$ and $Ar^4$ have the same structure.

6. The benzoxazole derivative according to claim 1, wherein $R^{11}$ and $R^{15}$ have the same structure, $R^{12}$ and $R^{16}$ have the same structure, $R^{13}$ and $R^{17}$ have the same structure, and $R^{14}$ and $R^{18}$ have the same structure.

7. A light-emitting element comprising a benzoxazole derivative represented by a general formula (G1) between a pair of electrodes

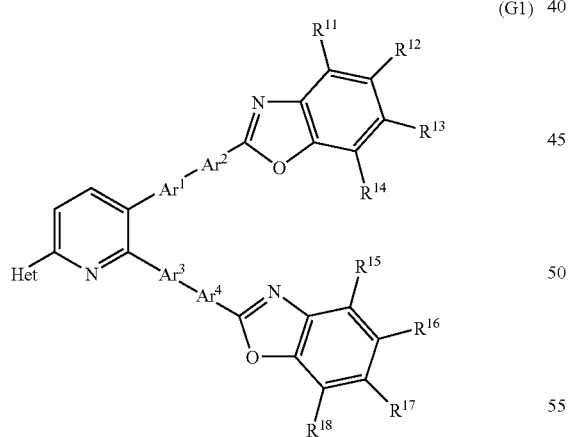

(G1)

wherein Het represents a pyridyl group or a pyrimidinyl group, $Ar^1$ to $Ar^4$ are independently a substituted or unsubstituted arylene group having 6 to 13 carbon atoms, and $R^{11}$ to $R^{18}$ are independently hydrogen, an alkyl group having 1 to 4 carbon atoms, a haloalkyl group having 1 to 4 carbon atoms, a substituted or unsubstituted aryl group having 6 to 13 carbon atoms, or halogen.

8. A light-emitting device comprising the light-emitting element according to claim 7, and a control circuit configured to control light emission of the light-emitting element.

9. The light-emitting element according to claim 7, wherein Het is a substituent represented by a general formula (G1-1),

(G1-1)

wherein one or two of $A^1$ to $A^3$ is/are nitrogen, and the other(s) is/are carbon.

10. The light-emitting element according to claim 7, wherein the benzoxazole derivative is represented by a general formula (G2)

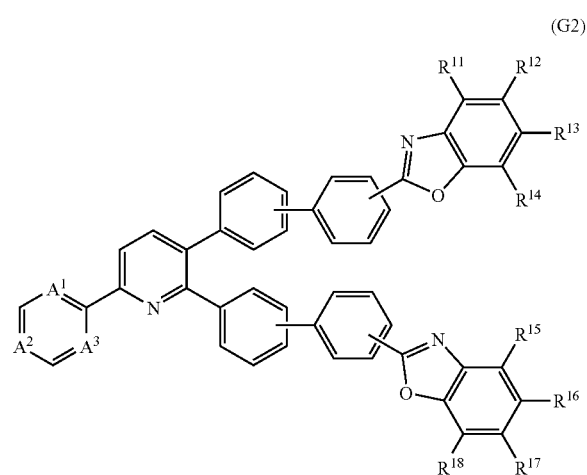

(G2)

wherein, one or two of $A^1$ to $A^3$ is/are nitrogen, and the other(s) is/are carbon.

11. The light-emitting element according to claim 7, wherein the benzoxazole derivative is represented by a general formula (G3)

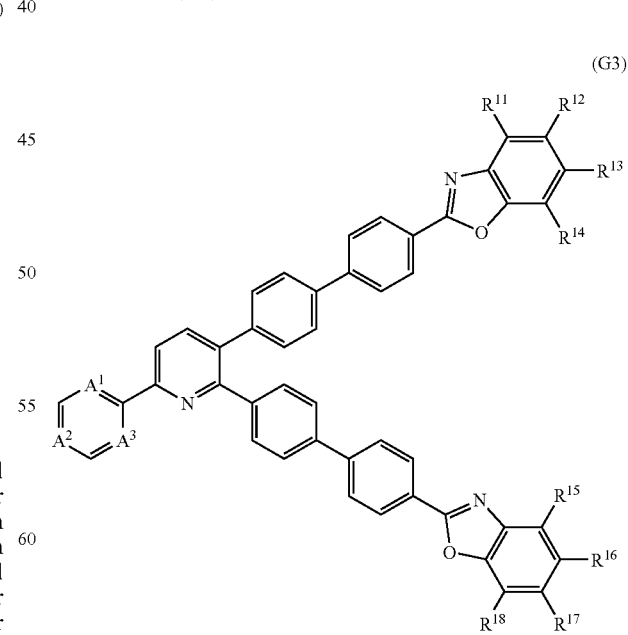

(G3)

wherein one or two of $A^1$ to $A^3$ is/are nitrogen, and the other(s) is/are carbon.

12. The light-emitting element according to claim 7, wherein $Ar^1$ and $Ar^3$ have the same structure, and $Ar^2$ and $Ar^4$ have the same structure.

13. The light-emitting element according to claim 7, wherein $R^{11}$ and $R^{15}$ have the same structure, $R^{12}$ and $R^{16}$ have the same structure, $R^{13}$ and $R^{17}$ have the same structure, and $R^{14}$ and $R^{18}$ have the same structure.

14. An electronic device comprising a display portion, the display portion including:
a light-emitting element comprising a benzoxazole derivative represented by a general formula (G1) between a pair of electrodes,

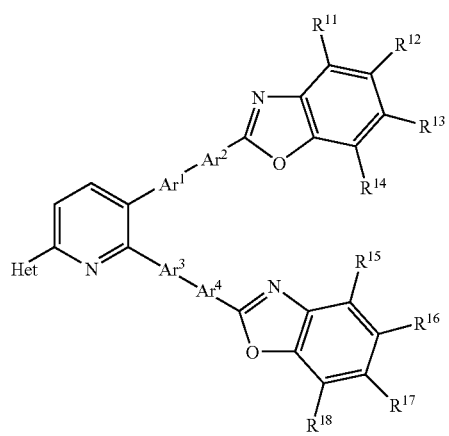

(G1)

wherein Het represents a pyridyl group or a pyrimidinyl group, $Ar^1$ to $Ar^4$ are independently a substituted or unsubstituted arylene group having 6 to 13 carbon atoms, and $R^{11}$ to $R^{18}$ are independently hydrogen, an alkyl group having 1 to 4 carbon atoms, a haloalkyl group having 1 to 4 carbon atoms, a substituted or unsubstituted aryl group having 6 to 13 carbon atoms, or halogen.

15. The electronic device according to claim 14, wherein Het is a substituent represented by a general formula (G1-1),

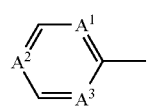

(G1-1)

wherein one or two of $A^1$ to $A^3$ is/are nitrogen, and the other(s) is/are carbon.

16. The electronic device according to claim 14, wherein the benzoxazole derivative is represented by a general formula (G2)

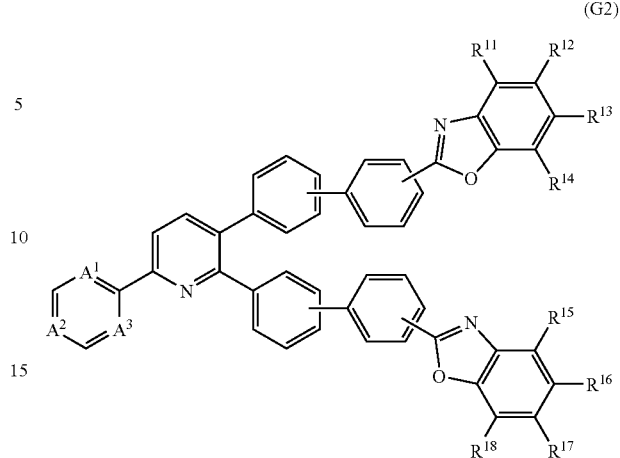

(G2)

wherein, one or two of $A^1$ to $A^3$ is/are nitrogen, and the other(s) is/are carbon.

17. The electronic device according to claim 14, wherein the benzoxazole derivative is represented by a general formula (G3)

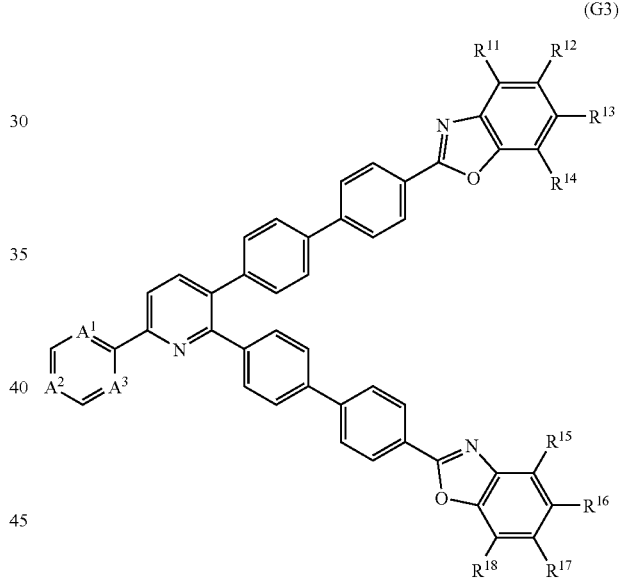

(G3)

wherein one or two of $A^1$ to $A^3$ is/are nitrogen, and the other(s) is/are carbon.

18. The electronic device according to claim 14, wherein $Ar^1$ and $Ar^3$ have the same structure, and $Ar^2$ and $Ar^4$ have the same structure.

19. The electronic device according to claim 14, wherein $R^{11}$ and $R^{15}$ have the same structure, $R^{12}$ and $R^{16}$ have the same structure, $R^{13}$ and $R^{17}$ have the same structure, and $R^{14}$ and $R^{18}$ have the same structure.

* * * * *

UNITED STATES PATENT AND TRADEMARK OFFICE
CERTIFICATE OF CORRECTION

PATENT NO. : 8,142,911 B2
APPLICATION NO. : 12/466076
DATED : March 27, 2012
INVENTOR(S) : Hiroshi Kadoma et al.

It is certified that error appears in the above-identified patent and that said Letters Patent is hereby corrected as shown below:

In the Specification:

Column 98, Line 18; Change "MFDATA" to --MTDATA--.

Column 99, Line 53; Change "iridium(II)acetylacetonate" to --iridium(III)acetylacetonate--.

Column 99, Line 56; Change "iridium(II)acetylacetonate" to --iridium(III)acetylacetonate--.

Column 99, Line 58; Change "iridium(II)acetylacetonate" to --iridium(III)acetylacetonate--.

Column 101, Line 27; Change "DPHPA" to --DPhPA--.

Column 102, Line 57; Change "(g)" to --(Mg)--.

Column 139, Line 57; Change "104 Pa" to --$10^{-4}$ Pa--.

Column 140, Line 21; Change "20 m" to --20 nm--.

Signed and Sealed this
Fourth Day of September, 2012

David J. Kappos
*Director of the United States Patent and Trademark Office*